(12) United States Patent
McKerrecher et al.

(10) Patent No.: US 7,943,607 B2
(45) Date of Patent: May 17, 2011

(54) HETEROARYL BENZAMIDE DERIVATIVES FOR USE AS GLK ACTIVATORS IN THE TREATMENT OF DIABETES

(75) Inventors: Darren McKerrecher, Cheshire (GB); Kurt Gordon Pike, Cheshire (GB); Michael James Waring, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 448 days.

(21) Appl. No.: 11/913,114

(22) PCT Filed: May 23, 2006

(86) PCT No.: PCT/GB2006/001887
§ 371 (c)(1),
(2), (4) Date: Jun. 27, 2008

(87) PCT Pub. No.: WO2006/125972
PCT Pub. Date: Nov. 30, 2006

(65) Prior Publication Data
US 2009/0105214 A1    Apr. 23, 2009

(30) Foreign Application Priority Data

May 27, 2005  (GB) .................................. 0510852.7
Jul. 9, 2005   (GB) .................................. 0514177.5
Aug. 9, 2005   (GB) .................................. 0516295.3
Nov. 24, 2005  (GB) .................................. 0523861.3

(51) Int. Cl.
| C07D 405/12 | (2006.01) |
| C07D 413/12 | (2006.01) |
| C07D 411/12 | (2006.01) |
| C07D 413/14 | (2006.01) |
| C07D 419/12 | (2006.01) |
| C07D 403/12 | (2006.01) |
| C07D 409/12 | (2006.01) |
| C07D 417/12 | (2006.01) |
| A61K 31/4155 | (2006.01) |
| A61P 3/10 | (2006.01) |

(52) U.S. Cl. ............. 514/211.05; 514/211.1; 514/230.5; 514/255.05; 514/407; 540/490; 540/552; 544/92; 544/336; 548/364.4; 548/364.7

(58) Field of Classification Search .................. 540/490, 540/552; 544/92, 336; 548/364.4, 364.7; 514/211.05, 211.1, 230.5, 255.05, 407
See application file for complete search history.

(56) References Cited

U.S. PATENT DOCUMENTS

| 2,750,393 | A | 6/1956 | Elpern |
| 2,967,194 | A | 1/1961 | Hauptschein |
| 3,917,625 | A | 11/1975 | Lee et al. |
| 3,950,351 | A | 4/1976 | Rossignol et al. |
| 4,009,174 | A | 2/1977 | Cluzan et al. |
| 4,105,785 | A | 8/1978 | Mauvernay et al. |
| 4,146,631 | A | 3/1979 | Ford et al. |
| 4,434,170 | A | 2/1984 | Dostert et al. |
| 4,474,792 | A | 10/1984 | Erickson |
| 4,634,783 | A | 1/1987 | Fujii et al. |
| 4,966,891 | A | 10/1990 | Fujiu et al. |
| 5,258,407 | A | 11/1993 | Washburn et al. |
| 5,273,986 | A | 12/1993 | Holland et al. |
| 5,399,702 | A | 3/1995 | Holland et al. |
| 5,466,715 | A | 11/1995 | Washburn et al. |
| 5,510,478 | A | 4/1996 | Sabb |
| 5,661,153 | A | 8/1997 | Isobe et al. |
| 5,672,750 | A | 9/1997 | Perry |
| 5,712,270 | A | 1/1998 | Sabb |
| 5,849,735 | A | 12/1998 | Albright et al. |
| 6,110,945 | A | 8/2000 | Head et al. |
| 6,197,798 | B1 | 3/2001 | Fink et al. |
| 6,200,995 | B1 | 3/2001 | De la Brouse-Elwood et al. |
| 6,207,693 | B1 | 3/2001 | Setoi et al. |
| 6,214,878 | B1 | 4/2001 | Bernardon et al. |
| 6,242,474 | B1 | 6/2001 | Yamasaki et al. |
| 6,255,335 | B1 | 7/2001 | Himmler et al. |
| 6,316,482 | B1 | 11/2001 | Setoi et al. |

(Continued)

FOREIGN PATENT DOCUMENTS

CA    2605738    11/2006

(Continued)

OTHER PUBLICATIONS

Coghlan et al., "Glucokinase activators in diabetes management" Expert Opin. Investig. Drugs 17(2):145-167 (2008).
Leighton, "Pre-clinical disease models—challenges and success stories"44th Drug Information Association Annual Meeting, Boston, MA, US (2008).
Lith, "Evaluation of the effects on whole body glucose metabolism after single doses of X2000—A glucose lowering agent" Poster presentation, Master thesis in Pharmaceutical Bioscience, Goteborgs University (2008).

(Continued)

*Primary Examiner* — Bruck Kifle
(74) *Attorney, Agent, or Firm* — Morgan Lewis & Bockius LLP

(57) ABSTRACT

Compounds of formula (I), wherein $R^1$, $R^4$, HET-1 and HET-2 are as described in the specification, and their salts and pro-drugs, are activators of glucokinase (GLK) and are thereby useful in the treatment of, for example, type 2 diabetes. Processes for preparing compounds of formula (I) are also described.

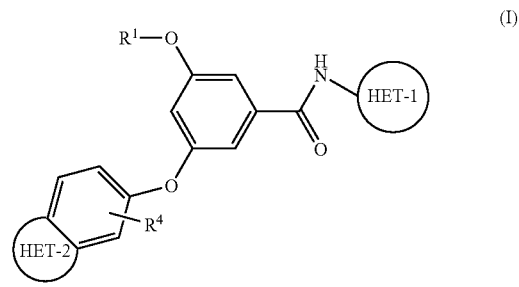

17 Claims, No Drawings

U.S. PATENT DOCUMENTS

| | | |
|---|---|---|
| 6,320,050 B1 | 11/2001 | Bizzarro et al. |
| 6,348,474 B1 | 2/2002 | Kayakiri et al. |
| 6,369,229 B1 | 4/2002 | Head et al. |
| 6,376,515 B2 | 4/2002 | Zhu et al. |
| 6,388,071 B2 | 5/2002 | Mahaney |
| 6,448,399 B1 | 9/2002 | Corbett et al. |
| 6,486,349 B1 | 11/2002 | Flitter et al. |
| 6,528,543 B1 | 3/2003 | Bizzarro et al. |
| 6,545,155 B2 | 4/2003 | Corbett et al. |
| 6,610,846 B1 | 8/2003 | Bizzarro et al. |
| 6,613,942 B1 | 9/2003 | Ling et al. |
| 7,132,546 B2 | 11/2006 | Kato et al. |
| 7,199,140 B2 | 4/2007 | Hayter et al. |
| 7,230,108 B2 | 6/2007 | Hargreaves et al. |
| 7,390,908 B2 | 6/2008 | Boyd et al. |
| 7,524,957 B2 | 4/2009 | Boyd et al. |
| 7,642,259 B2 | 1/2010 | McKerrecher et al. |
| 7,642,263 B2 | 1/2010 | McKerrecher et al. |
| 7,671,060 B2 | 3/2010 | Martin et al. |
| 7,696,191 B2 | 4/2010 | McCabe et al. |
| 7,700,640 B2 | 4/2010 | Cornwall et al. |
| 7,709,505 B2 | 5/2010 | McKerrecher et al. |
| 7,745,475 B2 | 6/2010 | Johnstone et al. |
| 2001/0027200 A1 | 10/2001 | De la Brouse-Elwood et al. |
| 2002/0002183 A1 | 1/2002 | Zhu et al. |
| 2002/0095044 A1 | 7/2002 | Jagtap et al. |
| 2003/0162690 A1 | 8/2003 | Zhu et al. |
| 2004/0014968 A1 | 1/2004 | Bizzarro et al. |
| 2004/0077555 A1 | 4/2004 | Ishihara et al. |
| 2004/0214868 A1 | 10/2004 | Hayter et al. |
| 2005/0080106 A1 | 4/2005 | Boyd et al. |
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0167053 A1 | 7/2006 | Iino et al. |
| 2006/0258728 A1 | 11/2006 | Tani et al. |
| 2007/0078168 A1 | 4/2007 | Caulkett |
| 2007/0093535 A1 | 4/2007 | Hayter et al. |
| 2007/0112040 A1 | 5/2007 | Hayter et al. |
| 2007/0255062 A1 | 11/2007 | Johnstone et al. |
| 2007/0287693 A1 | 12/2007 | Johnstone et al. |
| 2008/0171734 A1 | 7/2008 | Campbell et al. |
| 2008/0234273 A1 | 9/2008 | McKerrecher et al. |
| 2008/0280872 A1 | 11/2008 | Johnstone et al. |
| 2008/0280874 A1 | 11/2008 | Johnstone et al. |
| 2008/0300412 A1 | 12/2008 | Hopes et al. |
| 2008/0312207 A1 | 12/2008 | Johnstone et al. |
| 2009/0018157 A1 | 1/2009 | Johnstone et al. |
| 2009/0062351 A1 | 3/2009 | Caulkett et al. |
| 2009/0105263 A1 | 4/2009 | Caulkett et al. |
| 2009/0111790 A1 | 4/2009 | McKerrecher et al. |
| 2009/0227592 A1 | 9/2009 | Boyd et al. |
| 2009/0253676 A1 | 10/2009 | Johnstone et al. |
| 2009/0264336 A1 | 10/2009 | McKerrecher et al. |
| 2010/0093757 A1 | 4/2010 | Bennett et al. |
| 2010/0094009 A1 | 4/2010 | McCabe et al. |
| 2010/0160286 A1 | 6/2010 | McKerrecher et al. |
| 2010/0173825 A1 | 7/2010 | Martin et al. |
| 2010/0210621 A1 | 8/2010 | Bowden et al. |
| 2010/0210841 A1 | 8/2010 | Butters et al. |
| 2010/0261704 A1 | 10/2010 | Waring et al. |
| 2010/0261733 A1 | 10/2010 | Bennett et al. |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1600442 | 11/2005 |
| EP | 1702919 | 9/2006 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00375 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |

| | | |
|---|---|---|
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |
| WO | WO 02/051831 | 7/2002 |
| WO | WO 02/064545 | 8/2002 |
| WO | WO 02/079145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/051366 | 6/2003 |
| WO | WO 03/055482 | 7/2003 |
| WO | WO 03/066613 | 8/2003 |
| WO | WO 03/048152 | 9/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/081001 | 8/2004 |
| WO | WO 2004/076420 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/031739 | 3/2007 |
| WO | WO 2007/053657 | 5/2007 |
| WO | WO 2007/060448 | 5/2007 |
| WO | WO 2008/050101 | 5/2008 |
| WO | WO 2008/050117 | 5/2008 |
| WO | WO 2008/075073 | 6/2008 |

OTHER PUBLICATIONS

Ralph et al. "Glucose Modulation of Glucokinase Activation by Small Molecules" Biochemistry 47(17):5028-5036 (2008).
Sarabu et al., "Glucokinase activators as new type 2 diabetes therapeutic agents" Expert Opinion on Therapeutic Patents 18(7):759-768 (2008).
Shorvon, "Pyrrolidone derivatives" Lancet 358(9296):1885-1892 (2001).
Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.
Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).
West, Anthony R., "Solid State Chemistry and its Applications" Wiley, New York, pp. 358 and 365 (1988).
Wolff, Manfred E. "Burger's Medicinal Chemistry", 5th Edition, Part I, John Wiley & Sons, pp. 975-977 (1995).
Alvarez et al, "Evidence that glucokinase regulatory protein is expressed and interacts with glucokinase in rat brain" J. Neurochem. 80(1):45-53 (2002).
Alvarez et al, "Expression of the glucagon-like peptide-1 receptor gene in brain" J. Neurochem, 66(3)-920-927 (1996).
Anderson et al "Pyridopyrimidines. 6. Nucleophilic substitutions in the pyrido[2,3-d]pyrimidine series" J. Org. Chem. 42(6):993-996 (1977).
Ando et al. "Fluoride salts on alumina as reagents for alkylation of phenols and alcohols" Bull. Chem. Jpn. 55(8):2504-2507 (1982).
Atwell et al, "Potential antitumor agents. VI. Bisquaternary salts" J. Med. Chem. 11(2):295-300 (1968).
Baker et al, "Structure and synthesis of Pallescansin E utilising a modified Wadsworth-Emmons reaction" J. Chem. Soc., Perkin. Trans. 1, 12:3087-3091 (1981).
Baker et al, "Synthesis of Pallescensin-E: Use of crown ether in the Wadsworth procedure for olefin formation" Tetrahedron Letters 22:161-162 (1981).
Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).
Beilstein Registry Number 6511458 (Apr. 18, 1994) [XP002272206].
Bell et al. "Glucokinase mutations, insulin secretion, and diabetes mellitus" Annu. Rev. Physiol. 58:171-186 (1996).
Beller et al, "Photochemical synthesis of benzo[f]quinolines" J Org Chem. 42(22):3514-3518 (1977).
Berl et al. "Induced fit selection of a barbiturate receptor from a dynamic structural and conformational/ configurational library" European J. Org. Chem. (11):3089-3094 (1999)
Berl et al. "Template-induced and molecular recognition directed hierarchical generation of supramolecular assemblies from molecular strands" Chem. Eur. J. 6(11):1938-1946 (2000).
Bonina: et al. "Synthesis and pharmacologic activity of 2-arylethenylthinazol-4-acetic and 4-carboxylic acids" II Farmaco 40(11):875-884 (1985).
Boucherle et al. "Recherches dans la serie des cetones polyphenoliques IV. Thiazoles" Chimica, Therapeutica. 3(5):360-363 (1968) (Translation enclosed).
Bowden et al. "Structure-activity relations. Part 10. Metal-ion-complexation studies of a series of substituted benzamidotetrazoles" J. Chem. Research (Synopses) 11:304 (1991).

Bowden et al. "Structure-activity relations. Part 13. Inhibitors of cyclic nucleotide phosphodiestcrase and anaphylaxis. Inhibition by a series of substituted benzamidotetrazoles" J. Chem. Research (Synopses) 6:206 (1992).

Brenner et al. "Imino-bridged heterocycles. VII. (I) N-aminobenzocycloheptapyridinimines" J. Heterocyclic Chem. 23:1331-1332 (1986).

Brocklehurst et al. "Stimulation of hepatocyte glucose metabolism by novel small molecule glucokinase activators" Diabetes 53:535-541 (2004).

Caro et al. "Liver glucokinase: Decreased activity in patients with type II diabetes" Horm. Metab. Res. 27(1):19-22 (1995).

Carroll et al, "The in vitro characterisation of a novel Glucokinase activator" Stress, Signalling and Control, Biochemical Society Meeting 679, University of Essex, UK (Jul. 2-4, 2003).

Caulfield et al, "The first potent and selective inhibitors of the glycine transporter type 2" J. Med. Chem. 44(17):2679-2682 (2001).

Cavier et al. "Recherches sur les derives mitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).

Chemical Abstracts Service, Columbus, Ohio, US: CAS Registry No. 438028-05-8 (Nov. 15, 2001); CAS Registry No. 438024-90-9 (Nov. 15, 2001), [XP002272448].

Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-9 (Jul. 9, 2002); CAS Registry No. 455017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-03 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002) [XP002272449].

Chemical Abstracts Service, Columbus, Ohio, US: CAS Registry No. 354767-51-4 (Sep. 5, 2001).

Chemical Abstracts Service, Columbus, Ohio, US: CAS Registry No. 354767-66-1 (Sep. 5, 2001).

Christesen at al. "The second activating glucokinase mutation (A456V): Implications for glucose homeostasis and diabetes therapy" Diabetes 51(4):1240-1246 (2002).

Claceri et al. "Analgesic, antipyretic and anti-inflammatory action of some new acids of the phenylethylenethiazole series" Minerva Medica 63(42):2409-2413 (1972).

Coburn et al. "Meseionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences, 62(11):1785-1789 (1973).

Coghlan "Small Molecule Glucokinase Activators (GKAs) as novel anti-diabetic agents" CIDEM seminar (May 2005).

Coghlan "Small Molecule Glucokinase Activators (GKAs) as novel anti-diabetic agents" Society for Medicines Research Seminar (Jun. 2004).

Coope et al, "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Fancisco, CA (Mar. 24-26, 2004).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Fancisco, CA (Mar. 24-26, 2004).

Cushman et al. "Synthesis and evaluation of new protein-tyrosine kinase inhibitors, Part 1, Pyridine-containing stilbenes and amides" Bioorganic & Medicinal Chemistry Letters, 1(4):211-214 (1991).

De Paulis et al, "Potential antipsychotic agents. 6, Synthesis and antidopaminergic properties of substituted N-(1-benzyl-4-piperidinyl)salicylamides and related compounds. QSAR based design of more active members" Eur. J. Med. Chem. 25:507-517 (1990).

DeFronzo et al, "The triumvirate: β-cell, muscle, liver. A collusion responsible for NIDDM" Diabetes 37:667-687 (1988).

DeJohn et al. "Functionalization of Substituted 2(1H)- and 4(1H)-Pyridoncs. III. The preparation of substituted 6-vinyl-1,2-dihydro-2-oxo- and 1,4-dihydro-4-oxo-3-pyridinecarboxylic acids through the chemistry of pyridone dianions" J. Heterocyclic Chem. 20(5):1295-1302 (1983).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22: 1686 (1957).

Ferre et al. "Correction of diabectic alterations by Glucokinase" PNAS USA 93(14):7225-7230 (1996).

Ford et al. "Synthesis and quantitative structure-activity relationships of antiallergic 2-hydroxy-N-1H-tetrazel-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993)

Fujimoto et al. "Administration of D-glucosamine into the third cerebroventricle induced feeding accompanied hyperglycemia in rats" Life Sciences 37(26):2475-2482 (1985).

Gill et al, "Stimulation of insulin release by a small molecule glucokinase activator" EASD Islet Study Group, Abstract (Nov. 2005).

Gill et al. "Stimulation of Insulin Release MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S2818 (2007).

Glaseret et al. "Familial hyperinsulinism cause by an activating glucokinase mutation" The New England Journal of Medicine 338(4):226-230 (1998).

Gorman et al. "Effect of high-fat diet on glucokinase homeostasis and gene expression in Glucokinase (GK) heterozygous knock-outs" Abstract No. 0108-OR, 67th Annual Scientific Sessions, American Diabetes Association, Chicago, IL (Jun. 22-26, 2007).

Grimsby "Glucokinase activators: Potential for type 2 diabetes" Roche, SMi Diabetes, London, UK (Oct. 28-29, 2002).

Grimsby et al. "Allosteric activators of glucokinase: Potential role in diabetes therapy" Science 301 (5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding, and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244;939-942 (1994).

Johnson et al. "Glucose-dependent modulation of insulin secretion and intracellular calcium ions by GKA50—A glucokinase activator" Abstract No. 0592-P, 67th Annual Scientific Sessions, American Diabetes Association, Chicago, IL (Jun. 22-26, 2007).

Julia et al. "Synthesis of a 2,3,4,4a,5,6-hexahydronbenzo[f]quinline system by "aryne substitution"" Bull Chem Soc France 11:4463-4467 (1968) (Translation enclosed).

Kamata et al. "Pyroelectricity of noncentrosymmetric Languir-Blodgeti films of phenylpyranzine derivatives" Japan J. Appl. Phys. 33(2):1074-1078 (1994).

Kar "Cinchophen analogues as potenial CNS agents" J Pharm Sci, 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem 60(13):4291-4293 (1995).

Kunishima et al. "4-(4,6-Dimethoxy-1,3,5-triazin-2-yl)-4-methyl-morpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al, "Structural evaluation of glucose analogues on feeding elicitation in rat" Metabolism 38(1):46-51. (1989).

Lai et al. "Formation of columnar arrangements in copper(ii) complexes of 2-phenylazomethinopyridine derivatives" Materials Chemistry 8(11):2379-2383 (1998).

Leighton et al, "Improved glycemic control after sub-acute administration of a Glucokinase activator to male zucker (fa/fa) rats" Abstract No. 0377-OR, 67th Annual Scientific Sessions, American Diabetes Association, Chicago, IL (Jun. 22-26, 2007).

Leighton et al. "Small molecule glucokinase activators as novel antidiabetic agents" Biochemical Society Transactions 33(Part 2):371-374 (2005).

Levin "Glucosensing neurons do more than just sense glucose" International Journal of Obesity 25(Suppl 5): S68-S72 (2001).

Levin et al, "Brain glucose sensing and body energy homeostasis: role in obesity and diabetes" Am. J. Physiol. 276(5 Pt2):R123-R1231 (1999).

Levin et al. "Differential effects of diet and obesity on high and low affinity sulfonylurea binding sites in the rat brain" Brain Research 739(1-2):293-300 (1996).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al, "Research on cyanide dyes 11. 7.7'-Dimethylthiacarboctanines" Zhurnal Obshchei Khimii 27:3097-3107 (1957) (Translation enclosed).

Lynch et al. "Localization of gincokinase gene expression in the rat brain" Diabetes 49(5):693-700 (2000).

Mastafanova et al. "Features of the reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).

Mastafanova et al. "Synthesis and study of the antihypertensive activity of substituted N-acetylmercatopropionyl-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6- Substituted Picotinic Acids" Khimiko Farmatsevticheskii Zhurnal 22(4) 428-431.

Mazik et al. "Molecular recognition of carbohydrates by artificial receptors: systematic studies towards recognition motifs for carbohydrates" Chem. Eur. J. 7(3):664-670 (2001).

Mazik et al. "Molecular recognition of carbohydrates by artificial polypyridine and polyliyrimidine receptors" Angewandte Chemie International Edition 39(3):551-554 (2000).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Lett. 16(10):2705-2709 (May 15, 2006) Epub Feb. 28, 2006.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, $12^{th}$ SCI-RSC Medicinal Chemistry Symposium, Cambridge, UK, Sep. 7-10, 2003, (poster 21) and $227^{th}$ American Chemical Society National Meeting and Exposition, San Francisco, California, Mar. 28-Apr. 1, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al. "Chiral amplification in supramolecular stacks" Polymer Preprints 41(1):902-903 (2000)

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11): 1882-1887 (2001).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328-7316 (1998).

Palmans "Extended-core discotic liquid crystals based on the intramolecular H-bonding in N-acylated 2,2'-bipyridine-3,3'-diamine moieties" Chem. Eur. J. 3(2)300-307 (1997).

Plieninger et al. "Synthesis of 7,8-dihydro-5,6-benzoquinoline-(3)-carboxylic acid" Chemische Berichte 87:882-887 (1954) (Translation enclosed).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1(5-nitro-2-thienyl)-, and 1-(4-nitrophenyl)-2-R ethylenes" Collect Czech. Chem. Commun. 54:1575-1682 (1989).

Qian-Cutrone et al. "Glucolipsin A and B, two new glucokinase activators produced by Streptomyces purpurogeniscleroticus and Nocardia vaccinii" Journal of Antibiotics (Tokyo), 52(3):245-255 (1999).

Rivalle et al, "2,3 Disubstituted furans and pyrroles—XVIII: Synthesis annd rearrangement of 4H-dihydro-9,10 benzo[4,5]cycloheptal[1,2-b]furannones-4" Tetrahedron 32(7):829-834 (1976).

Rogers et al, "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497,2:365-377 (1996).

Schuit et al. "Glucose sensing in pancreatic β-Cells. A model for the study of other glucose-regulated cells in gut, pancreas, and hypothalamus" Diabetes 50:1-11 (2001).

Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).

Seoane et al, "Glucokinase overexpression restores glucose utilization and storage in cultured hepatocytes from male Zucker diabetic fatty rats" J Biol Chem. 274(45):31833-31838 (1999).

Shiota et al, "Glucokinase gene locus transgenic mice are resistant to the development of obesity-induced type 2 diabetes" Diabetes 50(3):622-629 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted. 3. Modifications to the linkage region (region 3)" J. Med. Chem. 28(3):295-298 (1985).

Suhua et al, "Synthesis and biological activity of tyrosine protein kinase inhibitors" Acta Pharmaceutica Sinica 32(7): 515-523 (1997).

Tecilla et al. "Hydrogen-bonding self-assembly of multichromophore structures" J. Am. Chem. Soc. 112:9408-9410 (1990).

Tecilla et al "Synthetic hydrogen bonding receptors as models of transacylase enzymes" Tetrahedron 51(2):435-448 (1995).

Tecilla et al, "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al, "C3-symmetrical supramolecular architectures: fibers and organic gels from discotic trisamides and trisureas" J Am. Chem. Soc. 124(49):14759-14769 (2002).

Vanderstelt et al. "Synthesis and pharmacological properties of some derivatives of 5H-benzo[4,5] cycloheptal[1,2-b] pyridine and of 11H-benzo[5, 6] cycloheptal[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulation of hepatocyte glucose metabolism by pharmacological agents" Diabetologia, 47 Supp 1, A 214, 589 (2004).

Williams et al, "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al, "Glucokinase Activation Reduces Glycemia and Improves Glucose Tolerance in Mice with High-fat Diet-induced Insulin Resistance" Abstract Number: 1482-P, 67th Annual Scientific Sessions, American Diabetes Association; Chicago, IL (Jun. 22-26, 2007) and Diabetes vol. 56 (Supplement 1) 1482-P (2007).

Yakushijin et al. "Intramolecular ring formation of phenyl azide and furan" Heterocycles 12(8):1021-1026 (1979).

Yakushijin et al, "Intramolecular ring formation of phenyl azide and furan moieties" Chem. Pharm. Bull. 30(1):140-151 (1982).

Yang et al. "Hypothalamic glucose sensor: similarities to and differences from pancreatic beta-cell mechanisms" Diabetes 48(9):1763-1772 (1999).

Yoshina et al, "Studies of heterocyclic compounds, II. Synthesis of 2-furylvinyl-benzenes and studies of polarography" Yakugaku Zasshi 88(4):398-404 (1968).

Yoshina et al. "Studies of heterocyclic compounds, III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2-(2-furyl)vinylbenzenes and 2-(2-furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

HETEROARYL BENZAMIDE DERIVATIVES FOR USE AS GLK ACTIVATORS IN THE TREATMENT OF DIABETES

The present invention relates to a group of benzoyl amino heterocyclyl compounds which are useful in the treatment or prevention of a disease or medical condition mediated through glucokinase (GLK or GK), leading to a decreased glucose threshold for insulin secretion. In addition the compounds are predicted to lower blood glucose by increasing hepatic glucose uptake. Such compounds may have utility in the treatment of Type 2 diabetes and obesity. The invention also relates to pharmaceutical compositions comprising said compounds and to methods of treatment of diseases mediated by GLK using said compounds.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6-10 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, Maturity-Onset Diabetes of the Young Type 2 (MODY-2), the diabetes is caused by GLK loss of function mutations [3,4]. Hyperglycaemia in MODY-2 patients results from defective glucose utilisation in both the pancreas and liver [5]. Defective glucose utilisation in the pancreas of MODY-2 patients results in a raised threshold for glucose stimulated insulin secretion. Conversely, rare activating mutations of GLK reduce this threshold resulting in familial hyperinsulinism [6, 6a, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9-12]. Moreover, acute treatment of type 2 diabetics with fructose improves glucose tolerance through stimulation of hepatic glucose utilisation [13]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is dominant in the post-absorptive state whereas F1P predominates in the post-prandial state. In contrast to the hepatocyte, the pancreatic β-cell expresses GLK in the absence of GLKRP. Therefore, β-cell GLK activity is regulated extensively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act selectively in the liver. However, compounds with either profile are predicted to be of therapeutic benefit in treating Type 2 diabetes as this disease is characterised by defective glucose utilisation in both tissues.

GLK, GLKRP and the $K_{ATP}$ channel are expressed in neurones of the hypothalamus, a region of the brain that is important in the regulation of energy balance and the control of food intake [14-18]. These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23-28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "Diabesity" target (of benefit in both Diabetes and Obesity).

GLK is also expressed in specific entero-endocrine cells where it is believed to control the glucose sensitive secretion of the incretin peptides GIP (glucose-dependent insulinotropic polypeptide) and GLP-1 (Glucagon-Like Peptide-1) from gut K-cells and L-cells respectively (32, 33, 34). Therefore, small molecule activators of GLK may have additional beneficial effects on insulin secretion, b-cell function and survival and body weight as a consequence of stimulating GIP and GLP-1 secretion from these entero-endocrine cells.

In WO00/58293 and WO01/44216 (Roche), a series of benzylcarbamoyl compounds are described as glucokinase activators. The mechanism by which such compounds activate GLK is assessed by measuring the direct effect of such compounds in an assay in which GLK activity is linked to NADH production, which in turn is measured optically—see details of the in vitro assay described hereinafter. Compounds of the present invention may activate GLK directly or may activate GLK by inhibiting the interaction of GLKRP with GLK.

Further GLK activators have been described in WO03/095438 (substituted phenylacetamides, Roche), WO03/055482 (carboxamide and sulphonamide derivatives, Novo Nordisk), WO2004/002481 (arylcarbonyl derivatives, Novo Nordisk), and in WO03/080585 (amino-substituted benzoylaminoheterocycles, Banyu).

Our International application Number: WO03/000267 describes a group of benzoyl amino pyridyl carboxylic acids which are activators of the enzyme glucokinase (GLK).

Our International application Number: WO 2005/054233 describes a group of benzoyl amino pyridyl carboxylic acids which are substituted on the phenyl ring by oxy linked benzofused diethers to give compounds such as 6-{[(3-(2,3-dihydro-1,4-benzodioxin-6-yloxy)-5-{[(1S)-1-methyl-2-(methyloxy)ethyl]oxy}phenyl)carbonyl]amino}pyridine-3-carboxylic acid and 6-{[(3-(1,3-benzodioxol-5-yloxy)-5-{[(1S)-1-methyl-2-(methyloxy)ethyl]oxy}phenyl)carbonyl]amino}pyridine-3-carboxylic acid. The present invention excludes benzoyl amino pyridyl carboxylic acids.

Our International application Number: WO03/015774 describes compounds of the Formula (A):

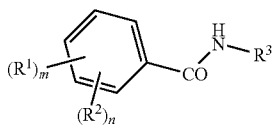

wherein $R^3$ is a substituted heterocycle other than a carboxylic acid substituted pyridyl.

International application WO2004/076420 (Banyu) describes compounds which are generally a subset of those described in WO03/015774, wherein for example $R^1$ is an (substituted) alkyl ether and $R^2$ is (substituted) phenoxy.

We have surprisingly found a small group of compounds, generally a selected subgroup of those described in WO 03/015774, which have generally superior potency for the GLK enzyme, and more advantageous physical properties, including, for example, higher aqueous solubility, higher permeability, and/or lower plasma protein binding. Consequently, such compounds having a balance of these properties would be expected to display higher plasma free drug levels and superior in vivo efficacy after oral dosing as determined, for example, by activity in Oral Glucose Tolerance Tests (OGTTs). Therefore this group of compounds would be expected to provide superior oral exposure at a lower dose and thereby be particularly suitable for use in the treatment or prevention of a disease or medical condition mediated through GLK. The compounds of the invention may also have superior potency and/or advantageous physical properties (as described above) and/or favourable toxicity profiles and/or favourable metabolic profiles in comparison with other GLK activators known in the art, as well as those described in WO 03/015774.

Thus, according to the first aspect of the invention there is provided a compound of Formula (I):

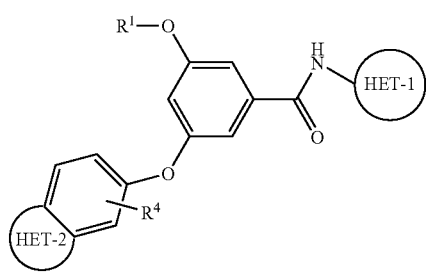

wherein:
$R^1$ is selected from isopropyl, but-2-yl, 1,1,1-trifluoroprop-2-yl, 1,3-difluoroprop-2-yl, but-1-yn-3-yl, 1-hydroxyprop-2-yl, hydroxybut-3-yl, 1-hydroxybut-2-yl, tetrahydrofuranyl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl, 1-fluoromethoxyprop-2-yl, 1,1-difluoromethoxyprop-2-yl and 1-trifluoromethoxyprop-2-yl;
HET-1 is a 5- or 6-membered, C-linked heteroaryl ring containing a nitrogen atom in the 2-position and optionally 1 or 2 further ring heteroatoms independently selected from O, N and S; which ring is optionally substituted on any nitrogen atom by a substituent selected from $R^7$ and/or on any available carbon atom by 1 or 2 substituents independently selected from $R^6$;
HET-2 is a 5-7 membered heterocyclic ring fused to the benzene ring, containing 1, 2 or 3 ring hetereoatoms independently selected from O, S and N (provided that there are no O—O, S—O or S—S bonds within the ring), wherein any ring carbon or sulfur atom may optionally be oxidised and wherein HET-2 is optionally substituted on any nitrogen atom by a substituent selected from $R^2$ and/or on any available carbon atom by 1 or 2 substituents independently selected from $R^3$;
$R^2$ is selected from (1-4C)alkyl, (3-6C)cycloalkyl, benzyl, (1-4C)alkylcarbonyl, (1-4C)alkylsulphonyl, hydroxy(1-4C)alkyl and (1-4C)alkoxy(1-4C)alkyl;
$R^3$ is selected from (1-4C)alkyl, (3-6C)cycloalkyl, (1-4C)alkoxy, hydroxy, fluoro and chloro;
$R^4$ is selected from hydrogen, fluoro and chloro;
$R^6$ is independently selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, di(1-4C)alkylamino(1-4C)alkyl and HET-3;
$R^7$ is independently selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, di(1-4C)alkylamino(1-4C)alkyl and HET-3;
HET-3 is a 5- or 6-membered, C- or N-linked unsubstituted heteroaryl ring containing 1, 2 or 3 ring heteroatoms independently selected from O, N and S;
p is (independently at each occurrence) 0, 1 or 2;
or a salt or pro-drug thereof.

In a further aspect of the invention, there is provided a compound of formula (I) as hereinbefore defined wherein $R^1$ is selected from isopropyl, but-2-yl, 1,1,1-trifluoroprop-2-yl, 1,3-difluoroprop-2-yl, but-1-yn-3-yl, 1-hydroxyprop-2-yl, hydroxybut-3-yl, 1-hydroxybut-2-yl, tetrahydrofuranyl, tetrahydropyranyl, 1-methoxyprop-2-yl, 1-methoxybut-2-yl, 1-fluoromethoxyprop-2-yl, 1,1-difluoromethoxyprop-2-yl and 1-trifluoromethoxyprop-2-yl.

In a further aspect of the invention, there is provided a compound of formula (I) as hereinbefore defined wherein $R^1$ is selected from isopropyl, 1,1,1-trifluoroprop-2-yl, 1,3-difluoroprop-2-yl, but-1-yn-3-yl, 1-hydroxyprop-2-yl, hydroxybut-3-yl, tetrahydrofuranyl, 1-methoxyprop-2-yl, 1-fluoromethoxyprop-2-yl, 1,1-difluoromethoxyprop-2-yl and 1-trifluoromethoxyprop-2-yl; and $R^2$ is selected from (1-4C)alkyl, (3-6C)cycloalkyl and benzyl.

It will be understood that HET-2 may be an unsaturated (including aromatic where possible), partially or fully saturated ring system.

It will be understood that $R^2$ can be present on any nitrogen atom so if there is more than one nitrogen atom in the HET-2 ring, any or all may be substituted by an $R^2$ group, which may be the same or different, provided that the substituted nitrogen is not thereby quaternised.

It will be understood that $R^3$ can be present on any or all available carbon atoms in the heterocyclic ring; each carbon atom can be substituted with 1 or 2 $R^3$ groups which may be the same or different, provided the structure thereby formed is stable (so, for example, it is not intended to cover gem-dihydroxy substitution).

Compounds of Formula (I) may form salts which are within the ambit of the invention. Pharmaceutically acceptable salts are preferred although other salts may be useful in, for example, isolating or purifying compounds.

In another aspect, the invention relates to compounds of formula (I) as hereinabove defined or to a pharmaceutically acceptable salt.

In another aspect, the invention relates to compounds of formula (I) as hereinabove defined or to a pro-drug thereof. Suitable examples of pro-drugs of compounds of formula (I) include in-vivo hydrolysable esters of compounds of formula (I). Therefore in another aspect, the invention relates to compounds of formula (I) as hereinabove defined or to an in-vivo hydrolysable ester thereof.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "(1-4C)alkyl" includes methyl, ethyl, propyl, isopropyl and t-butyl. An analogous convention applies to other generic terms.

For the avoidance of doubt, reference to the group HET-1 containing a nitrogen in the 2-position, is intended to refer to the 2-position relative to the point of attachment of HET-1 to the amide nitrogen atom. For example, HET-1 encompasses but is not limited to the following structures:

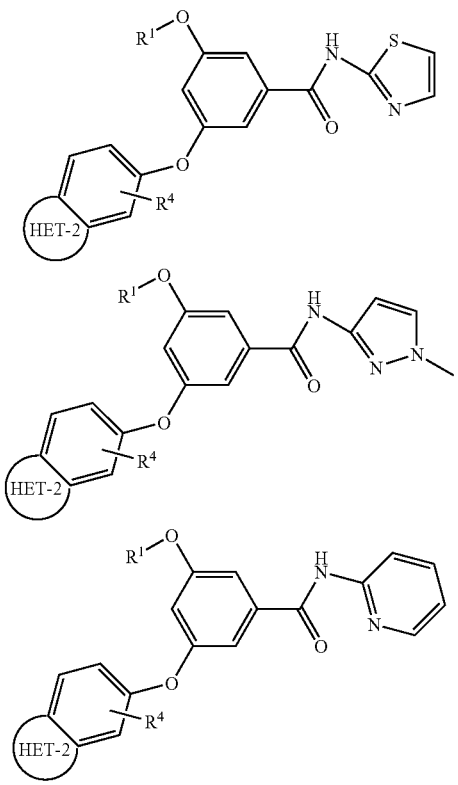

Suitable examples of HET-1 as a 5- or 6-membered, C-linked heteroaryl ring as hereinbefore defined, include thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl.

Suitable values for the bicyclic system formed by HET-2 fused to the benzo ring include those where HET-2 is furyl, thienyl, pyrrolyl, pyrrolidinyl, 1,3-dioxolyl, 1,4-dioxolanyl, oxazolyl, thiazolyl, imidazolyl, imidazolidinyl, pyrazolyl, isoxazolyl, isothiazolyl, pyranyl, piperazinyl, homopiperazinyl, morpholinyl, homomorpholinyl, thiomorpholinyl, homothiomorpholinyl, oxathianyl and homooxathianyl. Further suitable values include those wherein HET-2 is oxathiazepinyl, dihydrothienyl, dihydrofuryl, and piperidinyl. Still further suitable values include those wherein HET-2 is selected from furyl, thienyl, dihydrothienyl, dihydrofuryl, piperidinyl, pyrrolyl, pyrrolidinyl, oxazolyl, thiazolyl, isoxazolyl, isothiazolyl, morpholinyl, homomorpholinyl, thiomorpholinyl, homothiomolpholinyl, oxathiazepinyl, oxathianyl and homooxathianyl. Further suitable values include such ring systems where one or more carbon atoms in the HET-2 ring have been oxidised to a carbonyl group, and/or where one or more sulfur atoms in the HET-2 ring have been oxidised to an S(O) or S(O)$_2$ group.

It will be understood that references herein to the system formed by HET-2 fused to the benzo ring when HET-2 is 1,3-dioxolyl are intended to refer to the following structure:

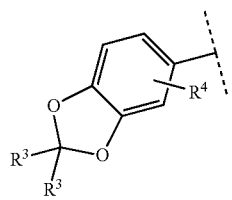

It will be understood that references herein to the system formed by HET-2 fused to the benzo ring when HET-2 is 1,4-dioxolanyl are intended to refer to the following structure:

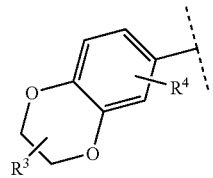

For example suitable values for the bicyclic system formed by HET-2 fused to the benzo ring include the following (wherein each $R^{2a}$ is hydrogen or is selected from $R^2$ as hereinbefore defined, $R^{3a}$ is hydrogen or is selected from $R^3$ as hereinbefore defined and each $R^4$ is as hereinbefore defined):

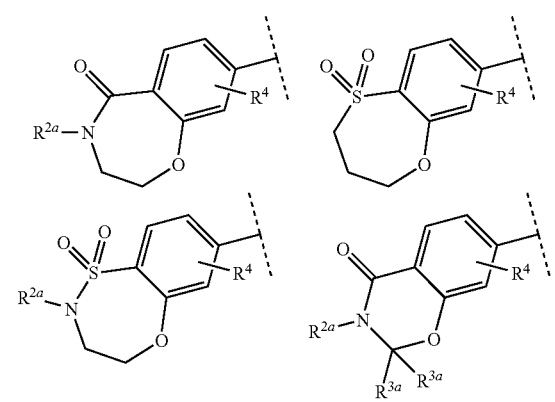

-continued
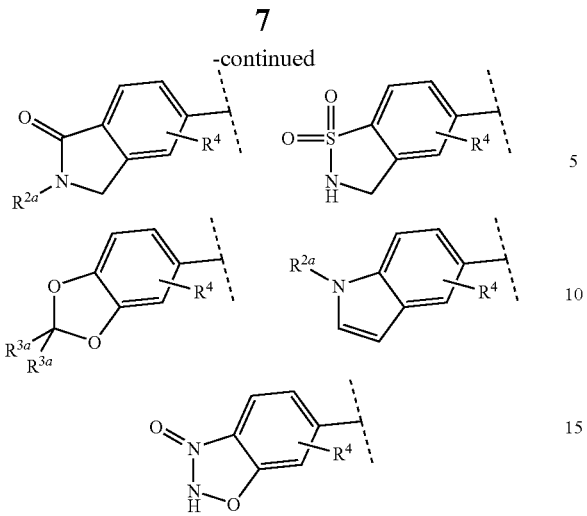
A further example is:
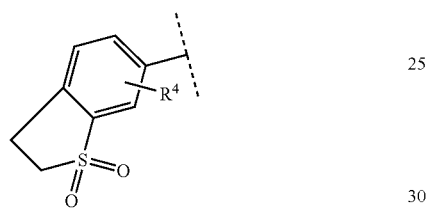
Further examples include:
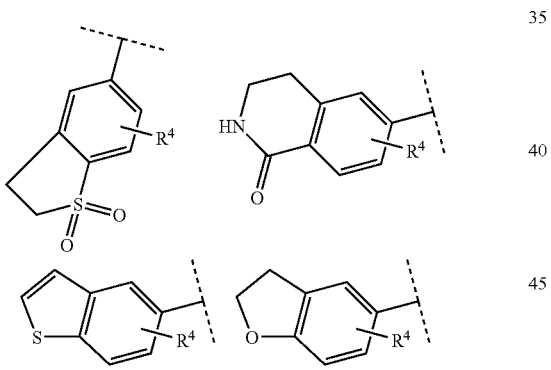
In another aspect, the bicyclic system formed by HET-2 fused to the benzo ring is selected from formulae A to M (wherein $R^{2a}$ is hydrogen or is selected from $R^2$ as hereinbefore defined, $R^{3a}$ is hydrogen or is selected from $R^3$ as hereinbefore defined and each $R^4$ is as hereinbefore defined)
A
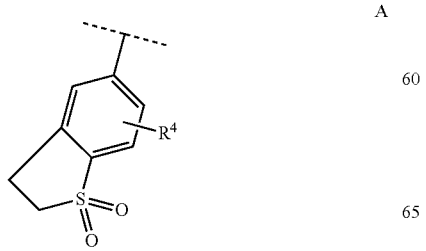
B
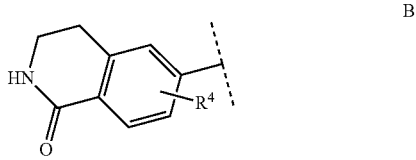
C
D
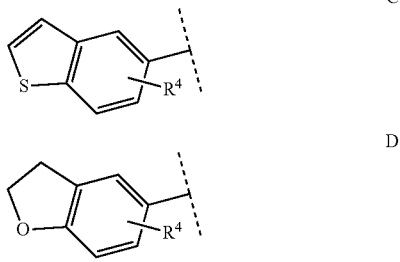
E
F
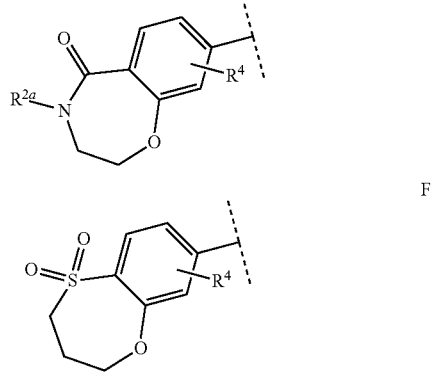
G
H
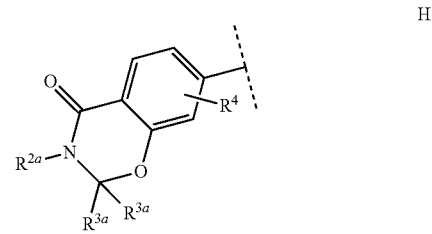
J
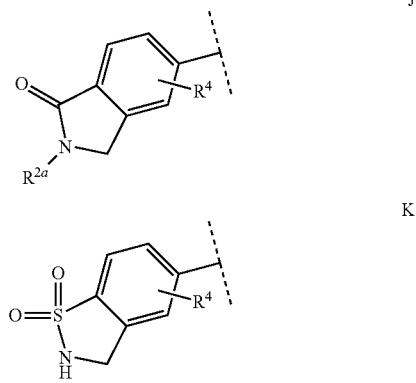
K In one aspect, the bicyclic system formed by HET-2 fused to the benzo ring is selected from:

L

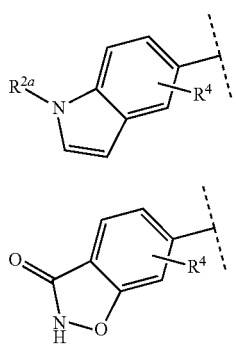

M

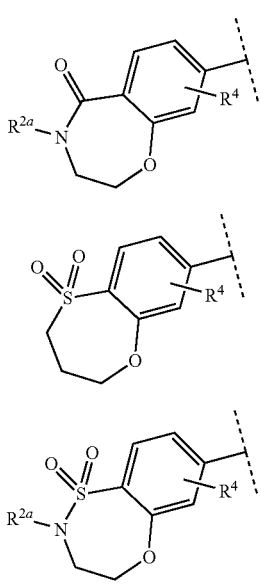

E

F

G particularly wherein R$^{2a}$ is hydrogen or is methyl and R$^4$ is as hereinbefore defined, for example R$^4$ is hydrogen or fluoro, or for example R$^4$ is hydrogen.

In another aspect, the bicyclic system formed by HET-2 fused to the benzo ring is selected from

E

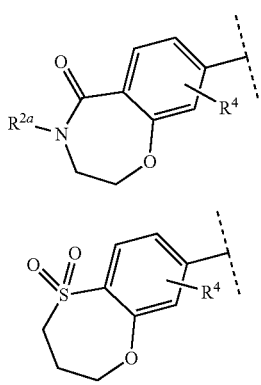

F

G

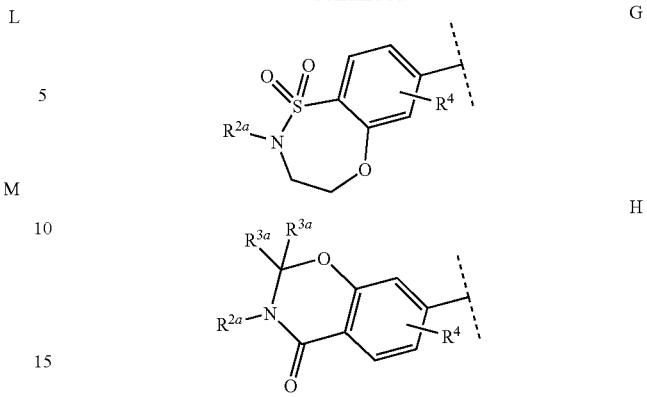

H particularly, wherein both R$^{3a}$ are hydrogen, R$^{2a}$ is hydrogen or is methyl and R$^4$ is as hereinbefore defined, for example R$^4$ is hydrogen or fluoro, or for example R$^4$ is hydrogen. In one embodiment of this aspect, the bicyclic system formed by HET-2 fused to the benzo ring is of formula E. In another embodiment of this aspect, the bicyclic system formed by HET-2 fused to the benzo ring is of formula F. In another embodiment of this aspect, the bicyclic system formed by HET-2 fused to the benzo ring is of formula G. In another embodiment of this aspect, the bicyclic system formed by HET-2 fused to the benzo ring is of formula H.

In another aspect, the bicyclic system formed by HET-2 fused to the benzo ring is of formula (Z):

Z

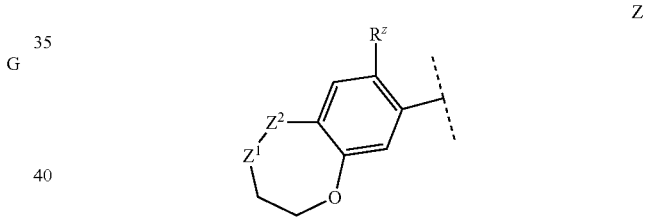

wherein R$^z$ is hydrogen or fluoro, Z$^1$ is CH$_2$ or NR$^{2a}$, R$^{2a}$ is hydrogen or methyl, and Z$^2$ is C(=O) or SO$_2$.

In a further aspect, HET-2 is an optionally substituted 5-7 membered heterocyclic ring fused to the benzene ring, containing 1, 2 or 3 ring hetereoatoms independently selected from O, S and N (provided that there are no O—O, S—O or S—S bonds within the ring), wherein any ring carbon or sulfur atom may optionally be oxidised, provided that where HET-2 contains two ring heteroatoms they are not both oxygen (such that for example, HET-2 is not dioxolyl or dioxolanyl).

It will be appreciated that, where definitions of heterocylyl groups HET-1 to HET-3 encompass heteroaryl rings which may be substituted on nitrogen, such substitution may not result in charged quaternary nitrogen atoms or unstable structures. It will be appreciated that the definitions of HET-1 to HET-3 are not intended to include any O—O, O—S or S—S bonds. It will be appreciated that the definitions of HET-1 to HET-3 are not intended to include unstable structures.

Examples of (1-4C)alkyl include methyl, ethyl, propyl, isopropyl, butyl and tert-butyl; examples of (3-6C)cycloalkyl include cyclopropyl, cyclobutyl, cyclopentyl and cyclohexyl; examples of halo include fluoro, chloro, bromo and iodo; examples of (1-4C)allkylcarbonyl include methylcarbonyl, ethylcarbonyl, propylcarbonyl, isopropylcarbonyl and tert-butylcarbonyl; examples of hydroxy(1-4C)alkyl include hydroxymethyl, 1-hydroxyethyl, 2-hydroxyethyl, 2-hydroxypropyl, 3-hydroxypropyl, 1-hydroxyisopropyl and 4-hydroxybutyl; examples of (1-4C)alkoxy include methoxy, ethoxy, prop oxy, isopropoxy and tert-butoxy; examples of (1-4C)alkoxy(1-4C)alkyl include methoxymethyl, ethoxymethyl, tert-butoxymethyl, 2-methoxyethyl, 2-ethoxyethyl, methoxypropyl, 2-methoxypropyl and methoxybutyl; examples of (1-4C)alkylS(O)p(1-4C)alkyl (where p is 0, 1 or 2) include methylsulfinylmethyl, ethylsulfinylmethyl, ethylsulfinylethyl, methylsulfinylpropyl, methylsulfinylbutyl, methylsulfonylmethyl, ethylsulfonylmethyl, ethylsulfonylethyl, methylsulfonylpropyl, methylsulfonylbutyl, methylthiomethyl, ethylthiomethyl, ethylthioethyl, methylthiopropyl, and methylthiobutyl; examples of (1-4C)alkylsulphonyl include methylsulfonyl, ethylsulfonyl, propylsulfonyl, isopropylsulfonyl and tertbutylsulfonyl; examples of amino(1-4C)alkyl include aminomethyl, aminoethyl, 2-aminopropyl, 3-aminopropyl, 1-aminoisopropyl and 4-aminobutyl; examples of (1-4C)alkylamino(1-4C)alkyl include (N-methyl)aminomethyl, (N-ethyl)aminomethyl, 1-((N-methyl)amino)ethyl, 2-((N-methyl)amino)ethyl, (N-ethyl)aminoethyl, (N-methyl)aminopropyl, and 4-((N-methyl)amino)butyl; examples of di(1-4C)alkylamino(1-4C)alkyl include dimethylaminomethyl, methyl(ethyl)aminomethyl, methyl(ethyl)aminoethyl, (N,N-diethyl)aminoethyl, (N,N-dimethyl)aminopropyl and (N,N-dimethyl)aminobutyl.

It is to be understood that, insofar as certain of the compounds of Formula (I) defined above may exist in optically active or racemic forms by virtue of one or more asymmetric carbon atoms, the invention includes in its definition any such optically active or racemic form which possesses the property of stimulating GLK directly or inhibiting the GLK/GLKRP interaction. The synthesis of optically active forms may be carried out by standard techniques of organic chemistry well known in the art, for example by synthesis from optically active starting materials or by resolution of a racemic form. It is also to be understood that certain compounds may exist in tautomeric forms and that the invention also relates to any and all tautomeric forms of the compounds of the invention which activate GLK.

It is to be understood that certain compounds of the formula (I) and salts thereof can exist in solvated as well as unsolvated forms such as, for example, hydrated forms. It is to be understood that the invention encompasses all such solvated forms which activate GLK.

In one embodiment of the invention are provided compounds of formula (I), in an alternative embodiment are provided salts of compounds of formula (I), in an alternative embodiment are provided pharmaceutically-acceptable salts of compounds of formula (I), in a further alternative embodiment are provided in-vivo hydrolysable esters of compounds of formula (I), and in a further alternative embodiment are provided pharmaceutically-acceptable salts of in-vivo hydrolysable esters of compounds of formula (I).

Preferred values of each variable group are as follows. Such values may be used where appropriate with any of the values, definitions, claims, aspects or embodiments defined hereinbefore or hereinafter. In particular, each may be used as an individual limitation on the broadest definition of formula (I). Further, each of the following values may be used in combination with one or more of the other following values to limit the broadest definition of formula (I) or to limit any narrower definitions of formula (I) in any of the aspects hereinbefore or hereinafter.

(1) $R^1$ is of sub-formula X:

wherein $R^x$ is selected from methyl, trifluoromethyl, ethynyl, hydroxymethyl, hydroxyethyl, methoxymethyl, fluoromethoxymethyl, difluoromethoxymethyl and trifluoromethoxymethyl (2) $R^1$ is of sub-formula X and $R^x$ is selected from methyl, ethyl, trifluoromethyl, ethynyl, hydroxymethyl, hydroxyethyl, methoxymethyl, fluoromethoxymethyl, difluoromethoxymethyl and trifluoromethoxymethyl; preferably $R^x$ is selected from methyl, ethyl, trifluoromethyl, ethynyl, hydroxymethyl, hydroxyethyl, methoxymethyl, fluoromethoxymethyl and difluoromethoxymethyl (3) $R^1$ is of sub-formula Y:

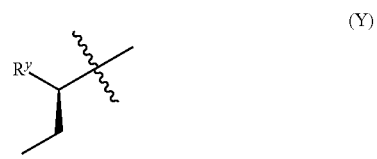

wherein $R^y$ is selected from hydroxymethyl and methoxymethyl (4) $R^1$ is 1-hydroxyprop-2-yl and the configuration is preferably (S), that is $R^1$—O— is:

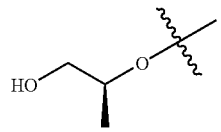

(5) $R^1$ is 1-methoxyprop-2-yl and the configuration is preferably (S), that is $R^1$—O— is:

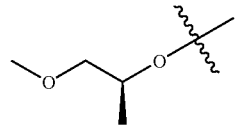

(6) $R^1$ is selected from isopropyl, 1,3-difluoroprop-2-yl, but-1-yn-3-yl, 1-hydroxyprop-2-yl, hydroxybut-3-yl and 1-methoxyprop-2-yl (7) $R^1$ is 1,1,1-trifluoroprop-2-yl, 1-fluoromethoxyprop-2-yl, 1,1-difluoromethoxyprop-2-yl or 1-trifluoromethoxyprop-2-yl (8) $R^1$ is 1-fluoromethoxyprop-2-yl, 1,1-difluoromethoxyprop-2-yl or 1-trifluoromethoxyprop-2-yl, preferably 1-fluoromethoxyprop-2-yl or 1,1-difluoromethoxyprop-2-yl (9) $R^1$ is 1,1-difluoromethoxyprop-2-yl, particularly with the stereochemistry:

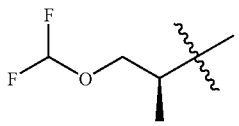

(10) $R^1$ is tetrahydrofuranyl or tetrahydropyranyl
(11) $R^1$ is tetrahydrofuranyl
(12) $R^1$ is tetrahydrofuranyl in the (S) configuration, that is:

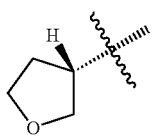

(13) $R^1$ is tetrahydrofuranyl in the (R) configuration, that is:

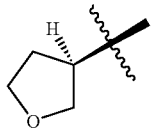

(14) $R^1$ is 4-tetrahydropyranyl

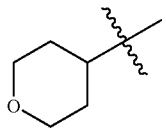

(11) $R^1$ is 2-hydroxy-but-3-yl and the configuration is preferably such that $R^1$—O— is:

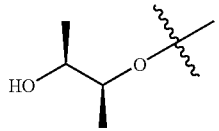

(15) $R^1$ is 1-hydroxybut-2-yl or 1-methoxybut-2-yl
(16) $R^1$ is selected from isopropyl, but-2-yl, 1,1,1-trifluoroprop-2-yl, 1,3-difluoroprop-2-yl, but-1-yn-3-yl, 1-hydroxyprop-2-yl, 2-hydroxybut-3-yl, tetrahydrofuranyl, tetrahydropyranyl, 1-methoxyprop-2-yl, 1-fluoromethoxyprop-2-yl, 1,1-difluoromethoxyprop-2-yl and 1-trifluoromethoxyprop-2-yl
(17) $R^1$ is selected from 2-hydroxyprop-1-yl, 2-methoxyprop-1-yl, 2-hydroxybut-1-yl and 2-methoxybut-1-yl
(18) $R^1$ is selected from 1-hydroxyprop-2-yl, 1-methoxyprop-2-yl, 1-hydroxybut-2-yl, isopropyl, tetrahydrofuranyl and 1,3-difluoroprop-2-yl
(19) $R^1$ is selected from 1-hydroxyprop-2-yl, 1-methoxyprop-2-yl, 1-hydroxybut-2-yl, isopropyl and tetrahydrofuranyl
(20) $R^1$ is selected from 1,3-difluoroprop-2-yl, tetrahydrofuranyl and difluoromethoxyprop-2-yl
(21) HET-1 is a 5-membered heteroaryl ring
(22) HET-1 is a 6-membered heteroaryl ring
(23) HET-1 is substituted with 1 or 2 substituents independently selected from $R^6$
(24) HET-1 is substituted with 1 substituent selected from $R^6$
(25) HET-1 is substituted with 1 substituent selected from $R^7$
(26) HET-1 is unsubstituted
(27) HET-1 is selected from thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, and triazolyl
(28) HET-1 is selected from methylpyrazinyl, pyrazinyl, pyrazolyl, 5-methyl-NH-pyrazolyl, thiadiazolyl (particularly 1,2,4-thiadiazol-5-yl, more particularly 3-methyl-1,2,4-thiadiazol-5-yl), thiazolyl, pyridyl, fluoropyridyl, isoxazolyl and methylthiazolyl
(29) HET-1 is selected from thiazolyl, isothiazolyl, thiadiazolyl, pyrazolyl, imidazolyl, oxazolyl, isoxazolyl and oxadiazolyl
(30) HET-1 is selected from pyridyl, pyrazinyl, pyridazinyl and pyrimidinyl
(31) HET-1 is selected from thiazolyl, pyrazolyl and oxazolyl
(32) HET-1 is selected from thiadiazolyl and oxadiazolyl
(33) HET-1 is selected from 1,3,4-thiadiazolyl and 1,3,4-oxadiazolyl
(34) HET-1 is selected from 1,2,4-oxadiazolyl and 1,2,4-oxadiazolyl
(35) HET-1 is pyrazolyl, particularly N-methylpyrazole
(36) HET-1 is pyrazinyl, particularly methylpyrazinyl
(37) HET-1 is selected from thiazolyl, pyrazolyl, thiadiazolyl and pyrazinyl;
(38) HET-1 is selected from pyrazolyl, thiadiazolyl and pyrazinyl, optionally substituted on carbon or nitrogen (provided the nitrogen is not thereby quaternised) by methyl or ethyl
(39) HET-1 is selected from pyrazolyl, N-methylpyrazolyl, N-ethylpyrazolyl, methylthiadiazolyl (particularly 3-methyl-1,2,4-thiadiazol-5-yl) and methylpyrazinyl (particularly 5-methyl-pyrazin-2-yl)
(40) HET-1 is selected from pyrazolyl, methylthiadiazolyl (particularly 3-methyl-1,2,4-thiadiazol-5-yl) and methylpyrazinyl (particularly 5-methyl-pyrazin-2-yl)
(41) HET-1 is selected from pyrazolyl, thiadiazolyl and pyrazinyl, optionally substituted on carbon or nitrogen (provided the nitrogen is not thereby quaternised) by methyl or ethyl; and $R^1$ is selected from 1-hydroxyprop-2-yl, 1-methoxyprop-2-yl, 1-hydroxybut-2-yl, isopropyl, tetrahydrofuranyl and 1,3-difluoroprop-2-yl; when HET-1 is unsubstituted pyrazolyl (i.e. NH-pyrazolyl), particularly $R^1$ is selected from 1-methoxyprop-2-yl, isopropyl, and tetrahydrofuranyl
(42) HET-1 is selected from pyrazolyl, methylthiadiazolyl (particularly 3-methyl-1,2,4-thiadiazol-5-yl) and methylpyrazinyl (particularly 5-methyl-pyrazin-2-yl) and $R^1$ is selected from 1-hydroxyprop-2-yl, 1-methoxyprop-2-yl, 1-hydroxybut-2-yl, isopropyl, tetrahydrofuranyl and 1,3-difluoroprop-2-yl; when HET-1 is unsubstituted pyrazolyl (i.e. NH-pyrazolyl), particularly $R^1$ is selected from 1-methoxyprop-2-yl, isopropyl, and tetrahydrofuranyl
(43) $R^6$ is selected from (1-4C)alkyl, halo, hydroxy(1-4C)alkyl, di(1-4C)alkylamino(1-4C)alkyl and HET-3
(44) $R^6$ is selected from methyl, ethyl, bromo, chloro, fluoro, hydroxymethyl, methoxymethyl, aminomethyl, N-methylaminomethyl, dimethylaminomethyl
(45) $R^6$ is selected from (1-4C)alkyl, halo, hydroxy(1-4C)alkyl, (1-4C)alkoxy(1-4C)alkyl, (1-4C)alkylS(O)p(1-4C)

alkyl, amino(1-4C)alkyl, (1-4C)alkylamino(1-4C)alkyl, and di(1-4C)alkylamino(1-4C)alkyl
(46) $R^6$ is selected from methyl, ethyl, bromo, chloro, fluoro, aminomethyl, N-methylaminomethyl, and dimethylaminomethyl
(47) $R^6$ is selected from methyl, ethyl, bromo, chloro, fluoro, hydroxymethyl and methoxymethyl
(48) $R^6$ is selected from methyl, ethyl, bromo, chloro and fluoro
(49) $R^6$ is methyl
(50) $R^6$ is selected from methyl, ethyl, bromo, chloro, fluoro, aminomethyl, N-methylaminomethyl, dimethylaminomethyl, hydroxymethyl and methoxymethyl
(51) $R^6$ is selected from methyl, ethyl, aminomethyl, N-methylaminomethyl, dimethylaminomethyl, hydroxymethyl and methoxymethyl
(52) $R^6$ is selected from methyl, ethyl, isopropyl and methoxymethyl
(53) when 2 substituents $R^6$ are present, both are selected from methyl, ethyl, bromo, chloro and fluoro; preferably both are methyl
(54) $R^6$ is selected from (1-4C)alkylS(O)p(1-4C)alkyl, (1-4C)alkylamino(1-4C)alkyl, di(1-4C)alkylamino(1-4C)alkyl and HET-3
(55) $R^6$ is HET-3
(56) $R^7$ is selected from (1-4C)alkyl, hydroxy(1-4C)alkyl, di(1-4C)alkylamino(1-4C)alkyl and HET-3
(57) $R^7$ is selected from methyl, ethyl, hydroxymethyl, methoxymethyl, aminomethyl, N-methylaminomethyl, dimethylaminomethyl
(58) $R^7$ is selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, and di(1-4C)alkylamino(1-4C)alkyl
(59) $R^7$ is selected from methyl, ethyl, aminomethyl, N-methylaminomethyl, and dimethylaminomethyl
(60) $R^7$ is selected from methyl, ethyl, hydroxymethyl and methoxymethyl
(61) $R^7$ is selected from methyl and ethyl
(62) $R^7$ is methyl
(63) HET-3 is selected from furyl, pyrrolyl and thienyl
(64) HET-3 is furyl
(65) $R^2$ is (1-4C)alkyl, preferably methyl
(66) $R^2$ is selected from (1-4C)alkyl, (3-6C)cycloalkyl and benzyl
(67) $R^2$ is benzyl
(68) $R^2$ is (3-6C)cycloalkyl
(69) $R^2$ is selected from (1-4C)alkylcarbonyl, (1-4C)alkylsulphonyl, hydroxy(1-4C)alkyl and (1-4C)alkoxy(1-4C)alkyl
(70) $R^2$ is selected from (1-4C)alkyl (such as methyl or ethyl), benzyl and (1-4C)alkoxy(1-4C)alkyl (such as methoxymethyl)
(71) $R^3$ is (1-4C)alkyl, preferably methyl
(72) $R^3$ is hydroxy
(73) $R^3$ is fluoro or chloro
(74) $R^3$ is (3-6C)cycloalkyl
(75) $R^3$ is (1-4C)alkoxy
(76) $R^3$ is (1-4C)alkyl or halo, for example methyl or fluoro
(77) HET-2 is substituted by two $R^3$ and both are either methyl or fluoro
(78) HET-2 is gem di-substituted by $R^3$ and both are either methyl or fluoro
(79) $R^4$ is hydrogen
(80) $R^4$ is fluoro
(81) $R^4$ is chloro
(82) $R^4$ is hydrogen or fluoro
(83) HET-2 is a 5-membered ring
(84) HET-2 is a 6-membered ring
(85) HET-2 is a 7-membered ring
(86) HET-2 is unsubstituted
(87) HET-2 is substituted on an available nitrogen atom by $R^2$
(88) HET-2 is substituted on each available nitrogen atom by a substituent $R^2$, wherein each $R^2$ is independently selected from (1-4C)alkyl and benzyl
(89) HET-2 is substituted on an available carbon atom by 1 or 2 $R^3$
(90) HET-2 is substituted on more than one available carbon atom by substituents independently selected from $R^3$ According to a further feature of the invention there is provided the following preferred groups of compounds of the invention:

In one aspect there is provided a compound of formula (I) as hereinbefore defined wherein $R^1$ is selected from isopropyl, but-2-yl, 1,1,1-trifluoroprop-2-yl, 1,3-difluoroprop-2-yl, but-1-yn-3-yl, 1-hydroxyprop-2-yl, hydroxybut-3-yl, 1-hydroxybut-2-yl, tetrahydrofuranyl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl, 1-fluoromethoxyprop-2-yl and 1,1-difluoromethoxyprop-2-yl;

HET-1 is a 5- or 6-membered, C-linked heteroaryl ring containing a nitrogen atom in the 2-position and optionally 1 or 2 further ring heteroatoms independently selected from O, N and S; which ring is optionally substituted by (1-4C)alkyl;

HET-2 is a 5-7 membered heterocyclic ring fused to the benzene ring, containing 1, 2 or 3 ring hetereoatoms independently selected from O, S and N (provided that there are no O—O, S—O or S—S bonds within the ring), wherein any ring carbon or sulfur atom may optionally be oxidised and wherein HET-2 is optionally substituted on any nitrogen atom by a substituent selected from $R^2$ and/or on any available carbon atom by 1 or 2 substituents independently selected from $R^3$;

$R^2$ is selected from (1-4C)alkyl, (3-6C)cycloalkyl and benzyl;
$R^3$ is selected from (1-4C)alkyl, (3-6C)cycloalkyl, (1-4C)alkoxy, hydroxy, fluoro and chloro;
$R^4$ is selected from hydrogen, fluoro and chloro;
p is (independently at each occurrence) 0, 1 or 2;
or a salt or pro-drug thereof.

In another aspect there is provided a compound of formula (I) as hereinbefore defined wherein $R^1$ is selected from isopropyl, but-2-yl, 1,1,1-trifluoroprop-2-yl, 1,3-difluoroprop-2-yl, but-1-yn-3-yl, 1-hydroxyprop-2-yl, hydroxybut-3-yl, tetrahydrofuranyl, tetrahydropyranyl, 1-methoxyprop-2-yl, 1-fluoromethoxyprop-2-yl and 1,1-difluoromethoxyprop-2-yl;

HET-1 is a 5- or 6-membered, C-linked heteroaryl ring containing a nitrogen atom in the 2-position and optionally 1 or 2 further ring heteroatoms independently selected from O, N and S; which ring is optionally substituted by (1-4C)alkyl;

HET-2 is a 5-7 membered heterocyclic ring fused to the benzene ring, containing 1, 2 or 3 ring hetereoatoms independently selected from O, S and N (provided that there are no O—O, S—O or S—S bonds within the ring), wherein any ring carbon or sulfur atom may optionally be oxidised and wherein HET-2 is optionally substituted on any nitrogen atom by a substituent selected from $R^2$ and/or on any available carbon atom by 1 or 2 substituents independently selected from $R^3$;

$R^2$ is selected from (1-4C)alkyl, (3-6C)cycloalkyl and benzyl;
$R^3$ is selected from (1-4C)alkyl, (3-6C)cycloalkyl, (1-4C)alkoxy, hydroxy, fluoro and chloro;
$R^4$ is selected from hydrogen, fluoro and chloro;
p is (independently at each occurrence) 0, 1 or 2;
or a salt or pro-drug thereof.

In another aspect there is provided a compound of formula (I) or a salt or pro-drug thereof, wherein:
HET-1 is selected from thiazolyl, thiadiazolyl, pyrazinyl and pyrazolyl; wherein HET-1 is optionally substituted with (1-4C)alkyl;
$R^1$ is 1-hydroxyprop-2-yl, 1-methoxyprop-2-yl or isopropyl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl and (1-4C)alkyl; and
$R^3$ is selected from (1-4C)alkyl, chloro and fluoro.

In a further aspect there is provided a compound of formula (I) or a salt or pro-drug thereof, wherein:
HET-1 is selected from thiazolyl, thiadiazolyl, pyrazinyl and pyrazolyl; wherein HET-1 is optionally substituted with (1-4C)alkyl;
$R^1$ is 1-hydroxyprop-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl, methyl and ethyl; and
$R^3$ is selected from methyl and fluoro.

In a further aspect there is provided a compound of formula (I) or a salt or pro-drug thereof, wherein:
HET-1 is selected from thiazolyl, thiadiazolyl, pyrazinyl and pyrazolyl; wherein HET-1 is optionally substituted with (1-4C)alkyl;
$R^1$ is 1-fluoromethoxyprop-2-yl, 1,1-difluoromethoxyprop-2-yl or 1-trifluoromethoxyprop-2-yl, particularly 1-fluoromethoxyprop-2-yl or 1,1-difluoromethoxyprop-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^1$ and a ring carbon atom is optionally substituted by 1 or 2 substituents independently selected from $R^3$;
$R^2$ is selected from benzyl and (1-4C)alkyl; and
$R^3$ is selected from (1-4C)alkyl, chloro and fluoro.

In a further aspect there is provided a compound of formula (I) or a salt or pro-drug thereof, wherein:
HET-1 is selected from thiazolyl, thiadiazolyl, pyrazinyl and pyrazolyl; wherein HET-1 is optionally substituted with (1-4C)alkyl;
$R^1$ is 1-fluoromethoxyprop-2-yl, 1,1-difluoromethoxyprop-2-yl or 1-trifluoromethoxyprop-2-yl, particularly 1-fluoromethoxyprop-2-yl or 1,1-difluoromethoxyprop-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl, methyl and ethyl; and
$R^3$ is selected from methyl and fluoro.

In another aspect there is provided a compound of formula (I) or a salt or pro-drug thereof, wherein:
HET-1 is selected from thiazolyl, thiadiazolyl, pyrazinyl and pyrazolyl; wherein HET-1 is optionally substituted with (1-4C)alkyl;
$R^1$ is 1-hydroxyprop-2-yl, 1-methoxyprop-2-yl, isopropyl, 1,3-difluoroprop-2-yl or 1-hydroxy-but-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl and (1-4C)alkyl; and
$R^3$ is selected from (1-4C)alkyl, chloro and fluoro.

In another aspect there is provided a compound of formula (I) or a salt or pro-drug thereof, wherein:
HET-1 is selected from thiazolyl, thiadiazolyl, pyrazinyl and pyrazolyl; wherein HET-1 is optionally substituted with (1-4C)alkyl;
$R^1$ is 1-hydroxyprop-2-yl, 1-methoxyprop-2-yl, isopropyl or 1,3-difluoroprop-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl and (1-4C)alkyl; and
$R^3$ is selected from (1-4C)alkyl, chloro and fluoro.

In another aspect there is provided a compound of formula (I) or a salt or pro-drug thereof, wherein:
HET-1 is pyrazolyl, optionally substituted with methyl or ethyl;
$R^1$ is 1-hydroxyprop-2-yl, 1-methoxyprop-2-yl, isopropyl or 1,3-difluoroprop-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl and (1-4C)alkyl; and
$R^3$ is selected from (1-4C)alkyl, chloro and fluoro.

In another aspect there is provided a compound of formula (I) or a salt or pro-drug thereof, wherein:
HET-1 is pyrazolyl, optionally substituted with methyl or ethyl;
$R^1$ is 1-hydroxyprop-2-yl, 1-methoxyprop-2-yl, tetrahydrofuranyl, 1,3-difluoroprop-2-yl, isopropyl or 1-hydroxybut-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl and (1-4C)alkyl; and
$R^3$ is selected from (1-4C)alkyl, chloro and fluoro.

In a further aspect there is provided a compound of formula (I) or a salt or pro-drug thereof, wherein:
HET-1 is pyrazolyl, optionally substituted with methyl or ethyl;
$R^1$ is 1-hydroxyprop-2-yl, 1-methoxyprop-2-yl or isopropyl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl and (1-4C)alkyl; and
$R^3$ is selected from (1-4C)alkyl, chloro and fluoro.

In a further aspect there is provided a compound of formula (I) or a salt or pro-drug thereof, wherein:
HET-1 is N-methylpyrazolyl;
$R^1$ is 1-hydroxyprop-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl, methyl and ethyl; and
$R^3$ is selected from methyl and fluoro.

In a further aspect there is provided a compound of formula (I) or a salt or pro-drug thereof, wherein:
HET-1 is pyrazolyl, optionally substituted with methyl or ethyl;
$R^1$ is 1-fluoromethoxyprop-2-yl, 1,1-difluoromethoxyprop-2-yl or 1-trifluoromethoxyprop-2-yl, particularly 1-fluoromethoxyprop-2-yl or 1,1-difluoromethoxyprop-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl and (1-4C)alkyl; and
$R^3$ is selected from (1-4C)alkyl, chloro and fluoro.

In a further aspect there is provided a compound of formula (I) or a salt or pro-drug thereof, wherein:
HET-1 is N-methylpyrazolyl;
$R^1$ is 1-fluoromethoxyprop-2-yl, 1,1-difluoromethoxyprop-2-yl or 1-trifluoromethoxyprop-2-yl, particularly 1-fluoromethoxyprop-2-yl or 1,1-difluoromethoxyprop-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl, methyl and ethyl; and
$R^3$ is selected from methyl and fluoro.

In another aspect there is provided a compound of formula (I) or a salt or pro-drug thereof, wherein:
HET-1 is pyrazolyl, pyrazinyl or thiadiazolyl, optionally substituted with methyl or ethyl;

$R^1$ is 1-hydroxyprop-2-yl, 1-methoxyprop-2-yl, tetrahydrofuranyl, 1,3-difluoroprop-2-yl, isopropyl or 1-hydroxybut-2-yl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl, (1-4C)alkoxy(1-4C)alkyl and (1-4C)alkyl; and
$R^3$ is selected from (1-4C)alkyl, chloro and fluoro, (particularly (1-4C)alkyl and fluoro).

In another aspect there is provided a compound of formula (I) or a salt or pro-drug thereof, wherein:
HET-1 is pyrazolyl, pyrazinyl or thiadiazolyl, optionally substituted with methyl or ethyl;
$R^1$ is 1-hydroxyprop-2-yl, 1-methoxyprop-2-yl, tetrahydrofuranyl, 1,3-difluoroprop-2-yl, isopropyl or 1-hydroxybut-2-yl; except that when HET-1 is unsubstituted pyrazolyl (i.e. NH-pyrazolyl), $R^1$ is selected from 1-methoxyprop-2-yl, isopropyl, and tetrahydrofuranyl;
$R^4$ is hydrogen, fluoro or chloro;
HET-2 is a 5 to 7 membered ring containing 1 to 3 heteroatoms independently selected from O, N and S, wherein a ring carbon or sulfur atom is optionally oxidised and a ring nitrogen atom is optionally substituted by a substituent selected from $R^2$ and a ring carbon atom is optionally substituted by 1 or 2 substituents independently selected from $R^3$;
$R^2$ is selected from benzyl, (1-4C)alkoxy(1-4C)alkyl and (1-4C)alkyl; and
$R^3$ is selected from (1-4C)alkyl, chloro and fluoro, (particularly (1-4C)alkyl and fluoro).

In another aspect there is provided a compound of formula (I) or a salt or pro-drug thereof, wherein:
HET-1 is pyrazolyl, pyrazinyl or thiadiazolyl, optionally substituted with methyl or ethyl;
$R^1$ is 1-hydroxyprop-2-yl, 1-methoxyprop-2-yl, tetrahydrofuranyl, 1,3-difluoroprop-2-yl, isopropyl or 1-hydroxybut-2-yl; except that when HET-1 is unsubstituted pyrazolyl (i.e. NH-pyrazolyl), $R^1$ is selected from 1-methoxyprop-2-yl, isopropyl, and tetrahydrofuranyl;
$R^4$ is hydrogen, fluoro or chloro;
the bicyclic system formed by HET-2 fused to the benzo ring is selected from formulae A to L as hereinbefore defined;
$R^2$ is selected from benzyl, (1-4C)alkoxy(1-4C)alkyl and (1-4C)alkyl; and
$R^3$ is selected from (1-4C)alkyl, chloro and fluoro, (particularly (1-4C)alkyl and fluoro).

In another aspect there is provided a compound of formula (I) or a salt or pro-drug thereof, wherein:
HET-1 is pyrazolyl, pyrazinyl or thiadiazolyl, optionally substituted with methyl or ethyl;
$R^1$ is 1-hydroxyprop-2-yl, 1-methoxyprop-2-yl, tetrahydrofuranyl, 1,3-difluoroprop-2-yl, isopropyl or 1-hydroxybut-2-yl; except that when HET-1 is unsubstituted pyrazolyl (i.e. NH-pyrazolyl), $R^1$ is selected from 1-methoxyprop-2-yl, isopropyl, and tetrahydrofuranyl; the bicyclic system formed by HET-2 fused to the benzo ring is of formula Z;

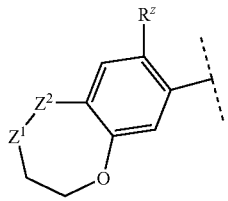

Z wherein $R^z$ is hydrogen or fluoro, $Z^1$ is $CH_2$ or $NR^{2a}$, $R^{2a}$ is hydrogen or methyl, and $Z^2$ is C(=O) or $SO_2$.

In another aspect, Aspect A, there is provided a compound of formula (I) or a salt or pro-drug thereof, wherein:

HET-1 is pyrazolyl, methylthiadiazolyl (particularly 3-methyl-1,2,4-thiadiazol-5-yl), or optionally substituted pyrazinyl, wherein optional substituents are selected from methyl and ethyl;

$R^1$ is 1-hydroxyprop-2-yl, 1-methoxyprop-2-yl, tetrahydrofuranyl, 1,3-difluoroprop-2-yl, isopropyl or 1-hydroxybut-2-yl; except that when HET-1 is unsubstituted pyrazolyl (i.e. NH-pyrazolyl), $R^1$ is selected from 1-methoxyprop-2-yl, isopropyl, and tetrahydrofuranyl; the bicyclic system formed by HET-2 fused to the benzo ring is of formula Z;

wherein $R^z$ is hydrogen or fluoro, $Z^1$ is $CH_2$ or $NR^{2a}$, $R^{2a}$ is hydrogen or methyl, and $Z^2$ is C(=O) or $SO_2$.

In another aspect there is provided a compound of formula (I) or a salt or pro-drug thereof, wherein:

HET-1 is pyrazolyl, pyrazinyl or thiadiazolyl, optionally substituted with methyl or ethyl;

$R^1$ is 1-hydroxyprop-2-yl, 1-methoxyprop-2-yl, tetrahydrofuranyl, 1,3-difluoroprop-2-yl, isopropyl or 1-hydroxybut-2-yl; except that when HET-1 is unsubstituted pyrazolyl (i.e. NH-pyrazolyl), $R^1$ is selected from 1-methoxyprop-2-yl, isopropyl, and tetrahydrofuranyl; the bicyclic system formed by HET-2 fused to the benzo ring is selected from formulae E, F, G and H, particularly E, F and G;

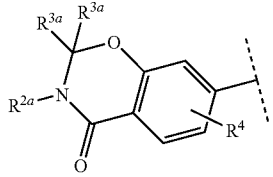

H both $R^{3a}$ are hydrogen;
$R^{2a}$ is hydrogen or methyl;
$R^4$ is hydrogen or fluoro, particularly hydrogen.

In another aspect, Aspect B, there is provided a compound of formula (I) or a salt or pro-drug thereof, wherein:

HET-1 is pyrazolyl, methylthiadiazolyl (particularly 3-methyl-1,2,4-thiadiazol-5-yl), or optionally substituted pyrazinyl, wherein optional substituents are selected from methyl and ethyl;

$R^1$ is 1-hydroxyprop-2-yl, 1-methoxyprop-2-yl, tetrahydrofuranyl, 1,3-difluoroprop-2-yl, isopropyl or 1-hydroxybut-2-yl; except that when HET-1 is unsubstituted pyrazolyl (i.e. NH-pyrazolyl), $R^1$ is selected from 1-methoxyprop-2-yl, isopropyl, and tetrahydrofuranyl; the bicyclic system formed by HET-2 fused to the benzo ring is selected from formulae E, F, G and H, particularly E, F and G;

both $R^{3a}$ are hydrogen;
$R^{2a}$ is hydrogen or methyl;
$R^4$ is hydrogen or fluoro, particularly hydrogen.

In another aspect, Aspect C, there is provided a compound of formula (I) or a salt or pro-drug thereof, wherein:

HET-1 is selected from pyrazinyl (optionally substituted with methyl), pyrazolyl (optionally substituted on carbon by methyl), methylthiadiazolyl (particularly 3-methyl-1,2,4-thiadiazol-5-yl), thiazolyl (optionally substituted with methyl), pyridyl (optionally substituted by fluoro) and isoxazolyl;

$R^1$ is 1-hydroxyprop-2-yl, 1-methoxyprop-2-yl, tetrahydrofuranyl, 1,3-difluoroprop-2-yl, isopropyl or 1-hydroxybut-2-yl; except that when HET-1 is unsubstituted pyrazolyl (i.e. NH-pyrazolyl), $R^1$ is selected from 1-methoxyprop-2-yl, isopropyl, and tetrahydrofuranyl; the bicyclic system formed by HET-2 fused to the benzo ring is of formula Z; wherein $R^z$ is hydrogen or fluoro, $Z^1$ is $CH_2$ or $NR^{2a}$, $R^{2a}$ is hydrogen or methyl, and $Z^2$ is C(=O) or $SO_2$.

In another aspect, Aspect D, there is provided a compound of formula (I) or a salt or pro-drug thereof, wherein:

HET-1 is selected from pyrazinyl (optionally substituted with methyl), pyrazolyl (optionally substituted on carbon by methyl), methylthiadiazolyl (particularly 3-methyl-1,2,4-thiadiazol-5-yl), thiazolyl (optionally substituted with methyl), pyridyl (optionally substituted by fluoro) and isoxazolyl;

$R^1$ is 1-hydroxyprop-2-yl, 1-methoxyprop-2-yl, tetrahydrofuranyl, 1,3-difluoroprop-2-yl, isopropyl or 1-hydroxybut-2-yl; except that when HET-1 is unsubstituted pyrazolyl (i.e. NH-pyrazolyl), $R^1$ is selected from 1-methoxyprop-2-yl, isopropyl, and tetrahydrofuranyl; the bicyclic system formed by HET-2 fused to the benzo ring is selected from formulae E, F, G and H, particularly E, F and G;

both $R^{3a}$ are hydrogen;
$R^{2a}$ is hydrogen or methyl;
$R^4$ is hydrogen or fluoro, particularly hydrogen.

Further preferred compounds of the invention are each of the Examples (and their salts and pro-drugs), each of which provides a further independent aspect of the invention. In further aspects, the present invention also comprises any two or more compounds of the Examples and salts and pro-drugs thereof.

Particular compounds of the invention include any one or more of:

3-[(2,2-difluoro-1,3-benzodioxol-5-yl)oxy]-5-[(1S)-2-hydroxy-1-methylethoxy]-N-(1-methyl-1H-pyrazol-3-yl)benzamide;

3-(1,3-benzodioxol-5-yloxy)-5-[(1S)-2-hydroxy-1-methylethoxy]-N-(1-methyl-1H-pyrazol-3-yl)benzamide;

3-[(8-fluoro-2,3-dimethyl-4-oxo-3,4-dihydro-2H-1,3-benzoxazin-7-yl)oxy]-5-[(1S)-2-hydroxy-1-methylethoxy]-N-(1-methyl-1H-pyrazol-3-yl)benzamide;

3-[(7-fluoro-5,5-dioxido-3,4-dihydro-2H-1,5-benzoxathiepin-8-yl)oxy]-5-[(1S)-2-hydroxy-1-methylethoxy]-N-(1-methyl-1H-pyrazol-3-yl)benzamide;

3-[(1S)-2-hydroxy-1-methylethoxy]-5-[(1-methyl-1H-indol-5-yl)oxy]-N-(1-methyl-1H-pyrazol-3-yl)benzamide;

3-(2,3-dihydro-1-benzofuran-5-yloxy)-5-[(1S)-2-hydroxy-1-methylethoxy]-N-(1-methyl-1H-pyrazol-3-yl)benzamide;

3-[(1S)-2-hydroxy-1-methylethoxy]-5-(1H-indol-5-yloxy)-N-(1-methyl-1H-pyrazol-3-yl)benzamide;

3-(1-benzothien-5-yloxy)-5-[(1S)-2-hydroxy-1-methylethoxy]-N-(1-methyl-1H-pyrazol-3-yl)benzamide;

3-[(9-chloro-4-methyl-5-oxo-2,3,4,5-tetrahydro-1,4-benzoxazepin-8-yl)oxy]-5-[(1S)-2-hydroxy-1-methylethoxy]-N-(1-methyl-1H-pyrazol-3-yl)benzamide;

3-[(4-benzyl-9-fluoro-5-oxo-2,3,4,5-tetrahydro-1,4-benzoxazepin-8-yl)oxy]-5-[(1S)-2-hydroxy-1-methylethoxy]-N-(1-methyl-1H-pyrazol-3-yl)benzamide;

3-[(8-chloro-3-ethyl-2-methyl-4-oxo-3,4-dihydro-2H-1,3-benzoxazin-7-yl)oxy]-5-[(1S)-2-hydroxy-1-methylethoxy]-N-(1-methyl-1H-pyrazol-3-yl)benzamide; and 3-[(1S)-2-hydroxy-1-methylethoxy]-5-[(4-methyl-5-oxo-2,3,4,5-tetrahydro-1,4-benzoxazepin-8-yl)oxy]-N-(1-methyl-1H-pyrazol-3-yl)benzamide; and/or 3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-(1-methyl-1H-pyrazol-3-yl)benzamide; and 3-[(1,1-dioxido-3,4-dihydro-2H-5,1,2-benzoxathiazepin-7-yl)oxy]-5-{[(1S)-2-hydroxy-1-methylethyl]oxy}-N-(1-methyl-1H-pyrazol-3-yl)benzamide; and/or 3-[(9-chloro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide;

3-[(8-chloro-2,3-dimethyl-4-oxo-3,4-dihydro-2H-1,3-benzoxazin-7-yl)oxy]-5-{[(1S)-1-methyl-2-(methyloxy)ethyl]oxy}-N-(1-methyl-1H-pyrazol-3-yl)benzamide;

3-[(9-chloro-4-methyl-5-oxo-2,3,4,5-tetrahydro-1,4-benzoxazepin-8-yl)oxy]-N-(1-ethyl-1H-pyrazol-3-yl)-5-{[(1S)-1-methyl-2-(methyloxy)ethyl]oxy}benzamide;

3-[(2,3-dimethyl-4-oxo-3,4-dihydro-2H-1,3-benzoxazin-7-yl)oxy]-5-{[(1S)-1-methyl-2-(methyloxy)ethyl]oxy}-N-(1-methyl-1H-pyrazol-3-yl)benzamide;

N-(1-ethyl-1H-pyrazol-3-yl)-3-{[(1S)-1-methyl-2-(methyloxy)ethyl]oxy}-5-[(4-methyl-5-oxo-2,3,4,5-tetrahydro-1,4-benzoxazepin-8-yl)oxy]benzamide;

3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(1-methyl-1H-pyrazol-3-yl)benzamide;

3-{[2-fluoro-1-(fluoromethyl)ethyl]oxy}-5-[(9-fluoro-4-methyl-5-oxo-2,3,4,5-tetrahydro-1,4-benzoxazepin-8-yl)oxy]-N-(1-methyl-1H-pyrazol-3-yl)benzamide;

3-[(9-chloro-4-methyl-5-oxo-2,3,4,5-tetrahydro-1,4-benzoxazepin-8-yl)oxy]-N-(1-ethyl-1H-pyrazol-3-yl)-5-{[(1S)-2-hydroxy-1-methylethyl]oxy}benzamide;

3-[(9-chloro-4-methyl-5-oxo-2,3,4,5-tetrahydro-1,4-benzoxazepin-8-yl)oxy]-5-[(1-methylethyl)oxy]-N-(1-methyl-1H-pyrazol-3-yl)benzamide;

3-[(1-methylethyl)oxy]-5-[(4-methyl-5-oxo-2,3,4,5-tetrahydro-1,4-benzoxazepin-8-yl)oxy]-N-(1-methyl-1H-pyrazol-3-yl)benzamide; and 3-[(8-chloro-2,3-dimethyl-4-oxo-3,4-dihydro-2H-1,3-benzoxazin-7-yl)oxy]-5-{[(1S)-1-(hydroxymethyl)propyl]oxy}-N-(1-methyl-1H-pyrazol-3-yl)benzamide; and/or 3-[(1,1-dioxido-2,3-dihydro-1-benzothien-5-yl)oxy]-5-{[(1S)-1-methyl-2-(methyloxy)ethyl]oxy}-N-(1-methyl-1H-pyrazol-3-yl)benzamide;

N-(1-ethyl-1H-pyrazol-3-yl)-3-{[(1S)-2-hydroxy-1-methylethyl]oxy}-5-[(4-methyl-5-oxo-2,3,4,5-tetrahydro-1,4-benzoxazepin-8-yl)oxy]benzamide;

N-(1-ethyl-1H-pyrazol-3-yl)-3-[(9-fluoro-4-methyl-5-oxo-2,3,4,5-tetrahydro-1,4-benzoxazepin-8-yl)oxy]-5-{[(1S)-1-methyl-2-(methyloxy)ethyl]oxy}benzamide;

3-[(9-fluoro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide;

3-[(7-fluoro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide;

3-[(9-chloro-4-methyl-5-oxo-2,3,4,5-tetrahydro-1,4-benzoxazepin-8-yl)oxy]-N-(1-methyl-1H-pyrazol-3-yl)-5-[(3S)-tetrahydrofuran-3-yloxy]benzamide;

3-[(4-methyl-5-oxo-2,3,4,5-tetrahydro-1,4-benzoxazepin-8-yl)oxy]-N-(1-methyl-1H-pyrazol-3-yl)-5-[(3S)-tetrahydrofuran-3-yloxy]benzamide; and/or 3-{[(1S)-1-methyl-2-(methyloxy)ethyl]oxy}-N-(1-methyl-1H-pyrazol-3-yl)-5-[(2,2,3-trimethyl-4-oxo-3,4-dihydro-2H-1,3-benzoxazin-7-yl)oxy]benzamide;

N-(1-methyl-1H-pyrazol-3-yl)-3-[(3S)-tetrahydrofuran-3-yloxy]-5-[(2,2,3-trimethyl-4-oxo-3,4-dihydro-2H-1,3-benzoxazin-7-yl)oxy]benzamide;

3-{[(1S)-1-methyl-2-(methyloxy)ethyl]oxy}-N-(5-methylpyrazin-2-yl)-5-[(2,2,3-trimethyl-4-oxo-3,4-dihydro-2H-1,3-benzoxazin-7-yl)oxy]benzamide;

3-{[(1S)-1-methyl-2-(methyloxy)ethyl]oxy}-5-[(3-methyl-4-oxo-3,4-dihydro-2H-1,3-benzoxazin-7-yl)oxy]-N-(1-methyl-1H-pyrazol-3-yl)benzamide;

3-[(3-methyl-4-oxo-3,4-dihydro-2H-1,3-benzoxazin-7-yl)oxy]-N-(1-methyl-1H-pyrazol-3-yl)-5-[(3S)-tetrahydrofuran-3-yloxy]benzamide;

3-{[(1S)-1-methyl-2-(methyloxy)ethyl]oxy}-5-[(3-methyl-4-oxo-3,4-dihydro-2H-1,3-benzoxazin-7-yl)oxy]-N-(5-methylpyrazin-2-yl)benzamide;

3-({2,2-dimethyl-3-[(methyloxy)methyl]-4-oxo-3,4-dihydro-2H-1,3-benzoxazin-7-yl}oxy)-5-{[(1S)-1-methyl-2-(methyloxy)ethyl]oxy}-N-(1-methyl-1H-pyrazol-3-yl)benzamide;

3-({2,2-dimethyl-3-[(methyloxy)methyl]-4-oxo-3,4-dihydro-2H-1,3-benzoxazin-7-yl}oxy)-N-(5-methylpyrazin-2-yl)-5-[(3S)-tetrahydrofuran-3-yloxy]benzamide;

3-({2,2-dimethyl-3-[(methyloxy)methyl]-4-oxo-3,4-dihydro-2H-1,3-benzoxazin-7-yl}oxy)-N-(5-methylpyrazin-2-yl)-5-[(3S)-tetrahydrofuran-3-yloxy]benzamide;

3-{[(1S)-2-hydroxy-1-methylethyl]oxy}-5-[(3-methyl-4-oxo-3,4-dihydro-2H-1,3-benzoxazin-7-yl)oxy]-N-(5-methylpyrazin-2-yl)benzamide;

3-{[(1S)-2-hydroxy-1-methylethyl]oxy}-5-[(3-methyl-4-oxo-3,4-dihydro-2H-1,3-benzoxazin-7-yl)oxy]-N-(3-methyl-1,2,4-thiadiazol-5-yl)benzamide;

3-[(2,2-dimethyl-4-oxo-3,4-dihydro-2H-1,3-benzoxazin-7-yl)oxy]-N-(5-methylpyrazin-2-yl)-5-[(3S)-tetrahydrofuran-3-yloxy]benzamide;

3-[(2,2-dimethyl-4-oxo-3,4-dihydro-2H-1,3-benzoxazin-7-yl)oxy]-5-{[(1S)-1-methyl-2-(methyloxy)ethyl]oxy}-N-(5-methylpyrazin-2-yl)benzamide;

3-[(2-methyl-1,1-dioxido-3,4-dihydro-2H-5,1,2-benzoxathiazepin-7-yl)oxy]-5-{[(1S)-1-methyl-2-(methyloxy)ethyl]oxy}-N-(5-methylpyrazin-2-yl)benzamide;

3-[(1,1-dioxido-3,4-dihydro-2H-5,1,2-benzoxathiazepin-7-yl)oxy]-5-{[(1S)-1-methyl-2-(methyloxy)ethyl]oxy}-N-(5-methylpyrazin-2-yl)benzamide;

3-{[(1S)-1-methyl-2-(methyloxy)ethyl]oxy}-5-[(3-methyl-4-oxo-3,4-dihydro-2H-1,3-benzoxazin-7-yl)oxy]-N-1H-pyrazol-3-ylbenzamide;

3-[(3-methyl-4-oxo-3,4-dihydro-2H-1,3-benzoxazin-7-yl)oxy]-N-1H-pyrazol-3-yl-5-[(3S)-tetrahydrofuran-3-yloxy]benzamide;

3-[(1-methylethyl)oxy]-5-[(3-methyl-4-oxo-3,4-dihydro-2H-1,3-benzoxazin-7-yl)oxy]-N-1H-pyrazol-3-ylbenzamide;

3-[(3-methyl-4-oxo-3,4-dihydro-2H-1,3-benzoxazin-7-yl)oxy]-N-(5-methylpyrazin-2-yl)-5-[(3S)-tetrahydrofuran-3-yloxy]benzamide;

3-[(9-chloro-4-methyl-5-oxo-2,3,4,5-tetrahydro-1,4-benzoxazepin-8-yl)oxy]-N-(5-methylpyrazin-2-yl)-5-[(3S)-tetrahydrofuran-3-yloxy]benzamide;

N-(5-methylpyrazin-2-yl)-3-[(1-oxo-1,2,3,4-tetrahydroisoquinolin-6-yl)oxy]-5-[(3S)-tetrahydrofuran-3-yloxy]benzamide;

3-[(4-methyl-5-oxo-2,3,4,5-tetrahydro-1,4-benzoxazepin-8-yl)oxy]-N-1H-pyrazol-3-yl-5-[(3S)-tetrahydrofuran-3-yloxy]benzamide;

3-[(2-methyl-1,1-dioxido-3,4-dihydro-2H-5,1,2-benzoxathiazepin-7-yl)oxy]-5-{[(1S)-1-methyl-2-(methyloxy)ethyl]oxy}-N-1H-pyrazol-3-ylbenzamide;

3-[(1,1-dioxido-3,4-dihydro-2H-5,1,2-benzoxathiazepin-7-yl)oxy]-5-{[(1S)-1-methyl-2-(methyloxy)ethyl]oxy}-N-1H-pyrazol-3-ylbenzamide;

3-[(5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide;

3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(5-methylpyrazin-2-yl)benzamide;

3-{[(1S)-1-methyl-2-(methyloxy)ethyl]oxy}-5-[(4-methyl-5-oxo-2,3,4,5-tetrahydro-1,4-benzoxazepin-8-yl)oxy]-N-1H-pyrazol-3-ylbenzamide;

3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(3-methyl-1,2,4-thiadiazol-5-yl)benzamide;

3-[(1-methylethyl)oxy]-5-[(4-methyl-5-oxo-2,3,4,5-tetrahydro-1,4-benzoxazepin-8-yl)oxy]-N-1H-pyrazol-3-ylbenzamide;

3-{[(1S)-2-hydroxy-1-methylethyl]oxy}-5-[(4-methyl-5-oxo-2,3,4,5-tetrahydro-1,4-benzoxazepin-8-yl)oxy]-N-(5-methylpyrazin-2-yl)benzamide;

3-[(2,3-dimethyl-4-oxo-3,4-dihydro-2H-1,3-benzoxazin-7-yl)oxy]-5-{[(1S)-2-hydroxy-1-methylethyl]oxy}-N-(3-methyl-1,2,4-thiadiazol-5-yl)benzamide;

3-{[(1S)-2-hydroxy-1-methylethyl]oxy}-5-[(4-methyl-5-oxo-2,3,4,5-tetrahydro-1,4-benzoxazepin-8-yl)oxy]-N-(3-methyl-1,2,4-thiadiazol-5-yl)benzamide;

3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide;

3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-1H-pyrazol-3-ylbenzamide;

3-[(7-fluoro-5,5-dioxido-3,4-dihydro-2H-1,5-benzoxathiepin-8-yl)oxy]-5-{[(1S)-2-hydroxy-1-methylethyl]oxy}-N-(5-methylpyrazin-2-yl)benzamide;

3-[(5,5-dioxido-3,4-dihydro-2H-1,5-benzoxathiepin-8-yl)oxy]-5-{[(1S)-2-hydroxy-1-methylethyl]oxy}-N-(5-methylpyrazin-2-yl)benzamide; and 3-[(5,5-dioxido-3,4-dihydro-2H-1,5-benzoxathiepin-8-yl)oxy]-5-{[(1S)-1-methyl-2-(methyloxy)ethyl]oxy}-N-1H-pyrazol-3-ylbenzamide;

or a pharmaceutically-acceptable salt or pro-drug thereof.

Further particular compounds of the invention include any one or more of:

3-[(1S)-2-hydroxy-1-methylethoxy]-5-[(4-methyl-5-oxo-2,3,4,5-tetrahydro-1,4-benzoxazepin-8-yl)oxy]-N-(1-methyl-1H-pyrazol-3-yl)benzamide;

3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-(1-methyl-1H-pyrazol-3-yl)benzamide;

3-[(1,1-dioxido-3,4-dihydro-2H-5,1,2-benzoxathiazepin-7-yl)oxy]-5-{[(1S)-2-hydroxy-1-methylethyl]oxy}-N-(1-methyl-1H-pyrazol-3-yl)benzamide;

N-(1-ethyl-1H-pyrazol-3-yl)-3-{[(1S)-1-methyl-2-(methyloxy)ethyl]oxy}-5-[(4-methyl-5-oxo-2,3,4,5-tetrahydro-1,4-benzoxazepin-8-yl)oxy]benzamide;

3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(1-methyl-1H-pyrazol-3-yl)benzamide;

N-(1-ethyl-1H-pyrazol-3-yl)-3-{[(1S)-2-hydroxy-1-methylethyl]oxy}-5-[(4-methyl-5-oxo-2,3,4,5-tetrahydro-1,4-benzoxazepin-8-yl)oxy]benzamide;

3-[(4-methyl-5-oxo-2,3,4,5-tetrahydro-1,4-benzoxazepin-8-yl)oxy]-N-(1-methyl-1H-pyrazol-3-yl)-5-[(3S)-tetrahydrofuran-3-yloxy]benzamide;

3-{[(1S)-1-methyl-2-(methyloxy)ethyl]oxy}-5-[(3-methyl-4-oxo-3,4-dihydro-2H-1,3-benzoxazin-7-yl)oxy]-N-(1-methyl-1H-pyrazol-3-yl)benzamide;

3-[(3-methyl-4-oxo-3,4-dihydro-2H-1,3-benzoxazin-7-yl)oxy]-N-(1-methyl-1H-pyrazol-3-yl)-5-[(3S)-tetrahydrofuran-3-yloxy]benzamide;

3-{[(1S)-1-methyl-2-(methyloxy)ethyl]oxy}-5-[(3-methyl-4-oxo-3,4-dihydro-2H-1,3-benzoxazin-7-yl)oxy]-N-(5-methylpyrazin-2-yl)benzamide;

3-{[(1S)-2-hydroxy-1-methylethyl]oxy}-5-[(3-methyl-4-oxo-3,4-dihydro-2H-1,3-benzoxazin-7-yl)oxy]-N-(5-methylpyrazin-2-yl)benzamide;

3-[(2-methyl-1,1-dioxido-3,4-dihydro-2H-5,1,2-benzoxathiazepin-7-yl)oxy]-5-{[(1S)-1-methyl-2-(methyloxy)ethyl]oxy}-N-(5-methylpyrazin-2-yl)benzamide;

3-[(1,1-dioxido-3,4-dihydro-2H-5,1,2-benzoxathiazepin-7-yl)oxy]-5-{[(1S)-1-methyl-2-(methyloxy)ethyl]oxy}-N-(5-methylpyrazin-2-yl)benzamide;

3-{[(1S)-1-methyl-2-(methyloxy)ethyl]oxy}-5-[(3-methyl-4-oxo-3,4-dihydro-2H-1,3-benzoxazin-7-yl)oxy]-N-1H-pyrazol-3-ylbenzamide;

3-[(3-methyl-4-oxo-3,4-dihydro-2H-1,3-benzoxazin-7-yl)oxy]-N-1H-pyrazol-3-yl-5-[(3S)-tetrahydrofuran-3-yloxy]benzamide;

3-[(1-methylethyl)oxy]-5-[(3-methyl-4-oxo-3,4-dihydro-2H-1,3-benzoxazin-7-yl)oxy]-N-1H-pyrazol-3-ylbenzamide;

3-[(2-methyl-1,1-dioxido-3,4-dihydro-2H-5,1,2-benzoxathiazepin-7-yl)oxy]-5-{[(1S)-1-methyl-2-(methyloxy)ethyl]oxy}-N-1H-pyrazol-3-ylbenzamide;

3-[(1,1-dioxido-3,4-dihydro-2H-5,1,2-benzoxathiazepin-7-yl)oxy]-5-{[(1S)-1-methyl-2-(methyloxy)ethyl]oxy}-N-1H-pyrazol-3-ylbenzamide;

3-[(5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide;

3-{[(1S)-1-methyl-2-(methyloxy)ethyl]oxy}-5-[(4-methyl-5-oxo-2,3,4,5-tetrahydro-1,4-benzoxazepin-8-yl)oxy]-N-1H-pyrazol-3-ylbenzamide;

3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide;

3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-1H-pyrazol-3-ylbenzamide;

3-[(7-fluoro-5,5-dioxido-3,4-dihydro-2H-1,5-benzoxathiepin-8-yl)oxy]-5-{[(1S)-2-hydroxy-1-methylethyl]oxy}-N-(5-methylpyrazin-2-yl)benzamide;

3-[(5,5-dioxido-3,4-dihydro-2H-1,5-benzoxathiepin-8-yl)oxy]-5-{[(1S)-2-hydroxy-1-methylethyl]oxy}-N-(5-methylpyrazin-2-yl)benzamide; and 3-[(5,5-dioxido-3,4-dihydro-2H-1,5-benzoxathiepin-8-yl)oxy]-5-{[(1S)-1-methyl-2-(methyloxy)ethyl]oxy}-N-1H-pyrazol-3-ylbenzamide;

or a pharmaceutically-acceptable salt or pro-drug thereof.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in-vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen;

c) H. Bundgaard, Chapter 5 "Design and Application of Prodrugs", by H. Bundgaard p. 113-191 (1991);

d) H. Bundgaard, Advanced Drug Delivery Reviews, 8, 1-38 (1992);

e) H. Bundgaard, et al., Journal of Pharmaceutical Sciences, 77, 285 (1988); and f) N. Kakeya, et al., Chem Pharm Bull, 32, 692 (1984).

The contents of the above cited documents are incorporated herein by reference.

Examples of pro-drugs are as follows. An in-vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $C_6$alkanoyloxymethyl esters for example pivaloyloxymethyl, phthalidyl esters, $C_3$ to $C_8$cycloalkoxycarbonyloxy $C_1$ to $C_6$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

A further feature of the invention is a pharmaceutical composition comprising a compound of Formula (I) as defined above, or a salt or prodrug thereof, together with a pharmaceutically-acceptable diluent or carrier.

According to another aspect of the invention there is provided a compound of Formula (I) as defined above, or a salt or prodrug thereof for use as a medicament.

According to another aspect of the invention there is provided a compound of Formula (I) as defined above, or a salt or prodrug thereof for use as a medicament for the treatment of a disease mediated through GLK, in particular type 2 diabetes.

Further according to the invention there is provided the use of a compound of Formula (I), or a salt or prodrug thereof in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of a compound of Formula (I) or salt or pro-drug thereof, to a mammal in need of such treatment.

Specific diseases which may be treated by a compound or composition of the invention include: blood glucose lowering in Type 2 Diabetes Mellitus without a serious risk of hypoglycaemia (and potential to treat type 1), dyslipidemia, obesity, insulin resistance, metabolic syndrome X and impaired glucose tolerance.

As discussed above, thus the GLK/GLKRP system can be described as a potential "Diabesity" target (of benefit in both Diabetes and Obesity). Thus, according to another aspect of the invention there if provided the use of a compound of Formula (I) or salt, solvate or pro-drug thereof, in the preparation of a medicament for use in the combined treatment or prevention of diabetes and obesity.

According to another aspect of the invention there is provided a compound of Formula (I) as defined above, or a salt or prodrug thereof for use as a medicament for the combined treatment or prevention, particularly treatment, of diabetes (particularly type 2 diabetes) and obesity.

According to another aspect of the invention there is provided the use of a compound of Formula (I) or salt or pro-drug thereof, in the preparation of a medicament for use in the treatment or prevention of obesity.

According to a further aspect of the invention there is provided a method for the combined treatment of obesity and diabetes by administering an effective amount of a compound of Formula (I) or salt or pro-drug thereof, to a mammal in need of such treatment.

According to a further aspect of the invention there is provided a method for the treatment of obesity by administering an effective amount of a compound of Formula (I) or salt or pro-drug thereof, to a mammal in need of such treatment.

Compounds of the invention may be particularly suitable for use as pharmaceuticals because of advantageous physical and/or pharmacokinetic properties, and/or favourable toxicity profile and/or favourable metabolic profile.

Favourable toxicity profile may be demonstrated, for example, by use of an Ames test assay, and/or by testing against the hERG ion channel. A favourable metabolic profile may mean, for example, reduced rate of metabolism, leading to reduction in clearance of the compound from the body and hence increased exposure to the compound, or a favourable metabolic profile may mean, for example, not forming active metabolites (which might be considered undesirable in some circumstances).

For example, compounds of Aspects A to D may have favourable toxicological profiles.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I) will naturally vary according to the nature and severity of the conditions, the age and sex of the animal or patient and the route of administration, according to well known principles of medicine.

In using a compound of the Formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example in the treatment of diabetes mellitus, chemotherapy may include the following main categories of treatment:

1) Insulin and insulin analogues;
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors, and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1,6 bisphosphatase inhibitors, glycogen phosphorylase inhibitors, glycogen synthase kinase inhibitors);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);
9) Anti-obesity agents (for example sibutramine and orlistat);
10) Anti-dyslipidaemia agents such as, HMG-CoA reductase inhibitors (e.g. statins); PPARα agonists (fibrates, e.g. gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
11) Antihypertensive agents such as, β blockers (e.g. atenolol, inderal); ACE inhibitors (e.g. lisinopril); Calcium antagonists (e.g. nifedipine); Angiotensin receptor antagonists (e.g. candesartan), α antagonists and diuretic agents (e.g. furosemide, benzthiazide);
12) Haemostasis modulators such as, antithrombotics, activators of fibrinolysis and antiplatelet agents; thrombin antagonists; factor Xa inhibitors; factor VIIa inhibitors); antiplatelet agents (e.g. aspirin, clopidogrel); anticoagulants (heparin and Low molecular weight analogues, hirudin) and warfarin;
13) Agents which antagonise the actions of glucagon; and
14) Anti-inflammatory agents, such as non-steroidal anti-inflammatory drugs (e.g. aspirin) and steroidal anti-inflammatory agents (e.g. cortisone).

According to another aspect of the present invention there is provided individual compounds produced as end products in the Examples set out below and salts and pro-drugs thereof.

In the above other pharmaceutical composition, process, method, use and medicament manufacture features, the alternative and preferred embodiments of the compounds of the invention described herein also apply.

A compound of the invention, or a salt thereof, may be prepared by any process known to be applicable to the preparation of such compounds or structurally related compounds. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991.

Processes for the synthesis of compounds of Formula (I) are provided as a further feature of the invention. Thus, according to a further aspect of the invention there is provided a process for the preparation of a compound of Formula (I), which comprises a process a) to e) (wherein the variables are as defined hereinbefore for compounds of Formula (I) unless otherwise defined):

(a) reaction of an acid of Formula (III) or activated derivative thereof with a compound of Formula (IV), wherein $R^1$ is as hereinbefore defined or a protected version thereof;

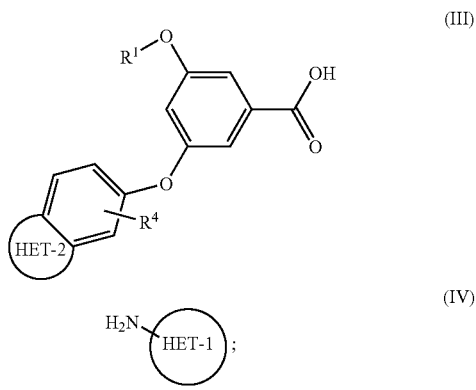

or (b) reaction of a compound of Formula (V) with a compound of Formula (VI),

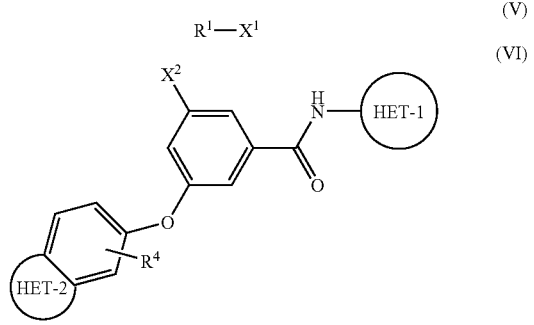

(V)

(VI)

wherein $X^1$ is a leaving group and $X^2$ is a hydroxyl group or $X^1$ is a hydroxyl group and $X^2$ is a leaving group, and wherein $R^1$ is as hereinbefore defined or a protected version thereof;

process (b) could also be accomplished using the intermediate ester Formula (VII), wherein $P^1$ is a protecting group as hereinafter described, followed by ester hydrolysis and amide formation by procedures described elsewhere and well known to those skilled in the art;

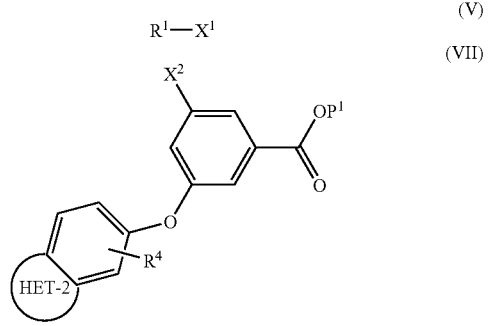

(V)

(VII)

or (c) reaction of a compound of Formula (VIII) with a compound of Formula (IX)

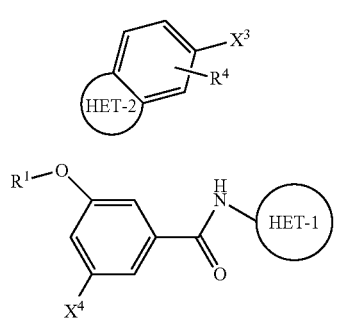

(VIII)

(IX)

wherein $X^3$ is a leaving group or an organometallic reagent and $X^4$ is a hydroxyl group or $X^3$ is a hydroxyl group and $X^4$ is a leaving group or an organometallic reagent, and wherein $R^1$ is as hereinbefore defined or a protected version thereof;

process (c) could also be accomplished using the intermediate ester Formula (X), followed by ester hydrolysis and amide formation by procedures described elsewhere and well known to those skilled in the art;

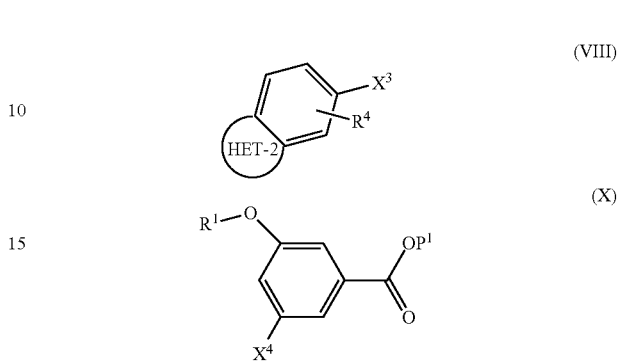

(VIII)

(X)

or (d) reaction of a compound of Formula (XI) with a compound of Formula (XII),

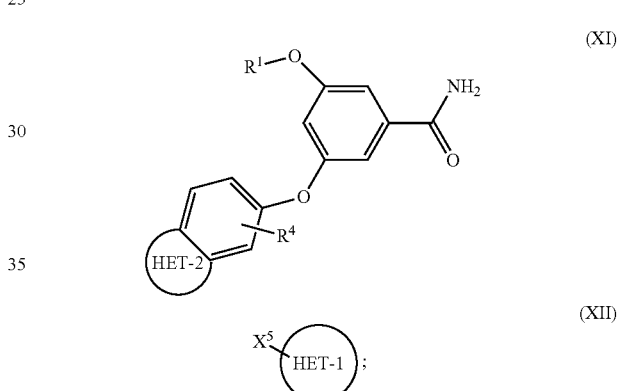

(XI)

(XII)

wherein $X^5$ is a leaving group; and wherein $R^1$ is as hereinbefore defined or a protected version thereof; or e) cyclisation of a compound of formula (XIII) to a compound of formula (I)

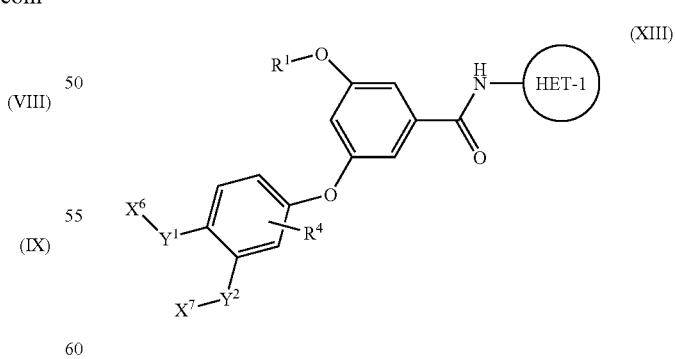

(XIII)

wherein $Y^1$ and $Y^2$ are 0-4 atom linkers, wherein each linker atom is independently selected from C, N, S or O (wherein any C or S can be optionally oxidised and any atom can be optionally substituted provided it is not quaternised and there are no S—S or O—O bonds), $X^6$ can be any nucleophilic species and $X^7$ a leaving group or vice versa, and wherein $R^1$ is as hereinbefore defined or a protected version thereof;

process (e) could also be accomplished using the intermediate ester Formula (XIV), followed by ester hydrolysis and amide formation by procedures described elsewhere and well known to those skilled in the art;

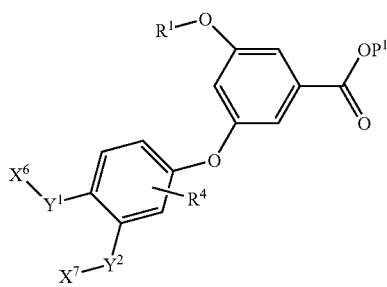

(XIV)

and thereafter, if necessary:
i) converting a compound of Formula (I) into another compound of Formula (I);
ii) removing any protecting groups; and/or
iii) forming a salt or pro-drug thereof.

Suitable leaving groups $X^1$ to $X^7$ for processes b) to e) are any leaving group known in the art for these types of reactions, for example halo, alkoxy, trifluoromethanesulfonyloxy, methanesulfonyloxy, or p-toluenesulfonyloxy; or a group (such as a hydroxy group) that may be converted into a leaving group (such as an oxytriphenylphosphonium group) in situ.

Suitable values for $R^1$ containing a protected hydroxy group are any suitable protected hydroxy group known in the art, for example simple ethers such as a methyl ether, tert-butyl ether or silylethers such as —OSi[(1-4C)alkyl]$_3$ (wherein each (1-4C)alkyl group is independently selected from methyl, ethyl, propyl, isopropyl, and tertbutyl). Examples of such trialkylsilyl groups are trimethylsilyl, triethylsilyl, triisopropylsilyl and tert-butyldimethylsilyl. Further suitable silyl ethers are those containing phenyl and substituted phenyl groups, such as —Si(PhMe$_2$) and —Si(TolMe$_2$) (wherein Tol=methylbenzene). Further suitable values for hydroxy protecting groups are given hereinafter.

Compounds of Formulae (III) to (XV) are commercially available, or are known in the art, or may be made by processes known in the art, for example as shown in the accompanying Examples, or as described below. For further information on processes for making such compounds, we refer to our PCT publications WO 03/000267, WO 03/015774 and WO 03/000262 and references therein. In general it will be appreciated that any aryl-O or alkyl-O bond may be formed by nucleophilic substitution or metal catalysed processes, optionally in the presence of a suitable base.

The group $R^1$ in the compounds of formulae (III), (IX), (X) and (XI) may be made by reaction of suitable precursors with compounds of formula (V) or derivatives thereof, depending on the nature of the $R^1$ group, for example, by nucleophilic displacement of a leaving group $X^1$ in a compound of formula (V). Compounds of formula (V) are generally commercially available or may be made by simple functional group interconversions from commercially available compounds, or by literature methods. Further information is available in WO2004/076420, WO2005/054200, WO2005/054233, WO 2005/044801 and WO 2005/056530. Some illustrative examples using various $R^1$ groups are given in the Schemes below, and/or in the accompanying examples, and may generally be applied analogously to $R^1$ groups not shown below.

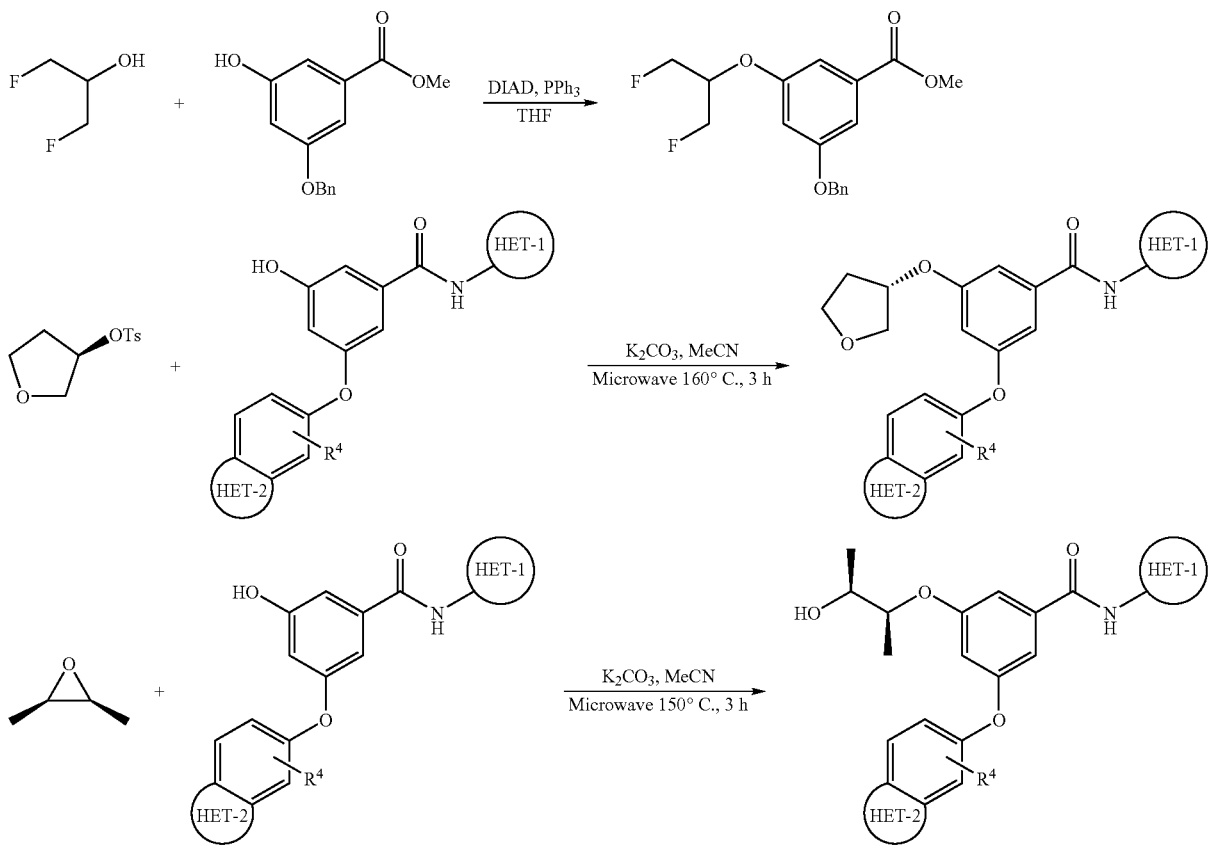

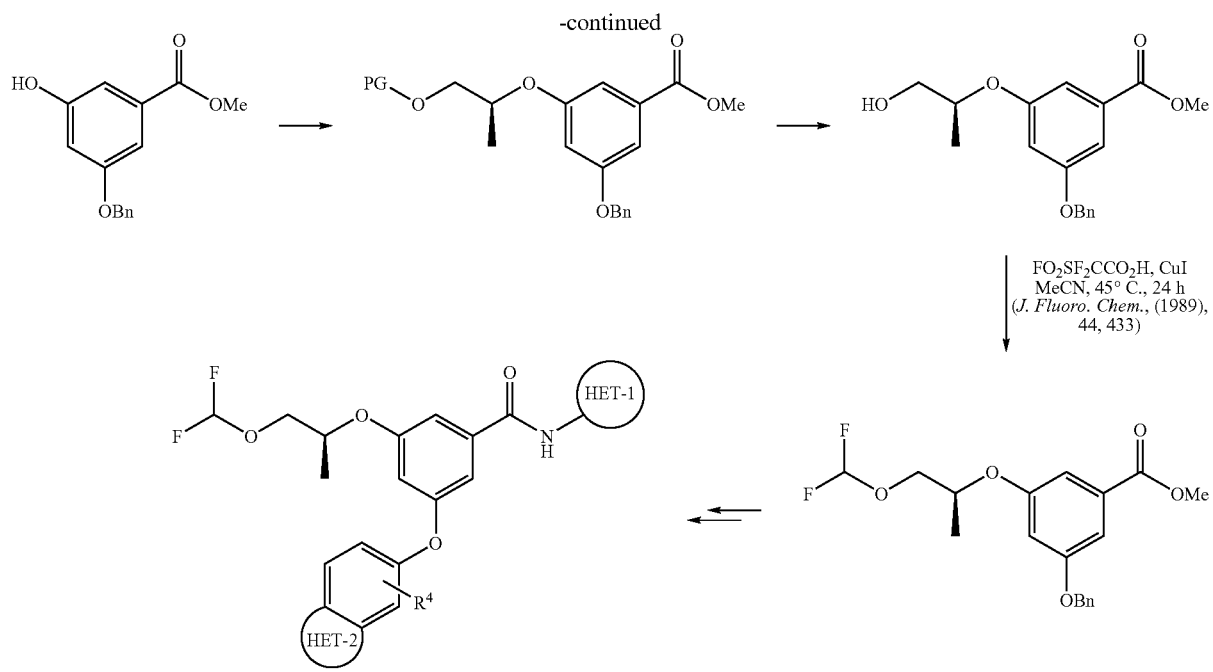

[PG is protecting group, Ts is p-toluenesulfonyl].

Examples of conversions of a compound of Formula (I) into another compound of Formula (I), well known to those skilled in the art, include functional group interconversions such as hydrolysis, hydrogenation, hydrogenolysis, oxidation or reduction, and/or further functionalisation by standard reactions such as amide or metal-catalysed coupling, or nucleophilic displacement reactions.

It will be understood that substituents $R^2$, $R^3$, $R^4$, $R^6$ and/or $R^7$ may be introduced into the molecule at any convenient point in the synthetic sequence or may be present in the starting materials. A precursor to one of these substituents may be present in the molecule during the process steps a) to e) above, and then be transformed into the desired substituent as a final step to form the compound of formula (I); followed where necessary by i) converting a compound of Formula (I) into another compound of Formula (I);
ii) removing any protecting groups; and/or
iii) forming a salt or pro-drug thereof.

Specific reaction conditions for the above reactions are as follows, wherein when $P^1$ is a protecting group $P^1$ is preferably (1-4C)alkyl, for example methyl or ethyl:

Process a)—coupling reactions of amino groups with carboxylic acids to form an amide are well known in the art. For example, (i) using an appropriate coupling reaction, such as a carbodiimide coupling reaction performed with EDAC (1-(3-dimethylaminopropyl)-3-ethylcarbodiimide hydrochloride) in the presence of dimethylaminopyridine (DMAP) in a suitable solvent such as dichloromethane (DCM), chloroform or dimethylformamide (DMF) at room temperature; or (ii) reaction in which the carboxylic group is activated to an acid chloride by reaction with oxalyl chloride in the presence of a suitable solvent such as DCM. The acid chloride can then be reacted with a compound of Formula (IV) in the presence of a base, such as triethylamine or pyridine, in a suitable solvent such as chloroform or DCM at a temperature between 0° C. and 80° C.

Process b)—compounds of Formula (V) and (VI) can be reacted together in a suitable solvent, such as DMF or tetrahydrofuran (THF), with a base such as sodium hydride or potassium tert-butoxide, at a temperature in the range 0 to 200° C., optionally using microwave heating or metal catalysis such as palladium(II)acetate, palladium on carbon, copper(II)acetate or copper(I)iodide; alternatively, compounds of Formula (V) and (VI) can be reacted together in a suitable solvent, such as THF or DCM, with a suitable phosphine such as triphenylphosphine, and azodicarboxylate such as diethylazodicarboxylate; process b) could also be carried out using a precursor to the ester of formula (VII) such as an aryl-nitrile or trifluoromethyl derivative, followed by conversion to a carboxylic acid and amide formation as previously described;

Process c)—compounds of Formula (VIII) and (IX) can be reacted together in a suitable solvent, such as DMF or THF, with a base such as sodium hydride or potassium tert-butoxide, at a temperature in the range 0 to 200° C., optionally using microwave heating or metal catalysis such as palladium(II)acetate, palladium on carbon, copper(II)acetate or copper(I)iodide; process c) could also be carried out using a precursor to the ester of formula (X) such as an aryl-nitrile or trifluoromethyl derivative, followed by conversion to a carboxylic acid and amide formation as previously described;

compounds of the formula (VIII) are commercially available or can be prepared from commercially available materials by processes well known to those skilled in the art, for example functional group interconversions (such as hydrolysis, hydrogenation, hydrogenolysis, oxidation or reduction), and/or further functionalisation and/or cyclisation by standard reactions (such as amide or sulphonamide or metal-catalysed coupling, or nucleophilic displacement or electrophilic substitution reactions);

for example, by addition of a formyl group to a hydroxybenzamide compound as shown below:

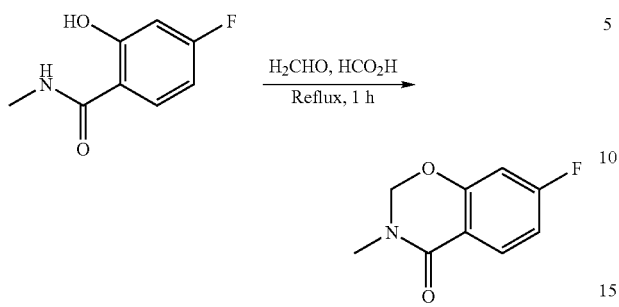

or by a nucleophilic displacement reaction as shown below:

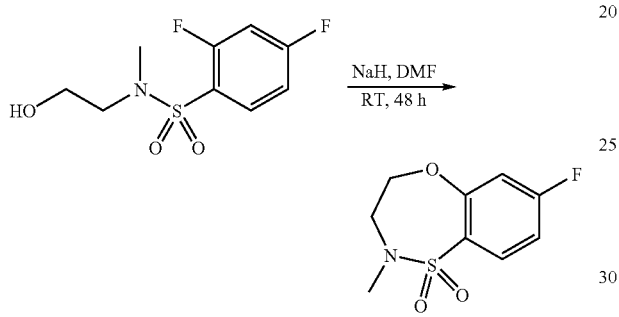

Process d)—reaction of a compound of Formula (XI) with a compound of Formula (XII) can be performed in a polar solvent, such as DMF or a non-polar solvent such as THF with a strong base, such as sodium hydride or potassium tert-butoxide at a temperature between 0 and 200° C., optionally using microwave heating or metal catalysis, such as palladium(II)acetate, palladium on carbon, copper (II)acetate or copper(I)iodide;

Process e)—cyclisation of a compound of formula (XIII) to a compound of formula (I) are well known in the art; for example, i) a coupling reaction of amino groups with carboxylic acids using coupling reagents or acid chlorides (see process a) to form amide bonds;

ii) a coupling reaction of an amino group with a sulphonyl chloride in the presence of a suitable base, such as pyridine or triethylamine, in a suitable solvent such as DCM, toluene or pyridine at a temperature between 0° C. and 80° C., to form a sulphonamide group;

iii) reaction with a suitable solvent, such as DMF or tetrahydrofuran (THF), with a base such as sodium hydride or potassium tert-butoxide, at a temperature in the range 0 to 200° C., optionally using microwave heating or metal catalysis such as palladium(II)acetate, palladium on carbon, copper(II)acetate or copper(I)iodide; alternatively, reaction in a suitable solvent, such as THF or DCM, with a suitable phosphine such as triphenylphosphine, and azodicarboxylate such as diethylazodicarboxylate;

iv) electrophilic substitution reactions (such as Friedel Crafts reactions, for compounds of Formula (XIII) where either $Y^1$ is a direct bond and $X^6$=H or $Y^2$ is a direct bond and $X^7$ is H);

compounds of the Formula (XIII) may be made from compounds of Formula (XV), wherein each R group is independently a simple substituent (such as halo or cyano) or hydrogen, by processes well known to those skilled in the art such as functional group interconversions (for example hydrolysis, hydrogenation, hydrogenolysis, oxidation or reduction), and/or further functionalisation by standard reactions (such as amide or sulphonamide or metal-catalysed coupling, or nucleophilic displacement or electrophilic substitution reactions); compounds of formula (XV) may be made from commercially available materials by processes such as those described herein in processes a) to e).

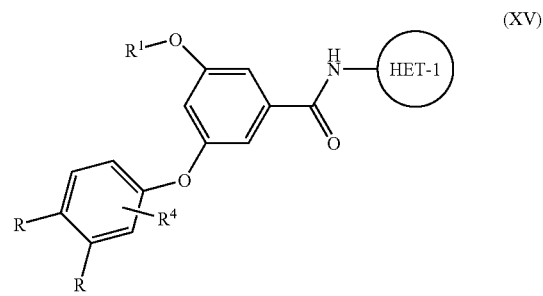

It will be appreciated that it is possible to form the HET-2 ring from a pre-cursor and form the phenoxy link in a one-pot reaction, so that it is unclear whether process c) or process e) is actually the final step. This is illustrated in the scheme below which illustrates that the $S_NAr$ reaction, deprotection and cyclisation to form HET-2 may occur in the same reaction pot:

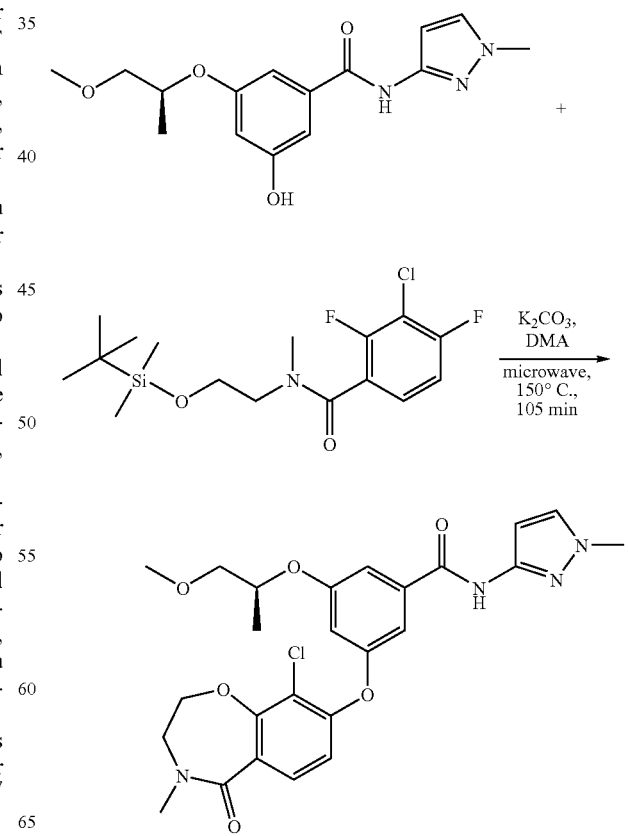

Rearrangement of the HET-2 ring may also occur in some circumstances, for example:

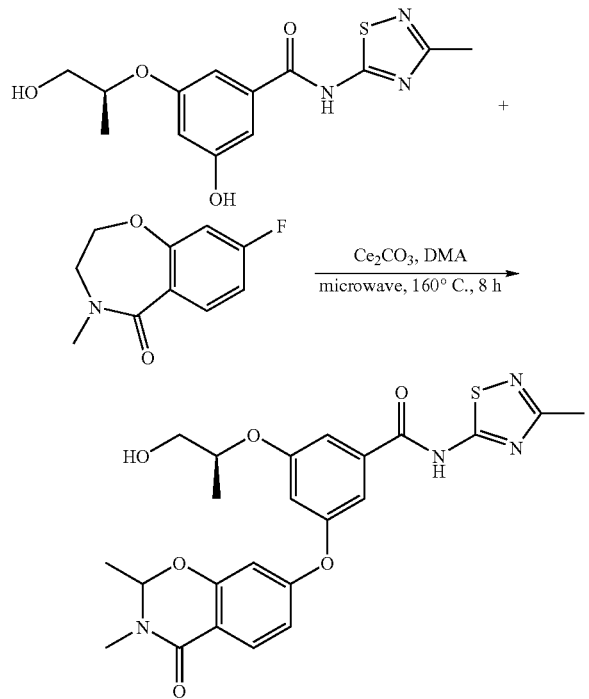

Certain intermediates of formula (III), (VI), (VII), (IX), (XI) and/or (XIII) are believed to be novel and comprise an independent aspect of the invention.

Certain intermediates of formula (III), (IX) and/or (XI) wherein $R^1$ is as defined herein for a compound of formula (I) are believed to be novel and comprise an independent aspect of the invention.

During the preparation process, it may be advantageous to use a protecting group for a functional group within the molecule. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms). Examples of carboxy protecting groups include straight or branched chain (1-12C)alkyl groups (e.g. isopropyl, t-butyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl) silyl groups (e.g. trimethylsilyl and t-butyldimethylsilyl); tri (lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, metal- or enzymically-catalysed hydrolysis. Hydrogenation may also be used.

Examples of hydroxy protecting groups include methyl, t-butyl, lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); tetrahydropyran-2-yl; aryl lower alkyl groups (e.g. benzyl) groups; and triaryl lower alkyl groups (e.g. triphenylmethyl). Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, hydrogenation, nucleophilic displacement, acid-, base, metal- or enzymically-catalysed hydrolysis, catalytic hydrogenolysis or photolytically for groups such as o-nitrobenzyloxycarbonyl, or with fluoride ions for silyl groups. For example, methylether protecting groups for hydroxy groups may be removed by trimethylsilyliodide. A tert-butyl ether protecting group for a hydroxy group may be removed by hydrolysis, for example by use of hydrochloric acid in methanol.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

EXAMPLES

The following examples are for illustration purposes and are not intended to limit the scope of this application. Each exemplified compound represents a particular and independent aspect of the invention. In the following non-limiting Examples, unless otherwise stated:
(i) evaporations were carried out by rotary evaporation in vacuo and work-up procedures were carried out after removal of residual solids such as drying agents by filtration;
(ii) operations were carried out at room temperature, that is in the range 18-25° C. and under an atmosphere of an inert gas such as argon or nitrogen;
(iii) yields are given for illustration only and are not necessarily the maximum attainable;
(iv) the structures of the end-products of the Formula (I) were confirmed by nuclear (generally proton) magnetic resonance (NMR) with a field strength (for proton) of 300 MHz (generally using a Varian Gemini 2000) or 400 MHz (generally using a Bruker Avance DPX400), unless otherwise stated, and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;
(v) intermediates were not generally fully characterised and purity was assessed by thin layer chromatography (TLC), high-performance liquid chromatography (HPLC), infra-red (IR) or NMR analysis;
(vi) Purification by chromatography generally refers to flash column chromatography, on silica unless otherwise stated. Column chromatography was generally carried out using prepacked silica cartridges (from 4 g up to 400 g) such as Redisep™ (available, for example, from Presearch Ltd, Hitchin, Herts, UK) or Biotage (Biotage UK Ltd, Hertford, Herts, UK), eluted using a pump and fraction collector system. Purification by Solid Phase Extraction (SPE) methods generally refers to the use of chromatography cartridges packed with SPE materials such as ISOLUTE® SCX-2 columns (available, for example, From International Sorbent Technology Ltd, Dryffryn Business Park, Hengoed, Mid Glamorgan, UK);
(vii) Mass spectra (MS) data was generated on an LCMS system where the HPLC component comprised generally either a Agilent 1100 or Waters Alliance HT (2790 & 2795) equipment and was run on a Phemonenex Gemini C18 5 µm, 50×2 mm column (or similar) eluting with either acidic eluent (for example, using a gradient between 0-95% water/acetonitrile with 5% of a 1% formic acid in 50:50 water:acetonitrile (v/v) mixture; or using an equivalent solvent system with methanol instead of acetonitrile), or basic eluent (for example, using a gradient between 0-95% water/acetonitrile with 5% of a 0.1% 880 Ammonia in acetonitrile mixture); and the MS component comprised generally a Waters ZQ spectrometer. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is (M−H)−;
(viii) Suitable microwave reactors include "Smith Creator", "CEM Explorer", "Biotage Initiator sixty" and "Biotage Initiator eight".

| Abbreviations | |
|---|---|
| DCM | dichloromethane; |
| DEAD | diethylazodicarboxylate; |
| DIAD | diisopropylazodicarboxylate; |
| DIPEA | N,N-Diisopropylethylamine; |
| DMSO | dimethyl sulphoxide; |
| DMF | dimethylformamide; |
| DMA | dimethylacetamide; |
| EDAC | 1-(3-dimethylaminopropyl)-3-ethylcarbodiimide hydrochloride; |
| HATU | O-(7-Azabenzotriazol-1-yl)-N,N,N',N'-tetramethyluronium hexafluorophosphate |
| HPLC | high pressure liquid chromatography |
| HPMC | Hydroxypropylmethylcellulose; |
| LCMS | liquid chromatography/mass spectroscopy; |
| NMP | N-methyl-2-pyrrolidone; |
| NMR | nuclear magnetic resonance spectroscopy; |
| RT | room temperature; |
| THF | tetrahydrofuran; |
| TFA | trifluoroacetic acid; |
| CDCl$_3$ | deuterochloroform. |

All compound names were derived using ACD NAME computer package.

Example 1

3-[(2,2-Difluoro-1,3-benzodioxol-5-yl)oxy]-5-[(1S)-2-hydroxy-1-methylethoxy]-N-(1-methyl-1H-pyrazol-3-yl)benzamide

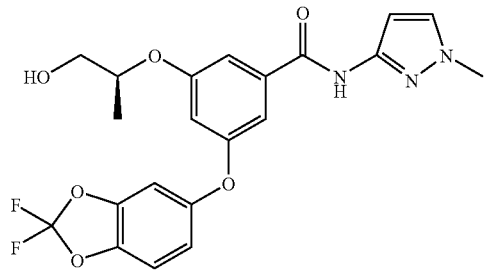

A solution of 3-((1S)-2-{[tert-butyl(dimethyl)silyl]oxy}-1-methylethyloxy)-5-hydroxy-N-(1-methyl-1H-pyrazol-3-yl)benzamide (0.20 g, 0.493 mmol), (2,2-difluoro-1,3-benzodioxol-5-yl)boronic acid (303 mg, 1.5 mmol), copper (II) acetate (0.202 g, 1.11 mmol), triethylamine (0.52 mL, 3.71 mmol) and freshly activated 4 Å molecular sieves (1 g) in DCM (40 mL) was stirred at ambient temperature and under ambient atmosphere for 2 days. The reaction mixture was filtered through celite, washed with DCM (2×10 mL), the DCM removed in vacuo. 3.5M Hydrochloric acid (0.5 mL) was added to a solution of the residual oil dissolved in methanol (5 mL) and the mixture stirred at room temperature for 20 minutes. The solution was neutralised with saturated sodium bicarbonate solution, the methanol removed in vacuo and the residual solution partitioned between ethyl acetate (50 mL) and water (10 mL). The ethyl acetate layer was separated, washed with brine, dried (MgSO$_4$), and evaporated to a residue which was chromatographed on silica, eluting with 3% methanol in DCM, to give the desired compound (3.1 mg).

$^1$H NMR δ (CDCl$_3$): 1.30 (d, 3H), 1.95 (t, 1H), 3.78 (m, 2H), 3.81 (s, 3H), 4.55 (m, 1H), 6.72 (m, 1H), 6.78 (m, 2H), 6.80 (m, 1H), 6.98 (m, 1H), 7.00 (d, 1H), 7.18 (s, 1H), 7.26 (m, 1H), 8.30 (brs, 1H); m/z 448 (M+H)$^+$ In a similar manner to that described above, the following compounds were also prepared from 3-((1S)-2-{[tert-butyl(dimethyl)silyl]oxy}-1-methylethyloxy)-5-hydroxy-N-(1-methyl-1H-pyrazol-3-yl)benzamide and the appropriate boronic acid:—

| Example | Structure | m/z | ¹H NMR (CDCl₃) |
|---|---|---|---|
| 1a | 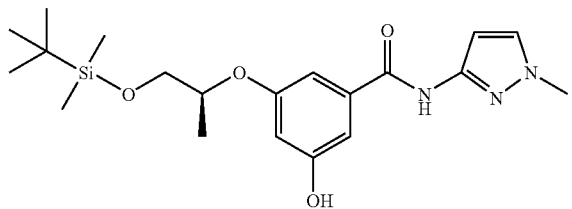 | 412 (M + H)⁺ | δ: 1.26 (d, 3 H), 1.98 (brs, 1 H), 3.90-3.98 (m, 5 H), 4.48-4.58 (m, 1 H), 6.00 (s, 2 H), 6.48 (d, 1 H), 6.58 (m, 1 H), 6.67 (m, 1 H), 6.77 (m, 2 H), 6.97 (m, 1 H), 7.14 (m, 1 H), 7.23 (m, 1 H), 8.60 (s, 1 H) |

The preparation of 3-((1S)-2-{[tert-butyl(dimethyl)silyl]oxy}-1-methylethyloxy)-5-hydroxy-N-(1-methyl-1H-pyrazol-3-yl)benzamide is described below:

3-((1S)-2-{[tert-Butyl(dimethyl)silyl]oxy}-1-methylethyloxy)-5-hydroxy-N-(1-methyl-1H-pyrazol-3-yl)benzamide 3-((1S)-2-{[tert-Butyl(dimethyl)silyl]oxy}-1-methylethyloxy)-5-(phenylmethyl)oxy-N-(1-methyl-1H-pyrazol-3-yl)benzamide (1.8 g, 3.64 mmol) was dissolved in methanol (50 mL) and the flask evacuated and purged with nitrogen (3 times). 10% Palladium on carbon (0.2 g) was added and the flask further evacuated and finally purged with hydrogen gas. The reaction mixture was stirred at ambient temperature for 16 hours until completion. The reaction mixture was evacuated and purged with nitrogen (3 times). The catalyst was filtered off, and the filtrate concentrated in vacuo to give the desired compound (1.45 g).
¹H NMR δ (d₆-DMSO): 0.02 (d, 6H), 0.83 (s, 9H), 1.18 (d, 3H), 3.66 (m, 2H), 3.72 (s, 3H), 4.51 (m, 1H), 6.42 (m, 1H), 6.52 (m, 1H), 6.90 (s, 1H), 7.02 (s, 1H), 7.55 (m, 1H), 9.58 (br s, 1H), 10.59 (br s, 1H). m/z 406 (M+H)⁺

3-((1S)-2-{[tert-Butyl(dimethyl)silyl]oxy}-1-methylethyloxy-5-(phenylmethyl)oxy-N-(1-methyl-1H-pyrazol-3-yl)benzamide

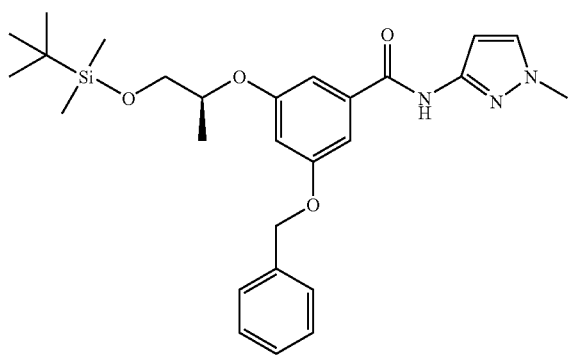

DIPEA (4.06 g, 23.4 mmol) was added to a suspension of 3-{(phenylmethyl)oxy}-5-((1S)-2-{[tert-butyl(dimethyl)silyl]oxy}-1-methylethoxy)benzoic acid (2.43 g, 5.84 mmol), 1-methyl-1H-pyrazole-3-amine (0.85 g, 8.76 mmol) and HATU (4.66 g, 12.3 mmol) in DMF (50 mL) and stirred at ambient temperature for 16 hours. The resultant mixture was partially reduced in vacuo, poured onto water (100 mL) and extracted with diethyl ether (2×50 mL). The extracts were washed with water and brine then dried (MgSO₄), filtered and reduced to an opaque gum which partially crystallized. The crude product was purified by column chromatography, eluting with 0-100% ethyl acetate in isohexane, to give the title compound as a colourless oil (1.87 g).
¹H NMR δ (d₆-DMSO): 0.02 (d, 6H), 0.84 (s, 9H), 1.21 (d, 3H), 3.68 (d, 2H), 3.76 (s, 3H), 4.58 (m, 1H), 5.13 (s, 2H), 6.56 (m, 1H), 6.70 (m, 1H), 7.18 (s, 1H), 7.24 (s, 1H), 7.29-7.46 (m, 5H), 7.57 (m, 1H), 10.74 (br s, 1H). m/z 496 (M+H)⁺

3-{(Phenylmethyl)oxy}-5-((1S)-2-{[tert-butyl(dimethyl)silyl]oxy}-1-methylethoxy)benzoic acid

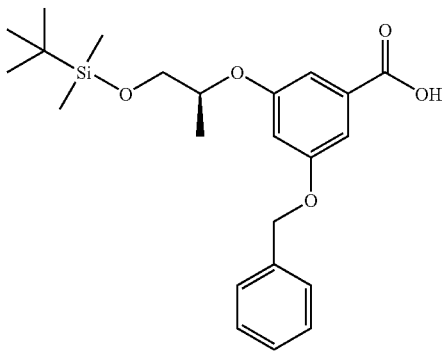

Methyl 3-((1S)-2-{[tert-butyl(dimethyl)silyl]oxy}-1-methylethoxy)-5-[(phenylmethyl)oxy]benzoate (3.0 g, 6.98 mmol) was dissolved in THF (50 mL) and water (10 mL) and lithium hydroxide monohydrate (586 mg, 13.95 mmol) added. The resultant mixture was heated with stirring at 45° C. for 2 hours, then at ambient temperature for 16 hours, and at 45° C. for a further 4 hours. Water (40 mL) was added and the solvent removed in vacuo. The resultant solution was acidified carefully with 1M citric acid (2 equivalents), washed with water and brine then dried (MgSO₄), filtered and evaporated in vacuo to give the title compound as a colourless gum (2.58 g).

¹H NMR δ (d₆-DMSO): 0.02 (d, 6H), 0.84 (s, 9H), 1.17 (d, 3H), 3.66 (m, 2H), 4.43 (m, 1H), 5.05 (s, 2H), 6.56 (br s, 1H), 7.10 (br s, 1H), 7.17 (br s, 1H), 7.25-7.44 (m, 5H), 7.60 (br s, 1H).

Methyl 3-((1S)-2-{[tert-butyl(dimethyl)silyl]oxy}-1-methylethoxy)-5-[(phenylmethyl)oxy]benzoate

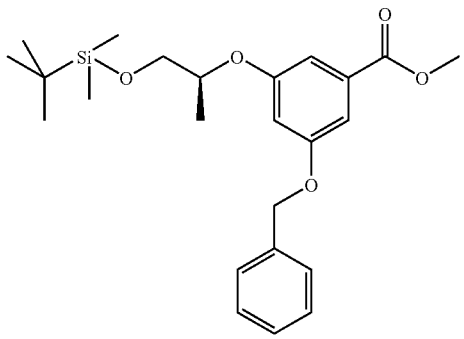

(2R)-1-{[tert-Butyl(dimethyl)silyl]oxy}propan-2-ol (3.31 g, 17.4 mmol) was added to a solution of methyl 3-hydroxy-5-{[phenylmethyl]oxy}benzoate (3.00 g, 11.6 mmol) in THF (50 mL) at 0° C. followed by addition of triphenylphosphine (4.57 g, 17.4 mmol) then DIAD (3.43 mL, 17.4 mmol) and the reaction was warmed to RT and stirred for 16 h. The reaction was quenched with water (100 mL) and diethyl ether (400 mL) and the organic layer was separated then dried (MgSO₄) and evaporated. Purification by column chromatography, eluting with 1:15 to 1:5 ethyl acetate:hexane, afforded the title compound as a colourless oil (4.00 g, 80%).

¹H NMR δ (CDCl₃): 0.03 (s, 3H), 0.05 (s, 3H), 0.89 (s, 9H), 1.29 (d, 3H), 3.63 (dd, 1H), 3.78 (dd, 1H), 3.92 (s, 3H), 4.44 (m, 1H), 5.08 (s, 2H), 6.77 (m, 1H), 7.40 (m, 7H)

Methyl 3-hydroxy-5-{[phenylmethyl]oxy}benzoate

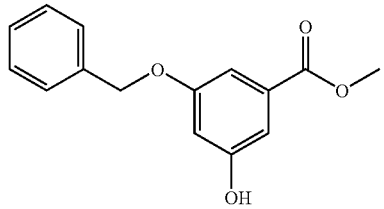

To a stirred solution of methyl 3,5-dihydroxybenzoate (5.95 mol) in DMF (6 L) was added potassium carbonate (9 mol), and the suspension stirred at ambient temperature under argon. To this was added benzyl bromide (8.42 mol) slowly over 1 hour, with a slight exotherm, and the reaction mixture stirred overnight at ambient temperature. The reaction was quenched cautiously with ammonium chloride solution (5 L) followed by water (35 L). The aqueous suspension was extracted with DCM (1×3 L and 2×5 L). The combined extracts were washed with water (10 L) and dried overnight (MgSO₄). The solution was evaporated in vacuo, and the crude product chromatographed in 3 batches (flash column, 3×2 kg silica, eluting with a gradient consisting of hexane containing 10% DCM, to neat DCM, to DCM containing 50% ethyl acetate) to eliminate starting material. The crude eluant was further chromatographed in 175 g batches (Amicon HPLC, 5 kg normal-phase silica, eluting with isohexane containing 20% v/v of ethyl acetate) to give the desired compound (21% yield); ¹H NMR δ (d₆-DMSO): 3.8 (s, 3H), 5.1 (s, 2H), 6.65 (m, 1H), 7.0 (m, 1H), 7.05 (m, 1H), 7.3-7.5 (m, 5H), 9.85 (br s, 1H).

(2R)-1-{[tert-Butyl(dimethyl)silyl]oxy}propan-2-ol

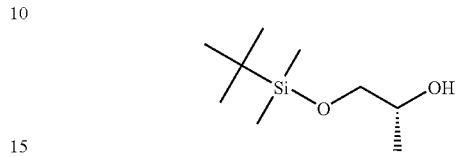

tert-Butyl(dimethyl)silyl chloride (5.90 g, 39.5 mmol) was added to a solution of (2R)-propane-1,2-diol (3.00 g, 39.5 mmol) in DCM (100 mL) followed by diisopropylethylamine (7.10 g, 55.3 mmol) and the reaction was stirred under argon for 72 h. The reaction was diluted with diethyl ether (500 mL) and water (140 mL) and the organic layer was separated then dried (MgSO₄), filtered and evaporated. Purification by column chromatography, eluting with 1:15 to 1:10 ethyl acetate:hexane, afforded the title compound as a colourless oil (6.00 g, 80%).

¹H NMR δ (CDCl₃): 0.10 (m, 6H), 0.92 (s, 9H), 1.14 (d, 3H), 2.42 (d, 1H), 3.38 (dd, 1H), 3.60 (dd, 1H), 3.82 (m, 1H).

The data matched that reported in the literature (*J. Org. Chem.*, 1998, 53, 2300).

Example 2

3-[(8-Fluoro-2,3-dimethyl-4-oxo-3,4-dihydro-2H-1,3-benzoxazin-7-yl)oxy]-5-[(1S)-2-hydroxy-1-methylethoxy]-N-(1-methyl-1H-pyrazol-3-yl)benzamide

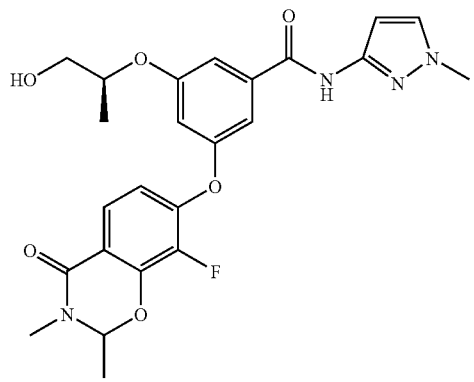

Potassium carbonate (152 mg, 1.1 mmol) was added to a solution of 8,9-difluoro-4-methyl-3,4-dihydro-1,4-benzoxazepin-5(2H)-one (117 mg, 0.55 mmol) and 3-((1S)-2-{[tert-butyl(dimethyl)silyl]oxy}-1-methylethyloxy)-5-hydroxy-N-(1-methyl-1H-pyrazol-3-yl)benzamide (223 mg, 0.55 mmol) in 1-methyl-2-pyrrolidinone (10 mL) and the mixture heated at 140° C. for 3 days. The mixture was concentrated in vacuo and the residue suspended in ethyl acetate (20 mL). The suspension was filtered through Celite® and evaporated. The residue was purified by column chromatography (eluting with 0-20% methanol in DCM) to afford a colourless gum which solidified on evaporation from 30% methanol in DCM to afford the title compound as a colourless solid (109 mg, 33%).

$^1$H NMR δ (CDCl$_3$): 1.22 (d, 3H), 1.59 (d, 3H), 2.97 (s, 3H), 3.52 (m, 2H), 3.75 (s, 3H), 4.55 (m, 1H), 4.85 (m, 1H), 5.75 (q, 1H), 6.53 (d, 1H), 6.78-6.87 (m, 2H), 7.20 (m, 1H), 7.42 (m, 1H), 7.56-7.61 (m, 2H), 10.83 (s, 1H); m/z 485 (M+H)$^+$

The preparation of 3-((1S)-2-{[tert-butyl(dimethyl)silyl]oxy}-1-methylethyloxy)-5-hydroxy-N-(1-methyl-1H-pyrazol-3-yl)benzamide was described in Example 1. The preparation of 8,9-difluoro-4-methyl-3,4-dihydro-1,4-benzoxazepin-5(2H)-one is described below:

8,9-Difluoro-4-methyl-3,4-dihydro-1,4-benzoxazepin-5(2H)-one

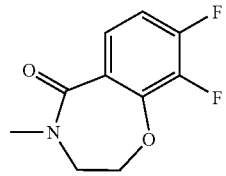

DIPEA (0.68 mL, 3.9 mmol) was added to a solution of 2,3,4-trifluorobenzoyl chloride (500 mg, 2.6 mmol) in DCM (5 mL) followed by the addition of N-methylethanolamine (0.31 mL, 3.9 mmol). The mixture was stirred for 20 hours. The solution was diluted with methanol (10 mL) and passed through an ISOLUTE® SCX-2 SPE column. The solution was evaporated. The residue was dissolved in DMF and sodium hydride (60% dispersion in mineral oil, 0.11 g, 2.7 mmol) was added portionwise over 5 minutes. The resulting mixture was stirred for 20 hours. Water (100 mL) was added dropwise and the mixture was extracted with ether (3×200 mL). Combined ethereal extracts were dried (MgSO$_4$) and evaporated. The residue was purified by column chromatography (eluting with 1:1 ethyl acetate:isohexane to neat ethyl acetate) to afford the title compound (117 mg, 20%) as a colourless solid.

$^1$H NMR δ (CDCl$_3$): 3.20 (s, 3H), 3.59 (t, 2H), 4.51 (t, 2H), 6.93 (m, 1H), 7.59 (m, 1H); m/z 214 (M+H)$^+$

Example 3

3-[(7-Fluoro-5,5-dioxido-3,4-dihydro-2H-1,5-benzoxathiepin-8-yl)oxy]-5-[(1S)-2-hydroxy-1-methylethoxy]-N-(1-methyl-1H-pyrazol-3-yl)benzamide

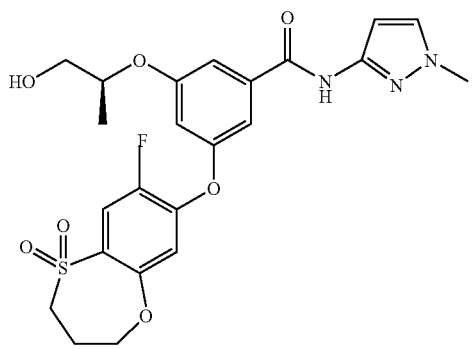

A solution of 3-[(2,4,5-trifluorophenyl)sulfonyl]dihydrofuran-2(3H)-one (126 mg, 0.45 mmol) and 3-((1S)-2-{[tert-butyl(dimethyl)silyl]oxy}-1-methylethyloxy)-5-hydroxy-N-(1-methyl-1H-pyrazol-3-yl)benzamide (203 mg, 0.50 mmol) in acetonitrile (3.5 mL) was treated with caesium carbonate (650 mg, 2.0 mmol) and heated in a microwave reactor at 150° C. for 1.5 hours. The reaction mixture was filtered and concentrated in vacuo. The residue was then chromatographed on silica, eluting with a gradient of 0 to 10% methanol in ethyl acetate, to afford the title compound (78 mg).

$^1$H NMR δ (d$_6$-DMSO): 1.23 (d, 3H), 2.17-2.26 (brm, 2H), 3.43-3.59 (brm, 4H), 3.76 (s, 3H), 4.15 (m, 2H), 4.57 (m, 1H), 4.85 (t, 1H), 6.55 (m, 1H), 6.92 (m, 2H), 7.23 (m, 1H), 7.45 (m, 1H), 7.57 (m, 1H), 7.73 (d, 1H), 10.84 (brs, 1H). m/z 506 (M+H)$^+$ 504 (M−H)$^-$ 3-[(2,4,5-Trifluorophenyl)sulfonyl]dihydrofuran-2 (3H)-one

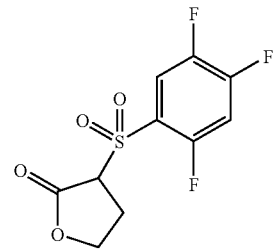

A solution of sodium sulfite (153 mg, 1.21 mmol) and sodium bicarbonate (306 mg, 3.63 mmol) in water (3 mL) was treated with 2,4,5-trifluorobenzenesulfonyl chloride (280 mg, 1.21 mmol) and heated in a microwave reactor at 150° C. for 400 seconds. The resulting mixture was treated with 3-bromodihydrofuran-2(3H)-one (299 mg, 1.82 mmol) and then heated in a microwave reactor at 150° C. for 500 seconds. The mixture was cooled to 10° C. and the resulting solid filtered off and dried in vacuo to give the title compound (60 mg).

$^1$H NMR δ (d$_6$-DMSO): 2.66-2.76 (brm, 2H), 4.31-4.45 (brm, 2H), 4.92 (t, 1H), 7.92-8.07 (brm, 2H) m/z 279 (M−H)$^-$ The preparation of 3-((1S)-2-{[tert-butyl(dimethyl)silyl]oxy}-1-methylethyloxy)-5-hydroxy-N-(1-methyl-1H-pyrazol-3-yl)benzamide was described in Example 1.

Example 4

3-[(1S)-2-Hydroxy-1-methylethoxy]-5-[(1-methyl-1H-indol-5-yl)oxy]-N-(1-methyl-1H-pyrazol-3-yl) benzamide

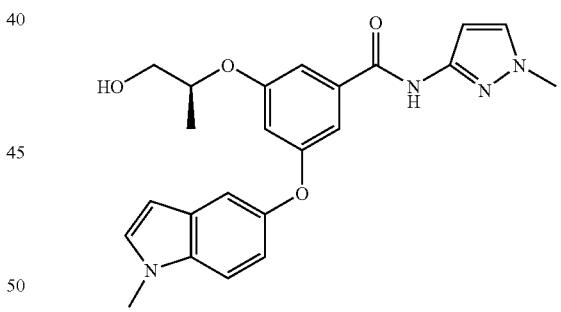

10% Hydrochloric acid (0.5 mL) was added to a solution of 3-((1S)-2-{[tert-butyl(dimethyl)silyl]oxy}-1-methylethoxy)-5-[(1-methyl-1H-indol-5-yl)oxy]-N-(1-methyl-1H-pyrazol-3-yl)benzamide (120 mg, 0.22 mmol) in methanol (5 mL). The reaction was stirred at ambient temperature for 1 hour, saturated sodium bicarbonate solution added and the methanol evaporated. The aqueous residue was taken to pH 2 and extracted with ethyl acetate. The extracts were combined, washed with brine, dried (MgSO$_4$), filtered and evaporated in vacuo to give the crude product which was chromatographed on silica, eluting with 1% methanol in ethyl acetate, to give the desired product (85 mg).

$^1$H NMR δ (CDCl$_3$): 1.3 (d, 3H), 2.2 (t, 1H), 3.6-3.7 (m, 2H), 3.7 (s, 3H), 3.8 (s, 3H), 4.5 (m, 1H), 6.4 (d, 1H), 6.7 (d, 1H), 6.8 (d, 1H), 6.9 (m, 2H), 7.1 (m, 2H), 7.20 (m, 3H) and 8.75 (s, 1H). m/z 421 (M+H)$^+$ The following compounds were prepared in an analogous fashion from the appropriate silyl ethers.

| Example | Structure | m/z | ¹H NMR (CDCl₃) |
|---|---|---|---|
| 4a | 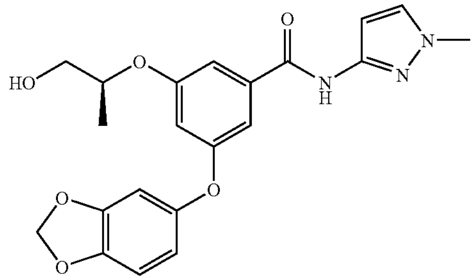 | 410 (M + H)⁺ | δ: 1.3 (d, 3 H), 2.4 (br, 1 H), 3.2 (t, 2 H), 3.7 (m, 2 H), 3.8 (s, 3 H), 4.5 (m, 1 H), 4.6 (t, 2 H), 6.65 (d, 1 H), 6.8 (m, 3 H), 6.85 (s, 1 H), 6.95 (s, 1 H), 7.1 (s, 1 H), 7.3 (s, 1 H), 8.75 (s, 1 H). |
| 4b | 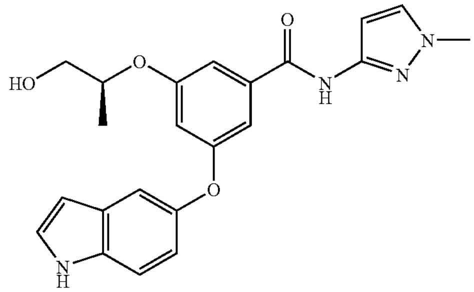 | 407 (M + H)⁺ | δ: 1.3 (d, 3 H), 2.2 (br, 1 H), 3.7 (m, 2 H), 3.75 (s, 3 H), 4.5 (m, 1 H), 6.5 (d, 1 H), 6.7 (m, 1 H), 6.8 (d, 1 H), 6.9 (dd, 1 H), 6.95 (s, 1 H), 7.1 (s, 1 H), 7.2-7.4 (m, 4 H), 8.3 (s, 1 H), 8.75 (s, 1 H). |
| 4c | 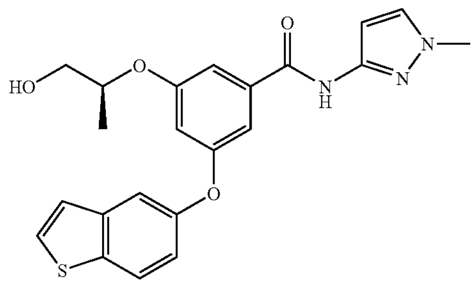 | 424 (M + H)⁺ | δ: 1.3 (d, 3 H), 2.4 (br, 1 H), 3.7 (dd, 2 H), 3.8 (s, 3 H), 4.55 (m, 1 H), 6.7 (s, 1 H), 6.8 (s, 1 H), 7.05 (s, 1 H), 7.1 (dd, 1 H), 7.2 (s, 1 H), 7.25 (d, 1 H), 7.45 (s, 1 H), 7.5 (d, 1 H) 7.6-7.7 (m, 1 H), 7.85 (d, 1 H), 8.8 (s, 1 H). |

The preparation of 3-((1S)-2-{[tert-butyl(dimethyl)silyl]oxy}-1-methylethoxy)-5-[(1-methyl-1H-indol-5-yl)oxy]-N-(1-methyl-1H-pyrazol-3-yl)benzamide is described below:

3-((1S)-2-{[tert-Butyl(dimethyl)silyl]oxy}-1-methylethoxy)-5-[(1-methyl-1H-indol-5-yl)oxy]-N-(1-methyl-1H-pyrazol-3-yl)benzamide

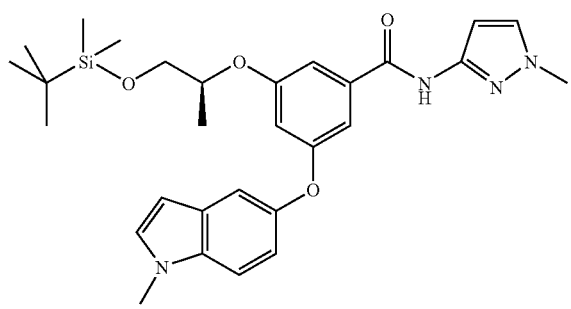

A solution of 3-((1S)-2-{[tert-butyl(dimethyl)silyl]oxy}-1-methylethyloxy)-5-hydroxy-N-(1-methyl-1H-pyrazol-3-yl)benzamide (202 mg, 0.5 mmol), 1-methylindole-5-boronic acid (131 mg, 0.75 mmol), copper (II) acetate (138 mg, 0.75 mmol), triethylamine (0.35 mL, 2.5 mmol) and freshly activated 4A molecular sieves (1 g) in DCM (10 mL) was stirred at ambient temperature and under ambient atmosphere for 2 days. The reaction mixture was filtered through Celite, washed with DCM (2×10 mL), the DCM removed in vacuo and the residual oil partitioned between ethyl acetate (25 mL) and water (25 mL). The ethyl acetate layer was separated, washed with aqueous sodium hydrogen carbonate solution, brine, dried (MgSO₄) and evaporated to a residue which was chromatographed on silica, eluting with 40% ethyl acetate in iso-hexane, to give the desired compound (128 mg).

¹H NMR δ (CDCl₃): 0.0 (m, 6H), 0.85 (s, 9H), 1.3 (d, 3H), 3.6-3.8 (m, 2H), 3.75 (s, 3H), 3.8 (s, 3H), 4.45 (m, 1H), 6.4 (d, 1H), 6.7 (d, 1H), 6.75 (d, 1H), 6.8 (m, 2H), 7.1 (m, 2H), 7.20 (m, 3H) and 8.4 (s, 1H). m/z 535 (M+H)⁺

The silyl ethers used in the preparation of Examples 4a and 4b were made in an analogous fashion from either 3-((1S)-2-{[tert-butyl(dimethyl)silyl]oxy}-1-methylethyloxy)-5-hydroxy-N-(1-methyl-1H-pyrazol-3-yl)benzamide or 3-hydroxy-N-(1-methyl-1H-pyrazol-3-yl)-5-{(1S)-1-methyl-2-[(triisopropylsilyl)oxy]ethoxy}benzamide.

| Structure | m/z |
|---|---|
| 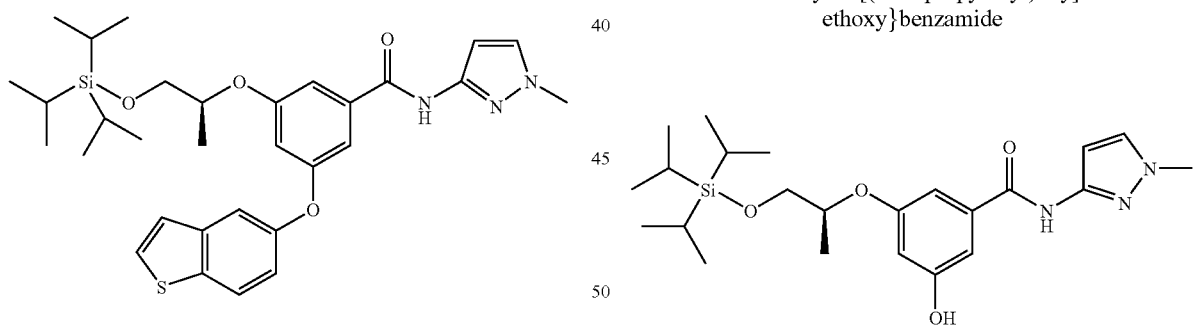 | 524 (M + H)+. |
| 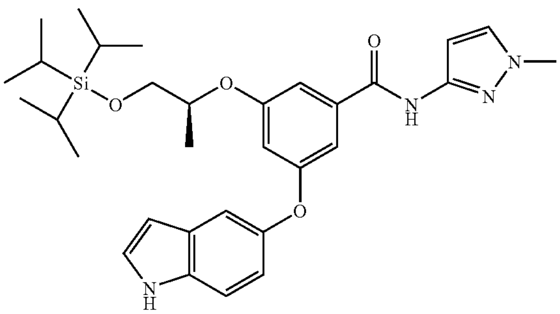 | 563 (M + H)+. |

The preparation of 3-(1-benzothien-5-yloxy)-N-(1-methyl-1H-pyrazol-3-yl)-5-{(1S)-1-methyl-2-[(triisopropylsilyl)oxy]ethoxy}benzamide used in the synthesis of Example 4c is described below:

3-(1-Benzothien-5-yloxy)-N-(1-methyl-1H-pyrazol-3-yl)-5-{(1S)-1-methyl-2-[(triisopropylsilyl)oxy]ethoxy}benzamide Cesium carbonate (163 mg, 0.05 mmol) was added to a solution of 3-hydroxy-N-(1-methyl-1H-pyrazol-3-yl)-5-{(1S)-1-methyl-2-[(triisopropylsilyl)oxy]ethoxy}benzamide (225 mg, 0.5 mmol), bromotris(triphenylphosphine)copper[1] (93 mg, 0.1 mmol) and 5-bromobenzothiophene (107 mg, 0.5 mmol) in dimethylacetamide (2.5 mL) and the stirred mixture heated at 200° C. in a "Biotage Initiator" microwave for 4 hours. The mixture was cooled to ambient temperature and pressure, poured onto water (40 mL) and extracted with ethyl acetate (3×15 mL), the combined organic layers washed with brine, dried (MgSO₄) and evaporated to a residue which was chromatographed on silica, eluting with 40% ethyl acetate in isohexane, to give the desired compound (100 mg).

m/z 580 (M+H)+.

The preparation of 3-((1S)-2-{[tert-butyl(dimethyl)silyl]oxy}-1-methylethyloxy)-5-hydroxy-N-(1-methyl-1H-pyrazol-3-yl)benzamide, used during the preparation of Examples 4 and 4a, was described in Example 1.

The synthesis of 3-hydroxy-N-(1-methyl-1H-pyrazol-3-yl)-5-{(1S)-1-methyl-2-[(triisopropylsilyl)oxy]ethoxy}benzamide, used in the preparation of Examples 4b and 4c, is described below:

3-Hydroxy-N-(1-methyl-1H-pyrazol-3-yl)-5-{(1S)-1-methyl-2-[(triisopropylsilyl)oxy]ethoxy}benzamide 10% Palladium on carbon was added to 3-(benzyloxy)-N-(1-methyl-1H-pyrazol-3-yl)-5-{(1S)-1-methyl-2-[(triisopropylsilyl)oxy]ethoxy}benzamide (21.7 g, 40.4 mmol) in dry THF (480 mL) under argon. The reaction mixture was degassed and placed under a hydrogen balloon and stirred for 16 hours. The atmosphere was replaced with argon and mixture was filtered through diatomaceous earth then the filtrate evaporated and dried under high vacuum for 1 hour to give the title compound (18.2 g).

$^1$H NMR δ (CDCl₃): 1.05 (s, 18H), 1.05-1.1 (m, 3H), 1.3 (d, 3H), 3.7 (m, 1H), 3.8 (s, 3H), 3.9 (m, 1H), 4.5 (m, 1H), 6.6

(s, 1H), 6.8 (s, 1H), 7.0 (m, 2H), 7.20 (s, 1H), 7.3 (s, 1H), 8.7 (s, 1H). m/z 448 (M+H)⁺, 446 (M−H)⁻

3-(Benzyloxy)-N-(1-methyl-1H-pyrazol-3-yl)-5-{(1S)-1-methyl-2-[(triisopropylsilyl)oxy]ethoxy}benzamide

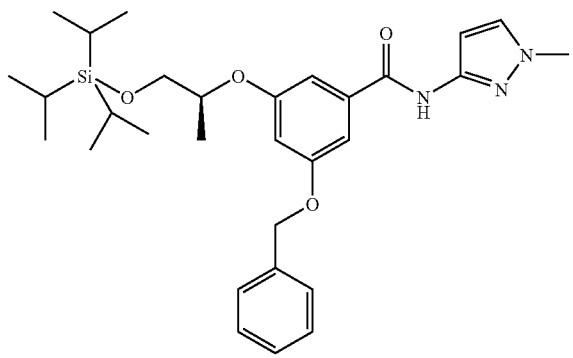

HATU (23.5 g, 61.8 mmol) was added to 3-(benzyloxy)-5-{(1S)-1-methyl-2-[(triisopropylsilyl)oxy]ethoxy}benzoic acid (23.6 g, 51.5 mmol), followed by addition of DMF (140 mL), and cooled to 0° C. 1-Methyl-1H-pyrazole-3-amine (6.00 g. 61.8 mmol) was added followed by DIPEA (21.3 mL) and the reaction was stirred under argon at 0° C. for 3 hours. The solvent was evaporated and the residue was dissolved in ethyl acetate (500 mL) and washed with citric acid solution (200 mL), sodium hydrogen carbonate solution (150 mL), and saturated brine solution (2×150 mL). The organic layer was separated and dried (MgSO₄), filtered and evaporated. Purification by column chromatography, eluting with 1:4 to 1:1 ethyl acetate:hexanes, afforded the title compound as a colourless oil (21.7 g). ¹H NMR δ (CDCl₃): 1.05 (s, 18H), 1.05-1.1 (m, 3H), 1.3 (d, 3H), 3.7 (m, 1H), 3.8 (s, 3H), 3.9 (m, 1H), 4.5 (m, 1H), 5.1 (s, 2H), 6.7 (s, 1H), 6.8 (s, 1H), 7.0 (m, 2H), 7.1 (s, 1H), 7.3 (s, 1H), 7.35-7.5 (m, 5H), 8.5 (s, 1H). m/z 538 (M+H)⁺

3-(Benzyloxy)-5-{(1S)-1-methyl-2-[(triisopropylsilyl)oxy]ethoxy}benzoic acid

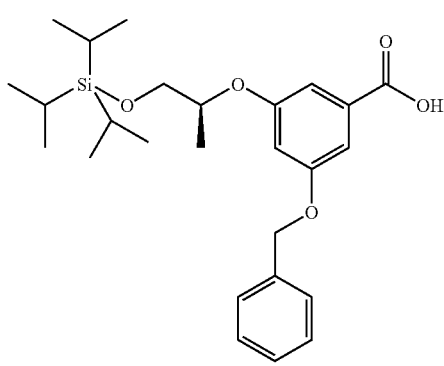

Lithium hydroxide monohydrate (12.14 g, 0.289 mol) in water (100 mL) was added to a solution of methyl 3-(benzyloxy)-5-{(s)-1-methyl-2-[(triisopropylsilyl)oxy]ethoxy}benzoate (62 g, 0.131 mol) in THF (300 mL) and warmed to 43° C. The reaction was stirred for 16 hours, the THF removed in vacuo and the resultant mixture acidified to pH 5 with 10% w/v citric acid. This was extracted with ethyl acetate (2×300 mL) and the combined organic layers were dried (MgSO₄), filtered and evaporated to afford the title compound (60.2 g).

¹H NMR δ (CDCl₃): 1.05 (s, 18H), 1.05-1.1 (m, 3H), 1.35 (d, 3H), 3.7 (m, 1H), 3.9 (m, 1H), 4.5 (m, 1H), 5.1 (s, 2H), 6.8 (s, 1H), 7.3-7.5 (m, 7H). m/z 457 (M−H)⁻

Methyl 3-(benzyloxy)-5-{(1S)-1-methyl-2-[(triisopropylsilyl)oxy]ethoxy}benzoate

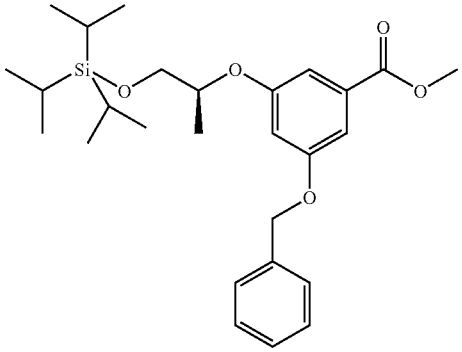

(2R)-1-[(Triisopropylsilyl)oxy]propan-2-ol (56.1 g, 242 mmol) was added to a solution of methyl 3-hydroxy-5-{[phenylmethyl]oxy}benzoate (50 g, 194 mmol) and triphenylphosphine (63.5 g, 242 mmol) in dry THF (500 mL), at 0° C., followed by addition of DIAD (47.6 mL, 242 mmol) over 45 minutes under an argon atmosphere. The reaction was stirred at 0° C. for 1 hour and allowed to warm up to RT over an hour then stirred at RT for 1 hour. The THF was evaporated and a mixture of ethyl acetate (80 mL) and hexane (120 mL) was added. This mixture stirred for 2 hours and filtered. The precipitate was washed with a mixture of ethyl acetate (20 mL) and hexane (180 mL) and the filtrate evaporated. The residue was purified by column chromatography, eluting with 1:20 to 1:10 ethyl acetate:hexanes, to afford the title compound (65.5 g). ¹H NMR δ (CDCl₃): 1.05 (s, 18H), 1.05-1.1 (m, 3H), 1.35 (d, 3H), 3.7 (m, 1H), 3.9 (m, 1H), 3.9 (s, 3H), 4.5 (m, 1H), 5.05 (s, 2H), 6.75 (s, 1H), 7.2 (s, 1H). 7.3-7.5 (m, 6H). m/z 471 (M−H)⁻

(2R)-1-[(Triisopropylsilyl)oxy]propan-2-ol

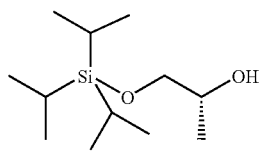

Triisopropylsilyl chloride (83.8 mL, 390 mmol) was added slowly over 15 minutes to a solution of (2R)-propane-1,2-diol (29.7 g, 390 mmol) in DMF at 0° C. (100 mL) keeping the internal temperature below 15° C. This was followed by addition of imidazole (66.4 g, 975 mmol) and the reaction mixture was allowed to warm to RT and stirred under argon for 20 hours. The reaction was quenched with 1M hydrochloric acid/diethyl ether (300 mL/800 mL). The organic layer was separated and washed with 1M hydrochloric acid followed by saturated brine solution. The organic layer was dried (MgSO₄), filtered and evaporated. Purification by distillation at 10 mmHg, 90-104° C., afforded the title compound as colourless oil (69.5 g). ¹H NMR δ (CDCl₃): 1.05 (s, 18H), 1.05-1.1 (m, 3H), 1.05 (d, 3H), 2.55 (s, 1H), 3.45 (dd, 1H), 3.7 (dd, 1H), 3.85 (m, 1H).

The preparation of methyl 3-hydroxy-5-{[phenylmethyl]oxy}benzoate was described in Example 1.

Example 5

3-[(9-Chloro-4-methyl-5-oxo-2,3,4,5-tetrahydro-1,4-benzoxazepin-8-yl)oxy]-5-[(1S)-2-hydroxy-1-methylethoxy]-N-(1-methyl-1H-pyrazol-3-yl)benzamide

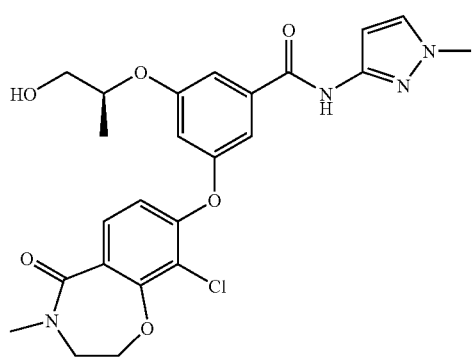

A suspension of 3-((1S)-2-{[tert-butyl(dimethyl)silyl]oxy}-1-methylethyloxy)-5-hydroxy-N-(1-methyl-1H-pyrazol-3-yl)benzamide (250 mg, 0.163 mmol), 9-chloro-8-fluoro-4-methyl-3,4-dihydro-1,4-benzoxazepin-5(2H)-one (140 mg, 0.611 mmol) and cesium carbonate (397 mg, 1.22 mmol) in DMF (3 mL) was heated in a microwave at 150° C. for 2 hours. Water (5 mL) was added and the mixture was extracted with DCM (3×15 mL). The combined organic extracts were washed with water (2×15 mL) and saturated brine solution (15 mL). The organic phase was dried (MgSO$_4$), filtered and evaporated to give an orange oil. This was purified by preparative HPLC, eluting with a gradient of 5-95% acetonitrile in water on a Phenomenex Luna 10u C18 (2) 100A column, to give an off-white foam (70 mg).

$^1$H NMR δ (CDCl$_3$): 1.22 (d, 3H), 3.09 (s, 3H), 3.44-3.54 (m, 2H), 3.58 (t, 2H), 3.76 (s, 3H), 4.47 (t, 2H), 4.52-4.59 (m, 1H), 4.82 (t, 1H), 6.53 (s, 1H), 6.77 (s, 1H), 6.87 (d, 1H), 7.15 (s, 1H), 7.42 (s, 1H), 7.57 (s, 1H), 7.59 (d, 2H), 10.82 (s, 1H). m/z 501 (M+H)$^+$

The preparation of 3-((1S)-2-{[tert-butyl(dimethyl)silyl]oxy}-1-methylethyloxy)-5-hydroxy-N-(1-methyl-1H-pyrazol-3-yl)benzamide was described in Example 1.

The preparation of 9-chloro-8-fluoro-4-methyl-3,4-dihydro-1,4-benzoxazepin-5(2H)-one is described below:

9-Chloro-8-fluoro-4-methyl-3,4-dihydro-1,4-benzoxazepin-5(2H)-one

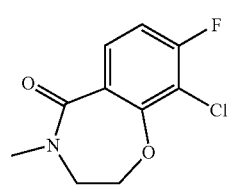

Sodium hydride (28 mg, 0.723 mmol, 60% dispersion in mineral oil) was added slowly to a solution of 3-chloro-2,4-difluoro-N-(2-hydroxyethyl)-N-methylbenzamide (180 mg, 0.723 mmol) in DMF (4 mL) and the reaction stirred at room temperature for 16 hours. Water was added to the reaction and the mixture was subsequently extracted with DCM (3×30 mL). The combined organic phases were washed with water (5×25 mL) and saturated brine solution then dried (MgSO$_4$), filtered and evaporated to give the desired product as an oil (140 mg). $^1$H NMR δ (CDCl$_3$): 3.21 (s, 3H), 3.54 (t, 2H), 4.52 (t, 2H), 6.97 (dd, 1H), 7.72 (dd, 1H). m/z 230 (M+H)$^+$ 3-Chloro-2,4-difluoro-N-(2-hydroxyethyl)-N-methylbenzamide

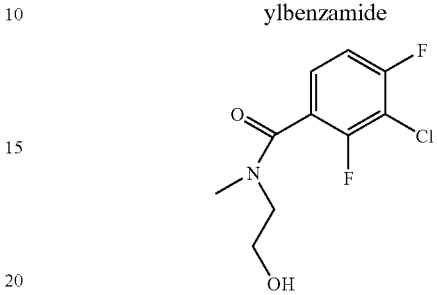

3-Chloro-2,4-difluorobenzoylchloride (211 mg, 1 mmol) in DCM (1 mL) was added to a stirred solution of N-methylaminoethanol (83 mg, 1.1 mmol) in a mixture of DCM (1 mL) and 10% sodium hydroxide solution (1 mL) at 0° C. After the addition of the acid chloride was complete, the mixture was warmed to RT and stirred for approximately 4 hours. The two layers were separated and the aqueous layer was extracted with DCM (3×30 mL). The organic layers were combined, dried (MgSO$_4$), filtered and evaporated to give a colourless oil (180 mg). $^1$H NMR δ (CDCl$_3$): 3.01 (s, 3H), 3.37 (t, 1H), 3.74 (t, 2H), 3.92 (t, 2H), 7.06 (td, 1H), 7.28-7.37 (m, 1H).

3-[(9-Chloro-4-methyl-5-oxo-2,3,4,5-tetrahydro-1,4-benzoxazepin-8-yl)oxy]-5-[(1S)-2-hydroxy-1-methylethoxy]-N-(1-methyl-1H-pyrazol-3-yl)benzamide can also be prepared by the route described below:

N-(2-{[tert-Butyl(dimethyl)silyl]oxy}ethyl)-3-chloro-2,4-difluoro-N-methylbenzamide (100 mg, 0.275 mmol) was added to 3-hydroxy-N-(1-methyl-1H-pyrazol-3-yl)-5-{(1S)-1-methyl-2-[(triisopropylsilyl)oxy]ethoxy}benzamide (123 mg, 0.275 mmol) and potassium carbonate (76 mg, 0.551 mmol) in dry dimethylacetamide. The mixture was heated in a Smith Creator microwave at 160° C. for 2 hours. Water (25 mL) was added to the reaction mixture and extracted with ethyl acetate (3×30 mL). The combined organic extracts were dried (MgSO$_4$), filtered and evaporated. Purification by column chromatography on silica, eluting with 50-100% ethyl acetate in hexanes, gave the title compound as a pale yellow oil (500 mg). $^1$H NMR δ (CDCl$_3$): 1.29 (d, 3H), 2.09 (t, 1H), 3.23 (s, 3H), 3.59 (t, 2H), 3.71-3.76 (m, 2H), 3.79 (s, 3H), 4.54 (t, 2H), 4.50-4.57 (m, 1H), 6.74 (t, 1H), 6.77 (d, 1H), 6.80 (d, 1H), 7.04 (t, 1H), 7.23 (t, 1H), 7.28 (d, 1H), 7.70 (d, 1H), 8.52 (s, 1H)

N-(2-{[tert-Butyl(dimethyl)silyl]oxy}ethyl)-3-chloro-2,4-difluoro-N-methylbenzamide

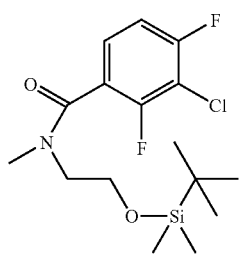

3-Chloro-2,4-difluorobenzoyl chloride (1.92 g, 9.1 mmol) was added slowly to a stirred solution of (2-{[tert-butyl(dimethyl)silyl]oxy}ethyl)methylamine (1.89 g, 10.0 mmol) in a 1:1 mixture of 10% sodium hydroxide solution and DCM at 0° C. The reaction mixture was then allowed to warm up to RT and left to stir for 5 hours. The phases were separated and the aqueous phase was extracted with DCM (3×50 mL). The combined extracts were dried (MgSO$_4$), filtered and evaporated to give a pale yellow oil. Purification by column chromatography on silica, eluting with 0-50% ethyl acetate in hexanes, gave the title compound as a colourless oil (2.26 g) $^1$H NMR δ (CDCl$_3$): 0.00 (s, 6H), 0.82 (s, 9H), 2.93 (s, 3H), 3.58 (t, 2H), 3.81 (t, 2H), 6.95 (dtd, 1H), 7.16-7.22 (m, 1H)

(2-{[tert-Butyl(dimethyl)silyl]oxy}ethyl)methylamine

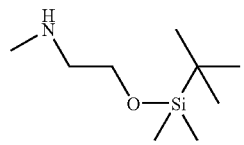

DIPEA (2.45 mL, 14.0 mmol) and tert-butyldimethylsilyl chloride (1.51 g, 10.0 mmol) were added to a solution of 2-(methylamino)ethanol (751 mg, 10.0 mmol) in dry DCM (25 mL) under argon and the reaction mixture allowed to stir at RT for 16 hours. Diethyl ether (50 mL) and water (50 mL) were added to the reaction mixture and the aqueous phase was extracted with diethyl ether (3×30 mL). The combined extracts were dried (MgSO$_4$), filtered and evaporated to give a pale yellow oil which was dried under high vacuum to give the title compound (1.91 g).
$^1$H NMR δ (CDCl$_3$): 0.00 (s, 6H), 0.84 (s, 9H), 2.38 (s, 3H), 2.61 (t, 2H), 3.65 (t, 2H)
The preparation of 3-hydroxy-N-(1-methyl-1H-pyrazol-3-yl)-5-{(1S)-1-methyl-2-[(triisopropylsilyl)oxy]ethoxy}benzamide is described in Example 4.

Example 6

3-[(4-Benzyl-9-fluoro-5-oxo-2,3,4,5-tetrahydro-1,4-benzoxazepin-8-yl)oxy]-5-[(1S)-2-hydroxy-1-methylethoxy]-N-(1-methyl-1H-pyrazol-3-yl)benzamide

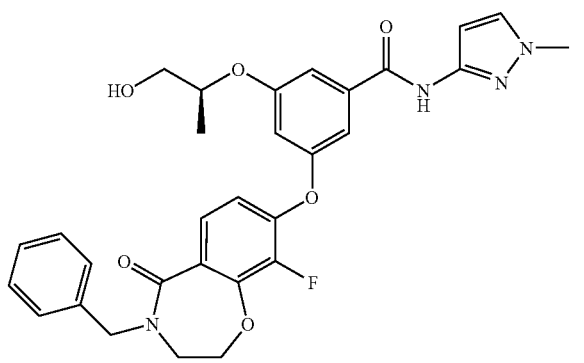

A suspension of 3-hydroxy-N-(1-methyl-1H-pyrazol-3-yl)-5-{(1S)-1-methyl-2-[(triisopropylsilyl)oxy]ethoxy}benzamide (200 mg, 0.447 mmol), 4-benzyl-8,9-difluoro-3,4-dihydro-1,4-benzoxazepin-5(2H)-one (140 mg, 0.611 mmol) and cesium carbonate (136 mg, 0.418 mmol) in DMA (3 mL) was heated in a microwave at 150° C. for 1 hour.

Water (5 mL) was added and the mixture was extracted with DCM (3×30 mL). The combined organic extracts were washed with water (2×20 mL) and saturated brine solution (15 mL). The organic phase was dried (MgSO$_4$), filtered and evaporated to give an orange oil. Purification was by column chromatography, eluting with 50-100% ethyl acetate in hexanes, and subsequently by preparative HPLC, eluting with a gradient 5-95% acetonitrile in water on a Phenomenex Luna 10u C18(2) 100A column, to give an off-white foam (20 mg).
$^1$H NMR δ (d$_6$-DMSO): 1.22 (d, 5H), 3.44-3.56 (m, 5H), 3.61 (t, 2H), 3.76 (s, 4H), 4.34 (t, 2H), 4.49-4.59 (m, 2H), 4.75 (s, 2H), 4.83 (t, 2H), 6.54 (s, 1H), 6.81 (s, 1H), 6.92 (dd, 1H), 7.18 (s, 1H), 6.92 (dd, 1H)), 7.41 (s, 1H), 7.55 (d, 1H), 7.57 (s, 1H), 10.82 (s, 1H). m/z 561 (M+H)$^+$, 559 (M−H)$^−$
The synthesis of 3-hydroxy-N-(1-methyl-1H-pyrazol-3-yl)-5-{(s)-1-methyl-2-[(triisopropylsilyl)oxy]ethoxy}benzamide was described in Example 4b.
The preparation of 4-benzyl-8,9-difluoro-3,4-dihydro-1,4-benzoxazepin-5(2H)-one is described below:

4-Benzyl-8,9-difluoro-3,4-dihydro-1,4-benzoxazepin-5(2H)-one

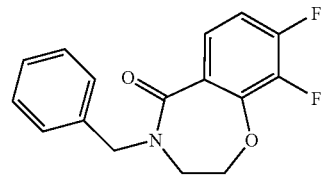

Sodium hydride (25 mg, 0.615 mmol, 60% dispersion in mineral oil) was added slowly to a solution of N-benzyl-2,3,4-trifluoro-N-(2-hydroxyethyl)benzamide (190 mg, 0.615 mmol) in DMF (3 mL) and the pale yellow solution was stirred at RT for 16 hours. Water was added to the reaction and the mixture was subsequently extracted with DCM (4×30 mL). The combined organic phases were washed with water (3×20 mL) and saturated brine solution then dried (MgSO$_4$), filtered and evaporated to give the desired product as a colourless oil (130 mg). $^1$H NMR δ (CDCl$_3$): 3.5 (t, 2H), 4.3 (t, 2H), 4.8 (s, 2H), 6.92 (dd, 1H), 7.3-7.4 (m, 5H), 7.7 (m, 1H)

N-Benzyl-2,3,4-trifluoro-N-(2-hydroxyethyl)benzamide

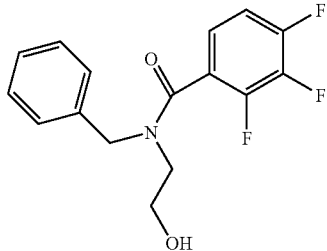

2,3,4-Trifluorobenzoylchloride (195 mg, 1 mmol) in DCM (1 mL) was added to a stirred solution of N-benzylaminoethanol (166 mg, 1.1 mmol) in a mixture of DCM (1 mL) and 10% sodium hydroxide solution (1 mL) at 0° C. After the addition of the acid chloride was complete, the mixture was warmed to RT and stirred for approximately 4 hours. The two layers were separated and the aqueous layer was extracted with DCM (3×30 mL). The organic layers were combined, dried (MgSO4), filtered and evaporated to give a colourless oil (190 mg). $^1$H NMR δ (CDCl$_3$): 3.74 (t, 2H), 3.82 (t, 2H), 4.5 (s, 2H), 4.85 (s, 1H), 7.06 (td, 1H), 7.15 (m, 1H), 7.28-7.37 (m, 1H). m/z 310 (M+H)$^+$ Example 7

3-[(8-Chloro-3-ethyl-2-methyl-4-oxo-3,4-dihydro-2H-1,3-benzoxazin-7-yl)oxy]-5-[(1S)-2-hydroxy-1-methylethoxy]-N-(1-methyl-1H-pyrazol-3-yl)benzamide

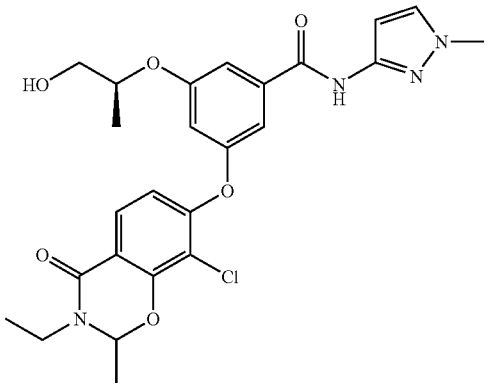

A suspension of 3-hydroxy-N-(1-methyl-1H-pyrazol-3-yl)-5-{(is)-1-methyl-2-[(triisopropylsilyl)oxy]ethoxy}benzamide (330 mg, 0.738 mmol), 9-chloro-4-ethyl-8-fluoro-3,4-dihydro-1,4-benzoxazepin-5(2H)-one (180 mg, 0.74 mmol) and cesium carbonate (240 mg, 0.74 mmol) in DMA (2 mL) was heated in a microwave at 150° C. for 1 hour. Water (5 mL) was added and the mixture was extracted with DCM (3×30 mL). The combined organic extracts were washed with water (2×20 mL) and saturated brine solution (15 mL). The organic phase was dried (MgSO$_4$), filtered and evaporated to give an orange oil. Purification was by column chromatography, eluting with 50-100% ethyl acetate in hexanes, and subsequently by preparative HPLC, eluting with a gradient 5-95% acetonitrile in water on a Phenomenex Luna 10u C18(2) 100A column, to give an off-white foam (56 mg). $^1$H NMR δ (d$_6$-DMSO): 1.14 (t, 3H), 1.22 (d, 3H), 1.54 (d, 3H), 3.44-3.58 (m, 2H), 3.70 (dd, 2H), 3.75 (s, 3H), 4.56 (sextet, 1H), 4.82 (t, 1H), 5.87 (q, 1H), 6.54 (d, 1H), 6.76 (d, 2H), 6.84 (t, 1H), 7.19 (t, 1H), 7.44 (s, 1H), 7.57 (d, 1H), 7.73 (d, 1H), 10.82 (s, 1H). m/z 515 (M+H)$^+$, 513 (M–H)$^-$ The synthesis of 3-hydroxy-N-(1-methyl-1H-pyrazol-3-yl)-5-{(is)-1-methyl-2-[(triisopropylsilyl)oxy]ethoxy}benzamide was described in Example 4b.

The preparation of 9-chloro-4-ethyl-8-fluoro-3,4-dihydro-1,4-benzoxazepin-5(2H)-one is described below:

9-Chloro-4-ethyl-8-fluoro-3,4-dihydro-1,4-benzoxazepin-5(2H)-one

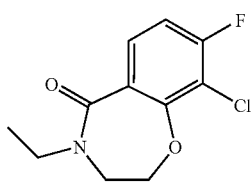

Sodium hydride (35 mg, 0.913 mmol, 60% dispersion in mineral oil) was added slowly to a solution of 3-chloro-2,4-difluoro-N-(2-hydroxyethyl)-N-methylbenzamide (220 mg, 0.836 mmol) in DMF (4 mL) and the pale yellow solution was stirred at RT for 16 hours. Water was added to the reaction and the mixture was subsequently extracted with DCM (3×30 mL). The combined organic phases were washed with water (3×20 mL) and saturated brine solution then dried (MgSO$_4$), filtered and evaporated to give the desired product as a colourless oil (180 mg). $^1$H NMR δ (CDCl$_3$): 1.25 (t, 3H), 3.5 (t, 3H), 3.65 (q, 2H), 4.52 (t, 2H), 6.97 (dd, 1H), 7.72 (dd, 1H). m/z 244 (M+H)$^+$, 242 (M–H)$^-$ 3-Chloro-N-ethyl-2,4-difluoro-N-(2-hydroxyethyl) benzamide

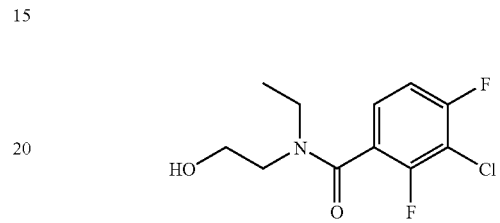

3-Chloro-2,4-difluorobenzoylchloride (211 mg, 1 mmol) in DCM (1 mL) was added to a stirred solution of 2-(ethylamino)ethanol (98 mg, 1.1 mmol) in a mixture of DCM (1 mL) and 10% sodium hydroxide solution (1 mL) at 0° C. After the addition of the acid chloride was complete, the mixture was warmed to RT and stirred for approximately 4 hours. The two layers were separated and the aqueous layer was extracted with DCM (3×30 mL). The organic layers were combined, dried (MgSO$_4$), filtered and evaporated to give a colourless oil (220 mg). The material was used without further purification or analysis.

Example 8

3-[(1S)-2-Hydroxy-1-methylethoxy]-5-[(4-methyl-5-oxo-2,3,4,5-tetrahydro-1,4-benzoxazepin-8-yl)oxy]-N-(1-methyl-1H-pyrazol-3-yl)benzamide

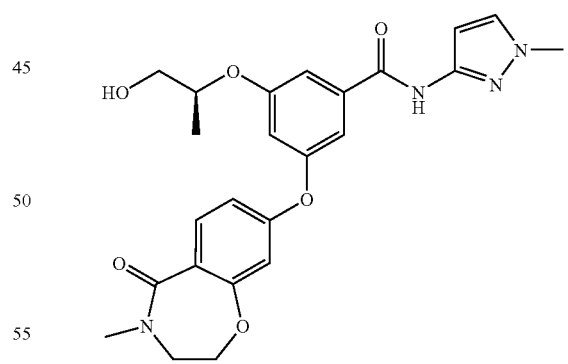

10% Palladium on carbon (30 mg) and triethylamine (2.0 mL) were added to a solution of 3-[(9-chloro-4-methyl-5-oxo-2,3,4,5-tetrahydro-1,4-benzoxazepin-8-yl)oxy]-5-[(1S)-2-hydroxy-1-methylethoxy]-N-(1-methyl-1H-pyrazol-3-yl)benzamide (160 mg; 0.32 mmol) in dry THF (4 mL) and dry ethanol (4 mL) under argon. The reaction was degassed and placed under a hydrogen balloon and stirred for 24 hours at RT. The mixture was filtered through diatomaceous earth and the filtrate was evaporated. Purification by column chromatography on silica, eluting with 0-5% methanol in DCM, yielded a colourless oil which solidified under vacuum to give the title compound as a white foam (62 mg, 33%). $^1$H NMR δ (CDCl$_3$): 1.23 (d, 3H), 2.00 (dd, 1H), 3.14 (s, 3H), 3.51 (t, 2H), 3.64-3.71 (m, 2H), 3.73 (s, 3H), 4.34 (t, 2H), 4.46 (dq, 1H), 6.51 (d, 1H), 6.69 (d, 1H), 6.70-6.72 (m, 2H), 7.02 (t, 1H), 7.18 (t, 1H), 7.21 (d, 1H), 7.81 (d, 1H), 8.38 (s, 1H) m/z 467 (M+H)$^+$ 465 (M−H)$^−$ The preparation of 3-[(9-chloro-4-methyl-5-oxo-2,3,4,5-tetrahydro-1,4-benzoxazepin-8-yl)oxy]-5-[(1S)-2-hydroxy-1-methylethoxy]-N-(1-methyl-1H-pyrazol-3-yl)benzamide is described in Example 5.

Example 9

3-[(7-Fluoro-5,5-dioxido-3,4-dihydro-2H-1,5-benzoxathiepin-8-yl)oxy]-5-{[(1S)-1-methyl-2-(methyloxy)ethyl]oxy}-N-(1-methyl-1H-pyrazol-3-yl)benzamide

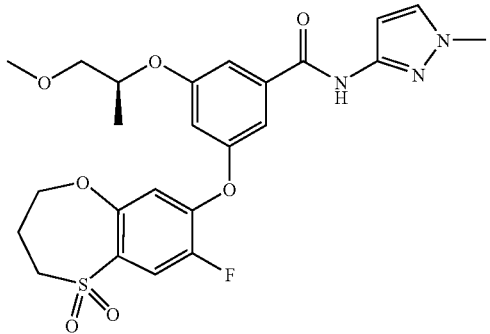

A suspension of 3-[(2,4,5-trifluorophenyl)sulfonyl]dihydrofuran-2(3H)-one (210 mg, 0.75 mmol), 3-hydroxy-5-[(1S)-2-methoxy-(1-methylethyl)oxy]-N-(1-methyl-1H-pyrazol-3-yl)benzamide (254 mg, 0.83 mmol), and potassium carbonate (414 mg, 3.0 mmol) in acetonitrile (4 mL) was heated to 150° C. in Smith Creator Microwave for 3.5 hours. The reaction mixture was filtered and evaporated to a brown oil which was purified by chromatography on a silica column, eluting 0-30% methanol in DCM, to give an orange oil. This was further purified on an alumina column, eluting with 0-10% methanol in DCM, to give a colourless oil which foamed under high vacuum to give a white solid (200 mg). $^1$H NMR δ (d$_6$-DMSO): 1.30 (d, 3H), 2.26-2.32 (m, 2H), 3.35 (s, 3H), 3.52-3.59 (m, 2H), 3.65 (t, 2H), 3.84 (s, 3H), 4.23 (t, 2H), 4.85 (sextet, 1H), 6.63 (d, 1H), 7.01 (d, 1H), 7.02 (d, 1H), 7.33 (s, 1H), 7.55 (s, 1H), 7.67 (d, 1H), 7.82 (d, 1H), 10.98 (s, 1H). m/z 520 (M+H)$^+$, 518 (M−H)$^−$ The preparation of 3-[(2,4,5-trifluorophenyl)sulfonyl]dihydrofuran-2(3H)-one was described in Example 3.

The preparation of 3-hydroxy-5-[(1S)-2-methoxy-(1-methylethyl)oxy]-N-(1-methyl-1H-pyrazol-3-yl)benzamide is described below:

3-Hydroxy-5-[(1S)-2-methoxy-(1-methylethyl)oxy]-N-(1-methyl-1H-pyrazol-3-yl)benzamide

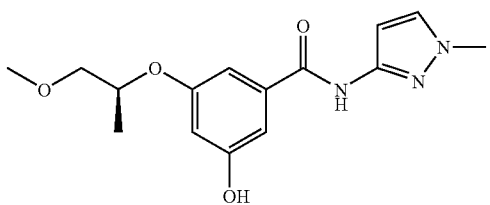

To a solution of 3-[(1S)-2-methoxy-(1-methylethyl)oxy]-N-(1-methyl-1H-pyrazol-3-yl)-5-[(phenylmethyl)oxy]benzamide (7.07 g) in THF (50 mL) and methanol (50 mL) was added 10% palladium on carbon (727 mg) as a slurry in THF (1 mL) and methanol (1 mL). The mixture was placed under vacuum and stirred under an atmosphere of hydrogen for 70 hours. The mixture was filtered through diatomaceous earth, and the diatomaceous earth washed with methanol (2×100 mL), followed by evaporation in vacuo. The residues were dissolved in ethyl acetate (10 mL), treated with isohexane (40 mL), the solid filtered off and washed with isohexane (50 mL) to afford the desired compound (5.17 g) which was used without further purification.

$^1$H NMR δ (d$_6$-DMSO): 1.22 (d, 3H), 3.28 (s, 3H, obscured by water), 3.38-3.53 (m, 2H), 3.76 (s, 3H), 4.65 (m, 1H), 6.44 (m, 1H), 6.54 (m, 1H), 6.93 (s, 1H), 7.04 (s, 1H), 7.57 (m, 1H), 9.63 (br s, 1H), 10.60 (s, 1H). m/z 306 (M+H)$^+$, 304 (M−H)$^−$ 3-[(1S)-2-Methoxy-(1-methylethyl)oxy]-N-(1-methyl-1H-pyrazol-3-yl)-5-[(phenylmethyl)oxy]benzamide

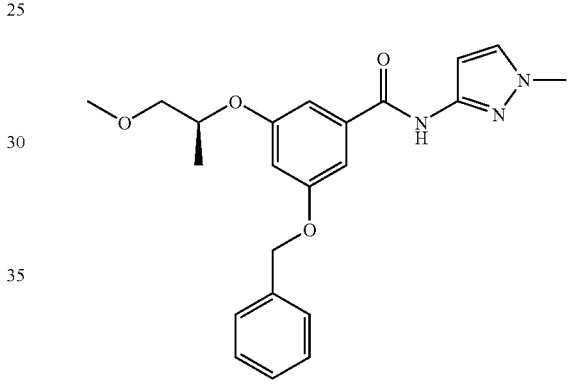

A solution of 3-[(1S)-2-methoxy-(1-methylethyl)oxy]-5-{[phenylmethyl]oxy}benzoic acid (8.73 g) in DCM (150 mL) was cooled to 0° C. Oxalyl chloride (4.81 mL) and DMF (0.15 mL) were slowly added with stirring. The mixture was allowed to warm to ambient temperature and stirred for 16 hours, following which the organics were removed in vacuo, and the residues azeotroped with toluene (75 mL). The crude material was dissolved in DCM (75 mL) and slowly added to a stirred suspension of 3-amino-1-methylpyrazole (3.35 g) and DIPEA (14.4 mL) in DCM (75 mL). The mixture was stirred at ambient temperature for 18 hours, before the organics were evaporated in vacuo and the residue dissolved in ethyl acetate (150 mL). The organics were washed with 1M aqueous hydrochloric acid (100 mL) and brine (50 mL), and dried (MgSO$_4$), before evaporation in vacuo to give crude material. This was chromatographed on a 200 g Biotage Flash 75 SiO$_2$ column (eluting with 30 to 90% ethyl acetate in isohexane), and evaporated in vacuo to afford the desired compound (7.07 g).

$^1$H NMR δ (d$_6$-DMSO): 1.23 (d, 3H), 3.28 (s, 3H, obscured by water), 3.40-3.52 (m, 2H), 3.77 (s, 3H), 4.70 (m, 1H), 5.03 (s, 2H), 6.56 (m, 1H), 6.71 (m, 1H), 7.18 (s, 1H), 7.24 (s, 1H), 7.32-7.47 (br m, 5H), 7.58 (m, 1H), 10.73 (s, 1H). m/z 396 (M+H)$^+$.

3-[(1S)-2-Methoxy-(1-methylethyl)oxy]-5-{[phenyl-methyl]oxy}benzoic acid

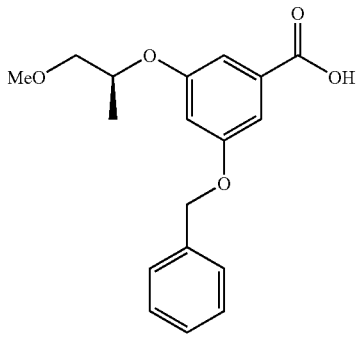

A solution of methyl 3-[(1S)-2-methoxy-(1-methylethyl)oxy]-5-{[phenylmethyl]oxy}benzoate (77.4 mmol) in a mixture of THF (232 mL) and methanol (232 mL) was treated with a solution of 2M sodium hydroxide (232 mmol), and the reaction mixture stirred for 4 hours at ambient temperature. The resulting solution was diluted with water (250 mL) and most of the organic solvent removed in vacuo. The resulting suspension was washed with diethyl ether (3×200 mL) and the organic washings discarded. The resulting aqueous solution was acidified to pH4 with 2M hydrochloric acid solution and extracted with ethyl acetate (2×200 mL). The extracts were combined, washed with brine, dried (MgSO$_4$), and evaporated to give the desired compound (99% yield).

$^1$H NMR δ (d$_6$-DMSO): 1.20 (d, 3H), 3.46 (m, 2H), 4.64 (m, 1H), 5.15 (s, 2H), 6.83 (app t, 1H), 7.06 (s, 1H), 7.13 (s, 1H), 7.30-7.49 (m, 5H), 12.67 (br s, 1H)

Methyl 3-[(1S)-2-methoxy-(1-methylethyl)oxy]-5-{[phenylmethyl]oxy}benzoate

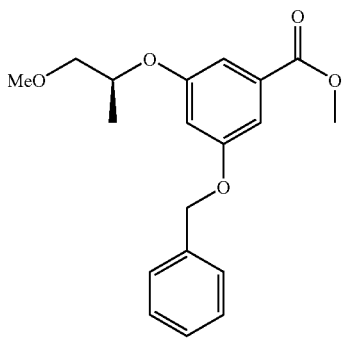

To a solution of methyl 3-hydroxy-5-{[phenylmethyl]oxy}benzoate (77.4 mmol) in THF was added polymer-supported triphenylphosphine (51.7 g of 3 mmol/g loading, 155 mmol) and (R)-(−)-1-methoxy-2-propanol (102 mmol). The stirred solution was blanketed with argon and cooled in an ice bath. A solution of DIAD (116 mmol) was added dropwise by syringe over 10 minutes. The solution was stirred for 20 minutes and filtered, washing the residue with THF (500 mL). The filtrate and washings were combined, and evaporated to give the desired compound which was used without further purification.

$^1$H NMR δ (d$_6$-DMSO): 3.26 (s, 3H), 3.44 (m, 2H), 3.82 (s, 3H), 4.63 (m, 1H), 5.14 (s, 2H), 6.85 (s, 1H), 7.05 (s, 1H), 7.11 (s, 1H), 7.30-7.47 (m, 5H)

The $^1$H NMR spectrum also contained signals consistent with a small amount of bis(1-methylethyl)hydrazine-1,2-dicarboxylate.

The preparation of methyl 3-hydroxy-5-{[phenylmethyl]oxy}benzoate is described in Example 1.

Example 10

3-[(1,1-Dioxido-3,4-dihydro-2H-5,1,2-benzoxathiazepin-7-yl)oxy]-5-{[(1S)-2-hydroxy-1-methylethyl]oxy}-N-(1-methyl-1H-pyrazol-3-yl)benzamide

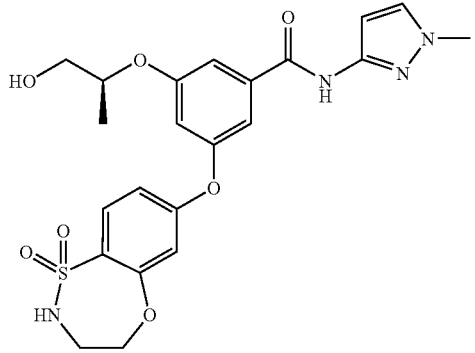

10% Palladium on carbon (30 mg) was added to 3-{[1,1-dioxido-2-(phenylmethyl)-3,4-dihydro-2H-5,1,2-benzoxathiazepin-7-yl]oxy}-5-{[(1S)-2-hydroxy-1-methylethyl]oxy}-N-(1-methyl-1H-pyrazol-3-yl)benzamide (100 mg; 0.17 mmol) in dry THF (4 mL) and dry ethanol (4 mL) under an argon atmosphere. The reaction was degassed and placed under a hydrogen atmosphere then stirred for 24 hours at 50° C. and 20 bar. The mixture was filtered through diatomaceous earth and the filtrate evaporated. Purification via column chromatography, eluting with 50-100% ethyl acetate in isohexane, yielded a colourless oil which solidified under vacuum to give the title compound as a white foam (21 mg).

$^1$H NMR δ (CDCl$_3$): 1.3 (d, 3H), 2.0 (t, 1H), 3.65 (m, 2H), 3.75 (m, 2H), 3.8 (s, 3H), 4.2 (m, 2H), 4.55 (m, 1H), 4.8 (t, 1H), 6.7 (d, 1H), 6.75 (d, 1H) 6.77 (m, 2H), 7.1 (s, 1H), 7.3 (m, 2H), 7.8 (d, 1H), 8.5 (brs, 1H). m/z 489 (M+H)$^+$, 487 (M−H)$^-$ The preparation of 3-{[1,1-dioxido-2-(phenylmethyl)-3,4-dihydro-2H-5,1,2-benzoxathiazepin-7-yl]oxy}-5-{[(1S)-2-hydroxy-1-methylethyl]oxy}-N-(1-methyl-1H-pyrazol-3-yl)benzamide is described below:

3-{[1,1-Dioxido-2-(phenylmethyl)-3,4-dihydro-2H-5,1,2-benzoxathiazepin-7-yl]oxy}-5-{[(1S)-2-hydroxy-1-methylethyl]oxy}-N-(1-methyl-1H-pyrazol-3-yl)benzamide

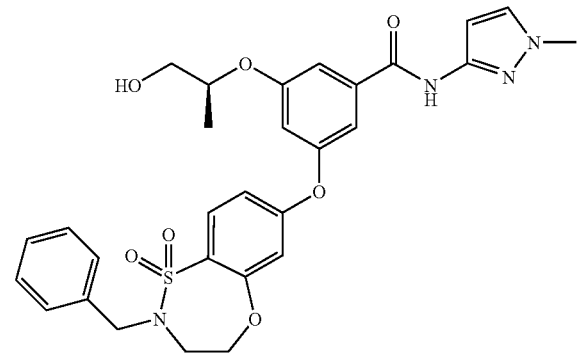

N-(2-{[(1,1-Dimethylethyl)(dimethyl)silyl]oxy}ethyl)-2,4-difluoro-N-(phenylmethyl)benzenesulfonamide (291 mg, 0.66 mmol) was added to 3-hydroxy-N-(1-methyl-1H-pyrazol-3-yl)-5-{(s)-1-methyl-2-[(triisopropylsilyl)oxy]ethoxy}benzamide (296 mg, 0.66 mmol) and potassium carbonate (183 mg, 1.31 mmol) in dry DMA (4 mL). The mixture was heated in a Smith Creator microwave at 150° C. for 45 mins. Water (25 mL) was added to the reaction mixture and extracted with ethyl acetate (3×30 mL). The combined organic extracts were dried (MgSO$_4$), filtered and evaporated. Purification by column chromatography on silica, eluting with 80-90% ethyl acetate in isohexane, afforded the title compound as a colourless oil (450 mg). $^1$H NMR δ (CDCl$_3$): 1.25 (d, 3H), 2.16-2.19 (m, 1H), 3.53 (t, 2H), 3.68-3.71 (m, 2H), 3.74 (s, 3H), 4.14 (t, 2H), 4.18 (s, 2H), 4.50 (ddd, 1H), 6.70 (d, 1H), 6.72 (d, 1H), 6.75 (t, 1H), 6.78 (dd, 1H), 7.09 (t, 1H), 7.22 (ddd, 1H), 7.24-7.26 (m, 1H), 7.28-7.29 (m, 5H), 7.78 (d, 1H), 8.45 (s, 1H). m/z 579 (M+H)$^+$ The preparation of 3-hydroxy-N-(1-methyl-1H-pyrazol-3-yl)-5-{(1S)-1-methyl-2-[(triisopropylsilyl)oxy]ethoxy}benzamide was described in Example 4b.

N-(2-{[(1,1-Dimethylethyl)(dimethyl)silyl]oxy}ethyl)-2,4-difluoro-N-(phenylmethyl)benzenesulfonamide

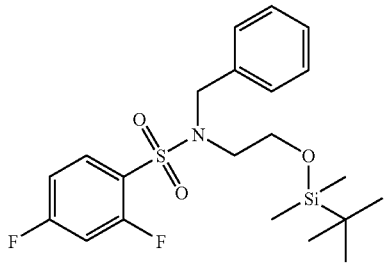

The following process was carried out according to literature precedent (JOC, 1988, 53 (7), 1372). 2,4-Difluorobenzenesulphonyl chloride (436 mg, 2.05 mmol) was added slowly to a stirred solution of 2-{[(1,1-dimethylethyl)(dimethyl)silyl]oxy}-N-(phenylmethyl)ethanamine (600 mg, 2.26 mmol) in a 1:1 mixture of 10% sodium hydroxide solution and DCM (80 mL) at 0° C. The reaction mixture was allowed to warm up to RT and left to stir for 5 hours. The phases were separated and the aqueous phase was extracted with DCM (3×50 mL). The combined extracts were dried (MgSO$_4$), filtered and evaporated to afford the title compound as a colourless oil (939 mg).

$^1$H NMR δ (CDCl$_3$): 0.00 (s, 6H), 0.88 (s, 9H), 3.39 (t, 2H), 3.60 (t, 2H), 4.64 (s, 2H), 6.96-7.04 (m, 2H), 7.31-7.39 (m, 5H), 7.98 (ddd, 1H). m/z 442 (M+H)$^+$ 2-{[(1,1-Dimethylethyl)(dimethyl)silyl]oxy}-3-N-(phenylmethyl)ethanamine

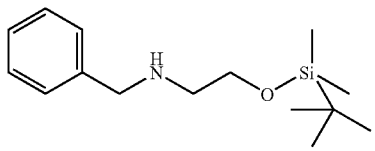

tert-Butyldimethylsilyl chloride (1.50 g, 10.0 mmol) and DIPEA (2.45 mL, 14.0 mmol) were added to a solution of 2-(benzylamino)ethanol (1.51 mg, 10.0 mmol) in dry DCM (25 mL) under an argon atmosphere and the reaction mixture allowed to stir at RT for 16 hours. Diethyl ether (50 mL) and water (50 mL) were added to the reaction mixture and the aqueous phase was extracted with diethyl ether (3×30 mL). The combined extracts were dried (MgSO$_4$), filtered and evaporated to give a pale yellow oil which was purified via column chromatography on silica, eluting with 0-50% ethyl acetate in isohexane, to give the title compound as a colourless oil (1.91 g). $^1$H NMR δ (CDCl$_3$): 0.00 (s, 6H), 0.85 (s, 9H), 2.7 (t, 2H), 3.7 (t, 2H), 3.75 (s, 2H), 7.25 (m, 5H). m/z 266 (M+H)$^+$ Example 11

3-[(9-Chloro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide

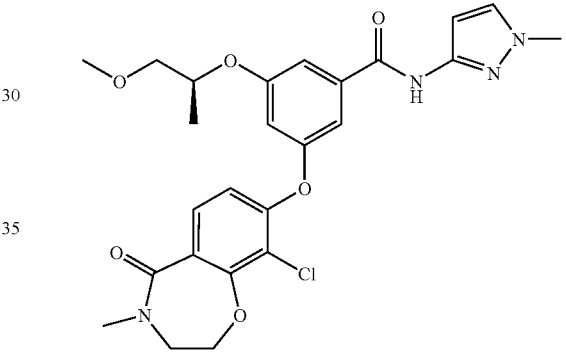

N-(2-{[tert-Butyl(dimethyl)silyl]oxy}ethyl)-3-chloro-2,4-difluoro-N-methylbenzamide (705 mg, 1.94 mmol) was added to 3-hydroxy-5-[(1S)-2-methoxy-(1-methylethyl)oxy]-N-(1-methyl-1H-pyrazol-3-yl)benzamide (592 mg, 1.94 mmol) and potassium carbonate (536 mg, 3.88 mmol) in DMA (4 mL). The mixture was heated in a Smith Creator microwave at 150° C. for 1 hour 45 mins. Water (25 mL) was added and the reaction mixture extracted with ethyl acetate (3×30 mL). The organic phases were washed with water (2×30 mL) and brine (2×30 mL). The combined organic extracts were dried (MgSO$_4$), filtered and evaporated. Purification by column chromatography on silica, eluting with 20-100% ethyl acetate:hexanes, afforded the desired material as a pale yellow oil (218 mg, 22%).

$^1$H NMR δ (CDCl$_3$): 1.25 (d, 3H), 3.17 (s, 3H), 3.32 (s, 3H), 3.43 (dd, 1H), 3.50 (dd, 1H), 3.53 (t, 2H), 3.72 (s, 3H), 4.48 (t, 2H), 4.50-4.55 (m, 1H), 6.69 (t, 1H), 6.71 (d, 1H), 6.73 (d, 1H), 6.97 (s, 1H), 7.16 (s, 1H), 7.21 (d, 1H), 7.62 (d, 1H), 8.41 (s, 1H); m/z 515 (M+H)$^+$ 513 (M−H)$^−$

The following compounds were prepared in an analogous fashion from N-(2-{[tert-butyl(dimethyl)silyl]oxy}ethyl)-3-chloro-2,4-difluoro-N-methylbenzamide and the corresponding phenol.

| Examples | Structure | m/z | ¹H NMR (CDCl₃) |
|---|---|---|---|
| 11a* | 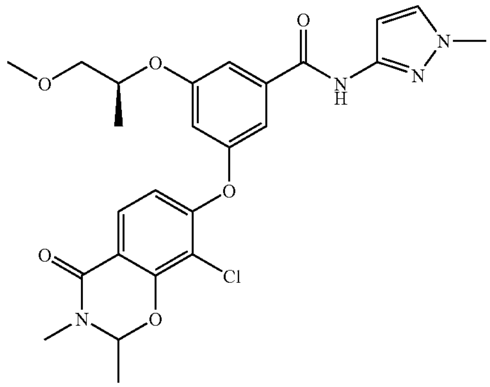 | 515 (M + H)⁺, 513 (M − H)⁻ | δ: 1.25 (d, 3 H), 1.60 (d, 3 H), 3.03 (s, 3 H), 3.33 (s, 3 H), 3.43 (dd, 1 H), 3.50 (dd, 1 H), 3.73 (s, 3 H), 4.49-4.54 (m, 1 H), 5.51 (q, 1 H), 6.61 (d, 1 H), 6.71 (d, 1 H), 6.71 (s, 1 H), 6.99 (s, 1 H), 7.18 (s, 1 H), 7.21 (d, 1 H), 7.75 (d, 1 H), 8.38 (s, 1 H) |
| 11b | 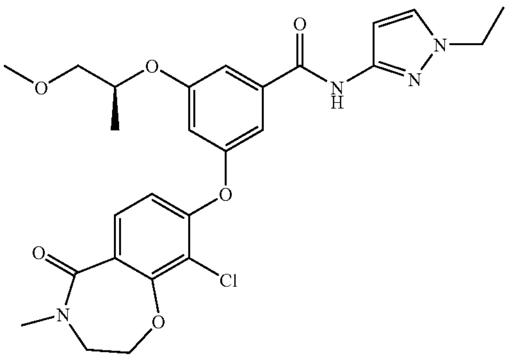 | 529 (M + H)⁺, 513 (M − H)⁻ | δ: 1.25 (3 H, d), 1.39 (3 H, t), 3.17 (3 H, s), 3.33 (3 H, s), 3.45-3.41 (1 H, m), 3.49-3.53 (1 H, m), 3.53 (2 H, t), 3.99 (2 H, q), 4.48 (2 H, t), 4.55-4.52 (1 H, m), 6.71-6.69 (2 H, m), 6.73 (1 H, d), 6.99 (1 H, s), 7.19 (1 H, s), 7.25 (1 H, s), 7.62 (1 H, d), 8.38 (1 H, s). |

*Example 11a was isolated in a 12% yield from the same reaction mixture as that from which Example 11 was isolated.

The preparation of N-(2-{[tert-butyl(dimethyl)silyl]oxy}ethyl)-3-chloro-2,4-difluoro-N-methylbenzamide and 3-hydroxy-5-[(1S)-2-methoxy-(1-methylethyl)oxy]-N-(1-methyl-1H-pyrazol-3-yl)benzamide are described earlier.

The preparation of N-(1-ethyl-1H-pyrazol-3-yl)-3-hydroxy-5-{[(1S)-1-methyl-2-(methyloxy)ethyl]oxy}benzamide, used in the synthesis of Example 11b, is described below.

N-(1-Ethyl-1H-pyrazol-3-yl)-3-hydroxy-5-{[(1S)-1-methyl-2-(methyloxy)ethyl]oxy}benzamide

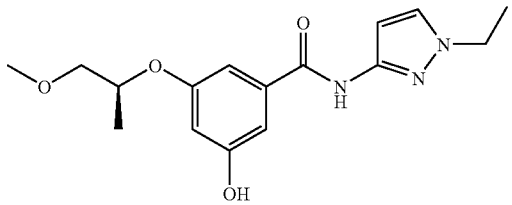

10% Palladium on carbon (1.9 g, 50% wet) was added under argon to N-(1-ethyl-1H-pyrazol-3-yl)-3-{[(1S)-1-methyl-2-(methyloxy)ethyl]oxy}-5-[(phenylmethyl)oxy]benzamide (19.1 g, 46.7 mmol) in dry THF (100 mL) and ethanol (100 mL). The reaction mixture was degassed, placed under a hydrogen balloon and stirred for 16 hours. The mixture was filtered through diatomaceous earth and the filtrate was evaporated to give a brown oil. The residue was purified by column chromatography on silica, eluting with 40-65% ethyl acetate in hexanes, to give the desired product as a clear oil which crystallized on standing (11.35 g). ¹H NMR δ (CDCl₃): 1.21 (d, 6H), 1.38 (t, 3H), 3.32 (s, 3H), 3.39-3.51 (m, 3H), 3.98 (q, 2H), 4.44-4.51 (m, 1H), 6.54 (s, 1H), 6.72 (d, 1H), 6.92 (s, 2H), 7.26 (d, 1H), 8.18 (s, 1H), 8.85 (s, 1H); m/z 320 (M+H)⁺ 318 (M−H)⁻

N-(1-Ethyl-1H-pyrazol-3-yl)-3-{[(1S)-1-methyl-2-(methyloxy)ethyl]oxy}-5-[(phenylmethyl)oxy]benzamide

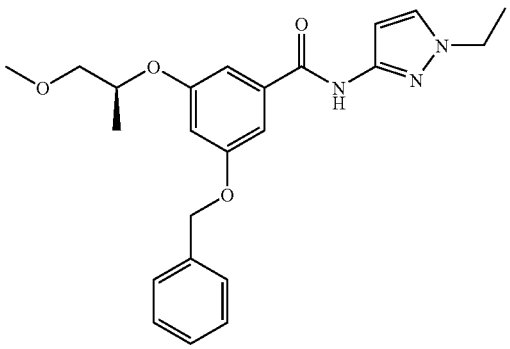

HATU (23.5 g, 61.83 mmol) was added to 3-[(1S)-2-methoxy-(1-methylethyl)oxy]-5-{[phenylmethyl]oxy}benzoic acid (16.28 g, 51.53 mmol) followed by addition of DMF (140 mL) and cooled to 0° C. 1-Ethyl-1H-pyrazol-3-amine (6.86 g, 61.8 mmol) was added followed by DIPEA (21.3 mL) and the reaction stirred under argon, at 0° C., for 3 hours. The solvent volume was reduced and the residue was dissolved in ethyl acetate (500 mL), washed with citric acid (200 mL), sodium hydrogen carbonate solution (150 mL) and saturated brine solution (2×150 mL). The organic layer was separated and dried (MgSO₄), filtered and evaporated. Purification by column chromatography on silica, eluting with 10-50% ethyl acetate in hexanes, afforded the title compound as a pale yellow oil (19.1 g). ¹H NMR δ (CDCl₃): 1.23 (d, 3H), 1.38 (t, 3H), 3.33 (s, 3H), 3.42 (dd, 1H), 3.50 (dd, 1H), 3.97 (q, 2H), 4.49 (sextet, 1H), 4.99 (s, 2H), 6.66 (t, 1H), 6.75 (d, 1H), 6.98

(s, 1H), 7.02 (s, 1H), 7.26 (d, 1H), 7.28-7.37 (m, 5H), 8.58 (s, 1H); m/z 410 (M+H)+

The preparation of 3-[(1S)-2-methoxy-(1-methylethyl)oxy]-5-{[phenylmethyl]oxy}benzoic acid was described earlier.

The preparation of 1-ethyl-1H-pyrazol-3-amine is described in the literature [*Chem. Heterocycl. Compd.* (*Engl. Transl.*), 11, 1975, 212].

Example 12

3-[(2,3-Dimethyl-4-oxo-3,4-dihydro-2H-1,3-benzoxazin-7-yl)oxy]-5-{[(1S)-1-methyl-2-(methyloxy)ethyl]oxy}-N-(1-methyl-1H-pyrazol-3-yl)benzamide

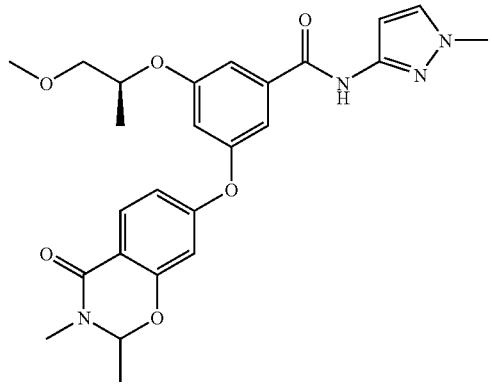

Ammonium formate (122 mg, 1.9 mmol) was added in one portion to a solution of 3-[(8-chloro-2,3-dimethyl-4-oxo-3,4-dihydro-2H-1,3-benzoxazin-7-yl)oxy]-5-{[(1S)-1-methyl-2-(methyloxy)ethyl]oxy}-N-(1-methyl-1H-pyrazol-3-yl)benzamide (100 mg, 0.19 mmol) in ethanol (3 mL). The reaction was blanketed with argon and 10% palladium on carbon (20 mg) was added. The mixture was heated to 140° C. for 10 minutes in a Smith Creator microwave after which complete conversion to desired product was observed. The reaction mixture was filtered through diatomaceous earth and the filter pad was washed well with ethyl acetate. The filtrate was evaporated in vacuo and the residue purified by column chromatography on silica, eluting with 60-100% ethyl acetate in hexanes, and then by chromatography on alumina, eluting with 20-60% ethyl acetate in hexanes, to afford the title compound as a colourless oil which foamed under high vacuum (50 mg).

$^1$H NMR δ (CDCl$_3$): 1.29 (d, 3H), 2.09 (t, 1H), 3.23 (s, 3H), 3.59 (t, 2H), 3.71-3.76 (m, 2H), 3.79 (s, 3H), 4.54 (t, 2H), 4.50-4.57 (m, 1H), 6.74 (t, 1H), 6.77 (d, 1H), 6.80 (d, 1H), 7.04 (t, 1H), 7.23 (t, 1H), 7.28 (d, 1H), 7.70 (d, 1H), 8.52 (s, 1H)

The following compounds were prepared in an analogous fashion from the corresponding chloro compounds.

| Example | Structure | m/z | $^1$H NMR (CDCl$_3$) |
|---|---|---|---|
| 12a | 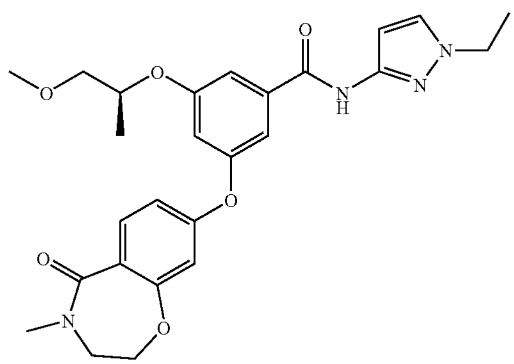 | 495 (M + H)+ 493 (M − H)− | δ: 1.25 (3 H, d), 1.39 (3 H, t), 3.15 (3 H, s), 3.34 (3 H, s), 3.45-3.42 (1 H, m), 3.51-3.49 (1 H, m), 3.55 (2 H, t), 4.00 (2 H, q), 4.34 (2 H, t), 4.56-4.50 (1 H, m), 6.50 (1 H, d), 6.74-6.70 (2 H, m), 6.73-6.72 (1 H, m), 7.03 (1 H, d), 7.20 (1 H, s), 7.25 (1 H, d), 7.8 (1 H, d), 8.32 (1 H, s) |
| 12b | 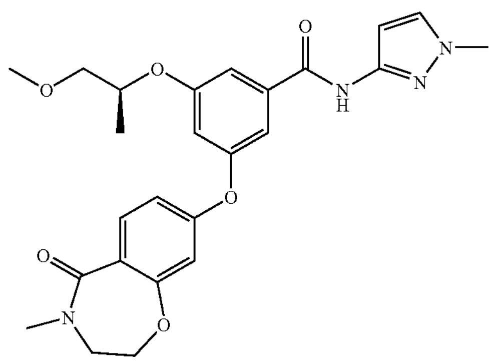 | 481 (M + H)+ 479 (M − H)− | δ: 1.27 (3 H, d), 3.17 (3 H, s), 3.38 (3 H, s), 3.46 (1 H, dd), 3.55 (1 H, dd), 3.55 (2 H, t), 3.77 (3 H, s), 4.4 (2 H, t), 4.55-4.60 (1 H, m), 6.55 (1 H, d), 6.73 (1 H, d), 6.74-6.75 (1 H, m), 6.77 (1 H, t), 7.06 (1 H, t), 7.23 (1 H, t), 7.26 (1 H, d), 7.85 (1 H, d), 8.3 (1 H, s br) |

The synthesis of 3-[(8-chloro-2,3-dimethyl-4-oxo-3,4-dihydro-2H-1,3-benzoxazin-7-yl)oxy]-5-{[(is)-1-methyl-2-(methyloxy)ethyl]oxy}-N-(1-methyl-1H-pyrazol-3-yl)benzamide, used in the preparation of Example 12, was described in Example 11a.

The synthesis of 3-[(9-chloro-4-methyl-5-oxo-2,3,4,5-tetrahydro-1,4-benzoxazepin-8-yl)oxy]-N-(1-ethyl-1H-pyrazol-3-yl)-5-{[(1S)-1-methyl-2-(methyloxy)ethyl]oxy}benzamide, used in the preparation of Example 12a, was described in Example 11b.

The synthesis of 3-[(9-chloro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide, used in the preparation of Example 12b, was described in Example 11.

Example 13

3-{[2-Fluoro-1-(fluoromethyl)ethyl]oxy}-5-[(9-fluoro-4-methyl-5-oxo-2,3,4,5-tetrahydro-1,4-benzoxazepin-8-yl)oxy]-N-(1-Methyl-1H-pyrazol-3-yl)benzamide

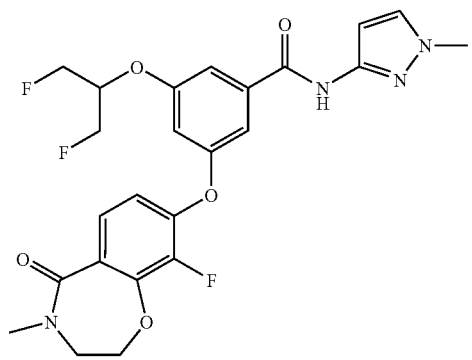

A solution of 3-{[2-fluoro-1-(fluoromethyl)ethyl]oxy}-5-hydroxy-N-(1-methyl-1H-pyrazol-3-yl)benzamide (100 mg, 0.32 mmol), N-(2-{[(1,1-dimethylethyl)(dimethyl)silyl]oxy}ethyl)-2,3,4-trifluoro-N-methylbenzamide (112 mg, 0.32 mmol) and potassium carbonate (89 mg, 0.64 mmol) in DMA (2 mL) was heated in a microwave reactor for 2 hours. Water (20 mL) was added and the solution extracted with ethyl acetate. The ethyl acetate layer was washed with brine (20 mL), dried (MgSO$_4$) and evaporated to a residue which was taken up in DCM (10 mL) and TFA (5 drops) added. The mixture was stirred at RT for 2 hours. The solvent was evaporated to a residue, which was chromatographed by preparative HPLC on C18 reversed phase, eluting with 5-95% acetonitrile (+0.2% TFA) in water (+0.2% TFA), to give the required product (5 mg).

$^1$H NMR δ (CDCl$_3$): 3.18 (s, 3H), 3.57 (t, 2H), 3.85 (s, 3H), 4.47 (t, 2H), 4.65 (m, 4H), 4.95 (m, 1H), 6.78 (m, 2H), 6.96 (d, 1H), 7.32 (m, 2H), 7.36 (t, 1H), 7.53 (m, 1H), 10.68 (s, 1H); m/z 506 (M+H)$^+$

The preparation of N-(2-{[(1,1-dimethylethyl)(dimethyl)silyl]oxy}ethyl)-2,3,4-trifluoro-N-methylbenzamide is described below:

N-(2-{[(1,1-Dimethylethyl)(dimethyl)silyl]oxy}ethyl)-2,3,4-trifluoro-N-methylbenzamide

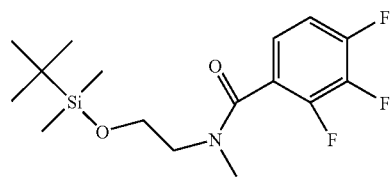

2,3,4-Trifluorobenzoyl chloride (2.32 mL, 18.16 mmol) was added slowly to a stirred mixture of (2-{[tert-butyl(dimethyl)silyl]oxy}ethyl)methylamine (3.44 g, 18.16 mmol) in DCM (200 mL) and 10% aqueous sodium hydroxide solution (200 mL) at 0° C. The reaction was allowed to warm to RT and stirred for a further 24 hours. The phases were separated and the aqueous phase further extracted with DCM (3×100 mL), the combined organics dried (MgSO$_4$), filtered and the solvent removed in vacuo to give a pale yellow oil. The residue was chromatographed on silica, eluting with 0-50% ethyl acetate in isohexane, to give the desired compound as a colourless oil (5.22 g).

$^1$H NMR δ (CDCl$_3$): 0.00 & 0.06 (2xs, 6H), 0.79 & 0.82 (2xs, 9H), 2.96 & 3.10 (2xs, 3H), 3.25 & 3.58 & 3.82 (3xt, 4H), 6.90-7.07 (m, 2H)

The NMR spectrum was complicated due to the presence of rotamers

The preparation of (2-{[tert-butyl(dimethyl)silyl]oxy}ethyl)methylamine was described earlier.

The preparation of 3-{[2-fluoro-1-(fluoromethyl)ethyl]oxy}-5-hydroxy-N-(1-methyl-1H-pyrazol-3-yl)benzamide is described below:

3-{[2-Fluoro-1-(fluoromethyl)ethyl]oxy}-5-hydroxy-N-(1-methyl-1H-pyrazol-3-yl)benzamide

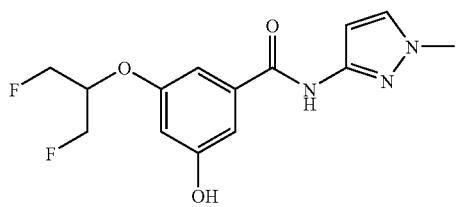

A solution of 3-{[2-fluoro-1-(fluoromethyl)ethyl]oxy}-N-(1-methyl-1H-pyrazol-3-yl)-5-[(phenylmethyl)oxy]benzamide (2.46 g, 6.13 mmol) and 10% by weigh palladium on carbon (0.246 g) in ethanol (100 mL) was allowed to stir at RT, under a hydrogen atmosphere overnight. The solution was filtered through Celite® and the residue was washed with methanol (100 mL). The solution was evaporated to give the desired compound (1.78 g). $^1$H NMR δ (d$_6$-DMSO): 3.78 (s, 3H), 4.72 (m, 4H), 4.97 (m, 1H), 6.57 (d, 2H), 7.03 (s, 1H), 7.16 (s, 1H), 7.59 (s, 1H). m/z 312 (M+H)⁺

3-{[2-Fluoro-1-(fluoromethyl)ethyl]oxy}-N-(1-methyl-1H-pyrazol-3-yl)-5-[(phenylmethyl)oxy]benzamide

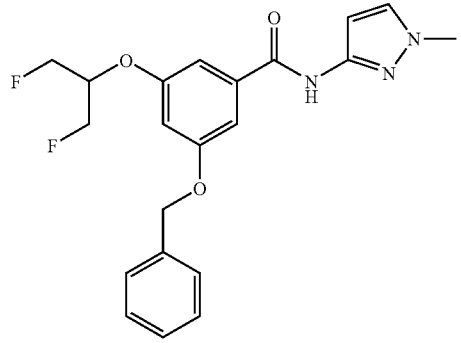

A solution 3-{[2-fluoro-1-(fluoromethyl)ethyl]oxy}-5-[(phenylmethyl)oxy]benzoic acid (3.00 g, 9.31 mmol), 3-amino-1-methylpyrazole (1.83 g, 18.6 mmol), HATU (4.60 g, 12.1 mmol) and DIPEA (3.25 mL, 18.6 mmol) in DMF (12 mL) was stirred at RT overnight. Water (150 mL) was added and the solution partitioned with ethyl acetate (250 mL). The ethyl acetate layer was separated, washed with brine and dried (MgSO₄), and evaporated to a residue which was chromatographed on silica, eluting with 50% ethyl acetate in isohexane, to give the desired product (2.46 g).

¹H NMR δ (CDCl₃): 3.69 (s, 3H), 4.57 (m, 5H), 5.00 (s, 2H), 6.70 (t, 1H), 6.74 (d, 1H), 7.01 (t, 1H), 7.08 (t, 1H), 7.21 (d, 1H), 7.30 (m, 5H), 8.68 (s, 1H); m/z 402 (M+H)⁺

3-{[2-Fluoro-1-(fluoromethyl)ethyl]oxy}-5-[(phenylmethyl)oxy]benzoic acid

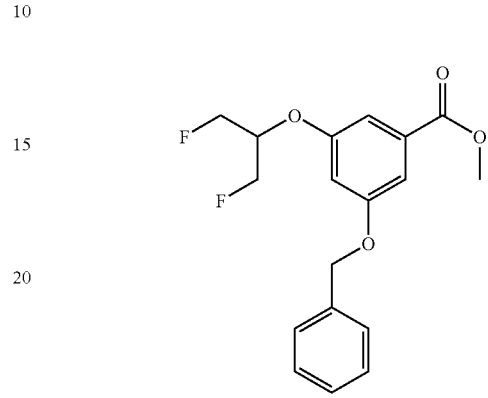

A solution of lithium hydroxide monohydrate (2.32 g, 55.1 mmol) in water (100 mL) was added to a solution of methyl 3-{[2-fluoro-1-(fluoromethyl)ethyl]oxy}-5-[(phenylmethyl) oxy]benzoate (7.41 g, 22.0 mmol) in THF (200 mL) and the mixture allowed to stir at RT overnight. The THF was removed in vacuo and the resulting solution partitioned between water (100 mL) and ethyl acetate (250 mL). The ethyl acetate layer was separated, washed with brine and dried (MgSO₄). The aqueous layer was then adjusted to pH 7 by addition of 1M hydrochloric acid and extracted with ethyl acetate (75 mL). The ethyl acetate layer was separated, washed with brine and dried (MgSO₄). The ethyl acetate layers were combined and evaporated to give the required product (6.404 g).

¹H NMR δ (d₆-DMSO): 4.74 (m, 4H), 5.08 (s, 2H), 6.67 (s, 1H), 6.67 (s, 1H), 7.23 (s, 1H), 7.37 (m, 5H). m/z 231 (M–H)⁻

Methyl 3-{[2-fluoro-1-(fluoromethyl)ethyl]oxy}-5-[(phenylmethyl)oxy]benzoate

DIAD (7.63 μL, 38.7 mmol) was added in a drop wise fashion to a solution of methyl 3-hydroxy-5-{[phenylmethyl] oxy}benzoate (5.00 g, 19.4 mmol), 1,3-difluoropropan-2-ol (3 mL, 38.7 mmol), and triphenylphosphine (10.16 g, 38.7 mmol) in THF (100 mL) under an inert atmosphere at 0° C. The solution was allowed to reach RT and left to stir for 2 days. The THF was removed in vacuo and the residual oil slurried with a mixture of 20% ethyl acetate in isohexane. After allowing to stir for 90 minutes the mixture was filtered and the filtrate evaporated. The residual was oil chromatographed on silica, eluting with 30% ethyl acetate in isohexane, to give the desired compound (7.41 g).

¹H NMR δ (d₆-DMSO): 3.85 (s, 3H), 4.71 (m, 4H), 5.03 (m, 1H), 5.17 (s, 2H), 7.01 (t, 1H), 7.20 (m, 2H), 7.40 (m, 5H). m/z 335 (M–H)⁻

The preparation of methyl 3-hydroxy-5-{[phenylmethyl] oxy}benzoate is described earlier.

Example 14

3-[(9-Chloro-4-methyl-5-oxo-2,3,4,5-tetrahydro-1,4-benzoxazepin-8-yl)oxy]-N-(1-ethyl-1H-pyrazol-3-yl)-5-{[(1S)-2-hydroxy-1-methylethyl]oxy}benzamide

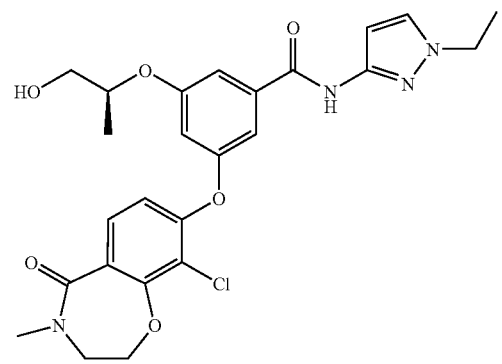

A solution of 3-[(9-chloro-4-methyl-5-oxo-2,3,4,5-tetrahydro-1,4-benzoxazepin-8-yl)oxy]-N-(1-ethyl-1H-pyrazol-3-yl)-5-{[(1S)-1-methyl-2-(methyloxy)ethyl]oxy}benzamide (300 mg, 0.57 mmol) in acetonitrile (10 mL) was treated with trimethylsilyl iodide (0.404 mL) and stirred at RT under argon for 3 hours. Sodium thiosulphate solution (30 mL) was added to quench the reaction and mixture was extracted with ethyl acetate (3×30 mL). The combined organic extracts were dried (MgSO$_4$), filtered and evaporated to give a yellow oil. Purification by column chromatography on silica, eluting with 50-100% ethyl acetate in hexanes, gave the desired compound as a pale yellow solid (230 mg).

$^1$H NMR δ (CDCl$_3$): 1.23 (d, 3H), 1.38 (t, 3H), 3.18 (s, 3H), 3.53 (t, 2H), 3.67-3.70 (m, 2H), 3.99 (q, 2H), 4.48 (t, 3H), 6.68 (t, 1H), 6.71 (d, 1H), 6.74 (d, 1H), 6.98 (d, 1H), 7.17 (t, 1H), 7.26 (d, 1H), 7.62 (d, 1H), 8.44 (s, 1H); m/z 515 (M+H)$^+$ 513 (M−H)$^−$

Example 15

3-[(9-Chloro-4-methyl-5-oxo-2,3,4,5-tetrahydro-1,4-benzoxazepin-8-yl)oxy]-5-[(1-methylethyl)oxy]-N-(1-methyl-1H-pyrazol-3-yl)benzamide

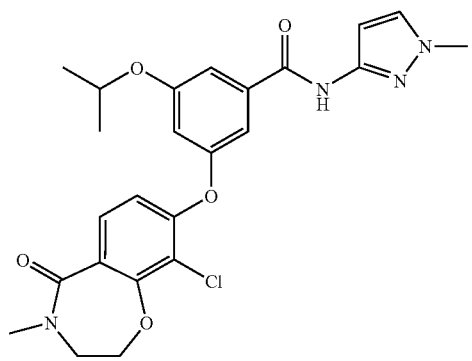

N-(2-{[tert-Butyl(dimethyl)silyl]oxy}ethyl)-3-chloro-2,4-difluoro-N-methylbenzamide (705 mg, 1.94 mmol) was added to 3-hydroxy-5-[(1-methylethyl)oxy]-N-(1-methyl-1H-pyrazol-3-yl)benzamide (512 mg, 1.86 mmol) and potassium carbonate (536 mg, 3.88 mmol) in DMA (25 mL) and the mixture was heated at 135° C. for 5 hours. Water (100 mL) was added and the reaction mixture extracted with ethyl acetate (3×30 mL). The combined organic phases were washed with water (2×30 mL), brine (2×30 mL), dried (MgSO$_4$), filtered and evaporated. Purification by column chromatography on silica, eluting with 40-100% ethyl acetate in hexanes, afforded the desired compound as a pale yellow oil (300 mg). $^1$H NMR δ (CDCl$_3$): 1.28 (d, 6H), 3.17 (s, 3H), 3.53 (t, 2H), 3.73 (s, 3H), 4.48 (t, 2H), 4.48-4.55 (m, 1H), 6.63 (t, 1H), 6.71 (d, 1H), 6.73 (d, 1H), 6.95 (t, 1H), 7.12 (t, 1H), 7.22 (d, 1H), 7.61 (d, 1H), 8.52 (s, 1H), m/z 485 (M+H)$^+$ 483 (M−H)$^−$ The preparation of N-(2-{[tert-butyl(dimethyl)silyl]oxy}ethyl)-3-chloro-2,4-difluoro-N-methylbenzamide is described earlier.

The preparation of 3-hydroxy-5-[(1-methylethyl)oxy]-N-(1-methyl-1H-pyrazol-3-yl)benzamide is described below:

3-Hydroxy-5-[(1-methylethyl)oxy]-N-(1-methyl-1H-pyrazol-3-yl)benzamide

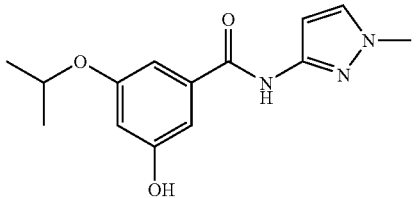

3-[(1-Methylethyl)oxy]-N-(1-methyl-1H-pyrazol-3-yl)-5-[(phenylmethyl)oxy]benzamide (51 g; 0.14 mol) was dissolved in methanol (500 mL) and THF (500 mL) and the flask evacuated and purged with argon (3 times). 10% Palladium on carbon (5.1 g) was added and the flask further evacuated and finally purged with hydrogen gas. The reaction mixture was stirred at ambient temperature for 20 hours. The reaction mixture was evacuated and purged with nitrogen (3 times). The catalyst was filtered off through celite, and the filtrate concentrated in vacuo. Ethyl acetate was added and filtered to give the desired compound. (30.5 g). A second crop of material was obtained in the same way (4.0 g).

$^1$H NMR δ (d$_6$-DMSO): 1.30 (d, 6H), 3.78 (s, 3H), 4.68 (sept, 1H), 6.47 (m, 1H), 6.60 (s, 1H), 6.94 (s, 1H), 7.05 (s, 1H), 7.60 (s, 1H), 10.63 (s, 1H). m/z 276 (M+H)$^+$ 3-[(1-Methylethyl)oxy]-N-(1-methyl-1H-pyrazol-3-yl)-5-[(phenylmethyl)oxy]benzamide

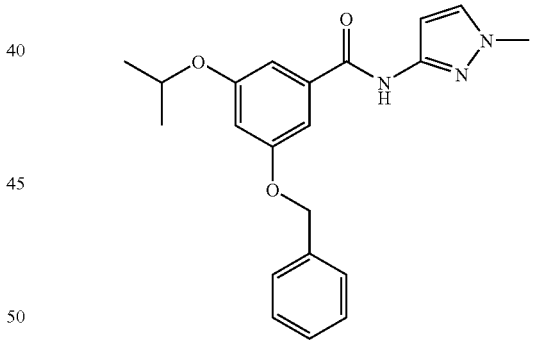

DMF (2 drops) was added to a solution of 3-[(1-methylethyl)oxy]-5-[(phenylmethyl)oxy]benzoic acid (40.0 g, 0.14 mol) and oxalyl chloride (14.6 mL, 0.17 mol) in DCM (700 mL). The mixture was stirred at ambient temperature for 4 hours and the DCM and excess oxalyl chloride were evaporated in vacuo. The residual acid chloride was dissolved in DCM (300 mL) and added dropwise to 1-methyl-3-aminopyrazole (14.25 g, 0.147 mol) and triethylamine (41 mL, 0.29 mol) in DCM (300 mL), at 0° C. Stirred at ambient temperature for 24 hours. The DCM was evaporated in vacuo, and the residue partitioned between ethyl acetate (400 mL) and 1N hydrochloric acid (200 mL). The ethyl acetate layer was washed sequentially with saturated aqueous sodium hydrogen carbonate (200 mL) and brine (100 mL), dried (MgSO$_4$) and evaporated in vacuo. The residue was chromatographed on silica, eluting with a gradient of 50% ethyl acetate in isohexane, to give the desired compound (51 g). ¹H NMR δ (CDCl₃): 1.30 (d, 6H), 3.61 (s, 3H), 4.50 (sept, 1H), 5.01 (s, 2H), 6.66 (m, 1H), 6.88 (m, 1H), 7.00 (m, 1H), 7.06 (m, 1H), 7.24 (m, 1H), 7.39 (m, 5H), 9.50 (s, 1H). m/z 366 (M+H)⁺

3-[(1-Methylethyl)oxy]-5-[(phenylmethyl)oxy]benzoic acid

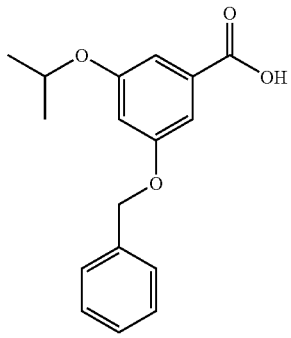

To a solution of methyl 3-[(1-methylethyl)oxy]-5-[(phenylmethyl)oxy]benzoate (37 g) in a 1:1 mixture of THF:methanol (300 mL) was added 4M sodium hydroxide solution (150 mL). The mixture was refluxed for 45 minutes, following which the organics were removed in vacuo. The aqueous was acidified to pH4 with hydrochloric acid (2M), and extracted with ethyl acetate. The organics were combined, washed with water and brine, dried (MgSO₄) and concentrated in vacuo to give the desired compound (33.5 g), which was used without further purification.

¹H NMR δ (d₆-DMSO): 1.26 (d, 6H), 4.59-4.69 (m, 1H), 5.15 (s, 2H), 6.80 (app t, 1H), 7.04 (m, 1H), 7.12 (m, 1H), 7.33 (app t, 1H), 7.40 (t, 2H), 7.46 (d, 2H), 12.95 (s, 1H)

Methyl 3-[(1-methylethyl)oxy]-5-[(phenylmethyl)oxy]benzoate

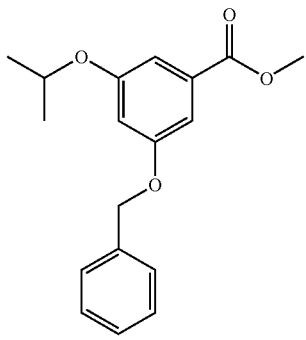

To a solution of methyl 3-hydroxy-5-[(1-methylethyl)oxy]benzoate (25 g) in DMF (250 mL) was added anhydrous potassium carbonate (297 mmol), and benzyl bromide (143 mmol). The mixture was stirred at 60° C. for 5 hours, then cooled to room temperature. The solvent was removed in vacuo and the residue partitioned between ethyl acetate and water. The organics were combined and washed with further water, brine, dried (MgSO₄) and concentrated in vacuo to give the desired compound (37 g) which was used without further purification.

¹H NMR δ (d₆-DMSO): 1.26 (d, 6H), 3.84 (s, 3H), 4.61-4.70 (m, 1H), 5.12 (s, 2H), 6.84 (t, 1H), 7.05 (app t, 1H), 7.12-7.15 (m, 1H), 7.31-7.37 (m, 1H), 7.40 (t, 2H), 7.46 (d, 2H)

Methyl 3-hydroxy-5-[(1-methylethyl)oxy]benzoate

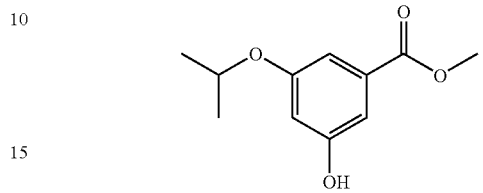

To a stirred solution of methyl 3,5-dihydroxybenzoate (0.1 mol) in DMF (180 mL) was added powdered potassium carbonate (0.2 mol) and 2-iodopropane (0.1 mol), and the resulting mixture stirred at ambient temperature for 16 hours. The reaction mixture was poured into water (1000 mL) and the mixture extracted with ether. The extracts were combined and washed sequentially with water (twice) and brine; the solution was dried (MgSO₄), filtered and evaporated in vacuo to give the crude product as a pale yellow oil (12.6 g). This was treated with toluene (40 mL) and allowed to stand overnight. The insoluble material (starting phenol) was removed by filtration, and the filtrate evaporated in vacuo. The resulting oil was chromatographed (2×90 g Biotage silica cartridges), eluting with hexane containing ethyl acetate (10% increasing to 15% v/v). The title compound was obtained as an oil (25% yield). ¹H NMR δ (d₆-DMSO): 1.2 (d, 6H), 3.8 (s, 3H), 4.5-4.6 (hept, 1H), 6.55 (m, 1H), 7.85 (m, 1H), 7.95 (m, 1H), 9.8 (s, 1H)

Example 16

3-[(1-Methylethyl)oxy]-5-[(4-methyl-5-oxo-2,3,4,5-tetrahydro-1,4-benzoxazepin-8-yl)oxy]-N-(1-methyl-1H-pyrazol-3-yl)benzamide

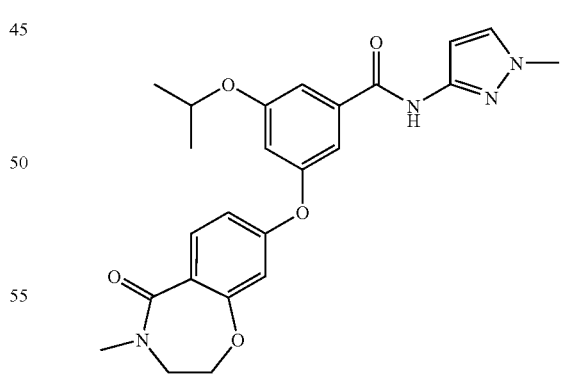

To a solution of 3-[(9-chloro-4-methyl-5-oxo-2,3,4,5-tetrahydro-1,4-benzoxazepin-8-yl)oxy]-5-[(1-methylethyl)oxy]-N-(1-methyl-1H-pyrazol-3-yl)benzamide (160 mg, 0.32 mmol) in ethanol (3 mL) was added ammonium formate (208 mg, 10 equivs) in one portion. The reaction was blanketed with argon and 10% Palladium on carbon (40 mg) was added. The mixture was heated to 140° C. for 10 minutes in a Smith Creator microwave. The reaction mixture was filtered

Example 17

3-[(8-Chloro-2,3-dimethyl-4-oxo-3,4-dihydro-2H-1,3-benzoxazin-7-yl)oxy]-5-{[(1S)-1-(hydroxymethyl)propyl]oxy}-N-(1-methyl-1H-pyrazol-3-yl)benzamide

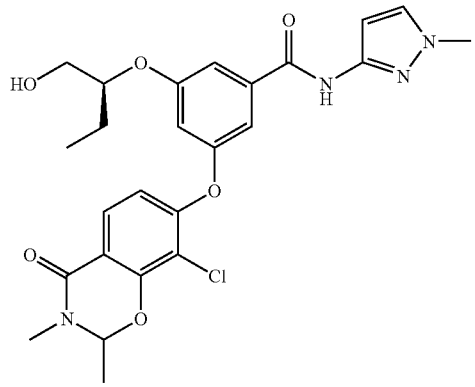

A solution of 3-hydroxy-5-{[(1S)-1-(hydroxymethyl)propyl]oxy}-N-(1-methyl-1H-pyrazol-3-yl)benzamide (200 mg, 0.66 mmol), N-(2-{[tert-butyl(dimethyl)silyl]oxy}ethyl)-3-chloro-2,4-difluoro-N-methylbenzamide (239 mg, 0.66 mmol) and potassium carbonate (181 mg, 1.31 mmol) in DMA (3 mL) was heated in a microwave reactor at 160° C. for 6 hours. Water (20 mL) was added and the reaction mixture extracted with ethyl acetate. The organic layer was washed with brine (20 mL), dried (MgSO$_4$) and evaporated to a residue which was chromatographed on silica, eluting with 2% methanol in ethyl acetate, and then chromatographed by preparative HPLC on C18 reversed phase, eluting with 5-95% acetonitrile (+0.2% TFA) in water (+0.2% TFA), to give the required product (542 mg).

$^1$H NMR δ (CDCl$_3$): 0.91 (t, 3H), 1.60 (d, 3H), 1.67 (quin, 2H), 3.03 (s, 3H), 3.74 (m, 2H), 3.84 (s, 3H), 4.45 (m, 1H), 5.51 (q, 1H), 6.64 (d, 1H), 6.77 (t, 1H), 6.93 (d, 1H), 7.31 (d, 1H), 7.36 (t, 1H), 7.75 (d, 1H), 10.32 (s, 1H); m/z 515 (M+H)$^+$ The preparation of N-(2-{[tert-butyl(dimethyl)silyl]oxy}ethyl)-3-chloro-2,4-difluoro-N-methylbenzamide was described earlier.

The preparation of 3-hydroxy-5-{[(1S)-1-(hydroxymethyl)propyl]oxy}-N-(1-methyl-1H-pyrazol-3-yl)benzamide is described below:

3-Hydroxy-5-{[(1S)-1-(hydroxymethyl)propyl]oxy}-N-(1-methyl-1H-pyrazol-3-yl)benzamide

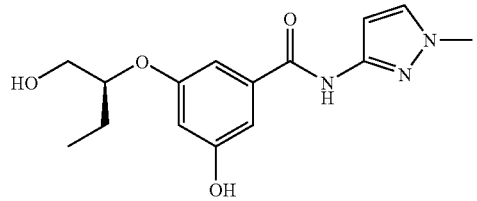

To a solution of 3-hydroxy-5-({(1S)-1-[(methyloxy)methyl]propyl}oxy)-N-(1-methyl-1H-pyrazol-3-yl)benzamide (500 mg, 1.6 mmol) in acetonitrile (25 mL), iodotrimethylsilane (1.11 mL, 7.8 mmol) was added and the resulting mixture stirred for 16 hours. Saturated sodium hydrogencarbonate solution (10 mL) was added, the solution stirred for 10 mins, saturated aqueous sodium thiosulfate (5 mL) was added then the acetonitrile was removed in vacuo. The residual aqueous layer was extracted with ethyl acetate (3×40 mL) and the organic layers combined, dried (MgSO$_4$), filtered and evaporated and purified by column chromatography, eluting with 85% ethyl acetate in isohexane, to give the title compound as a colourless foam (405 mg).

$^1$H NMR δ (d$_6$-DMSO): 0.95 (t, 3H), 1.5-1.8 (m, 2H), 3.5 (m, 2H), 3.8 (s, 3H), 4.3 (m, 1H), 4.8 (t, 1H), 6.45 (s, 1H), 6.55 (s, 1H), 6.9 (s, 1H), 7.05 (s, 1H), 7.55 (s, 1H), 9.6 (s, 1H); m/z 306 (M+H)$^+$

3-Hydroxy-5-({(1S)-1-[(methyloxy)methyl]propyl}oxy)-N-(1-methyl-1H-pyrazol-3-yl)benzamide

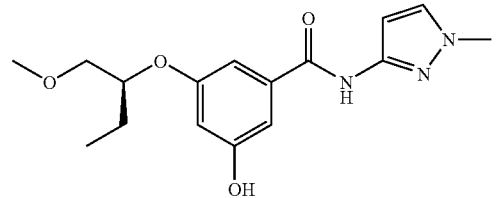

To a solution of 3-({(1S)-1-[(methyloxy)methyl]propyl}oxy)-N-(1-methyl-1H-pyrazol-3-yl)-5-[(phenylmethyl)oxy]benzamide (4.6 g, 11 mmol) in 1:1 THF:methanol (100 mL) was added 10% w/w palladium on carbon (450 mg) and the resulting mixture was stirred under an atmosphere of hydrogen for 6 hours. The atmosphere was replaced with argon and the mixture was filtered and evaporated to afford the title compound as a white solid (3.6 g).

$^1$H NMR δ (CDCl$_3$): 0.95 (t, 3H), 1.7 (m, 2H), 3.4 (s, 3H), 3.55 (m, 2H), 3.8 (s, 3H), 4.3 (m, 1H), 6.65 (s, 1H), 6.8 (s, 1H), 7.0 (m, 2H), 7.2 (m, 1H), 7.3 (s, 1H), 8.7 (s, 1H); m/z 320 (M+H)$^+$ 3-({(1S)-1-[(Methyloxy)methyl]propyl}oxy)-N-(1-methyl-1H-pyrazol-3-yl)-5-[(phenylmethyl)oxy]benzamide

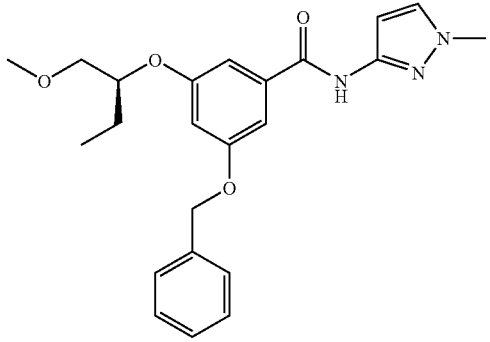

To a solution of 3-({(1S)-1-[(methyloxy)methyl]propyl}oxy)-5-[(phenylmethyl)oxy]benzoic acid (4.75 g, 14.4 mmol) and 3-amino-1-methyl-1H-pyrazole (2.04 g, 21 mmol) in DMF (25 mL) was added HATU (8.53 g, 22.4 mmol) then DIPEA (7.0 mL, 40 mmol) and the resulting mixture was stirred for 16 hours. The mixture was partitioned between ethyl acetate (100 mL) and water (30 mL). The organic layer was separated, washed with 1N citric acid (30 mL), water (30 mL), saturated sodium bicarbonate (30 mL), water (30 mL) and brine (30 mL) then dried (MgSO₄) and evaporated. The residue was purified by column chromatography, eluting with 50% ethyl acetate in isohexane, to give the title compound as a colourless oil (4.57 g).

¹H NMR δ (CDCl₃): 0.95 (t, 3H), 1.7 (m, 2H), 3.4 (s, 3H), 3.55 (m, 2H), 3.8 (s, 3H), 4.3 (m, 1H), 5.05 (s, 2H), 6.75 (s, 1H), 6.8 (s, 1H), 7.05 (d, 2H), 7.25 (s, 1H), 7.4 (m, 5H), 8.45 (s, 1H); m/z 410 (M+H)⁺

3-({(1S)-[(Methyloxy)methyl]propyl}oxy)-5-[(phenylmethyl)oxy]benzoic acid

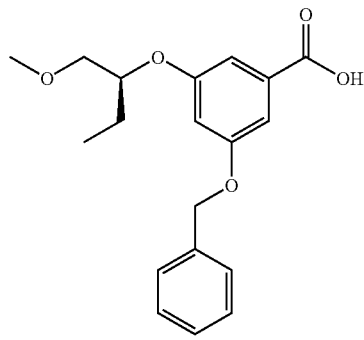

To a solution of methyl 3-({(s)-1-[(methyloxy)methyl]propyl}oxy)-5-[(phenylmethyl)oxy]benzoate (6.85 g, 20 mmol) in 3:1 THF:methanol (100 mL) was added 1N lithium hydroxide solution in water (40 mL, 40 mmol), then a further 100 mL water was added portionwise at intervals while the resulting mixture was stirred for 2 hours. The organic solvents were removed by evaporation and the cloudy solution filtered. The pH of the filtrate was adjusted to 3 by the addition of 2 M hydrochloric acid. This was extracted with ethyl acetate (3×70 mL). The combined organic extracts were dried (MgSO₄) and evaporated to afford the title compound as a colourless oil which solidified (6.36 g,).

¹H NMR δ (CDCl₃): 0.95 (t, 3H), 1.7 (m, 2H), 3.4 (s, 3H), 3.55 (m, 2H), 4.3 (m, 1H), 5.05 (s, 2H), 6.8 (s, 1H), 7.3-7.5 (m, 7H); m/z 329 (M−H)⁻

Methyl 3-({(1S)-1-[(methyloxy)methyl]propyl}oxy)-5-[(phenylmethyl)oxy]benzoate

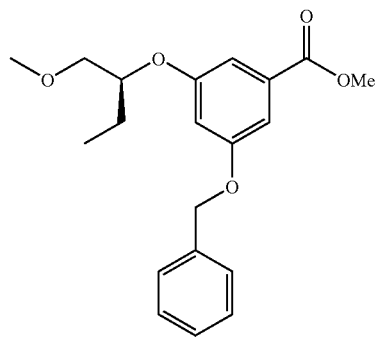

A stirred solution of methyl 3-hydroxy-5-{[phenylmethyl]oxy}benzoate (7.5 g, 29 mmol), (R)-1-methoxy-butan-2-ol (3.76 g, 36.25 mmol) and triphenylphosphine (9.5 g, 36.25 mmol) in dry THF (75 mL) was cooled in an ice-bath and a solution of 40% DEAD in toluene (15.8 mL, 36.25 mmol) was added dropwise over 30 minutes. The reaction mixture was allowed to warm slowly to 10° C. and stirred for 16 hours. The THF was evaporated. The residue was dissolved in 30% ethyl acetate in isohexane and cooled in ice. The resultant precipitate was removed by filtration and washed with 10% ethyl acetate in isohexane. The filtrate was evaporated and purified by column chromatography, eluting with 10% ethyl acetate in isohexane, to give the title compound as a colourless oil (6.85 g).

¹H NMR δ (CDCl₃): 0.95 (t, 3H), 1.7 (m, 2H), 3.35 (s, 3H), 3.55 (m, 2H), 3.9 (s, 3H), 4.3 (m, 1H), 5.05 (s, 2H), 6.8 (s, 1H), 7.25 (m, 2H), 7.4 (m, 5H); m/z 345 (M+H)⁺

The preparation of (R)-1-methoxy-butan-2-ol was described in the literature [Coke, J. L.; Shue, R. S., J. Org. Chem. 38, (1973), 2210-2211].

The preparation of methyl 3-hydroxy-5-{[phenylmethyl]oxy}benzoate was described earlier.

Example 18

3-[(1,1-Dioxido-2,3-dihydro-1-benzothien-5-yl)oxy]-5-{[(1S)-1-methyl-2-(methyloxy)ethyl]oxy}-N-(1-methyl-1H-pyrazol-3-yl)benzamide

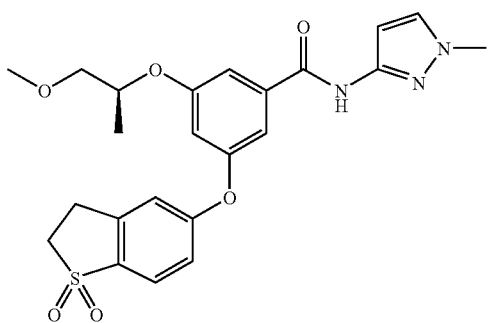

To a solution of 3-[(1,1-dioxido-1-benzothien-5-yl)oxy]-5-{[(1S)-1-methyl-2-(methyloxy)ethyl]oxy}-N-(1-methyl-1H-pyrazol-3-yl)benzamide (113 mg, 0.24 mmol) in ethanol (2.5 mL) was added ammonium formate (152 mg, 2.40 mmol) and 10% palladium on charcoal (25 mg) and the resultant mixture heated at 140° C. for 10 minutes in a microwave reactor. The catalyst was filtered and the residue reduced, taken up in DCM plus a little methanol and transferred to a silica cartridge, eluted with 0-3% methanol in DCM, to give the desired compound as a clear foam (65 mg).

$^1$H NMR δ (d$_6$-DMSO): 1.31 (d, 3H), 3.35 (s, 3H), 3.55 (m, 4H), 3.64 (t, 2H), 3.83 (s, 3H), 4.82 (m, 1H), 6.62 (d, 1H), 6.95 (t, 1H), 7.19 (d, 1H), 7.22 (m, 1H), 7.33 (t, 1H), 7.54 (t, 1H), 7.65 (m, 1H), 7.81 (d, 1H), 10.89 (s, 1H); m/z 472 (M+H)$^+$

The preparation of 3-[(1,1-dioxido-1-benzothien-5-yl)oxy]-5-{[(1S)-1-methyl-2-(methyloxy)ethyl]oxy}-N-(1-methyl-1H-pyrazol-3-yl)benzamide is described below:

3-[(1,1-Dioxido-1-benzothien-5-yl)oxy]-5-{[(1S)-1-methyl-2-(methyloxy)ethyl]oxy}-N-(1-methyl-1H-pyrazol-3-yl)benzamide

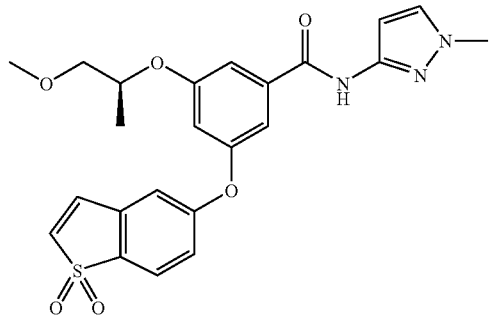

To a solution of 3-(1-benzothien-5-yloxy)-5-{[(1S)-1-methyl-2-(methyloxy)ethyl]oxy}-N-(1-methyl-1H-pyrazol-3-yl)benzamide (178 mg, 0.41 mmol) in methanol (3 mL) at 0° C. was added dropwise a solution of oxone (752 mg, 1.22 mmol) in water (3 mL). The resultant cloudy slurry was allowed to warm to RT and stir for 16 hours. Water (20 mL) was added and the mixture extracted with DCM (3×20 mL). The combined extracts were dried (MgSO$_4$), filtered and evaporated. The material was chromatographed on silica, eluting with 0-3% methanol in DCM, to give the desired compound as yellow oil (113 mg). m/z 470 (M+H)$^+$ 3-(1-Benzothien-5-yloxy)-5-{[(1S)-1-methyl-2-(methyloxy)ethyl]oxy}-N-(1-methyl-1H-pyrazol-3-yl)benzamide

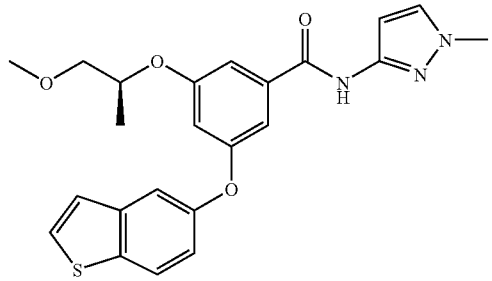

3-Hydroxy-5-[(1S)-2-methoxy-(1-methylethyl)oxy]-N-(1-methyl-1H-pyrazol-3-yl)benzamide (610 mg, 2.0 mmol), 5-bromobenzothiophene (639 mg, 3.0 mmol), copper bis (triphenylphosphine) bromide (372 mg, 0.40 mmol) and caesium carbonate (1.95 g, 6.0 mmol) in acetonitrile (7.5 mL) were heated at 160° C. for 15 hours. The mixture was concentrated in vacuo and re-dissolved in DCM (50 mL). The organics were washed with water (25 mL), brine (25 mL), dried (MgSO$_4$) and concentrated in vacuo. The residue was twice chromatographed on silica, eluting with 0-3% methanol in DCM, to give the desired material as a grey gum (178 mg). m/z 438 (M+H)$^+$ The preparation of 3-hydroxy-5-[(1S)-2-methoxy-(1-methylethyl)oxy]-N-(1-methyl-1H-pyrazol-3-yl)benzamide was described earlier.

Example 19

N-(1-Ethyl-1H-pyrazol-3-yl)-3-{[(1S)-2-hydroxy-1-methylethyl]oxy}-5-[(4-methyl-5-oxo-2,3,4,5-tetrahydro-1,4-benzoxazepin-8-yl)oxy]benzamide

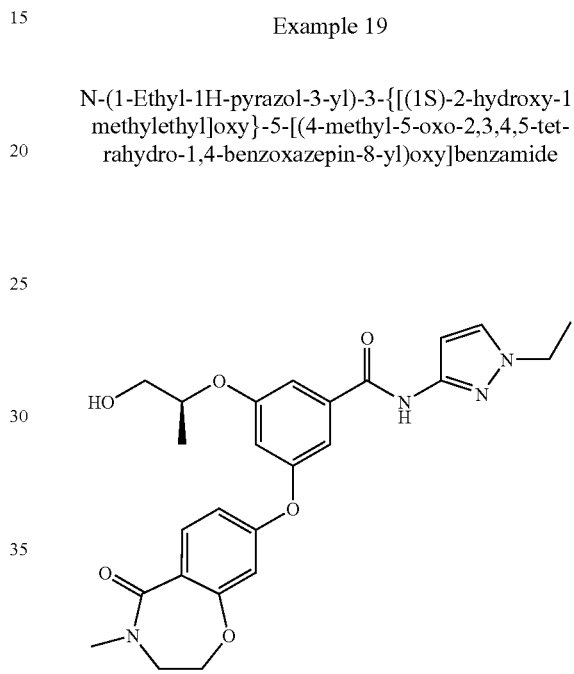

A solution of N-(1-ethyl-1H-pyrazol-3-yl)-3-{[(1S)-1-methyl-2-(methyloxy)ethyl]oxy}-5-[(4-methyl-5-oxo-2,3,4,5-tetrahydro-1,4-benzoxazepin-8-yl)oxy]benzamide (125 mg, 0.25 mmol) in acetonitrile (5 mL) was treated with trimethylsilyl iodide (0.178 mL) drop wise and stirred at RT under argon for 2.5 hours. Aqueous sodium thiosulphate solution (30 mL) was added to quench the reaction and the mixture was extracted with ethyl acetate (3×30 mL). The combined organic extracts were dried (MgSO$_4$), filtered and evaporated to give a yellow oil. Purification was carried out by column chromatography on silica, eluting with 50-100% ethyl acetate in isohexane, to give the desired compound as a pale yellow foam (50 mg).

$^1$H NMR δ (CDCl$_3$): 1.21 (d, 3H), 1.45 (t, 3H), 3.21 (s, 3H), 3.59 (t, 2H), 3.71-3.75 (m, 2H), 4.06 (q, 2H), 4.31 (t, 2H), 4.52-4.56 (m, 1H), 6.57 (d, 1H), 6.76-6.79 (m, 3H), 7.10 (t, 1H), 7.25 (s, 1H), 7.32 (d, 1H), 7.87 (d, 1H), 8.48 (s, 1H); m/z 481 (M+H)$^+$, 479 (M−H)$^−$

The preparation of N-(1-ethyl-1H-pyrazol-3-yl)-3-{[(is)-1-methyl-2-(methyloxy)ethyl]oxy}-5-[(4-methyl-5-oxo-2,3,4,5-tetrahydro-1,4-benzoxazepin-8-yl)oxy]benzamide was described earlier.

Example 20

N-(1-Ethyl-1H-pyrazol-3-yl)-3-[(9-fluoro-4-methyl-5-oxo-2,3,4,5-tetrahydro-1,4-benzoxazepin-8-yl)oxy]-5-{[(S)-1-methyl-2-(methyloxy)ethyl]oxy}benzamide

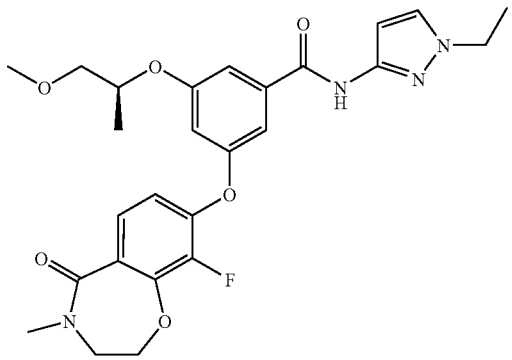

A suspension of N-(2-{[(1,1-dimethylethyl)(dimethyl)silyl]oxy}ethyl)-2,3,4-trifluoro-N-methylbenzamide (300 mg, 0.86 mmol), N-(1-ethyl-1H-pyrazol-3-yl)-3-hydroxy-5-{[(1S)-1-methyl-2-(methyloxy)ethyl]oxy}benzamide (290 mg, 0.91 mmol) and potassium carbonate (237 mg, 1.73 mmol) in DMA (20 mL) was heated to 140° C. for 4 hours. The reaction was poured into water (100 mL) and extracted with ethyl acetate (3×50 mL). The combined organic phases were washed with brine (50 mL) and dried (MgSO$_4$), filtered and evaporated to give an orange oil. This was purified by column chromatography on alumina, eluting with 30-100% ethyl acetate in isohexane, to give the desired product as a colourless oil (300 mg).

$^1$H NMR δ (CDCl$_3$): 1.25 (d, 3H), 1.38 (t, 3H), 2.77 (s, 3H), 3.33 (s, 3H), 3.43 (dd, 1H), 3.50 (dd, 1H), 3.73 (t, 2H), 3.98 (q, 2H), 4.25 (t, 2H), 4.52 (quind, 1H), 6.70 (d, 1H), 6.73 (t, 1H), 6.75 (dd, 1H), 7.05 (t, 1H), 7.21 (t, 1H), 7.25 (d, 1H), 7.47 (dd, 1H), 8.53 (s, 1H)

The preparations of N-(2-{[(1,1-dimethylethyl)(dimethyl)silyl]oxy}ethyl)-2,3,4-trifluoro-N-methylbenzamide and N-(1-ethyl-1H-pyrazol-3-yl)-3-hydroxy-5-{[(1S)-1-methyl-2-(methyloxy)ethyl]oxy}benzamide were described earlier.

Example 21

3-[(9-Fluoro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide

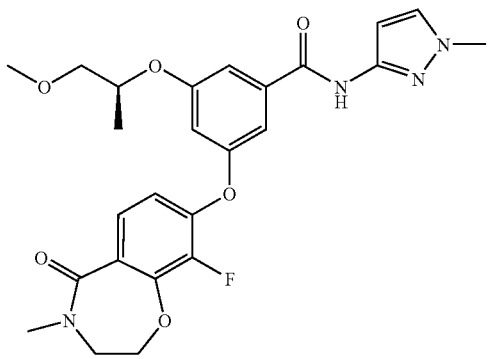

A suspension of N-(2-{[(1,1-dimethylethyl)(dimethyl)silyl]oxy}ethyl)-2,3,4-trifluoro-N-methylbenzamide (300 mg, 0.86 mmol), 3-hydroxy-5-[(1S)-2-methoxy-(1-methylethyl)oxy]-N-(1-methyl-1H-pyrazol-3-yl)benzamide (278 mg, 0.91 mmol) and potassium carbonate (237 mg, 1.73 mmol) in DMA (20 mL) was heated to 140° C. for 1 hour. The reaction mixture was poured into water (100 mL) and extracted with ethyl acetate (3×50 mL). The combined organic phases were washed with brine (50 mL) and dried (MgSO$_4$), filtered and evaporated to give an orange oil. This was purified via column chromatography on silica, eluting with 50-100% ethyl acetate in isohexane, to give the desired product as a colourless oil (322 mg). $^1$H NMR δ (CDCl$_3$): 1.25 (d, 3H), 2.77 (s, 3H), 3.33 (s, 3H), 3.44 (dd, 1H), 3.50 (dd, 1H), 3.71 (s, 3H), 3.74 (t, 2H), 4.25 (t, 2H), 4.49-4.56 (m, 1H), 6.71 (d, 1H), 6.73 (t, 1H), 6.75 (dd, 1H), 7.04 (t, 1H), 7.20-7.20 (m, 1H), 7.22 (d, 1H), 7.47 (dd, 1H), 8.68 (s, 1H); m/z 499 (M+H)$^+$ The preparations of N-(2-{[(1,1-dimethylethyl)(dimethyl)silyl]oxy}ethyl)-2,3,4-trifluoro-N-methylbenzamide and 3-hydroxy-5-[(1S)-2-methoxy-(1-methylethyl)oxy]-N-(1-methyl-1H-pyrazol-3-yl)benzamide were described earlier.

Example 22

3-[(7-Fluoro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide

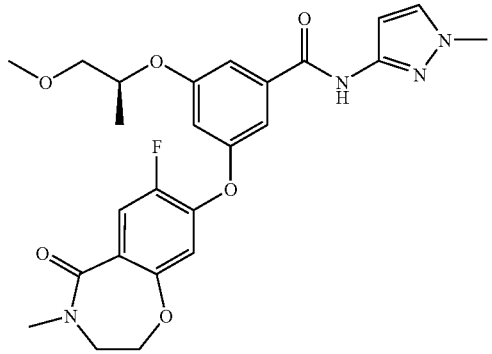

A mixture of 7,8-difluoro-4-methyl-3,4-dihydro-1,4-benzoxazepin-5(2H)-one (725 mg, 2.0 mmol), 3-hydroxy-5-[(1S)-2-methoxy-(1-methylethyl)oxy]-N-(1-methyl-1H-pyrazol-3-yl)benzamide (600 mg, 1.97 mmol) and potassium carbonate (550 mg, 3.88 mmol) in DMA (10 mL) was heated to 160° C. for 5 hours. Water (20 mL) was added to the reaction and extracted with ethyl acetate (3×30 mL). The combined organic phases were washed with water (2×30 mL) and brine (2×30 mL), dried (MgSO$_4$), filtered and evaporated to give a yellow oil. This was purified by column chromatography on silica, eluting with 20-100% ethyl acetate in isohexane, to give the desired compound as a foam (65 mg).

$^1$H NMR δ (CDCl$_3$): 1.25 (d, 3H), 3.14 (s, 3H), 3.33 (s, 3H), 3.42 (dd, 1H), 3.48-3.52 (m, 1H), 3.51 (t, 2H), 3.73 (s, 3H), 4.30 (t, 2H), 4.48-4.55 (m, 1H), 6.55 (d, 1H), 6.70-6.72 (m, 2H), 7.01 (t, 1H), 7.16 (t, 1H), 7.20 (d, 1H), 7.64 (d, 1H), 8.36 (s, 1H); m/z 499 (M+H)$^+$, 497 (M−H)$^−$

The preparation of 3-hydroxy-5-[(1S)-2-methoxy-(1-methylethyl)oxy]-N-(1-methyl-1H-pyrazol-3-yl)benzamide was described earlier.

The preparation of 7,8-difluoro-4-methyl-3,4-dihydro-1,4-benzoxazepin-5(2H)-one is described below:

7,8-Difluoro-4-methyl-3,4-dihydro-1,4-benzoxazepin-5(2H)-one

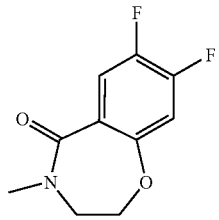

Sodium hydride (52 mg, 1.29 mmol) was added portionwise to a solution of 2,4,5-trifluoro-N-(2-hydroxyethyl)-N-methylbenzamide (300 mg, 1.29 mmol) in DMF (13 mL) and reaction was allowed to stir at RT for 2 hours. Water (30 mL) was added and the white solution was extracted with ethyl acetate (3×30 mL) and dried (MgSO₄), filtered and evaporated to give the desired compound as a colourless oil (275 mg). The compound was used without further purification.

2,4,5-Trifluoro-N-(2-hydroxyethyl)-N-methylbenzamide

2,4,5-Trifluorobenzoyl chloride (540 mg, 2.78 mmol) was added to a stirred solution of 2-methylaminoethanol (0.185 mL, 3.06 mmol) in DCM (5 mL) and 10% aqueous sodium hydroxide solution (5 mL) at 0° C. After addition was complete the icebath was removed and the reaction was allowed to warm up to RT and stirred for 3 hours. The phases were then separated and the aqueous phase extracted with DCM (3×30 mL). The combined organic layers were dried (MgSO₄), filtered and evaporated to give the desired compound as a colourless oil (686 mg). This material was used without further purification.

¹H NMR δ (CDCl₃): 2.48 (t, 1H), 2.95 (s, 2H), 3.07 (s, 1H), 3.31 (t, 1H), 3.65 (t, 2H), 3.84 (q, 1H), 6.86-6.95 (m, 1H), 7.14-7.24 (m, 1H).

Example 23

3-[(9-Chloro-4-methyl-5-oxo-2,3,4,5-tetrahydro-1,4-benzoxazepin-8-yl)oxy]-N-(1-methyl-1H-pyrazol-3-yl)-5-[(3S)-tetrahydrofuran-3-yloxy]benzamide

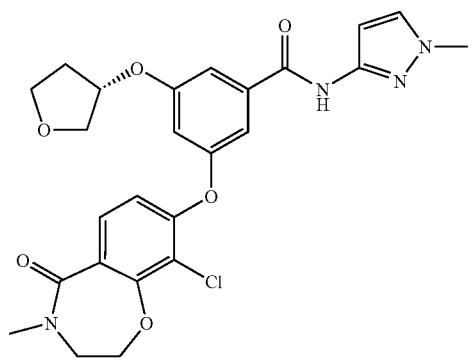

A mixture of 3-hydroxy-N-(1-methyl-1H-pyrazol-3-yl)-5-[(3S)-tetrahydrofuran-3-yloxy]benzamide (539 mg, 1.77 mmol), N-(2-{[tert-butyl(dimethyl)silyl]oxy}ethyl)-3-chloro-2,4-difluoro-N-methylbenzamide (539 mg, 1.77 mmol) and potassium carbonate (490 mg, 3.55 mmol) in acetonitrile (15 mL) was placed in a Smith Creator microwave reactor and heated to 140° C. for 6 hours. Distilled water was added to the reaction and the aqueous layer extracted with DCM (3×30 mL). The combined organic phase was washed with brine (30 mL), dried (MgSO₄), filtered and evaporated to give a yellow oil. This was purified by column chromatography, eluting with 20-100% ethyl acetate in isohexane, to give the title compound (290 mg). ¹H NMR δ (CDCl₃): 2.09-2.15 (1H, m), 2.18-2.27 (1H, m), 3.23 (3H, s), 3.59 (2H, t), 3.76 (3H, s), 3.86-3.92 (1H, m), 3.94-4.00 (3H, m), 4.54 (2H, t), 4.95 (1H, d), 6.68 (1H, d), 6.78-6.81 (2H, m), 7.04-7.05 (1H, m), 7.16-7.17 (1H, m), 7.28 (1H, d), 7.70 (1H, d), 8.75 (1H, s); m/z 513 (M+H)⁺.

The preparation of N-(2-{[tert-butyl(dimethyl)silyl]oxy}ethyl)-3-chloro-2,4-difluoro-N-methylbenzamide was described earlier.

The preparation of 3-hydroxy-N-(1-methyl-1H-pyrazol-3-yl)-5-[(3S)-tetrahydrofuran-3-yloxy]benzamide is described below:

3-Hydroxy-N-(1-methyl-1H-pyrazol-3-yl)-5-[(3S)-tetrahydrofuran-3-yloxy]benzamide

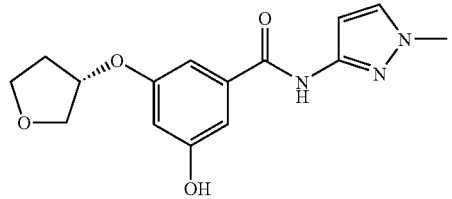

N-(1-Methyl-1H-pyrazol-3-yl)-3-[(phenylmethyl)oxy]-5-[(3S)-tetrahydrofuran-3-yloxy]benzamide (453 mg, 1.15 mmol) was dissolved in ethanol (5 mL) and ammonium formate (182 mg, 2.88 mmol) was added in one portion. The reaction was blanketed with argon and 10% Palladium on activated carbon (30 mg) was added. This mixture was heated to 140° C. for 10 minutes in a Smith Creator microwave. The catalyst was filtered off and the volatiles removed in vacuo to give the title product as a white solid (339 mg).

¹H NMR δ (CDCl₃): 2.06-2.14 (1H, m), 2.15-2.22 (1H, m), 3.72-3.73 (3H, s), 3.84-3.89 (1H, m), 3.92-3.98 (3H, m), 4.88 (1H, m), 6.53 (1H, t), 6.78 (1H, d), 6.89 (1H, s), 6.95 (1H, s), 7.28 (1H, d), 9.27 (1H, s); m/z 304 (M+H)⁺.

N-(1-Methyl-1H-pyrazol-3-yl)-3-[(phenylmethyl)oxy]-5-[(3S)-tetrahydrofuran-3-yloxy]benzamide

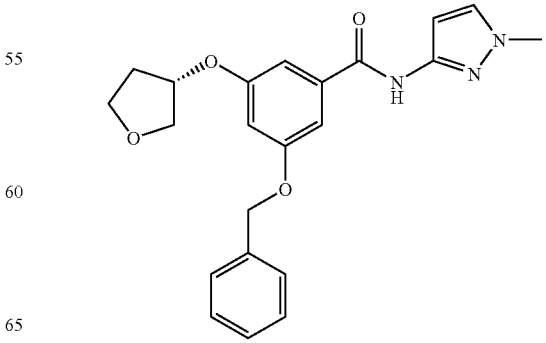

A suspension of 3-hydroxy-N-(1-methyl-1H-pyrazol-3-yl)-5-[(phenylmethyl)oxy]benzamide (450 mg, 1.39 mmol), (3R)-tetrahydrofuran-3-yl 4-methylbenzenesulfonate (507 mg, 2.09 mmol) and potassium carbonate (481 mg, 3.48 mmol) in acetonitrile (5 mL) was stirred in a Smith Creator microwave at 160° C. for 3 hours. The solvent was removed in vacuo and ethyl acetate added. The organics were washed with water (40 mL), brine (40 mL), dried (MgSO$_4$), filtered and the solvent removed in vacuo to give a yellow foam which was chromatographed on silica, eluting with a gradient of 0-100% ethyl acetate in iso-hexane, to give the title compound as a white foam (452 mg). $^1$H NMR δ (CDCl$_3$): 2.09-2.14 (1H, m), 2.14-2.24 (1H, m), 3.68 (3H, s), 3.86-3.91 (1H, m), 3.94-3.98 (3H, m), 4.89 (1H, s), 5.03 (2H, s), 6.64 (1H, t), 6.85 (1H, s), 6.96 (1H, d), 7.07 (1H, t), 7.27 (1H, m), 7.33-7.41 (5H, m), 9.31 (1H, s); m/z 394 (M+H)$^+$.

(3R)-Tetrahydrofuran-3-yl 4-methylbenzenesulfonate

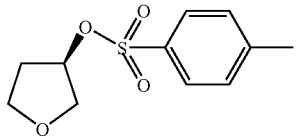

4-Toluene sulfonyl chloride (1.65 g, 8.63 mmol) was added to a solution of R-3-hydroxytetrahydrofuran (0.8 g, 9.08 mmol) and pyridine (0.88 mL, 10.9 mmol) in DCM (15 mL). The reaction was stirred at RT for 72 hours. Water (10 mL) and 1M hydrochloric acid (1 mL) were added and the mixture extracted with DCM (15 mL). The organic layer was washed with brine (20 mL), dried (MgSO$_4$), filtered and reduced in vacuo to give a yellow oil which was chromatographed on silica, eluting with a gradient of 0-50% ethyl acetate in iso-hexane, to give the desired compound (1.0 g). $^1$H NMR δ (CDCl$_3$): 2.13 (m, 2H), 2.47 (s, 3H), 3.80-3.95 (m, 4H), 5.15 (m, 1H), 7.37 (d, 2H), 7.81 (d, 2H).

3-Hydroxy-N-(1-methyl-1H-pyrazol-3-yl)-5-[(phenylmethyl)oxy]benzamide

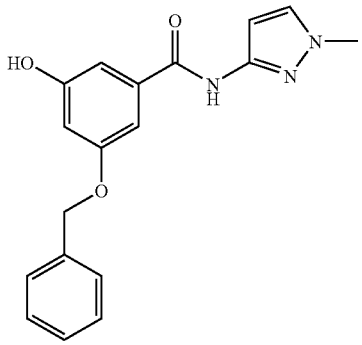

A suspension of N-(1-methyl-1H-pyrazol-3-yl)-3,5-bis[(phenylmethyl)oxy]benzamide (1.0 g, 2.42 mmol) was dissolved in ethanol (12 mL) and ammonium formate (229 mg, 3.63 mmol) was added in one portion. The reaction was blanketed with argon and 10% Palladium on activated carbon (10 mg) was added. This mixture was heated to 140° C. for 5 minutes in a Smith Creator microwave. The catalyst was filtered off and the volatiles removed in vacuo, the residue was chromatographed on silica, eluting with a gradient of 30-100% ethyl acetate in iso-hexane, to give the title compound as a white solid (378 mg). $^1$H NMR δ (d$_6$-DMSO): 3.78 (3H, s), 5.13 (2H, s), 6.55-6.57 (2H, m), 6.99 (1H, s), 7.17 (1H, s), 7.34-7.48 (5H, m), 7.60 (1H, d), 9.74 (1H, s), 10.70 (1H, s); m/z 324 (M+H)$^+$.

N-(1-Methyl-1H-pyrazol-3-yl)-3,5-bis[(phenylmethyl)oxy]benzamide

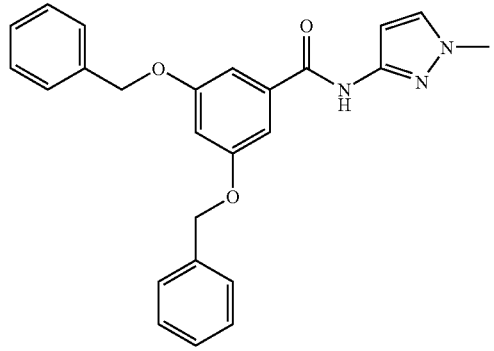

Oxalyl chloride (7.71 mL, 89.7 mmol) was added dropwise to a suspension of 3,5-dibenzyloxybenzoic acid (20.0 g, 59.8 mmol) in DCM (0.5 L) under argon. The reaction was stirred at RT for 6 hours after which time the volatiles were removed in vacuo. The residue was taken up in DCM (300 mL) and a solution of 1-methyl-1H-pyrazol-3-amine (5.81 g, 59.8 mmol) in DCM (50 mL) was added dropwise. The resulting solution was stirred for 16 hours at RT after which time a precipitate had formed. The solid was isolated by filtration and recrystallised from ethanol to give the title compound as a white solid (14.8 g). $^1$H NMR δ (d$_6$-DMSO): 3.84 (3H, s), 5.17 (4H, s), 6.59 (1H, d), 6.84 (1H, t), 7.33-7.46 (12H, m), 7.62 (1H, d), 10.83 (1H, s); m/z 414 (M+H)$^+$.

Example 24

3-[(4-Methyl-5-oxo-2,3,4,5-tetrahydro-1,4-benzoxazepin-8-yl)oxy]-N-(1-methyl-1H-pyrazol-3-yl)-5-[(3S)-tetrahydrofuran-3-yloxy]benzamide

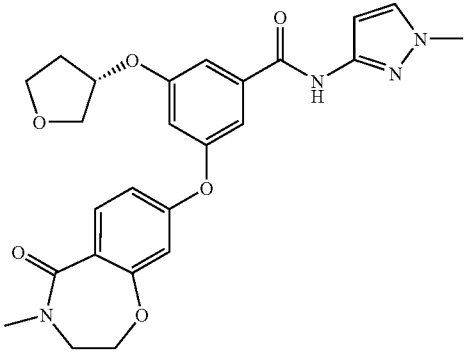

3-[(9-Chloro-4-methyl-5-oxo-2,3,4,5-tetrahydro-1,4-benzoxazepin-8-yl)oxy]-N-(1-methyl-1H-pyrazol-3-yl)-5-[(3S)-tetrahydrofuran-3-yloxy]benzamide (150 mg, 0.29 mmol) was dissolved in ethanol (5 mL) and ammonium formate (147 mg, 2.33 mmol) was added in one portion. The reaction was blanketed with argon and 10% palladium on charcoal (10 mg) was added. The mixture was heated to 140° C. for a total of 55 minutes in a Smith Creator microwave reactor after which time a further 100 mgs of ammonium formate and 10 mgs of catalyst were added and the suspension heated for a further hour. The catalyst was filtered off and the volatiles removed in vacuo to give the crude product as a colourless oil. This residue was purified by reverse phase preparative HPLC, eluting with 5-95% acetoniltrile in water (+0.2% TFA), to give the title compound as a colourless foam (95 mg). $^1$H NMR δ (CDCl$_3$): 2.12-2.19 (1H, m), 2.23-2.32 (1H, m), 3.23 (3H, s), 3.59 (2H, t), 3.88-3.91 (4H, m), 4.01 (3H, m), 4.42 (2H, t), 5.15-5.17 (1H, m), 6.61 (5H, d), 6.78-6.79 (1H, m), 6.80 (1H, t), 7.02 (1H, d), 7.33-7.36 (2H, m), 7.38-7.40 (1H, m), 7.85 (1H, d), 10.58 (1H, s); m/z 479 (M+H)$^+$.

The preparation of 3-[(9-chloro-4-methyl-5-oxo-2,3,4,5-tetrahydro-1,4-benzoxazepin-8-yl)oxy]-N-(1-methyl-1H-pyrazol-3-yl)-5-[(3S)-tetrahydrofuran-3-yloxy]benzamide was described earlier.

Example 25

3-{[(1S)-1-Methyl-2-(methyloxy)ethyl]oxy}-N-(1-methyl-1H-pyrazol-3-yl)-5-[(2,2,3-trimethyl-4-oxo-3,4-dihydro-2H-1,3-benzoxazin-7-yl)oxy]benzamide

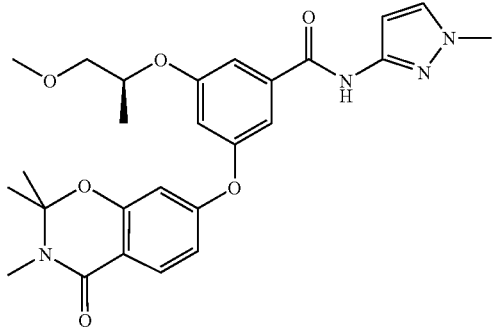

A mixture of 3-hydroxy-5-[(1S)-2-methoxy-(1-methyl-ethyl)oxy]-N-(1-methyl-1H-pyrazol-3-yl)benzamide (0.25 g, 0.82 mmol), 7-fluoro-2,2,3-trimethyl-2,3-dihydro-4H-1,3-benzoxazin-4-one (172 mg, 0.82 mmol) and potassium carbonate (226 mg, 1.64 mmol) in acetonitrile (5 mL) was stirred in a microwave reactor at 160° C. for 12 hours. The mixture was reduced in vacuo and ethyl acetate (50 mL) added. The mixture was washed with water (50 mL), brine (50 mL), dried (MgSO$_4$), and reduced in vacuo to give a brown oil which was chromatographed on silica, eluting with 0-10% methanol in DCM, to give the desired compound as a white foam (122 mg).

$^1$H NMR δ (CDCl$_3$): 1.25 (d, 3H), 1.56 (s, 6H), 2.99 (s, 3H), 3.33 (s, 3H), 3.42-3.53 (m, 2H), 3.76 (s, 3H), 4.53 (sextet, 1H), 6.37 (d, 1H), 6.61 (dd, 1H), 6.73-6.78 (m, 2H), 7.05-7.07 (m, 1H), 7.21-7.25 (m, 2H), 7.83 (d, 1H), 8.56 (s, 1H); m/z 495 (M+H)$^+$ The following compounds were synthesised in an analogous fashion from the appropriate phenol and aromatic fluoride.

| Example | Structure | m/z | $^1$H NMR (CDCl$_3$) |
|---|---|---|---|
| 25a | 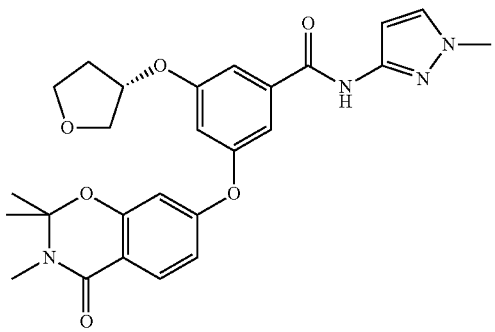 | 495 (M + H)$^+$ | δ: 1.57 (s, 6 H), 2.02-2.23 (m, 2 H), 2.99 (s, 3 H), 3.76 (s, 3 H), 3.81-3.96 (m, 4 H), 4.88-4.95 (m, 1 H), 6.38 (d, 1 H), 6.60-6.63 (m, 1 H), 6.69 (t, 1 H), 6.74-6.77 (m, 1 H), 7.06 (s, 1 H), 7.16 (s, 1 H), 7.24 (d, 1 H), 7.84 (d, 1 H), 8.59 (s, 1 H) |
| 25b | 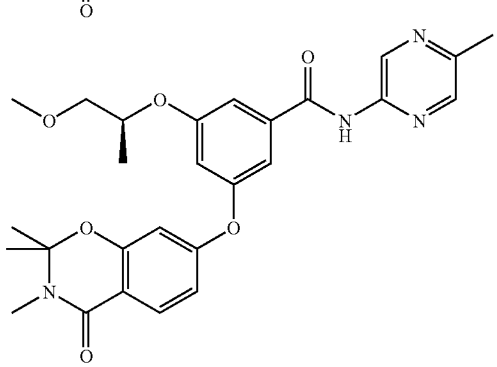 | 507 (M + H)$^+$ | δ: 1.35 (d, 3 H), 1.65 (s, 6 H), 2.58 (s, 3 H), 2.58 (s, 3 H), 3.43 (s, 3 H), 3.52-3.63 (m, 2 H), 4.60-4.67 (m, 1 H), 6.47 (d, 1 H), 6.70-6.72 (m, 1 H), 6.88 (t, 1 H), 7.19 (s, 1 H), 7.34 (s, 1 H), 7.93 (d, 1 H), 8.16 (s, 1 H), 8.39 (s, 1 H), 9.56 (s, 1 H) |
| 25c | 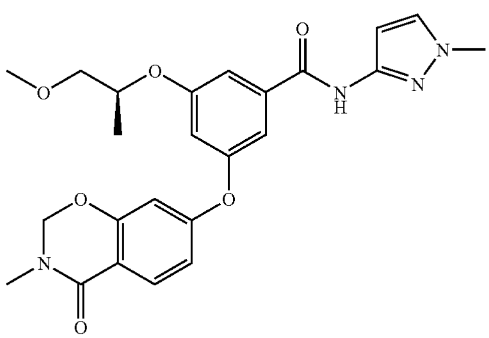 | 467 (M + H)$^+$ | δ: 1.23 (d, 3 H), 3.02 (s, 3 H), 3.32 (s, 3 H), 3.40-3.51 (m, 2 H), 3.66 (s, 3 H), 4.45-4.52 (m, 1 H), 5.10 (s, 2 H), 6.43 (d, 1 H), 6.64-6.67 (m, 1 H), 6.72-6.73 (m, 2 H), 7.02-7.03 (m, 1 H), 7.19-7.21 (m, 2 H), 7.85 (d, 1 H), 8.92 (s, 1 H) |

-continued

| Example | Structure | m/z | ¹H NMR (CDCl₃) |
|---------|-----------|-----|----------------|
| 25d | 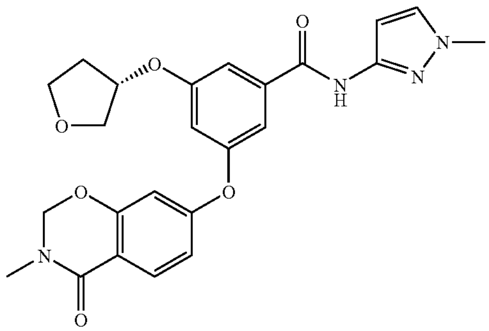 | 465 (M + H)⁺ | δ: 2.02-2.23 (m, 2 H), 3.03 (s, 3 H), 3.73 (s, 3 H), 3.80-3.86 (m, 1 H), 3.89-3.95 (m, 3 H), 4.88-4.91 (m, 1 H), 5.10 (s, 2 H), 6.46 (d, 1 H), 6.65-6.68 (m, 2 H), 6.72 (d, 1 H), 7.03 (t, 1 H), 7.14 (t, 1 H), 7.21 (d, 1 H), 7.87 (d, 1 H), 8.41 (s, 1 H) |
| 25e | 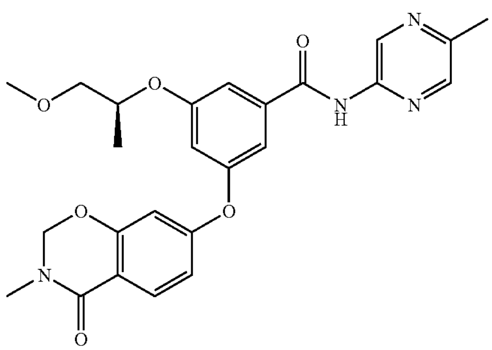 | 479 (M + H)⁺ | δ: 1.35 (d, 3 H), 2.57 (s, 3 H), 3.11 (s, 3 H), 3.42 (s, 3 H), 3.51-3.62 (m, 2 H), 4.60-4.65 (m, 1 H), 5.19 (s, 2 H), 6.55 (d, 1 H), 6.75-6.77 (m, 1 H), 6.86 (t, 1 H), 7.17 (t, 1 H), 7.34 (t, 1 H), 7.96 (d, 1 H), 8.14 (s, 1 H), 8.42 (s, 1 H), 9.54 (d, 1 H) |
| 25f | 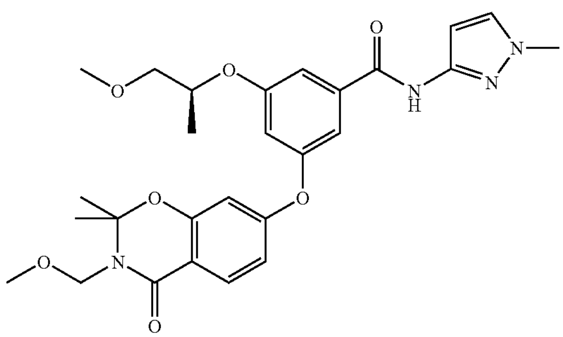 | 525 (M + H)⁺ | δ: 1.25 (d, 3 H), 1.64 (s, 6 H), 3.32 (s, 3 H), 3.33 (s, 3 H), 3.40-3.52 (m, 2 H), 3.71 (s, 3 H), 4.48-4.54 (m, 1 H), 5.01 (s, 2 H), 6.38 (d, 1 H), 6.61-6.64 (m, 1 H), 6.72 (d, 1 H), 6.75 (t, 1 H), 7.04 (t, 1 H), 7.20-7.22 (m, 2 H), 7.85 (d, 1 H), 8.51 (s, 1 H) |
| 25g | 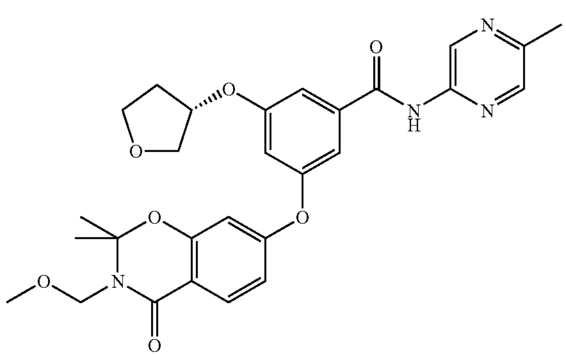 | 535 (M + H)⁺ | δ: 1.65 (s, 6 H), 2.06-2.24 (m, 2 H), 2.49 (s, 3 H), 3.32 (s, 3 H), 3.82-3.96 (m, 4 H), 4.90-4.94 (m, 1 H), 5.01 (s, 2 H), 6.40 (d, 1 H), 6.63-6.65 (m, 1 H), 6.73 (t, 1 H), 7.11 (t, 1 H), 7.19-7.20 (m, 1 H), 7.88 (d, 1 H), 8.07 (s, 1 H), 8.32 (s, 1 H), 9.47 (s, 1 H) |

| Example | Structure | m/z | ¹H NMR (CDCl₃) |
|---|---|---|---|
| 25h | 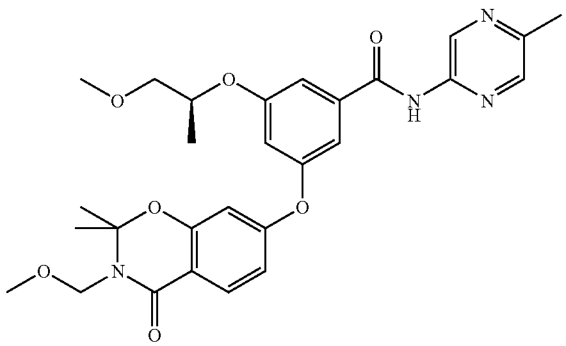 | 537 (M + H)⁺ | δ: 1.27 (d, 3 H), 1.65 (s, 6 H), 2.49 (s, 3 H), 3.32 (s, 3 H), 3.34 (s, 3 H), 3.40-3.54 (m, 2 H), 4.52-4.59 (m, 1 H), 5.01 (s, 2 H), 6.39 (d, 1 H), 6.63-6.65 (m, 1 H), 6.80 (t, 1 H), 7.11 (t, 1 H), 7.26 (t, 1 H), 7.87 (d, 1 H), 8.07 (s, 1 H), 8.32 (s, 1 H), 9.47 (d, 1 H) |
| 25i | 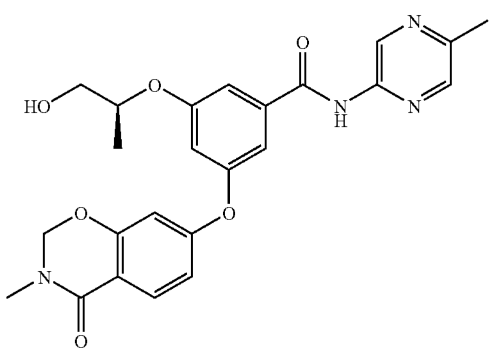 | 465 (M + H)⁺ | δ: 1.32 (d, 3 H), 2.12 (t, 1 H), 2.55 (s, 3 H), 3.10 (s, 3 H), 3.72-3.81 (m, 2 H), 4.52-4.61 (m, 1 H), 5.18 (s, 2 H), 6.54 (d, 1 H), 6.73-6.76 (m, 1 H), 6.83 (t, 1 H), 7.16 (t, 1 H), 7.33 (t, 1 H), 7.95 (d, 1 H), 8.14 (s, 1 H), 8.41 (s, 1 H), 9.53 (d, 1 H) |
| 25j | 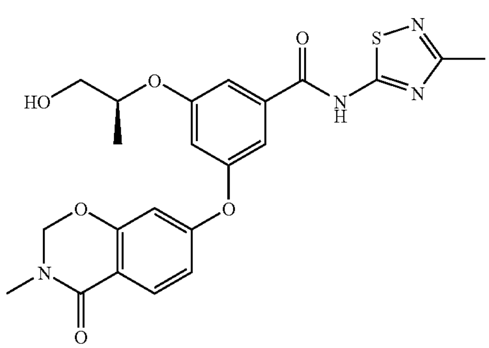 | 471 (M + H)⁺ | δ: 1.29 (d, 3 H), 2.46 (s, 3 H), 3.10 (s, 3 H), 3.73-3.80 (m, 2 H), 4.51-4.59 (m, 1 H), 5.17 (s, 2 H), 6.54 (d, 1 H), 6.69-6.71 (m, 1 H), 6.85 (t, 1 H), 7.20 (t, 1 H), 7.28 (t, 1 H), 7.92 (d, 1 H), 10.91 (s, 1 H) |

The preparations of 3-hydroxy-5-[(1S)-2-methoxy-(1-methylethyl)oxy]-N-(1-methyl-1H-pyrazol-3-yl)benzamide, 3-hydroxy-N-(1-methyl-1H-pyrazol-3-yl)-5-[(3S)-tetrahydrofuran-3-yloxy]benzamide and 3-hydroxy-5-{[(1S)-2-methoxy-(1-methylethyl)oxy}-N-(3-methyl-1,2,4-thiadiazol-2-yl)benzamide were described earlier. The preparation of 3-hydroxy-5-{[(1S)-1-methyl-2-(methyloxy)ethyl]oxy}-N-(5-methylpyrazin-2-yl)benzamide, used in Examples 25b, 25e and 25h is described below:

3-Hydroxy-5-{[(1S)-1-methyl-2-(methyloxy)ethyl]oxy}-N-(5-methylpyrazin-2-yl)benzamide

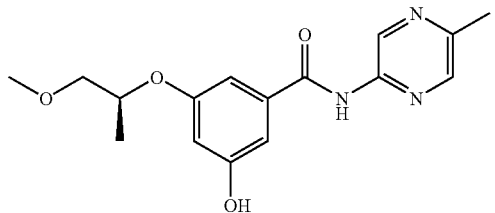

10% Palladium on charcoal (700 mg) was added to a solution of 3-{[(1S)-1-methyl-2-(methyloxy)ethyl]oxy}-N-(5-methylpyrazin-2-yl)-5-[(phenylmethyl)oxy]benzamide (7.0 g, 17.2 mmol) in ethanol (125 mL) and the mixture stirred at RT under a hydrogen atmosphere for 4 hours. The catalyst was removed by filtration and the ethanol evaporated in vacuo. The residue was crystallised from ethyl acetate to give the desired compound (4.22 g). $^1$H NMR δ (CDCl$_3$): 1.25 (d, 3H), 2.5 (s, 3H), 3.3 (s, 3H), 3.4-3.5 (m, 2H), 4.5 (m, 1H), 6.3 (br, 1H), 6.55 (s, 1H), 6.9 (s, 1H), 6.95 (s, 1H), 8.05 (s, 1H), 8.45 (s, 1H) and 9.5 (s, 1H). m/z 318 (M+H)$^+$.

3-{[(1S)-1-Methyl-2-(methyloxy)ethyl]oxy}-N-(5-methylpyrazin-2-yl)-5-[(phenylmethyl)oxy]benzamide

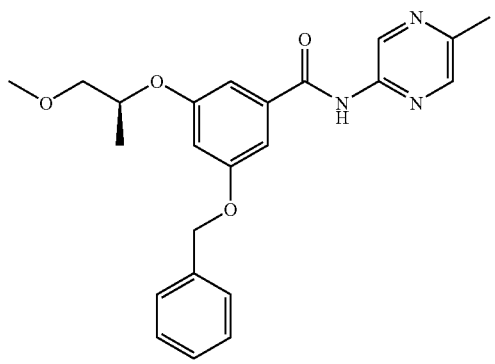

Oxalyl chloride (2.1 mL, 24.0 mmol) was added to a solution of 3-[(1S)-2-methoxy-(1-methylethyl)oxy]-5-{[phenylmethyl]oxy}benzoic acid (6.32 g, 20.0 mmol) in DCM (100 mL) and the mixture stirred at RT for 4 hours. The mixture was evaporated in vacuo to a residue, which was taken up in DCM (25 mL) and added to a stirred mixture of 2-amino-5-methylpyrazine (2.29 g, 21.0 mmol) and pyridine (1.94 mL, 24.0 mmol) in DCM (100 mL) at 5° C.-10° C. The mixture was stirred at RT for 18 hours, the DCM evaporated in vacuo. The residue was partitioned between water (50 mL) and ethyl acetate (150 mL), the organic layer washed with brine, dried (MgSO$_4$) and evaporated to a residue, which was chromatographed on silica, eluting with 50% ethyl acetate in isohexane, to give the desired compound (7.0 g). $^1$H NMR δ (CDCl$_3$): 1.3 (d, 3H), 2.5 (s, 3H), 3.3 (s, 3H), 3.4-3.5 (m, 2H), 4.5 (m, 1H), 5.0 (s, 2H), 6.7 (s, 1H), 7.0 (s, 1H), 7.05 (s, 1H), 7.35 (m, 5H), 8.05 (s, 1H), 8.3 (s, 1H) and 9.5 (s, 1H). m/z 408 (M+H)$^+$.

The preparation of 2-amino-5 methylpyrazine is described in the literature [*Tetrahedron Lett.* 2002, 9287].

The preparation of 3-[(1S)-2-methoxy-(1-methylethyl)oxy]-5-{[phenylmethyl]oxy}benzoic acid was described earlier.

The preparation of 3-hydroxy-N-(5-methylpyrazin-2-yl)-5-[(3S)-tetrahydrofuran-3-yloxy]benzamide, used in Example 25 g, is described below:

3-Hydroxy-N-(5-methylpyrazin-2-yl)-5-[(3S)-tetrahydrofuran-3-yloxy]benzamide

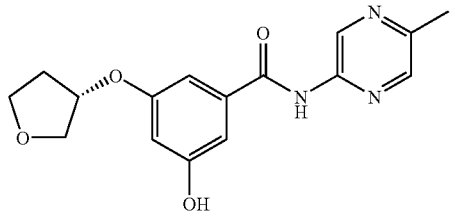

10% Palladium on charcoal (500 mg) was added to a solution of N-(5-methylpyrazin-2-yl)-3-[(phenylmethyl)oxy]-5-[(3S)-tetrahydrofuran-3-yloxy]benzamide (5.0 g, 12.34 mmol) in ethanol (50 mL) and THF (100 mL) and the mixture stirred under an atmosphere of hydrogen at RT for 16 hours. The mixture was filtered through Celite®, the solvents evaporated in vacuo to a residue which was crystallised from ethyl acetate to give the desired material (3.6 g). $^1$H NMR δ (d$_6$-DMSO): 2.0 (m, 1H), 2.25 (m, 1H), 2.5 (s, 3H), 3.75-3.95 (m, 4H), 5.1 (m, 1H), 6.5 (d, 1H), 7.0 (d, 1H), 7.05 (d, 1H), 8.35 (s, 1H), 9.25 (s, 1H), 9.75 (s, 1H), 10.8 (s, 1H); m/z 316 (M+H)$^+$.

N-(5-Methylpyrazin-2-yl)-3-[(phenylmethyl)oxy]-5-[(3S)-tetrahydrofuran-3-yloxy]benzamide

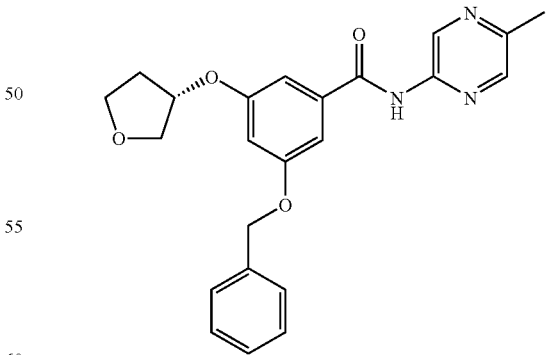

Oxalyl chloride (1.9 mL, 22.2 mmol) and DMF (1 drop) were added to a solution of 3-[(phenylmethyl)oxy]-5-[(3S)-tetrahydrofuran-3-yloxy]benzoic acid (5.8 g, 18.5 mmol) in DCM (100 mL) and the mixture stirred at RT for 16 hours. The mixture was evaporated in vacuo to a residue which was redissolved in DCM (25 mL) and added to a stirred mixture of 2-amino-5-methylpyrazine (2.22 g, 20.35 mmol) and pyridine (1.81 mL, 22.2 mmol) in DCM (100 mL) at 5° C.-10° C. The mixture was stirred at RT for 18 hours, the DCM evaporated in vacuo to give a residue which was partitioned between water (50 mL) and ethyl acetate (125 mL). The organic layer was washed with brine, dried (MgSO$_4$) and evaporated to a residue which was chromatographed on silica, eluting with 60% ethyl acetate in isohexane, to give the desired material (5.1 g). $^1$H NMR δ (CDCl$_3$): 2.1-2.2 (m, 2H), 2.5 (s, 3H), 3.8-3.95 (m, 4H), 4.9 (m, 1H), 5.0 (s, 2H), 6.6 (s, 1H), 6.95 (s, 1H), 7.05 (s, 1H), 7.35 (m, 5H), 8.05 (s, 1H), 8.3 (s, 1H), 9.5 (s, 1H); m/z 406 (M+H)$^+$.

3-[(Phenylmethyl)oxy]-5-[(3S)-tetrahydrofuran-3-yloxy]benzoic acid

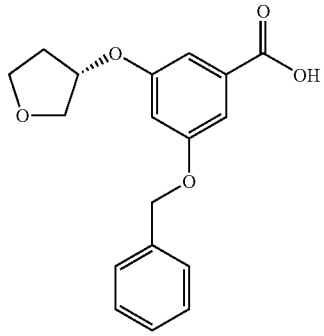

A solution of lithium hydroxide monohydrate (3.78 g; 90.0 mmol) in water (50 mL) was added to a solution of methyl 3-[(phenylmethyl)oxy]-5-[(3S)-tetrahydrofuran-3-yloxy] benzoate (10.0 g, 30 mmol) in THF (100 mL) and the mixture stirred at RT for 18 hours. The THF was removed in vacuo, the aqueous residue treated with 1M hydrochloric acid (90.0 mL) then extracted with ethyl acetate (3×100 mL). The combined organic extracts were washed with brine, dried (MgSO$_4$) and concentrated in vacuo to give the desired material (9.00 g). $^1$H NMR δ (CDCl$_3$): 2.0-2.2 (m, 2H), 3.7-3.95 (m, 4H), 4.85 (m, 1H), 5.0 (s, 2H), 6.65 (m, 1H), 7.15 (m, 1H), 7.25-7.4 (m, 6H); m/z 315 (M+H)$^+$.

Methyl 3-[(phenylmethyl)oxy]-5-[(3S)-tetrahydrofuran-3-yloxy]benzoate

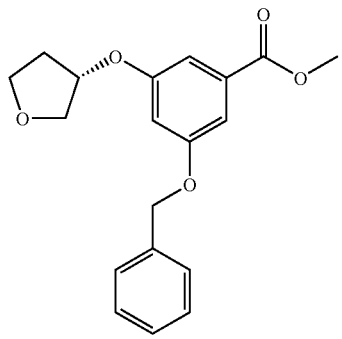

A mixture of methyl 3-hydroxy-5-{[phenylmethyl] oxy}benzoate (18.8 g, 72.75 mmol), (3R)-tetrahydrofuran-3-yl 4-methylbenzenesulfonate (18.5 g, 76.4 mmol) and potassium carbonate (20.08 g, 145.5 mmol) in butyronitrile (250 mL) was heated to 130° C. for 3 hours. The solvent was removed in vacuo and ethyl acetate added. The organics were washed with water (40 mL), 0.5M sodium hydroxide solution (40 mL), brine (40 mL), dried (MgSO$_4$), filtered and the solvent removed in vacuo. The residue was chromatographed on silica, eluting with a gradient of 0-5% methanol in DCM, to give the desired compound as a colourless oil (20.1 g). $^1$H NMR δ (CDCl$_3$): 2.08-2.26 (m, 2H), 3.78-4.01 (m, 4H), 3.90 (s, 3H), 4.92-4.96 (m, 1H), 5.08 (s, 2H), 6.69 (t, 1H), 7.15 (t, 1H), 7.29 (t, 1H), 7.34-7.44 (m, 5H); m/z 327 (M+H)$^+$ The preparations of methyl 3-hydroxy-5-{[phenylmethyl] oxy}benzoate and (3R)-tetrahydrofuran-3-yl 4-methylbenzenesulfonate were described earlier. The preparation of 3-hydroxy-5-{[(1S)-2-hydroxy-1-methylethyl]oxy}-N-(5-methylpyrazin-2-yl)benzamide, used in Example 25i, is described below:

3-Hydroxy-5-{[(1S)-2-hydroxy-1-methylethyl]oxy}-N-(5-methylpyrazin-2-yl)benzamide

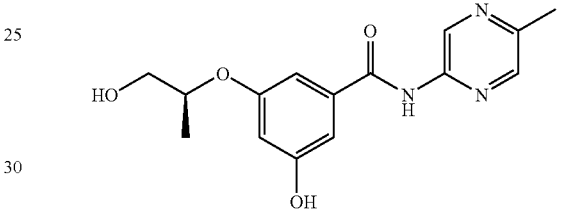

Iodotrimethylsilane (5.61 mL, 39.39 mmol) was added to 3-hydroxy-5-{[(1S)-1-methyl-2-(methyloxy)ethyl]oxy}-N-(5-methylpyrazin-2-yl)benzamide (2.5 g, 7.88 mmol) in acetonitrile (25 mL) and the reaction stirred at RT for 20 hours. Methanol (15 mL) was added and stirred for 1 hour then a saturated solution of sodium thiosulphate (10 mL) was added and stirred for a further 20 mins. The volatiles were removed in vacuo and the aqueous residue extracted into ethyl acetate (2×150 mL). The organics were washed with water (100 mL), brine (100 mL), dried (MgSO$_4$), and reduced in vacuo to give the desired compound as a white solid (2.03 g). $^1$H NMR δ (d$_6$-DMSO): 1.22 (d, 3H), 2.48 (s, 3H), 3.44-3.59 (m, 2H), 4.50 (sextet, 1H), 4.87 (t, 1H), 6.53 (t, 1H), 6.98 (s, 1H), 7.11 (s, 1H), 8.36 (s, 1H), 9.25 (s, 1H), 9.75 (s, 1H), 10.89 (s, 1H); m/z 304 (M+H)$^+$ The preparations of the aromatic fluorides are described below:

7-Fluoro-2,2,3-trimethyl-2,3-dihydro-4H-1,3-benzoxazin-4-one

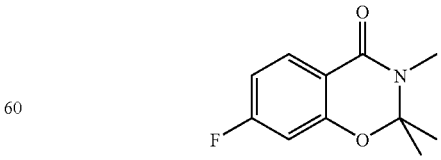

Sodium hydride (60% dispersion in oil) (112 mg, 2.82 mmol) was added to a solution of 7-fluoro-2,2-dimethyl-2,3-dihydro-4H-1,3-benzoxazin-4-one (0.5 g, 2.56 mmol) in THF (10 mL) at 0° C., under argon then the mixture allowed to warm to RT and methyl iodide (0.18 mL, 2.82 mmol) added. The reaction was stirred at RT for 24 hours, poured into ice/water (50 mL) and extracted into ethyl acetate (50 mL). The organic layer was washed with brine (50 mL), dried (MgSO$_4$), and the solvent removed in vacuo to give a yellow oil which was chromatographed on silica, eluting with 30-60% ethyl acetate in isohexane, to give the desired compound as a colourless oil (0.36 g). $^1$H NMR δ (CDCl$_3$): 1.65 (s, 6H), 3.08 (s, 3H), 6.61 (dd, 1H), 6.75-6.80 (m, 1H), 7.93-7.96 (m, 1H); m/z 210 (M+H)$^+$ 7-Fluoro-2,2-dimethyl-2,3-dihydro-4H-1,3-benzoxazin-4-one

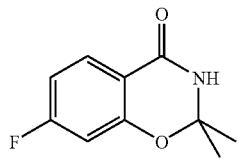

Pyridinium toluene-4-sulfonate (49 mg, 0.19 mmol) was added to a mixture of 4-fluoro-2-hydroxybenzamide (0.3 g, 1.93 mmol) in 2,2-dimethoxypropane (5 mL) and heated at 83° C. for 20 hours. The reaction mixture was reduced in vacuo and ethyl acetate (30 mL) added. The mixture was washed with 10% potassium carbonate solution (2×20 mL), brine (20 mL), dried (MgSO$_4$), and reduced in vacuo to give a white solid. The material was chromatographed on silica, eluting with 40-70% ethyl acetate in isohexane, to give the desired compound as a white solid (0.26 g).
$^1$H NMR δ (CDCl$_3$): 1.68 (s, 6H), 6.51 (s, 1H), 6.65 (d, 1H), 6.80 (t, 1H), 7.95 (t, 1H)

4-Fluoro-2-hydroxybenzamide

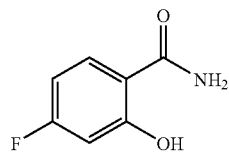

DMF (2 drops) was added to a mixture of 4-fluorosalicylic acid (5 g, 32.0 mmol) and oxalyl chloride (7.11 mL, 80.1 mmol) in THF (35 mL). The mixture was stirred for 2 hours then reduced in vacuo. The residue was dissolved in THF (20 mL) and added dropwise to concentrated ammonium hydroxide solution (30 mL) at 0° C. The reaction was stirred at RT for 20 hours and the THF removed in vacuo. The residue was acidified and a white solid was filtered off. The solid was dissolved in ethyl acetate (80 mL) and the solution washed with water (50 mL), saturated sodium bicarbonate solution (50 mL), dried (MgSO$_4$), and reduced in vacuo to give the desired compound as a yellow solid (2.4 g).
$^1$H NMR δ (d$_6$-DMSO): 6.70-6.76 (m, 2H), 7.90-7.95 (m, 2H), 8.37 (s, 1H), 13.50 (s, 1H); m/z 154 (M−H)$^−$ 7-Fluoro-3-methyl-2,3-dihydro-4H-1,3-benzoxazin-4-one

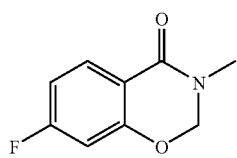

A mixture of 4-fluoro-2-hydroxy-N-methyl-benzamide (0.3 g, 1.77 mmol) in formaldehyde (37% aq. soln) (2 mL) and formic acid (2 mL) was refluxed for 1 hour then poured onto ice. The mixture was neutralised with sodium carbonate and extracted into chloroform (3×30 mL). The combined organics were dried (MgSO$_4$), and reduced in vacuo to give a white solid which was chromatographed on silica, eluting with 10-50% ethyl acetate in isohexane to give the desired compound as a white solid (0.24 g).
$^1$H NMR δ (CDCl$_3$): 3.12 (s, 3H), 5.21 (s, 2H), 6.69 (dd, 1H), 6.84 (td, 1H), 7.98 (dd, 1H)

4-Fluoro-2-hydroxy-N-methylbenzamide

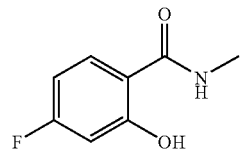

DMF (2 drops) was added to a mixture of 4-fluorosalicylic acid (2 g, 12.8 mmol) and oxalyl chloride (2.85 mL, 32.0 mmol) in THF (15 mL). The reaction was stirred for 2 hours then reduced in vacuo. The residue was dissolved in THF (10 mL) and added dropwise to 2M methylamine in THF (32 mL) at 0° C. The reaction was stirred at RT for 72 hours and the THF removed in vacuo. The residue was partitioned between ethyl acetate (80 mL) and water (80 mL). The aqueous layer was further extracted into ethyl acetate (80 mL) and the combined organics washed with brine (50 mL), dried (MgSO$_4$), and reduced in vacuo to give a white solid. The material was chromatographed on silica, eluting with 5-40% ethyl acetate in isohexane, to give the desired compound as a white solid (1.43 g).
$^1$H NMR δ (CDCl$_3$): 3.04 (d, 3H), 6.25 (s, 1H), 6.58 (td, 1H), 6.70 (dd, 1H), 7.34 (dd, 1H), 12.72 (s, 1H); m/z 170 (M+H)$^+$ 7-Fluoro-2,2-dimethyl-3-[(methyloxy)methyl]-2,3-dihydro-4H-1,3-benzoxazin-4-one

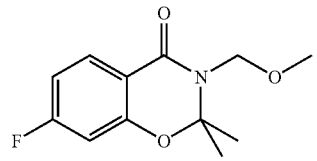

Sodium hydride (60% dispersion in oil) (45 mg, 1.13 mmol) was added to a solution of 7-fluoro-2,2-dimethyl-2,3-dihydro-4H-1,3-benzoxazin-4-one (0.2 g, 1.02 mmol) in THF (4 mL) at 0° C., under argon then allowed to warm to RT and chloromethylmethyl ether (0.086 mL, 1.13 mmol) added. The reaction was stirred at RT for 4 hours then poured into ice/water (50 mL) and extracted into ethyl acetate (50 mL). The organics were washed with brine (50 mL), dried (MgSO$_4$), and the solvent removed in vacuo. The crude oil was chromatographed on silica, eluting with 10-50% ethyl acetate in isohexane, to give the desired compound as a white solid (0.13 g). $^1$H NMR δ (CDCl$_3$): 1.66 (s, 6H), 3.31 (s, 3H), 5.00 (s, 2H), 6.53 (d, 1H), 6.67-6.72 (m, 1H), 7.89 (dd, 1H).

Example 26

3-[(2,2-Dimethyl-4-oxo-3,4-dihydro-2H-1,3-benzoxazin-7-yl)oxy]-N-(5-methylpyrazin-2-yl)-5-[(3S)-tetrahydrofuran-3-yloxy]benzamide

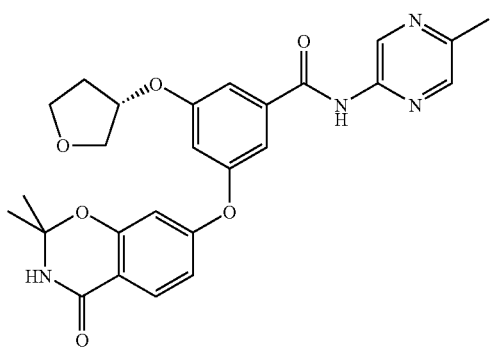

Trifluoroacetic acid (1 mL) was added to 3-({2,2-dimethyl-3-[(methyloxy)methyl]-4-oxo-3,4-dihydro-2H-1,3-benzoxazin-7-yl}oxy)-N-(5-methylpyrazin-2-yl)-5-[(3S)-tetrahydrofuran-3-yloxy]benzamide (54 mg, 0.1 mmol) and stirred at RT for 48 hours. DCM was added and the solvent removed in vacuo. Ethyl acetate (50 mL) was added and the mixture washed with water (50 mL), saturated sodium bicarbonate solution (50 mL), brine (50 mL), dried (MgSO$_4$), and reduced in vacuo. The crude oil was chromatographed on silica, eluting with 0-2.5% methanol in ethyl acetate, to give the desired compound as a white foam (14 mg).
$^1$H NMR δ (CDCl$_3$): 1.58 (s, 6H), 2.07-2.25 (m, 2H), 2.50 (s, 3H), 3.83-3.97 (m, 4H), 4.93-4.93 (m, 1H), 6.19 (s, 1H), 6.42 (d, 1H), 6.62-6.64 (m, 1H), 6.73 (t, 1H), 7.15 (t, 1H), 7.22 (t, 1H), 7.81 (d, 1H), 8.07 (s, 1H), 8.50 (s, 1H), 9.48 (s, 1H); m/z 491 (M+H)$^+$ The following compound was synthesised in an analogous fashion from 3-({2,2-dimethyl-3-[(methyloxy)methyl]-4-oxo-3,4-dihydro-2H-1,3-benzoxazin-7-yl}oxy)-N-(5-methylpyrazin-2-yl)-5-[(3S)-tetrahydrofuran-3-yloxy]benzamide.

Example 27

3-[(2-Methyl-1,1-dioxido-3,4-dihydro-2H-5,1,2-benzoxathiazepin-7-yl)oxy]-5-{[(1S)-1-methyl-2-(methyloxy)ethyl]oxy}-N-(5-methylpyrazin-2-yl)benzamide

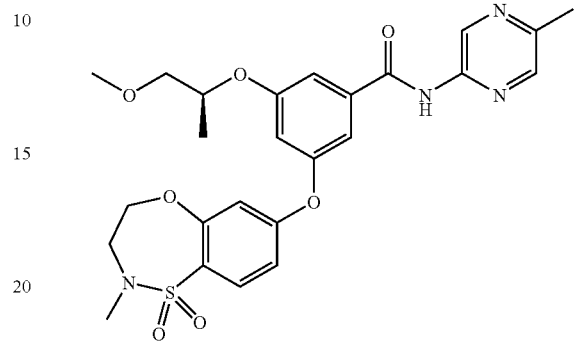

A mixture of 3-hydroxy-5-{[(is)-1-methyl-2-(methyloxy)ethyl]oxy}-N-(5-methylpyrazin-2-yl)benzamide (0.18 g, 0.57 mmol), N-(2-{[(1,1-dimethylethyl)(dimethyl)silyl]oxy}ethyl)-2,4-difluoro-N-methylbenzenesulfonamide (208 mg, 0.57 mmol) and potassium carbonate (157 mg, 1.13 mmol) in acetonitrile (5 mL) was stirred in a microwave reactor at 160° C. for 90 mins and at 150° C. for a further 5 hours. The mixture was reduced in vacuo and ethyl acetate (50 mL) added. The mixture was washed with water (50 mL), brine (50 mL), dried (MgSO$_4$), and reduced in vacuo to give a brown oil which was chromatographed on silica, eluting with 30-80% ethyl acetate in isohexane, to give the desired compound as a white foam (22 mg). $^1$H NMR δ (CDCl$_3$): 1.27 (d, 3H), 2.51 (s, 3H), 2.75 (s, 3H), 3.34 (s, 3H), 3.44-3.55 (m, 2H), 3.68 (t, 2H), 4.14 (t, 2H), 4.54-4.58 (m, 1H), 6.70 (d, 1H), 6.76-6.78 (m, 1H), 6.80 (t, 1H), 7.11 (t, 1H), 7.28 (t, 1H),

| Example | Structure | m/z | $^1$H NMR (CDCl$_3$) |
|---|---|---|---|
| 26a | 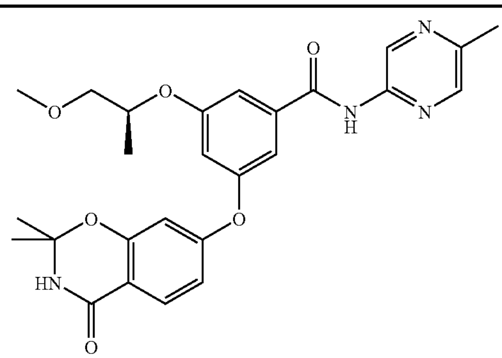 | 493 (M + H)$^+$ | δ: 1.27 (d, 3 H), 1.58 (s, 6 H), 2.49 (s, 3 H), 3.34 (s, 3 H), 3.42-3.54 (m, 2 H), 4.53-4.60 (m, 1 H), 6.27 (s, 1 H), 6.41 (d, 1 H), 6.61-6.63 (m, 1 H), 6.80 (t, 1 H), 7.14 (t, 1 H), 7.28 (t, 1 H), 7.80 (d, 1 H), 8.07 (s, 1 H), 8.50 (s, 1 H), 9.48 (s, 1 H) |

The preparations of 3-({2,2-dimethyl-3-[(methyloxy)methyl]-4-oxo-3,4-dihydro-2H-1,3-benzoxazin-7-yl}oxy)-N-(5-methylpyrazin-2-yl)-5-[(3S)-tetrahydrofuran-3-yloxy]benzamide and 3-({2,2-dimethyl-3-[(methyloxy)methyl]-4-oxo-3,4-dihydro-2H-1,3-benzoxazin-7-yl}oxy)-N-(5-methylpyrazin-2-yl)-5-[(3S)-tetrahydrofuran-3-yloxy]benzamide were described earlier.

7.74 (d, 1H), 8.10 (s, 1H), 8.37 (s, 1H), 9.50 (s, 1H); m/z 529 (M+H)$^+$

The following compound was synthesised in an analogous fashion from 3-hydroxy-5-{[(1S)-1-methyl-2-(methyloxy)ethyl]oxy}-N-(5-methylpyrazin-2-yl)benzamide and N-(2-{[(1,1-dimethylethyl)(dimethyl)silyl]oxy}ethyl)-2,4-difluorobenzenesulfonamide

| Example | Structure | m/z | ¹H NMR (CDCl₃) |
|---|---|---|---|
| 27a | 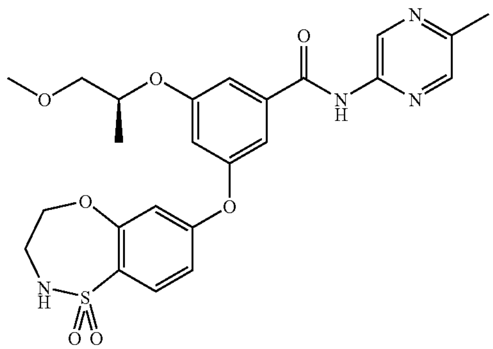 | 515 (M + H)⁺ | δ: 1.33 (d, 3 H), 2.55 (s, 3 H), 3.40 (s, 3 H), 3.50-3.61 (m, 2 H), 3.64-3.68 (m, 2 H), 4.23-4.25 (m, 2 H), 4.58-4.65 (m, 1 H), 4.86 (t, 1 H), 6.75 (d, 1 H), 6.79-6.81 (m, 1 H), 6.84 (t, 1 H), 7.15 (t, 1 H), 7.33 (t, 1 H), 7.79 (d, 1 H), 8.12 (s, 1 H), 8.42 (s, 1 H), 9.51 (d, 1 H) |

The preparation of 3-hydroxy-5-{[(S)-1-methyl-2-(methyloxy)ethyl]oxy}-N-(5-methylpyrazin-2-yl)benzamide was described earlier The preparation of N-(2-{[(1,1-dimethylethyl)(dimethyl)silyl]oxy}ethyl)-2,4-difluoro-N-methylbenzenesulfonamide is described below.

N-(2-{[(1,1-Dimethylethyl)(dimethyl)silyl]oxy}ethyl)-2,4-difluoro-N-methylbenzenesulfonamide

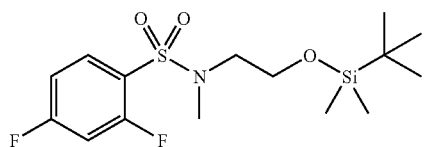

2,4-Difluorobenzenesulfonyl chloride (1 g, 4.70 mmol) in DCM (2 mL) was added slowly to a solution of (2-{[tert-butyl(dimethyl)silyl]oxy}ethyl)methylamine (980 mg, 5.17 mmol) in DCM (65 mL) and 10% sodium hydroxide solution (65 mL) at 0° C. The reaction was allowed to warm to RT and stirred for 20 hours. The DCM layer was separated and the aqueous re-extracted into DCM (2×50 mL). The combined organics were washed with brine (80 mL), dried (MgSO₄), and reduced in vacuo to give the desired compound as a colourless oil (0.7 g). ¹H NMR δ (CDCl₃): 0.00 (s, 6H), 0.83 (s, 9H), 2.91 (s, 3H), 3.24 (t, 2H), 3.73 (t, 2H), 6.87-6.96 (m, 2H), 7.82-7.88 (m, 1H)

N-(2-{[(1,1-dimethylethyl)(dimethyl)silyl]oxy}ethyl)-2,4-difluorobenzenesulfonamide was prepared in an analogous fashion.

| Structure | NMR |
|---|---|
| | ¹H NMR δ (CDCl₃): 0.00 (s, 6 H), 0.84 (s, 9 H), 3.06 (q, 2 H), 3.62 (t, 2 H), 5.10 (t, 1 H), 6.91-7.01 (m, 2 H), 7.86-7.92 (m, 1 H) |

The preparation of (2-{[tert-butyl(dimethyl)silyl]oxy}ethyl)methylamine was described earlier.

2-{[(1,1-Dimethylethyl)(dimethyl)silyl]oxy}ethanamine was prepared in an analogous fashion.

| Structure | NMR |
|---|---|
| | ¹H NMR δ (CDCl₃): 0.00 (s, 6 H), 0.84 (s, 9 H), 1.24 (s, 2 H), 2.70 (t, 2 H), 3.56 (t, 2 H) |

Example 28

3-{[(1S)-1-Methyl-2-(methyloxy)ethyl]oxy}-5-[(3-methyl-4-oxo-3,4-dihydro-2H-1,3-benzoxazin-7-yl)oxy]-N-1H-pyrazol-3-ylbenzamide

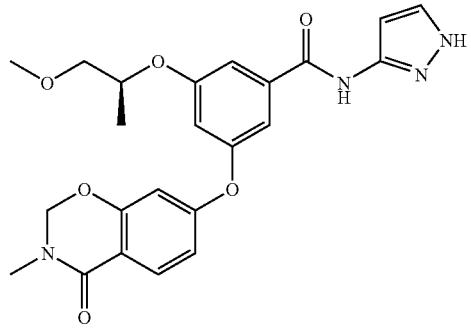

Trifluoroacetic acid (2 mL) was added to a solution of 1,1-dimethylethyl 3-[({3-{[(1S)-1-methyl-2-(methyloxy)ethyl]oxy}-5-[(3-methyl-4-oxo-3,4-dihydro-2H-1,3-benzoxazin-7-yl)oxy]phenyl}carbonyl)amino]-1H-pyrazole-1-carboxylate (190 mg, 0.34 mmol) in DCM (12 mL) and stirred at RT for 2 hours. The solvent was removed in vacuo and DCM (20 mL) added and the mixture washed with water (20 mL), saturated sodium bicarbonate solution (20 mL), brine (20 mL), dried (MgSO$_4$), and reduced in vacuo to give the desired compound as a white solid (54 mg). $^1$H NMR δ (CDCl$_3$): 1.32 (d, 3H), 3.09 (s, 3H), 3.40 (s, 3H), 3.47-3.63 (m, 2H), 4.56-4.63 (m, 1H), 5.16 (s, 2H), 6.52 (d, 1H), 6.71-6.74 (m, 1H), 6.81 (t, 1H), 6.85 (s, 1H), 7.18 (s, 1H), 7.37 (s, 1H), 7.49 (s, 1H), 7.92 (d, 1H), 9.46 (s, 1H), 9.46 (s, 1H); m/z 453 (M+H)$^+$ The following compounds were synthesised in an analogous fashion.

The preparation of 1,1-dimethylethyl 3-[({3-{[(1S)-1-methyl-2-(methyloxy)ethyl]oxy}-5-[(3-methyl-4-oxo-3,4-dihydro-2H-1,3-benzoxazin-7-yl)oxy]phenyl}carbonyl)amino]-1H-pyrazole-1-carboxylate is described below.

1,1-Dimethylethyl 3-[({3-{[(1S)-1-methyl-2-(methyloxy)ethyl]oxy}-5-[(3-methyl-4-oxo-3,4-dihydro-2H-1,3-benzoxazin-7-yl)oxy]phenyl}carbonyl)amino]-1H-pyrazole-1-carboxylate

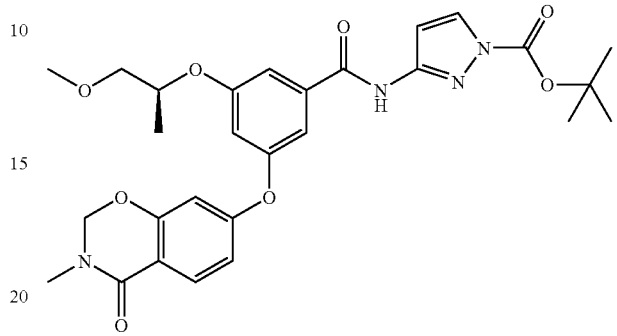

1-Chloro-N,N,2-trimethyl-1-propenylamine (0.13 mL, 0.97 mmol) was added to a solution of 3-{[(1S)-1-methyl-2-(methyloxy)ethyl]oxy}-5-[(3-methyl-4-oxo-3,4-dihydro-2H-1,3-benzoxazin-7-yl)oxy]benzoic acid (0.25 g, 0.65 mmol) in DCM (10 mL) and stirred for 1 hour. 1,1-Dimethylethyl 3-amino-1H-pyrazole-1-carboxylate (0.18 g, 0.97 mmol) then pyridine (0.11 mL, 1.29 mmol) were added and the reaction stirred for a further 45 mins then reduced in vacuo and partitioned between ethyl acetate (50 mL) and water (50 mL). The aqueous layer was further extracted into ethyl acetate (50 mL) and the combined organics washed with water (50 mL), brine (50 mL), dried (MgSO$_4$), and reduced in vacuo. The crude oil was chromatographed on silica, eluting with 40-100% ethyl acetate in isohexane, to give the desired

| Example | Structure | m/z | $^1$H NMR (CDCl$_3$) |
|---------|-----------|-----|----------------------|
| 28a | 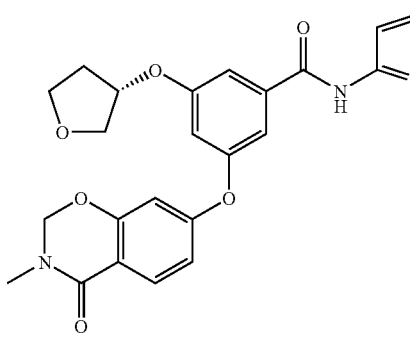 | 451 (M + H)$^+$ | δ: 2.11-2.29 (m, 2 H), 3.10 (s, 3 H), 3.86-4.00 (m, 4 H), 4.93-4.99 (m, 1 H), 5.17 (s, 2 H), 6.53 (d, 1 H), 6.72 (d, 1 H), 6.74-6.75 (m, 1 H), 6.83 (s, 1 H), 7.15 (s, 1 H), 7.26-7.27 (m, 1 H), 7.51 (d, 1 H), 7.94 (d, 1 H), 8.92 (s, 1 H), 10.00 (s, 1 H) |
| 28b | 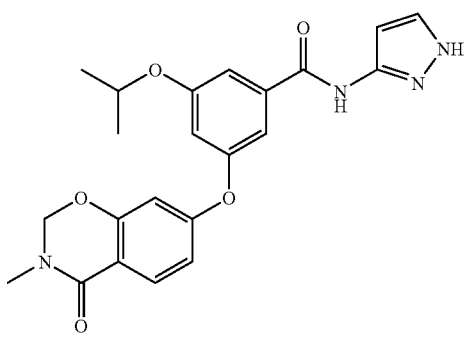 | 423 (M + H)$^+$ | δ: 1.35 (d, 6 H), 3.08 (s, 3 H), 4.55-4.61 (m, 1 H), 5.15 (s, 2 H), 6.51 (d, 1 H), 6.70-6.73 (m, 1 H), 6.75 (t, 1 H), 6.83 (s, 1 H), 7.16 (s, 1 H), 7.16 (s, 1 H), 7.49 (d, 1 H), 7.91 (d, 1 H), 9.40 (s, 1 H), 10.25 (s, 1 H) | compound as a golden oil (0.19 g). ¹H NMR δ (CDCl₃): 1.32 (d, 3H), 1.63 (s, 9H), 3.10 (s, 3H), 3.40 (s, 3H), 3.48-3.60 (m, 2H), 4.56-4.60 (m, 1H), 5.18 (s, 2H), 6.54 (d, 1H), 6.73-6.76 (m, 1H), 6.83 (t, 1H), 7.07-7.08 (m, 2H), 7.25-7.26 (m, 1H), 7.95 (d, 1H), 8.00 (d, 1H), 8.65 (s, 1H); m/z 551 (M−H)⁻

1,1-Dimethylethyl 3-[({3-[(3-methyl-4-oxo-3,4-dihydro-2H-1,3-benzoxazin-7-yl)oxy]-5-[(3S)-tetrahydrofuran-3-yloxy]phenyl}carbonyl)amino]-1H-pyrazole-1-carboxylate and 1,1-dimethylethyl 3-[({3-[(1-methylethyl)oxy]-5-[(3-methyl-4-oxo-3,4-dihydro-2H-1,3-benzoxazin-7-yl)oxy]phenyl}carbonyl)amino]-1H-pyrazole-1-carboxylate were prepared in an analogous fashion.

allowed to warm to room temperature and stirred for a further 2 h. The reaction was taken up in saturated aqueous sodium hydrogencarbonate (50 mL) and ethyl acetate (100 mL). The organic layer was separated then dried (MgSO₄), filtered and evaporated. Purification by column chromatography (eluting with 1:1 ethyl acetate:hexanes to neat ethyl acetate) afforded the title compound (117 mg) as a white solid. ¹H NMR δ (CDCl₃): 1.62 (s, 9H), 4.00 (br. s, 2H), 5.81 (d, 1H), 7.82 (d, 1H)

The preparation of 3-{[(S)-1-methyl-2-(methyloxy)ethyl]oxy}-5-[(3-methyl-4-oxo-3,4-dihydro-2H-1,3-benzoxazin-7-yl)oxy]benzoic acid is described below:

| Structure | m/z | ¹H NMR (CDCl₃) |
|---|---|---|
| | 549 (M − H)⁻ | δ: 1.64 (s, 9 H), 2.10-2.29 (m, 2 H), 3.10 (s, 3 H), 3.90-4.01 (m, 4 H), 4.93-5.00 (m, 1 H), 5.19 (s, 2 H), 6.55 (d, 1 H), 6.73-6.78 (m, 2 H), 7.06-7.09 (m, 2 H), 7.18-7.20 (m, 1 H), 7.96 (d, 1 H), 8.01 (d, 1 H), 8.62 (s, 1 H) |
| | 521 (M − H)⁻ | δ: 1.35 (d, 6 H), 1.63 (s, 9 H), 3.10 (s, 3 H), 4.55-4.61 (m, 1 H), 5.18 (s, 2 H), 6.54 (d, 1 H), 6.73-6.77 (m, 2 H), 7.05 (t, 1 H), 7.08 (d, 1 H), 7.20 (t, 1 H), 7.95 (d, 1 H), 8.00 (d, 1 H), 8.60 (s, 1 H) |

The preparation of 1,1-dimethylethyl 3-amino-1H-pyrazole-1-carboxylate is described below.

1,1-Dimethylethyl 3-amino-1H-pyrazole-1-carboxylate

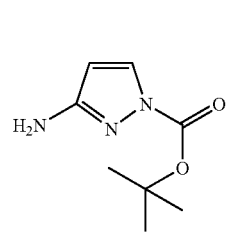

1H-Pyrazol-3-amine (428 mg, 5.15 mmol) was dissolved in DMF (5 mL) at 0° C. and treated with sodium hydride (206 mg, 5.15 mmol) followed by stirring for a further 30 min. Warmed di-tert-butyl dicarbonate (1.12 g, 5.15 mmol) was then slowly added via syringe over 5 min and the reaction was 3-{[(1S)-1-Methyl-2-(methyloxy)ethyl]oxy}-5-[(3-methyl-4-oxo-3,4-dihydro-2H-1,3-benzoxazin-7-yl)oxy]benzoic acid

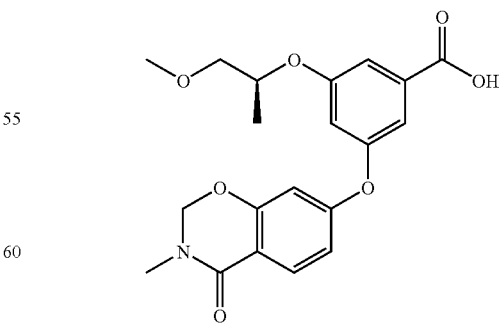

A mixture of 3-hydroxy-5-{[(1S)-1-methyl-2-(methyloxy)ethyl]oxy}benzoic acid (175 mg, 0.77 mmol), 7-fluoro-3-methyl-2,3-dihydro-4H-1,3-benzoxazin-4-one (141 mg, 0.77 mmol) and potassium carbonate (321 mg, 2.32 mmol) in acetonitrile (5 mL) was stirred in a microwave reactor at 160° C. for 16 hours then reduced in vacuo and ethyl acetate (50 mL) added. The mixture was washed with water (50 mL), the aqueous layer acidified with 1M citric acid and extracted into ethyl acetate (2×50 mL). The combined organics were washed with brine (50 mL), dried (MgSO$_4$), and reduced in vacuo to give the desired compound as a brown oil (0.24 g). m/z 453 (M+H)$^+$ 3-Hydroxy-5-{[(1S)-1-methyl-2-(methyloxy)ethyl]oxy}benzoic acid

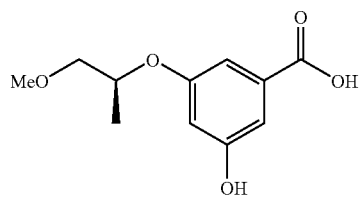

3-[(1S)-2-Methoxy-(1-methylethyl)oxy]-5-{[phenylmethyl]oxy}benzoic acid (25.2 g 79.7 mmol) was dissolved in ethanol (200 mL) and the reaction was blanketed with argon. 10% Palladium on charcoal (2.0 g) was added and the reaction vessel was flushed twice with hydrogen gas and allowed to stir under an atmosphere of hydrogen for 15 hours. The catalyst was filtered off and the volatiles removed in vacuo to give the product as a sticky gum which slowly crystallised on standing (17.3 g).

$^1$H NMR δ (CDCl$_3$): 1.21 (d, 3H), 3.29 (s, 3H), 3.43 (dd, 1H), 3.48 (dd, 1H), 4.55 (m, 1H), 6.55 (t, 1H), 6.91 (t, 1H), 6.95 (t, 1H), 9.70 (s, 1H), 12.77 (s, 1H); m/z 225 (M–H)$^-$

The preparation of 3-[(1S)-2-methoxy-(1-methylethyl)oxy]-5-{[phenylmethyl]oxy}benzoic acid was described earlier.

The preparation of 3-[(3-methyl-4-oxo-3,4-dihydro-2H-1,3-benzoxazin-7-yl)oxy]-5-[(3S)-tetrahydrofuran-3-yloxy]benzoic acid is described below.

3-[(3-Methyl-4-oxo-3,4-dihydro-2H-1,3-benzoxazin-7-yl)oxy]-5-[(3S)-tetrahydrofuran-3-yloxy]benzoic acid

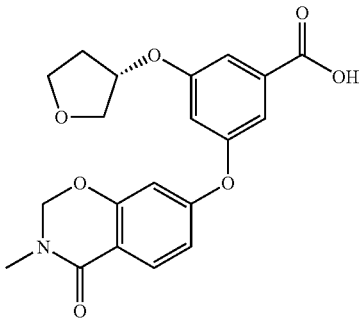

Lithium hydroxide monohydrate (13 mg, 0.3 mmol) in water (2.5 mL) was added to a solution of methyl 3-[(3-methyl-4-oxo-3,4-dihydro-2H-1,3-benzoxazin-7-yl)oxy]-5-[(3S)-tetrahydrofuran-3-yloxy]benzoate (0.12 g, 0.3 mmol) in THF (5 mL) and stirred at RT for 20 hours. The THF was removed in vacuo and the aqueous layer was washed with ethyl acetate (50 mL) to remove any impurities. The aqueous layer was acidified and extracted into ethyl acetate (2×50 mL), washed with brine (50 mL), dried (MgSO$_4$), and the solvent removed in vacuo to give the desired compound as a white solid (110 mg).

$^1$H NMR δ (CDCl$_3$): 2.13-2.30 (m, 2H), 3.11 (s, 3H), 3.89-4.04 (m, 4H), 4.94-5.00 (m, 1H), 5.17 (s, 2H), 6.53 (d, 1H), 6.72-6.74 (m, 1H), 6.82 (t, 1H), 7.37-7.39 (m, 2H), 7.95 (d, 1H); m/z 386 (M+H)$^+$

3-[(1-Methylethyl)oxy]-5-[(3-methyl-4-oxo-3,4-dihydro-2H-1,3-benzoxazin-7-yl)oxy]benzoic acid was prepared in an analogous fashion.

| Structure | m/z | $^1$H NMR (CDCl$_3$) |
|---|---|---|
| 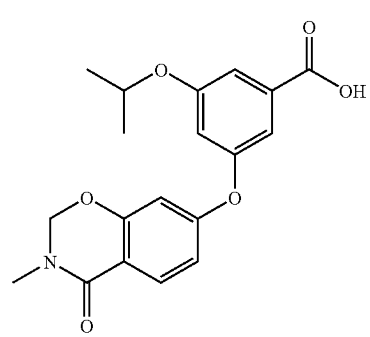 | 358 (M + H)$^+$ | δ: 1.35 (d, 6 H), 3.11 (s, 3 H), 4.59 (septet, 1 H), 5.17 (s, 2 H), 6.53 (d, 1 H), 6.72-6.75 (m, 1 H), 6.82 (t, 1 H), 7.33-7.34 (m, 1 H), 7.43-7.44 (m, 1 H), 7.94 (d, 1 H) |

The preparation of methyl 3-[(3-methyl-4-oxo-3,4-dihydro-2H-1,3-benzoxazin-7-yl)oxy]-5-[(3S)-tetrahydrofuran-3-yloxy]benzoate is described below.

Methyl 3-[(3-methyl-4-oxo-3,4-dihydro-2H-1,3-benzoxazin-7-yl)oxy]-5-[(3S)-tetrahydrofuran-3-yloxy]benzoate

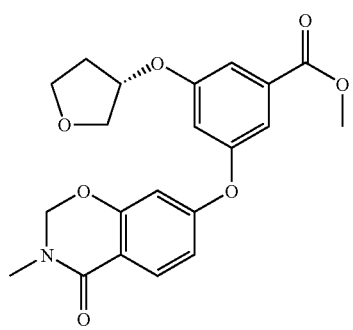

A mixture of methyl 3-hydroxy-5-[(3S)-tetrahydrofuran-3-yloxy]benzoate (184 mg, 0.77 mmol), 7-fluoro-3-methyl-2,3-dihydro-4H-1,3-benzoxazin-4-one (140 mg, 0.77 mmol) and potassium carbonate (214 mg, 1.54 mmol) in acetonitrile (5 mL) was stirred in a microwave reactor at 160° C. for 10 hours then reduced in vacuo and ethyl acetate (50 mL) added. The organics were washed with brine (50 mL), dried (MgSO$_4$), and reduced in vacuo and the crude oil purified by chromatography on silica, eluting with 30%-80% ethyl acetate in isohexane, to give the desired compound as a colourless oil (0.12 g).
$^1$H NMR δ (CDCl$_3$): 2.10-2.29 (m, 2H), 3.10 (s, 3H), 3.87-4.03 (m, 4H), 3.90 (s, 3H), 4.94-4.98 (m, 1H), 5.17 (s, 2H), 6.51 (d, 1H), 6.71-6.73 (m, 1H), 6.78 (t, 1H), 7.31-7.32 (m, 1H), 7.34-7.35 (m, 1H), 7.93 (d, 1H); m/z 400 (M+H)$^+$

Methyl 3-[(1-methylethyl)oxy]-5-[(3-methyl-4-oxo-3,4-dihydro-2H-1,3-benzoxazin-7-yl)oxy]benzoate was made in an analogous fashion.

The preparation of methyl 3-hydroxy-5-[(3S)-tetrahydrofuran-3-yloxy]benzoate is described below.

Methyl 3-hydroxy-5-[(3S)-tetrahydrofuran-3-yloxy]benzoate

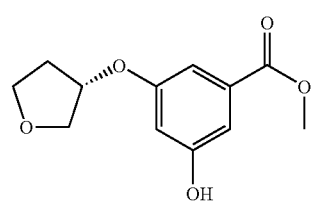

10% Palladium on carbon (1.2 g) was added to a mixture of methyl 3-[(phenylmethyl)oxy]-5-[(3S)-tetrahydrofuran-3-yloxy]benzoate (12 g, 36.54 mmol), in ethanol (80 mL) and THF (80 mL) in an argon filled flask. The flask was evacuated and the atmosphere replaced with hydrogen. The mixture was stirred for 20 hours, filtered through Celite® and the solvent removed in vacuo to give the desired compound as a white solid (8.41 g).
$^1$H NMR δ (CDCl$_3$): 2.11-2.31 (m, 2H), 3.92 (s, 3H), 3.94-4.10 (m, 4H), 4.98-5.01 (m, 1H), 6.57 (s, 1H), 6.65 (t, 1H), 7.10-7.12 (m, 1H), 7.18-7.20 (m, 1H); m/z 237 (M−H)$^−$ The preparation of methyl 3-[(phenylmethyl)oxy]-5-[(3S)-tetrahydrofuran-3-yloxy]benzoate was described earlier.

Example 29

3-[(3-Methyl-4-oxo-3,4-dihydro-2H-1,3-benzoxazin-7-yl)oxy]-N-(5-methylpyrazin-2-yl)-5-[(3S)-tetrahydrofuran-3-yloxy]benzamide

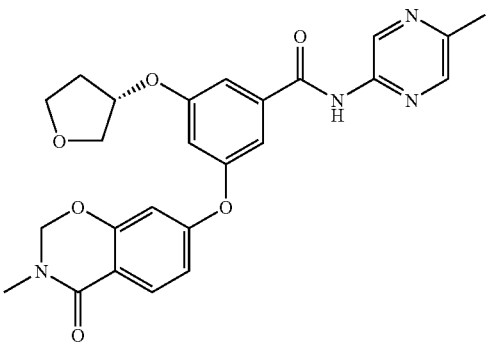

| Structure | m/z | $^1$NMR (CDCl$_3$) |
|---|---|---|
| 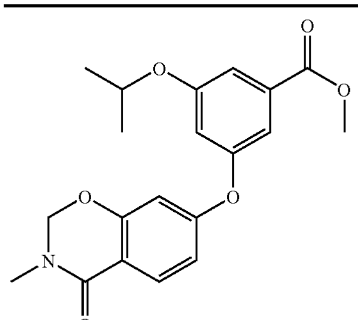 | 372 (M + H)$^+$ | δ: 1.34 (d, 6 H), 3.09 (s, 3 H), 3.89 (s, 3 H), 4.55-4.61 (m, 1 H), 5.16 (s, 2 H), 6.51 (d, 1 H), 6.71-6.73 (m, 1 H), 6.77 (t, 1 H), 7.26-7.28 (m, 1 H), 7.38-7.39 (m, 1 H), 7.93 (d, 1 H) |

Cesium carbonate (489 mg, 1.5 mmol) was added to a solution of 3-hydroxy-N-(5-methylpyrazin-2-yl)-5-[(3S)-tetrahydrofuran-3-yloxy]benzamide (157 mg, 0.5 mmol) and 7-fluoro-3-methyl-2,3-dihydro-4H-1,3-benzoxazin-4-one (100 mg, 0.55 mmol) in acetonitrile (5 mL) and the stirred mixture heated at 160° C. in a microwave reactor for 18 hours. The mixture was cooled to RT and pressure, the acetonitrile removed in vacuo and the residue partitioned between water (25 mL) and ethyl acetate (50 mL). The organic layer was washed with brine, dried (MgSO$_4$) and evaporated to a residue which was chromatographed on silica, eluting with ethyl acetate, to give a solid which was crystallised from ether to give the desired material (53 mg).
$^1$H NMR δ (CDCl$_3$): 2.1-2.2 (m, 2H), 2.5 (s, 3H), 3.0 (s, 3H), 3.85-3.95 (m, 2H), 3.95 (d, 2H), 4.9 (m, 1H), 5.1 (s, 2H), 6.45 (d, 1H), 6.65 (d, 1H), 6.7 (d, 1H), 7.05 (d, 1H), 7.2 (d, 1H), 7.9 (m, 1H), 8.1 (s, 1H), 8.4 (s, 1H), 9.45 (s, 1H); m/z 477 (M+H)$^+$.

The preparations of 7-fluoro-3-methyl-2,3-dihydro-4H-1,3-benzoxazin-4-one and 3-hydroxy-N-(5-methylpyrazin-2-yl)-5-[(3S)-tetrahydrofuran-3-yloxy]benzamide were described earlier.

Example 30

3-[(9-Chloro-4-methyl-5-oxo-2,3,4,5-tetrahydro-1,4-benzoxazepin-8-yl)oxy]-N-(5-methylpyrazin-2-yl)-5-[(3S)-tetrahydrofuran-3-yloxy]benzamide

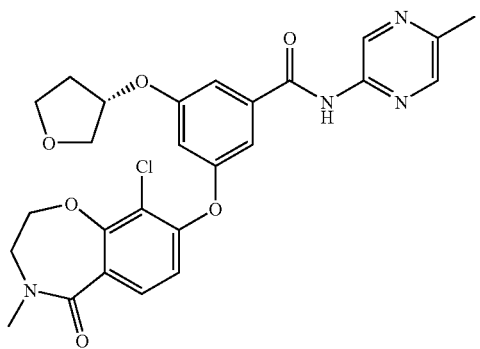

Cesium carbonate (489 mg, 1.5 mmol) was added to a solution of 3-hydroxy-N-(5-methylpyrazin-2-yl)-5-[(3S)-tetrahydro-3-yloxy]benzamide (157 mg, 0.5 mmol) and 9-chloro-8-fluoro-4-methyl-3,4-dihydro-1,4-benzoxazepin-5(2H)-one (200 mg, 0.55 mmol) in acetonitrile (5 mL) and the stirred mixture heated at 160° C. in a microwave reactor for 8 hours. The mixture was cooled to RT and pressure, the acetonitrile removed in vacuo and the residue partitioned between water (25 mL) and ethyl acetate (50 mL). The organic layer was washed with brine, dried (MgSO$_4$) and evaporated to a residue which was chromatographed on silica, eluting with ethyl acetate, to give the desired material (59 mg). $^1$H NMR δ (CDCl$_3$): 2.1-2.2 (m, 2H), 2.5 (s, 3H), 3.2 (s, 3H), 3.5 (t, 2H), 3.85-3.95 (m, 2H), 3.95 (d, 2H), 4.5 (t, 2H), 4.9 (m, 1H), 6.6 (s, 1H), 6.75 (d, 1H), 7.0 (s, 1H), 7.15 (s, 1H), 7.75 (d, 1H), 8.05 (s, 1H), 8.35 (s, 1H), 9.45 (s, 1H); m/z 525 (M+H)$^+$.

The preparations of 3-hydroxy-N-(5-methylpyrazin-2-yl)-5-[(3S)-tetrahydrofuran-3-yloxy]benzamide and 9-chloro-8-fluoro-4-methyl-3,4-dihydro-1,4-benzoxazepin-5(2H)-one were described earlier.

Example 31

N-(5-Methylpyrazin-2-yl)-3-[(1-oxo-1,2,3,4-tetrahydroisoquinolin-6-yl)oxy]-5-[(3S)-tetrahydrofuran-3-yloxy]benzamide

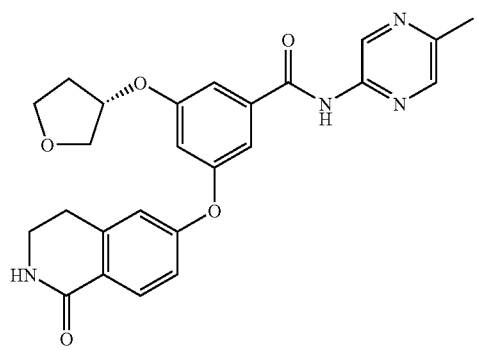

Cesium carbonate (812 mg, 2.50 mmol) was added to a solution of 3-hydroxy-N-(5-methylpyrazin-2-yl)-5-[(3S)-tetrahydrofuran-3-yloxy]benzamide (262 mg, 0.83 mmol), 6-bromo-3,4-dihydro-2H-isoquinolin-1-one (226 mg, 1.0 mmol), copper (I) iodide (158 mg, 0.83 mmol) and 2,2,6,6-tetramethyl-3,5-heptanedione (0.7 mL, 3.3 mmol) in NMP (9 mL) and the stirred mixture heated at 160° C. in a microwave reactor for 8 hours. The reaction mixture was filtered through diatomaceous earth and the filter pad washed thoroughly with DCM and methanol. The filtrate was concentrated in vacuo, water (20 mL) was added to the residue and the mixture extracted with ethyl acetate (3×50 mL). The combined organic phases were washed with water (2×10 mL), brine (20 mL), dried (MgSO$_4$) and evaporated in vacuo. The crude product was chromatographed on silica, eluting with a gradient of 0-5% methanol in DCM, to give the desired compound a white solid (190 mg). $^1$H NMR δ (CDCl$_3$): 2.17 (1H, m), 2.22-2.29 (1H, m), 2.56 (3H, s), 2.94-3.02 (2H, m), 3.49-3.59 (2H, m), 3.90-4.01 (4H, m), 5.00 (1H, s), 6.01 (1H, s), 6.77-6.80 (1H, m), 6.83 (1H, s), 6.96 (1H, d), 7.16 (1H, s), 7.26 (1H, d), 8.06 (1H, d), 8.15 (1H, s), 8.49 (1H, s), 9.54 (1H, s); m/z 461 (M+H)$^+$, 459 (M–H)$^-$ The preparation of 3-hydroxy-N-(5-methylpyrazin-2-yl)-5-[(3S)-tetrahydrofuran-3-yloxy]benzamide was described earlier.

Example 32

3-[(4-Methyl-5-oxo-2,3,4,5-tetrahydro-1,4-benzoxazepin-8-yl)oxy]-N-1H-pyrazol-3-yl-5-[(3S)-tetrahydrofuran-3-yloxy]benzamide

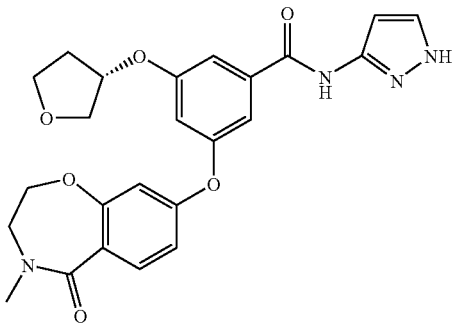

1,1-Dimethylethyl 3-[({3-[(9-chloro-4-methyl-5-oxo-2,3,4,5-tetrahydro-1,4-benzoxazepin-8-yl)oxy]-5-[(3S)-tetrahydrofuran-3-yloxy]phenyl}carbonyl)amino]-1H-pyrazole-1-carboxylate (107 mg, 0.17 mmol) was dissolved in ethanol (4 mL) and ammonium formate (125 mg, 1.7 mmol) was added in one portion. The reaction was blanketed with argon and 10% palladium on charcoal (30 mg) was added. The mixture was heated to 140° C. for 15 minutes in a microwave reactor then the mixture filtered through diatomaceous earth, washed well with ethanol and evaporated in vacuo. The crude product was chromatographed on silica, eluting with a gradient of 0-10% methanol in DCM, to give the desired compound as a white foam (60 mg). $^1$H NMR δ (CDCl$_3$): 2.12-2.29 (2H, m), 3.21 (3H, s), 3.57-3.60 (2H, m), 3.88-4.02 (5H, m), 4.41 (2H, t), 4.99 (1H, m), 6.58 (1H, d), 6.70-6.75 (1H, m), 6.76-6.79 (1H, m), 6.81 (1H, d), 7.19 (1H, s), 7.27 (1H, s), 7.51 (1H, d), 7.85 (1H, d), 9.23 (1H, s); m/z 465 (M+H)$^+$, 463 (M−H)$^−$ The preparation of 1,1-dimethylethyl 3-[({3-[(9-chloro-4-methyl-5-oxo-2,3,4,5-tetrahydro-1,4-benzoxazepin-8-yl)oxy]-5-[(3S)-tetrahydrofuran-3-yloxy]phenyl}carbonyl)amino]-1H-pyrazole-1-carboxylate is described below.

1,1-Dimethylethyl 3-[({3-[(9-chloro-4-methyl-5-oxo-2,3,4,5-tetrahydro-1,4-benzoxazepin-8-yl)oxy]-5-[(3S)-tetrahydrofuran-3-yloxy]phenyl}carbonyl)amino]-1H-pyrazole-1-carboxylate

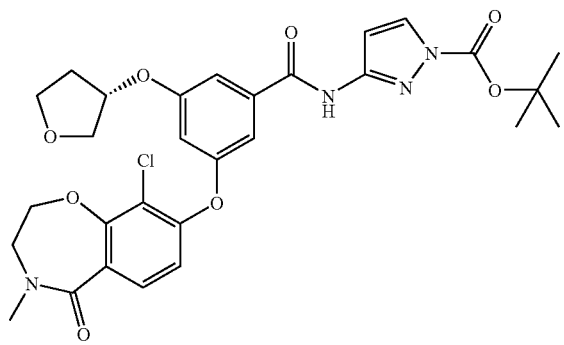

1-Chloro-N,N-2-trimethylpropenylamine (0.09 mL, 0.37 mmol) was added to a solution of 3-[(9-chloro-4-methyl-5-oxo-2,3,4,5-tetrahydro-1,4-benzoxazepin-8-yl)oxy]-5-[(3S)-tetrahydrofuran-3-yloxy]benzoic acid (145 mg, 0.34 mmol) in DCM (5 mL) and the reaction stirred at RT for 30-40 minutes. Pyridine (0.055 mL, 0.67 mmol) and 1,1-dimethylethyl 3-amino-1H-pyrazole-1-carboxylate (123 mg, 0.67 mmol) were added and the reaction stirred for 2 hours at RT. The reaction mixture was evaporated in vacuo and water (20 mL) added. The mixture was extracted with ethyl acetate (3×20 mL), washed with 1N hydrochloric acid (20 mL), a saturated solution of sodium hydrogen carbonate (20 mL), brine (20 mL), dried (MgSO$_4$) and evaporated in vacuo. The crude product was chromatographed on silica, eluting with a gradient of 0-5% methanol in DCM, to give the desired compound as a pale yellow oil (107 mg). m/z 611 (M−H)$^−$ The preparation of 1,1-dimethylethyl 3-amino-1H-pyrazole-1-carboxylate was described earlier.

3-[(9-Chloro-4-methyl-5-oxo-2,3,4,5-tetrahydro-1,4-benzoxazepin-8-yl)oxy]-5-[(3S)-tetrahydrofuran-b 3-yloxy]benzoic acid

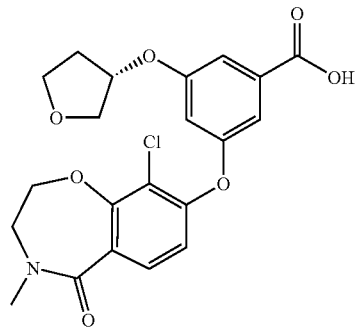

1M Sodium hydroxide solution (0.7 mL) was added to a solution of methyl 3-[(9-chloro-4-methyl-5-oxo-2,3,4,5-tetrahydro-1,4-benzoxazepin-8-yl)oxy]-5-[(3S)-tetrahydrofuran-3-yloxy]benzoate (310 mg, 0.69 mmol) in THF (5 mL) and water (5 mL). The reaction was stirred for 2-3 hours, the solvent removed in vacuo and filtered. The aqueous mixture was acidified using 2M hydrochloric acid, extracted with ethyl acetate, and the organic extract dried (MgSO$_4$) and concentrated in vacuo to give the desired compound as a pale yellow glassy gum (296 mg). $^1$H NMR δ (CDCl$_3$): 2.12-2.26 (m 2H), 3.25 (s, 3H), 3.57-3.61 (m, 2H), 3.90-4.03 (m, 4H), 4.55 (t, 2H), 4.96-4.99 (m, 1H), 6.78 (t, 1H), 6.80 (s, 1H), 7.29-7.30 (m, 1H), 7.35-7.36 (m, 1H), 7.70-7.72 (m, 1H); m/z 434 (M+H)$^+$, 432 (M−H)$^−$ Methyl 3-[(9-chloro-4-methyl-5-oxo-2,3,4,5-tetrahydro-1,4-benzoxazepin-8-yl)oxy]-5-[(3S)-tetrahydrofuran-3-yloxy]benzoate

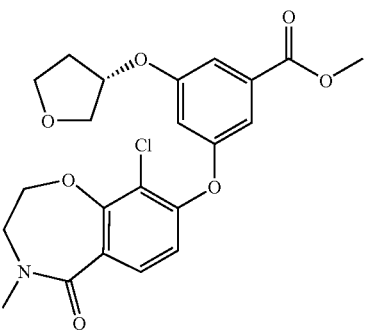

A solution of N-(2-{[tert-butyl(dimethyl)silyl]oxy}ethyl)-3-chloro-2,4-difluoro-N-methylbenzamide (647 mg, 1.78 mmol) in acetonitrile (10 mL) was heated with potassium carbonate (492 mg, 3.56 mmol) and methyl 3-hydroxy-5-[(3S)-tetrahydrofuran-3-yloxy]benzoate (424 mg, 1.78 mmol) at 160° C. for 2.5 hours in a microwave reactor. Water (15 mL) and ethyl acetate (20 mL) was added to the reaction mixture, the layers separated and the aqueous phase extracted with ethyl acetate (3×20 mL). The combined organic extract was washed with brine (10 mL) and dried (MgSO$_4$), filtered and evaporated to a residue which was chromatographed on silica, eluting with 40-100% ethyl acetate in isohexane, to give the desired compound as a clear oil (200 mg).

¹H NMR δ (CDCl₃): 2.12-2.27 (m, 2H), 3.24 (s, 3H), 3.59 (t, 2H), 3.89 (s, 3H), 3.90-4.03 (m, 4H), 4.55 (t, 2H), 4.96-4.98 (m, 1H), 6.74 (t, 1H), 6.79 (d, 1H), 7.24-7.24 (m, 1H), 7.31-7.32 (m, 1H), 7.69 (d, 1H); m/z 448 (M+H)⁺

The preparations of methyl 3-hydroxy-5-[(3S)-tetrahydrofuran-3-yloxy]benzoate and N-(2-{[tert-butyl(dimethyl)silyl]oxy}ethyl)-3-chloro-2,4-difluoro-N-methylbenzamide were described earlier.

Example 33

3-[(2-Methyl-1,1-dioxido-3,4-dihydro-2H-5,1,2-benzoxathiazepin-7-yl)oxy]-5-{[(1S)-1-methyl-2-(methyloxy)ethyl]oxy}-N-1H-pyrazol-3-ylbenzamide

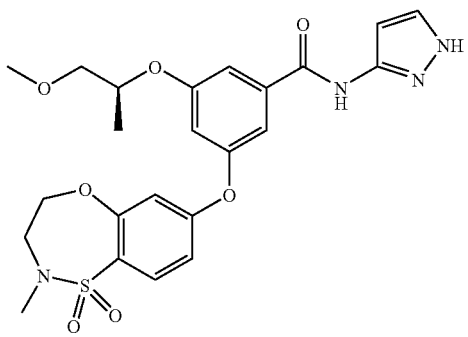

Trifluoroacetic acid (1 mL) was added to a solution of 1,1-dimethylethyl 3-{[(3-[(2-methyl-1,1-dioxido-3,4-dihydro-2H-5,1,2-benzoxathiazepin-7-yl)oxy]-5-{[(1S)-1-methyl-2-(methyloxy)ethyl]oxy}phenyl)carbonyl]amino}-1H-pyrazole-1-carboxylate (50 mg, 0.08 mmol) in DCM (8 mL) and stirred at RT for 2 hours. The solvent was removed in vacuo and DCM (20 mL). The mixture was washed with water (20 mL), a saturated solution of sodium bicarbonate (20 mL), brine (20 mL), dried (MgSO₄), filtered and reduced in vacuo to give the desired compound as a white foam (31 mg).
¹H NMR δ (CDCl₃): 1.33 (d, 3H), 2.80 (s, 3H), 3.40 (s, 3H), 3.51-3.61 (m, 2H), 3.71-3.73 (m, 2H), 4.17-4.22 (m, 2H), 4.57-4.65 (m, 1H), 6.72-6.74 (m, 1H), 6.79-6.84 (m, 2H), 6.86 (s, 1H), 7.20 (s, 1H), 7.41 (s, 1H), 7.49 (s, 1H), 7.78 (d, 1H), 9.59 (s, 1H), 10.20 (s, 1H); m/z 503 (M+H)⁺

The preparation of 1,1-dimethylethyl 3-{[(3-[(2-methyl-1,1-dioxido-3,4-dihydro-2H-5,1,2-benzoxathiazepin-7-yl)oxy]-5-{[(1S)-1-methyl-2-(methyloxy)ethyl]oxy}phenyl)carbonyl]amino}-1H-pyrazole-1-carboxylate is described below.

1,1-Dimethylethyl 3-{[(3-[(2-methyl-1,1-dioxido-3,4-dihydro-2H-5,1,2-benzoxathiazepin-7-yl)oxy]-5-{[(1S)-1-methyl-2-(methyloxy)ethyl]oxy}phenyl)carbonyl]amino}-1H-pyrazole-1-carboxylate

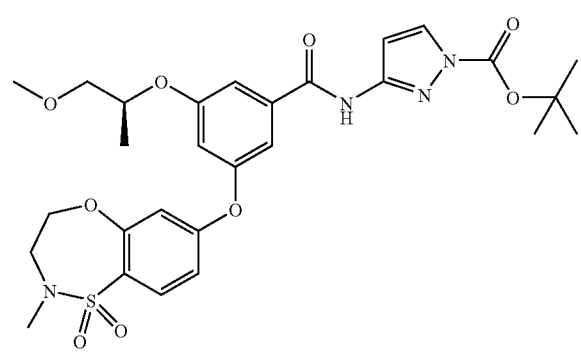

1-Chloro-N,N,2-trimethyl-1-propenylamine (0.13 mL, 1.01 mmol) was added to a solution of 3-[(2-methyl-1,1-dioxido-3,4-dihydro-2H-5,1,2-benzoxathiazepin-7-yl)oxy]-5-{[(1S)-1-methyl-2-(methyloxy)ethyl]oxy}benzoic acid (0.22 g, 0.50 mmol) in DCM (8 mL) and stirred for 1 hour. 1,1-Dimethylethyl 3-amino-1H-pyrazole-1-carboxylate (231 mg, 1.26 mmol) then pyridine (0.1 mL, 1.26 mmol) were added and the reaction stirred until the reaction was complete. The reaction mixture was reduced in vacuo and ethyl acetate (50 mL) and water (50 mL) were added. The aqueous layer was further extracted into ethyl acetate (50 mL) and the combined organics washed with water (50 mL), brine (50 mL), dried (MgSO₄), filtered and reduced in vacuo to give a golden oil which was chromatographed on silica, eluting with 25-70% ethyl acetate in isohexane then 0-5% methanol in DCM, to give the desired compound as a colourless oil (50 mg).
¹H NMR δ (CDCl₃): 1.33 (d, 3H), 1.63 (s, 9H), 2.81 (s, 3H), 3.40 (s, 3H), 3.49-3.60 (m, 2H), 3.74 (t, 2H), 4.21 (t, 2H), 4.57-4.61 (m, 1H), 6.75 (d, 1H), 6.81 (d, 1H), 6.83-6.85 (m, 1H), 7.08 (d, 1H), 7.11 (t, 1H), 7.28 (t, 1H), 7.80 (d, 1H), 8.01 (d, 1H), 8.68 (s, 1H); m/z 603 (M+H)⁺

The preparation of 1,1-dimethylethyl 3-amino-1H-pyrazole-1-carboxylate was described earlier 3-[(2-Methyl-1,1-dioxido-3,4-dihydro-2H-5,1,2-benzoxathiazepin-7-yl)oxy]-5-{[(1S)-1-methyl-2-(methyloxy)ethyl]oxy}benzoic acid

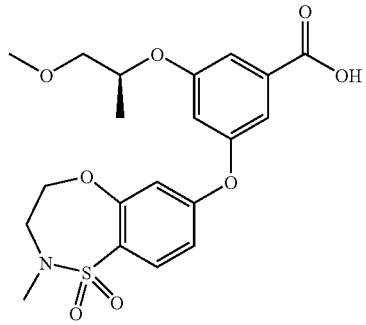

A mixture of 3-hydroxy-5-{[(1S)-1-methyl-2-(methyloxy)ethyl]oxy}benzoic acid (0.2 g, 0.88 mmol), 7-fluoro-2-methyl-3,4-dihydro-2H-5,1,2-benzoxathiazepine 1,1-dioxide (205 mg, 0.88 mmol) and potassium carbonate (244 mg, 1.77 mmol) in acetonitrile (5 mL) was stirred in a microwave reactor at 120° C. for 28 hours. The solvent was removed in vacuo and water (50 mL) and ethyl acetate (50 mL) added. The ethyl acetate layer was separated and discarded and the aqueous layer acidified and extracted into ethyl acetate (2×50 mL). The combined organics were washed with brine, dried (MgSO₄), filtered and the solvent removed in vacuo to give the desired compound as a brown oil (0.22 g) which was used in the following steps without further purification. m/z 436 (M−H)⁻

The preparation of 3-hydroxy-5-{[(1S)-1-methyl-2-(methyloxy)ethyl]oxy}benzoic acid was described earlier.

7-Fluoro-2-methyl-3,4-dihydro-2H-5,1,2-benzoxathiazepine 1,1-dioxide

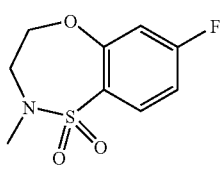

Sodium hydride (60% dispersion in mineral oil) (700 mg, 17.51 mmol) was added to a solution of 2,4-difluoro-N-(2-hydroxyethyl)-N-methylbenzenesulfonamide (2 g, 7.96 mmol) in DMF (200 mL) and the mixture stirred at RT for 48 hours. The solvent removed in vacuo, iced water (200 mL) added and the mixture extracted into ethyl acetate. The combined organic extract was washed with brine (40 mL), dried (MgSO$_4$), filtered and reduced in vacuo to give a white solid which was chromatographed on silica, eluting with 20-50% ethyl acetate in isohexane, to give the desired compound as a white solid (1.08 g).

$^1$H NMR δ (CDCl$_3$): 2.79 (s, 3H), 3.75 (t, 2H), 4.23 (t, 2H), 6.88-6.97 (m, 2H), 7.82-7.86 (m, 1H); m/z 230 (M−H)$^-$ 2,4-Difluoro-N-(2-hydroxyethyl)-N-methylbenzenesulfonamide

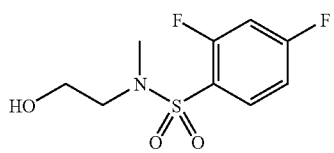

2,4-Difluorobenzenesulfonyl chloride (4 g, 18.81 mmol) in DCM (10 mL) was added slowly to a solution of 2-(methylamino)ethanol (1.66 mL, 20.70 mmol) in DCM (200 mL) and 10% sodium hydroxide solution (200 mL) at 0° C. The reaction was allowed to warm to RT and stirred for 20 hours. The DCM layer was separated and the aqueous re-extracted into DCM (2×50 mL). The combined organics were washed with brine, dried (MgSO$_4$), filtered and reduced in vacuo to give the desired compound as a colourless oil (4.7 g).

$^1$H NMR δ (CDCl$_3$): 1.98 (t, 1H), 2.94 (s, 3H), 3.32 (t, 2H), 3.79 (q, 2H), 6.94-7.03 (m, 2H), 7.89-7.95 (m, 1H)

Example 34

3-[(1,1-Dioxido-3,4-dihydro-2H-5,1,2-benzoxathiazepin-7-yl)oxy]-5-{[(1S)-1-methyl-2-(methyloxy)ethyl]oxy}-N-1H-pyrazol-3-ylbenzamide

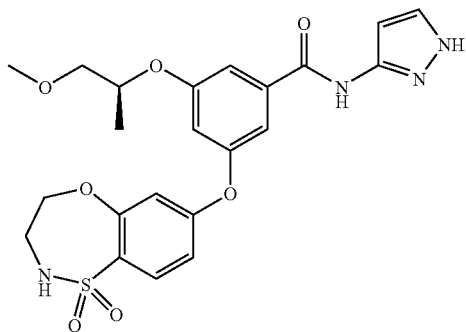

Trifluoroacetic acid (1 mL) was added to a solution of 1,1-dimethylethyl 3-{[(3-[(1,1-dioxido-3,4-dihydro-2H-5,1,2-benzoxathiazepin-7-yl)oxy]-5-{[(1S)-1-methyl-2-(methyloxy)ethyl]oxy}phenyl)carbonyl]amino}-1H-pyrazole-1-carboxylate (47 mg, 0.08 mmol) in DCM (8 mL) and stirred at RT for 2 hours. The solvent was removed in vacuo, DCM (20 mL) added and the mixture washed with water (20 mL), a saturated solution of sodium bicarbonate (20 mL), brine (20 mL), dried (MgSO$_4$), filtered and reduced in vacuo to give the desired compound as a white foam (39 mg).

$^1$H NMR δ (CDCl$_3$): 1.29 (d, 3H), 3.39 (s, 3H), 3.48-3.63 (m, 4H), 4.11-4.15 (m, 2H), 4.54-4.63 (m, 1H), 5.56 (t, 1H), 6.63-6.69 (m, 2H), 6.71 (s, 1H), 6.78 (t, 1H), 7.07 (s, 1H), 7.35 (s, 1H), 7.42 (d, 1H), 7.63 (d, 1H), 9.90 (s, 1H), 10.52 (s, 1H); m/z 489 (M+H)$^+$

The preparation of 1,1-dimethylethyl 3-{[(3-[(1,1-dioxido-3,4-dihydro-2H-5,1,2-benzoxathiazepin-7-yl)oxy]-5-{[(1S)-1-methyl-2-(methyloxy)ethyl]oxy}phenyl)carbonyl]amino}-1H-pyrazole-1-carboxylate is described below.

1,1-Dimethylethyl 3-{[(3-[(1,1-dioxido-3,4-dihydro-2H-5,1,2-benzoxathiazepin-7-yl)oxy]-5-{[(1S)-1-methyl-2-(methyloxy)ethyl]oxy}phenyl)carbonyl]amino}-1H-pyrazole-1-carboxylate

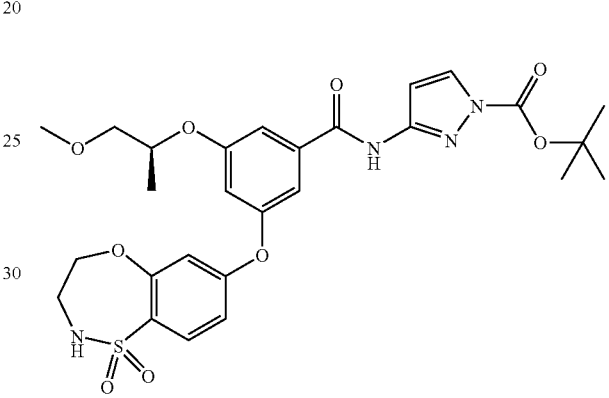

1-Chloro-N,N,2-trimethyl-1-propenylamine (0.1 mL, 0.74 mmol) was added to a solution of 3-[(1,1-dioxido-3,4-dihydro-2H-5,1,2-benzoxathiazepin-7-yl)oxy]-5-{[(S)-1-methyl-2-(methyloxy)ethyl]oxy}benzoic acid (0.21 g, 0.50 mmol) in DCM (5 mL) and stirred for 1 hour. 1,1-Dimethylethyl 3-amino-1H-pyrazole-1-carboxylate (137 mg, 0.74 mmol) then pyridine (0.08 mL, 0.99 mmol) were added and the reaction stirred for a further 45 minutes. The mixture was reduced in vacuo and ethyl acetate (50 mL) and water (50 mL) added. The aqueous layer was re-extracted into ethyl acetate (50 mL) and the combined organics washed with water (50 mL), brine (50 mL), dried (MgSO$_4$), filtered and reduced in vacuo to give a golden oil which was chromatographed on silica, eluting with 30-60% ethyl acetate in isohexane, to give a colourless oil. The oil was dissolved in ethyl acetate (30 mL) and washed with 1M hydrochloric acid, dried (MgSO$_4$), filtered and reduced in vacuo to give the desired compound as a colourless oil (47 mg).

$^1$H NMR δ (CDCl$_3$): 1.34 (d, 3H), 1.59 (s, 9H), 3.39 (s, 3H), 3.50-3.61 (m, 2H), 3.66-3.71 (m, 2H), 4.20-4.25 (m, 2H), 4.64-4.72 (m, 1H), 6.29 (s, 1H), 6.64-6.66 (m, 1H), 6.78 (d, 1H), 6.86 (t, 1H), 7.07 (d, 1H), 7.19 (t, 1H), 7.40 (t, 1H), 7.59 (d, 1H), 7.91 (d, 1H), 9.55 (s, 1H); m/z 589 (M+H)$^+$

The preparation of 1,1-dimethylethyl 3-amino-1H-pyrazole-1-carboxylate was described earlier.

3-[(1,1-Dioxido-3,4-dihydro-2H-5,12-benzoxathiazepin-7-yl)oxy]-5-{[(1S)-1-methyl-2-(methyloxy)ethyl]oxy}benzoic acid

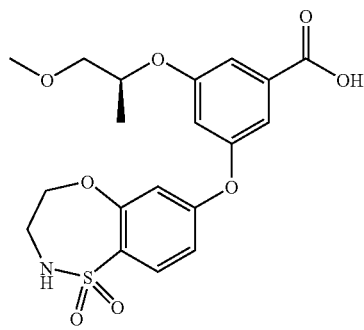

A mixture of 3-hydroxy-5-{[(1S)-1-methyl-2-(methyloxy)ethyl]oxy}benzoic acid (0.17 g, 0.75 mmol), 7-fluoro-3,4-dihydro-2H-5,1,2-benzoxathiazepine 1,1-dioxide (164 mg, 0.75 mmol) and potassium carbonate (208 mg, 1.50 mmol) in acetonitrile (5 mL) was stirred in a microwave reactor at 130° C. for 6 hours, then at 140° C. for 5 hours, and finally at 160° C. for 16 hours. The solvent was removed in vacuo and water (50 mL) and ethyl acetate (50 mL) added. The ethyl acetate layer was separated and discarded and the aqueous layer acidified and extracted into ethyl acetate (2×50 mL). The combined organics were washed with brine, dried (MgSO$_4$), filtered and the solvent removed in vacuo to give the desired compound as a brown foam (0.21 g) which was used in the next step without further purification.

The preparation of 3-hydroxy-5-{[(1S)-1-methyl-2-(methyloxy)ethyl]oxy}benzoic acid was described earlier.

7-Fluoro-3,4-dihydro-2H-5,1,2-benzoxathiazepine 1,1-dioxide

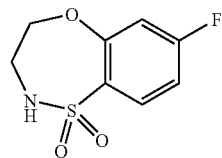

Sodium hydride (60% dispersion in mineral oil) (260 mg, 6.49 mmol) was added to a solution of 2,4-difluoro-N-(2-hydroxyethyl)benzenesulfonamide (0.7 g, 2.95 mmol) in DMF (100 mL) and the mixture stirred at RT for 48 hours. The solvent was removed in vacuo, iced water (200 mL) added and the mixture extracted into ethyl acetate. The combined organic extracts were washed with brine (40 mL), dried (MgSO$_4$), filtered and reduced in vacuo to give a white solid which was chromatographed on silica, eluting with 20-70% ethyl acetate in isohexane, to give the desired compound as a white solid (0.18 g). $^1$H NMR δ (CDCl$_3$): 3.65-3.70 (m, 2H), 4.25-4.27 (m, 2H), 4.69 (t, 1H), 6.86-6.94 (m, 2H), 7.82-7.86 (m, 1H); m/z 216 (M−H)$^-$

2,4-Difluoro-N-(2-hydroxyethyl)benzenesulfonamide

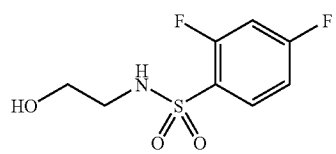

2,4-Difluorobenzenesulfonyl chloride (4 g, 18.81 mmol) in DCM (10 mL) was added slowly to a solution of ethanolamine (1.25 mL, 20.70 mmol) in DCM (200 mL) and 10% sodium hydroxide solution (200 mL) at 0° C. The reaction was allowed to warm to RT and stirred for 20 hours. The DCM layer was separated and the aqueous re-extracted into DCM (2×50 mL) then the combined organics discarded. The aqueous layer was acidified and extracted into DCM (4×100 mL) the combined organics washed with brine, dried (MgSO$_4$), filtered and reduced in vacuo to give the desired compound as a white solid (0.7 g). $^1$H NMR δ (CDCl$_3$): 1.75 (s, 1H), 3.17 (q, 2H), 3.72-3.73 (m, 2H), 5.16 (s, 1H), 6.94-7.03 (m, 2H), 7.90-7.97 (m, 1H); m/z 236 (M−H)$^-$

Example 35

3-[(5,5-Dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide

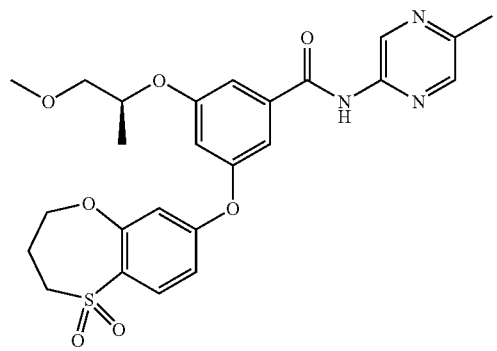

A mixture of 3-hydroxy-5-{[(1S)-1-methyl-2-(methyloxy)ethyl]oxy}-N-(5-methylpyrazin-2-yl)benzamide (0.15 g, 0.47 mmol), 8-fluoro-3,4-dihydro-2H-1,5-benzoxathiepine 5,5-dioxide (103 mg, 0.47 mmol) and potassium carbonate (131 mg, 0.95 mmol) in acetonitrile (5 mL) was stirred in a microwave reactor at 160° C. for 5 hours. The mixture was reduced in vacuo and ethyl acetate (50 mL) and water (50 mL) were added. The aqueous layer was re-extracted into ethyl acetate (50 mL) and the combined organics washed with water (50 mL), brine (50 mL), dried (MgSO$_4$), filtered and reduced in vacuo to give a golden oil. The oil was chromatographed on silica, eluting with 40-100% ethyl acetate in isohexane, to give the desired compound as a white foam (84 mg). $^1$H NMR δ (CDCl$_3$): 1.34 (d, 3H), 2.39-2.47 (m, 2H), 2.56 (s, 3H), 3.34-3.37 (m, 2H), 3.41 (s, 3H), 3.49-3.61 (m, 2H), 4.24-4.27 (m, 2H), 4.58-4.65 (m, 1H), 6.76 (d, 1H), 6.85-6.88 (m, 2H), 7.16 (t, 1H), 7.35 (t, 1H), 7.94 (d, 1H), 8.14 (s, 1H), 8.30 (s, 1H), 9.53 (s, 1H); m/z 514 (M+H)$^+$ The preparation of 3-hydroxy-5-{[(1S)-1-methyl-2-(methyloxy)ethyl]oxy}-N-(5-methylpyrazin-2-yl)benzamide was described earlier.

The preparation of 8-fluoro-3,4-dihydro-2H-1,5-benzoxathiepine 5,5-dioxide is described below.

8-Fluoro-3,4-dihydro-2H-1,5-benzoxathiepine 5,5-dioxide

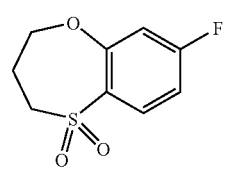

meta-Chloroperbenzoic acid (50-55%) (514 mg, 1.49 mmol) was added to a mixture of 8-fluoro-3,4-dihydro-2H-1,5-benzoxathiepine (110 mg, 0.6 mmol) and magnesium sulphate (1 spatula) in DCM (10 mL) and stirred at RT for 24 hours. Water was added and the mixture extracted into ethyl acetate. The combined organics were washed with a saturated solution of sodium bicarbonate (50 mL), brine (40 mL), dried (MgSO$_4$), filtered and reduced in vacuo to give a white solid which was chromatographed on silica, eluting with 0-10% ethyl acetate in isohexane to give a colourless oil. The oil was redissolved in organics, washed with 2M sodium hydroxide solution (40 mL), and concentrated in vacuo to give the desired compound as a white solid (100 mg).

$^1$H NMR δ (CDCl$_3$): 2.41-2.46 (m, 2H), 3.34-3.37 (m, 2H), 4.26-4.29 (m, 2H), 6.88-6.91 (m, 1H), 6.95-7.00 (m, 1H), 7.96-8.00 (m, 1H)

8-Fluoro-3,4-dihydro-2H-1,5-benzoxathiepine

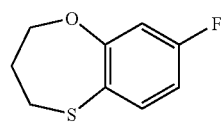

Sodium hydride (60% dispersion in mineral oil) (177 mg, 4.42 mmol) was added to a solution of 3-[(2,4-difluorophenyl)thio]propan-1-ol (0.41 g, 2.01 mmol) in DMF (40 mL) and the mixture stirred at RT for 24 hours. The solvent was removed in vacuo and iced water (200 mL) added. The mixture was extracted into ethyl acetate and the organics washed with brine (40 mL), dried (MgSO$_4$), filtered and reduced in vacuo to give a white solid which was chromatographed on silica, eluting with 0-10% ethyl acetate in isohexane, to give the desired compound as a colourless oil (110 mg).

$^1$H NMR δ (CDCl$_3$): 2.22-2.29 (m, 2H), 2.86-2.91 (m, 2H), 4.20-4.23 (m, 2H), 6.64-6.77 (m, 2H), 7.30-7.36 (m, 1H); m/z 185 (M+H)$^+$

3-[(2,4-Difluorophenyl)thio]propan-1-ol

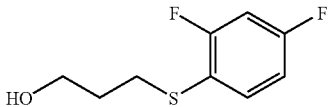

1M Hydrochloric acid (10 mL) was added to a solution of 2-({3-[(2,4-difluorophenyl)thio]propyl}oxy)tetrahydro-2H-pyran (610 mg, 2.12 mmol) in methanol (10 mL) and stirred at RT for 40 minutes. The methanol was removed in vacuo and the residue adjusted to pH 6 then extracted into ethyl acetate (3×50 mL). The combined organics were washed with brine (50 mL), dried (MgSO$_4$), filtered and reduced in vacuo to give the desired compound as a colourless oil (410 mg). $^1$H NMR δ (CDCl$_3$): 1.38 (t, 1H), 1.83 (quintet, 2H), 2.97 (t, 2H), 3.77 (q, 2H), 6.81-6.87 (m, 2H), 7.38-7.45 (m, 1H)

2-({3-[(2,4-Difluorophenyl)thio]propyl}oxy tetrahydro-2H-pyran

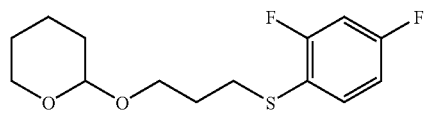

Sodium hydride (60% dispersion in mineral oil) (120 mg, 3.01 mmol) was added to a solution of 2,4-difluorothiophenol (0.4 g, 2.74 mmol) in THF (10 mL) at 0° C., under argon. The reaction was allowed to warm to RT and 2-(3-bromopropoxy) tetrahydro-2H-pyran (672 mg, 3.01 mmol) added. The reaction was stirred at RT for 4 hours then poured into iced water (50 mL) and extracted into ethyl acetate (50 mL). The organics were washed with brine (50 mL), dried (MgSO$_4$), filtered and the solvent removed in vacuo to give a yellow oil which was chromatographed on silica, eluting with 0-10% ethyl acetate in isohexane, to give the desired compound as a colourless oil (610 mg). $^1$H NMR δ (CDCl$_3$): 1.49-1.61 (m, 4H), 1.65-1.73 (m, 1H), 1.75-1.90 (m, 3H), 2.96 (t, 2H), 3.46-3.52 (m, 2H), 3.79-3.87 (m, 2H), 4.55-4.56 (m, 1H), 6.80-6.86 (m, 2H), 7.38-7.44 (m, 1H)

Example 36

3-{[(1S)-1-Methyl-2-(methyloxy)ethyl]oxy}-5-[(4-methyl-5-oxo-2,3,4,5-tetrahydro-1,4-benzoxazepin-8-yl)oxy]-N-(5-methylpyrazin-2-yl)benzamide

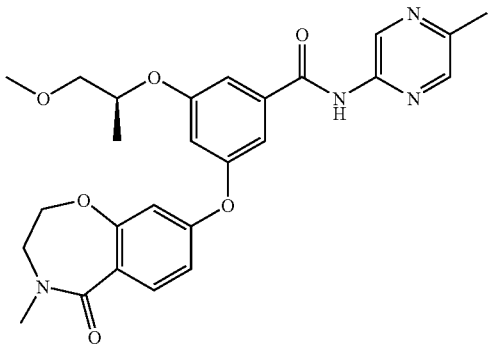

Oxalyl chloride (0.17 mL, 1.94 mmol) and DMF (1 drop) were added to a solution of 3-{[(1S)-1-methyl-2-(methyloxy) ethyl]oxy}-5-[(4-methyl-5-oxo-2,3,4,5-tetrahydro-1,4-benzoxazepin-8-yl)oxy]benzoic acid (625 mg, 1.56 mmol) in DCM (15 mL) and the mixture stirred at RT for 4 hours. The solvent was evaporated in vacuo to a residue which was added to a solution of 2-amino-5-methylpyrazine (255 mg, 2.34 mmol) and pyridine (0.64 mL, 7.8 mmol) in DCM (5 mL). The resultant mixture was heated at 60° C. in a microwave reactor for 5 minutes. The mixture was cooled to RT and pressure, the DCM was evaporated in vacuo to a residue which was partitioned between ethyl acetate (50 mL) and 1N citric acid (25 mL). The organic layer was washed with 1N citric acid (25 mL), brine, dried (MgSO$_4$) and evaporated in vacuo to a residue which was chromatographed on silica, eluting with ethyl acetate, to give the desired compound (352 mg).

$^1$H NMR δ (CDCl$_3$): 1.35 (d, 3H), 2.55 (s, 3H), 3.2 (s, 3H), 3.4 (s, 3H), 3.5 (m, 2H), 3.6 (t, 2H), 4.4 (t, 2H), 4.6 (m, 1H), 6.6 (d, 1H), 6.8 (dd, 1H), 6.85 (m, 1H), 7.15 (m, 1H), 7.3 (s, 1H), 7.9 (d, 1H), 8.1 (s, 1H), 8.45 (s, 1H), 9.5 (s, 1H); m/z 493 (M+H)$^+$

The following compounds were made by an analogous method using the appropriate aminoheterocycle.

| Example | Structure | m/z | ¹H NMR (CDCl₃) |
|---|---|---|---|
| 36a* | 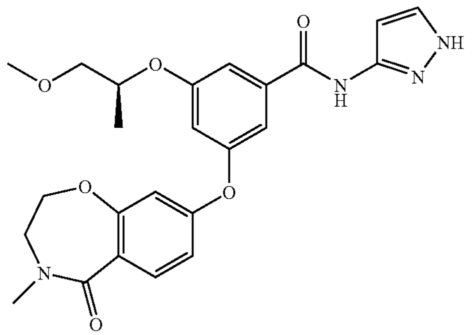 | 467 (M + H)⁺ | δ: 1.25 (d, 3 H), 3.15 (s, 3 H), 3.3 (s, 3 H), 3.45 (m, 2 H), 3.5 (t, 2 H), 4.3 (t, 2 H), 4.5 (m, 1 H), 6.5 (d, 1 H), 6.65 (dd, 1 H), 6.7 (s, 1 H), 6.75 (s, 1 H), 7.1 (s, 1 H), 7.3 (s, 1 H), 7.4 (s, 1 H), 7.8 (d, 1 H), 9.6 (s, 1 H) |
| 36b | 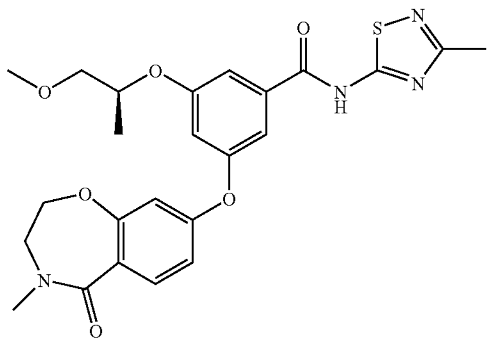 | 499 (M + H)⁺ | δ: 1.25 (d, 3 H), 2.4 (s, 3 H), 3.2 (s, 3 H), 3.3 (s, 3 H), 3.4 (m, 2 H), 3.5 (t, 2 H), 4.3 (t, 2 H), 4.5 (m, 1 H), 6.5 (d, 1 H), 6.65 (dd, 1 H), 6.8 (d, 1 H), 7.1 (m, 1 H), 7.25 (s, 1 H) and 7.8 (d, 1 H) |

*1,1-Dimethylethyl 3-amino-1H-pyrazole-1-carboxylate was used in this reaction and the isolated material was dissolved in methanol (2 mL) and heated at 140° C. in a microwave reactor for 30 minutes to give the desired compound following chromatography on silica.

The preparations of 2-amino-5-methylpyrazine and 1,1-dimethylethyl 3-amino-1H-pyrazole-1-carboxylate were described earlier.

The preparation of 3-{[(1S)-1-methyl-2-(methyloxy)ethyl]oxy}-5-[(4-methyl-5-oxo-2,3,4,5-tetrahydro-1,4-benzoxazepin-8-yl)oxy]benzoic acid is described below.

3-{[(1S)-1-Methyl-2-(methyloxy)ethyl]oxy}-5-[(4-methyl-5-oxo-2,3,45-tetrahydro-4-benzoxazepin-8-yl)oxy]benzoic acid Lithium hydroxide monohydrate (977 mg, 23.25 mmol) in water (25 mL) was added to a solution of methyl 3-{[(1S)-1-methyl-2-(methyloxy)ethyl]oxy}-5-[(4-methyl-5-oxo-2,3,4,5-tetrahydro-1,4-benzoxazepin-8-yl)oxy]benzoate (1.93 g, 4.65 mmol) in THF (25 mL) and the mixture stirred at RT for 18 hours. The THF was evaporated in vacuo, the aqueous residue filtered through Celite®, the filtrates treated with 1N hydrochloric acid (23.25 mL) then extracted into ethyl acetate (3×25 mL) The combined organic extracts were washed with brine (25 mL), dried (MgSO₄) and evaporated in vacuo to give the desired compound (1.82 g). ¹H NMR δ (CDCl₃): 1.3 (d, 3H), 3.2 (s, 3H), 3.4 (s, 3H), 3.5-3.6 (m, 2H), 3.6 (t, 2H), 3.8 (s, 3H), 4.4 (t, 2H), 4.6 (m, 1H), 6.55 (d, 1H), 6.75 (d, 1H), 6.85 (d, 1H), 7.35 (d, 1H), 7.45 (d, 1H), 7.85 (d, 1H); m/z 402 (M+H)⁺

Methyl 3-{[(1S)-1-methyl-2-(methyloxy)ethyl]oxy}-5-[(4-methyl-5-oxo-2,3,4,5-tetrahydro-1,4-benzoxazepin-8-yl)oxy]benzoate

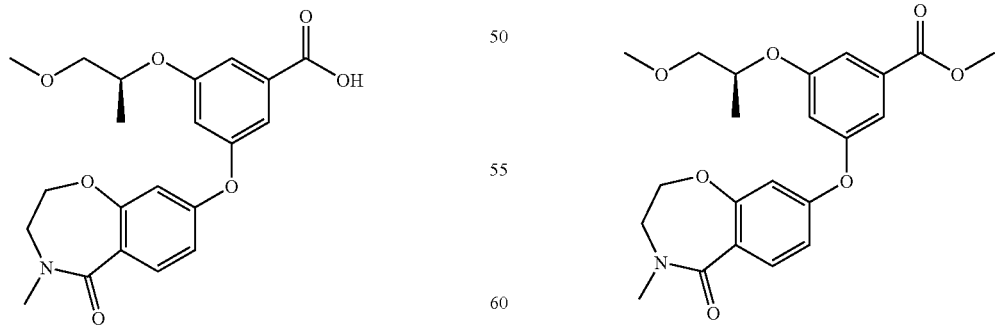

DIAD (1.18 mL, 6.0 mmol) was added to a stirred solution of methyl 3-hydroxy-5-[(4-methyl-5-oxo-2,3,4,5-tetrahydro-1,4-benzoxazepin-8-yl)oxy]benzoate (1.72 g, 5.0 mmol) and triphenylphosphine (2.62 g, 10.0 mmol) in THF (50 mL) at 0° C.-5° C. The mixture was stirred for 30 minutes, then treated with (R)-1-methoxy-2-propanol (675 mg, 7.5 mmol)

and the mixture stirred at RT for 18 hours. The mixture was evaporated in vacuo to a residue which was chromatographed on silica, eluting with 50% ethyl acetate in isohexane. The residue was slurried in ether (25 mL), filtered, and the filtrates evaporated in vacuo to give the desired compound (2.41 g) with a small amount of contaminating triphenylphosphine present. The material was used in the next steps without further purification. $^1$H NMR δ (CDCl$_3$): 1.25 (d, 3H), 3.15 (s, 3H), 3.3 (s, 3H), 3.4-3.5 (m, 2H), 3.5 (t, 2H), 3.8 (s, 3H), 4.3 (t, 2H), 4.5 (m, 1H), 6.5 (d, 1H), 6.7 (d, 1H), 6.75 (d, 1H), 7.2 (d, 1H), 7.35 (d, 1H), 7.8 (d, 1H); m/z 416 (M+H)$^+$ Methyl 3-hydroxy-5-[(4-methyl-5-oxo-2,3,4,5-tetrahydro-1,4-benzoxazepin-8-yl)oxy]benzoate

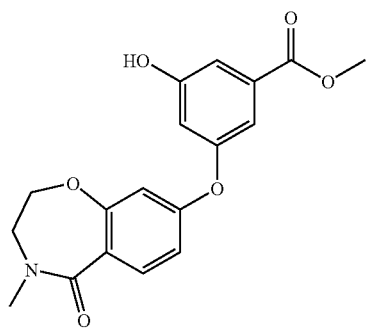

A mixture of methyl 3-[(9-chloro-4-methyl-5-oxo-2,3,4,5-tetrahydro-1,4-benzoxazepin-8-yl)oxy]-5-[(phenylmethyl)oxy]benzoate (8.8 g, 18.8 mmol), and ammonium formate (11.87 g, 188 mmol) in methanol (190 mL) was placed under an atmosphere of argon and 10% palladium on charcoal (880 mg) added. The mixture was heated under reflux for 2 hours, cooled to RT, filtered through Celite®, washed with methanol, and the filtrates evaporated in vacuo to a residue which was partitioned between water (150 mL) and ethyl acetate (200 mL). The organic layer was washed with brine, dried (MgSO$_4$), evaporated in vacuo to a residue which was chromatographed on basic alumina, eluting with ethyl acetate then methanol, to give a solid which was crystallised from ethyl acetate and isohexane to give the desired compound (3.25 g). $^1$H NMR δ (CDCl$_3$): 3.15 (s, 3H), 3.5 (t, 2H), 4.35 (t, 2H), 6.6 (dd, 1H), 6.75 (dt, 1H), 7.8 (t, 1H); m/z 344 (M+H)$^+$ Methyl 3-[(9-chloro-4-methyl-5-oxo-2,3,4,5-tetrahydro-1,4-benzoxazepin-8-yl)oxy]-5-[(phenylmethyl)oxy]benzoate

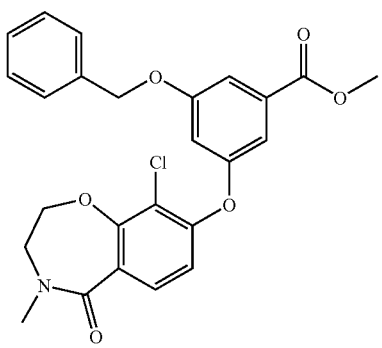

Cesium carbonate (41.2 g, 126.4 mmol) was added to a solution of methyl 3-hydroxy-5-{[phenylmethyl]oxy}benzoate (10.9 g, 42.25 mmol) and 3-chloro-2,4-difluoro-N-(2-hydroxyethyl)-N-methylbenzamide (11.6 g, 46.4 mmol) in acetonitrile (210 mL) and the stirred mixture heated at 160° C. in a microwave reactor for 8 hours. The mixture was cooled to RT and pressure, the acetonitrile evaporated in vacuo, and the residue partitioned between water (500 mL) and ethyl acetate (300 mL). The mixture was adjusted to pH 2, the organic layer washed with brine, dried (MgSO$_4$) and evaporated to a residue (shown to contain a large amount of acid). The mixture was added to a solution of thionyl chloride (11.7 mL, 160 mmol) in methanol (120 mL) at −35° C., the solution stirred at −35° C. for 1 hour then allowed to come to RT and stirred for 18 hours. The methanol was evaporated in vacuo to a residue which was partitioned between ethyl acetate (250 mL) and a saturated sodium hydrogen carbonate solution (175 mL). The organic layer was washed with a saturated sodium hydrogen carbonate solution (3×75 mL), brine, dried (MgSO$_4$) and evaporated in vacuo to a residue which was chromatographed on silica, eluting with 50% ethyl acetate in isohexane, to give the desired compound (8.8 g).

$^1$H NMR δ (CDCl$_3$): 3.15 (s, 3H), 3.5 (m, 2H), 3.8 (s, 3H), 4.45 (m, 2H), 5.0 (s, 2H), 6.7 (d, 1H), 6.75 (d, 1H), 7.2 (s, 1H), 7.3 (m, 5H), 7.4 (d, 1H), 7.6, (d, 1H); m/z 468 (M+H)$^+$

The preparations of methyl 3-hydroxy-5-{[phenylmethyl]oxy}benzoate and 3-chloro-2,4-difluoro-N-(2-hydroxyethyl)-N-methylbenzamide were described earlier.

Example 37

3-[(1-Methylethyl)oxy]-5-[(4-methyl-5-oxo-2,3,4,5-tetrahydro-1,4-benzoxazepin-8-yl)oxy]-N-1H-pyrazol-3-ylbenzamide

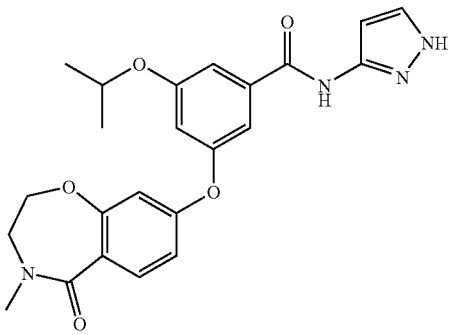

A solution of 1,1-dimethylethyl 3-[({3-[(1-methylethyl)oxy]-5-[(4-methyl-5-oxo-2,3,4,5-tetrahydro-1,4-benzoxazepin-8-yl)oxy]phenyl}carbonyl)amino]-1H-pyrazole-1-carboxylate (42 mg, 0.08 mmol), in methanol (2 mL) was heated at 140° C. in a microwave reactor for 30 minutes. The solution was cooled to RT and pressure, the methanol evaporated in vacuo to a residue which was chromatographed on silica, eluting with ethyl acetate, to give the desired compound (13 mg). $^1$H NMR δ (CDCl$_3$): 1.3 (d, 6H), 3.15 (s, 3H), 3.5 (t, 2H), 4.3 (t, 2H), 4.5 (m, 1H), 6.5 (s, 1H), 6.7 (m, 2H), 6.75 (s, 1H), 7.1 (d, 1H), 7.25 (d, 1H), 7.45 (d, 1H), 7.8 (d, 1H), 9.4 (s, 1H); m/z 437 (M+H)$^+$ The preparation of 1,1-dimethylethyl 3-[({3-[(1-methylethyl)oxy]-5-[(4-methyl-5-oxo-2,3,4,5-tetrahydro-1,4-benzoxazepin-8-yl)oxy]phenyl}carbonyl)amino]-1H-pyrazole-1-carboxylate is described below.

1,1-Dimethylethyl 3-[({3-[(1-methylethyl)oxy]-5-[(4-methyl-5-oxo-2,3,4,5-tetrahydro-1,4-benzoxazepin-8-yl)oxy]phenyl}carbonyl)amino]-1H-pyrazole-1-carboxylate

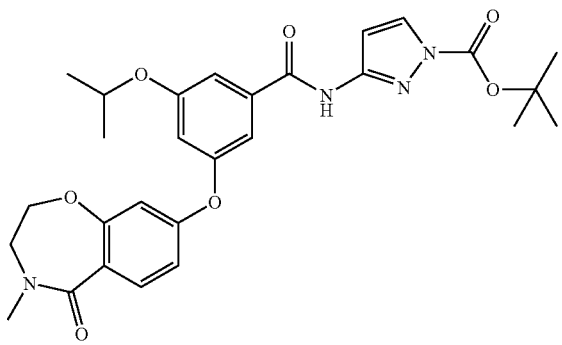

DIPEA (0.26 mL, 1.5 mmol) was added to a solution of 3-[(1-methylethyl)oxy]-5-[(4-methyl-5-oxo-2,3,4,5-tetrahydro-1,4-benzoxazepin-8-yl)oxy]benzoic acid (185 mg, 0.5 mmol), 1,1-dimethylethyl 3-amino-1H-pyrazole-1-carboxylate (110 mg, 0.6 mmol) and HATU (247 mg, 0.65 mmol) in DMF (2 mL) and the mixture stirred at RT for 16 hours. The mixture was poured onto water (30 mL), extracted with ethyl acetate (3×15 mL), the combined organic extracts washed with 1N citric acid, saturated sodium hydrogen carbonate, brine, dried (MgSO4) and evaporated in vacuo. The residue was chromatographed on silica, eluting with 60% ethyl acetate in isohexane, to give the desired compound (32 mg). $^1$H NMR δ (CDCl$_3$): 1.3 (d, 6H), 1.55 (s, 9H), 3.15 (s, 3H), 3.5 (t, 2H), 4.3 (t, 2H), 4.5 (m, 1H), 6.5 (s, 1H), 6.7 (m, 2H), 7.1 (d, 1H), 7.8 (d, 1H), 7.95 (d, 1H), 8.7 (s, 1H); m/z 535 (M−H)$^-$

3-[(1-Methylethyl)oxy]-5-[(4-methyl-5-oxo-2,3,4,5-tetrahydro-1,4-benzoxazepin-8-yl)oxy]benzoic acid

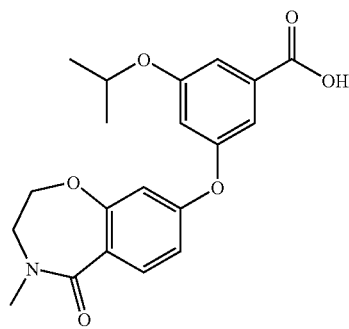

Cesium carbonate (1.96 g; 6.0 mmol) was added to a solution of methyl 3-hydroxy-5-[(4-methyl-5-oxo-2,3,4,5-tetrahydro-1,4-benzoxazepin-8-yl)oxy]benzoate (686 mg, 2.0 mmol) and 2-iodopropane (0.4 mL; 4.0 mmol) in DMA (5 mL) and the stirred mixture heated at 140° C. in a microwave reactor for 1 hour. Additional 2-iodopropane (0.4 mL, 4.0 mmol) was added and the reaction heated for a further 1 hour. The mixture was cooled to RT and pressure, the DMA evaporated in vacuo, and the residue partitioned between water (50 mL) containing 1N hydrochloric acid (12.0 mL) and ethyl acetate (100 mL). The organic layer was washed with aqueous sodium thiosulphate solution, brine, dried (MgSO$_4$) and evaporated in vacuo. The residue was added to a solution of thionyl chloride (0.73 mL, 10 mmol) in methanol (20 mL) at −35° C., the solution stirred at −35° C. for 1 hour then allowed to come to RT and stirred for 18 hours. The methanol was evaporated in vacuo to a residue which was partitioned between ethyl acetate (25 mL) and a saturated sodium hydrogen carbonate solution (15 mL). The organic layer was washed with a saturated sodium hydrogen carbonate solution (3×5 mL), brine, dried (MgSO$_4$) and evaporated in vacuo to a residue which was chromatographed on silica, eluting with ethyl acetate, to give an inseparable mixture of methyl 3-[(1-methylethyl)oxy]-5-[(4-methyl-5-oxo-2,3,4,5-tetrahydro-1,4-benzoxazepin-8-yl)oxy]benzoate (m/z 386 (M+H)$^+$) and 1-methylethyl 3-[(1-methylethyl)oxy]-5-[(4-methyl-5-oxo-2,3,4,5-tetrahydro-1,4-benzoxazepin-8-yl)oxy]benzoate (m/z 414 (M+H)$^+$) (650 mg). This mixture was dissolved in THF (20 mL) and a solution of lithium hydroxide monohydrate (346 mg, 8.23 mmol) in water (20 mL) added. The mixture was stirred at RT for 18 hours. The THF was evaporated in vacuo, the aqueous residue treated with 1N hydrochloric acid (14.0 mL), extracted with ethyl acetate (3×25 mL), the combined organic extracts washed with brine (25 mL), dried (MgSO$_4$) and evaporated in vacuo. The residue was crystallised from ethyl acetate and isohexane to give the desired material (430 mg). $^1$H NMR δ (d$_6$-DMSO): 1.3 (d, 6H), 3.1 (s, 3H), 3.6 (t, 2H), 4.4 (t, 2H), 4.7 (m, 1H), 6.6 (d, 1H), 6.8 (dd, 1H), 6.9 (d, 1H), 7.1 (d, 1H), 7.25 (d, 1H), 7.75 (d, 1H), 13.1 (s, 1H); m/z 372 (M+H)$^+$ The preparation of methyl 3-hydroxy-5-[(4-methyl-5-oxo-2,3,4,5-tetrahydro-1,4-benzoxazepin-8-yl)oxy]benzoate was described earlier.

Example 38

3-{[(1S)-2-Hydroxy-1-methylethyl]oxy}-5-[(4-methyl-5-oxo-2,3,4,5-tetrahydro-1,4-benzoxazepin-8-yl)oxy]-N-(5-methylpyrazin-2-yl)benzamide

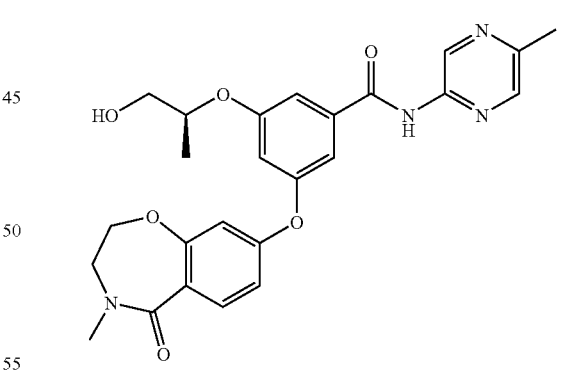

Trimethylsilyl iodide (0.35 mL, 2.4 mmol) was added to a solution of 3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(5-methylpyrazin-2-yl)benzamide (236 mg, 0.48 mmol) in acetonitrile (10 mL) under an atmosphere of argon and the mixture stirred at RT for 18 hours. The mixture was poured onto a saturated sodium hydrogen carbonate solution (25 mL), the acetonitrile removed in vacuo, and the aqueous layer extracted with ethyl acetate (3×25 mL). The combined organic layers were washed with sodium thiosulphate solution, brine, dried (MgSO$_4$) and evaporated in vacuo to a residue which was chromatographed on silica, eluting with 1% methanol in ethyl acetate, to give the desired compound (107 mg).

$^1$H NMR δ (CDCl$_3$): 1.35 (d, 3H), 1.6 (br, 1H), 2.5 (s, 3H), 3.15 (s, 3H), 3.5 (t, 2H), 3.7 (m, 2H), 4.35 (t, 2H), 4.5 (m, 1H), 6.5 (d, 1H), 6.7 (dd, 1H), 6.75 (d, 1H), 7.1 (s, 1H), 7.25 (s, 1H), 7.8 (d, 1H), 8.05 (s, 1H), 8.3 (s, 1H), 9.45 (s, 1H); m/z 479 (M+H)$^+$

The preparation of 3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(5-methylpyrazin-2-yl)benzamide was described earlier.

Example 39

3-[(2,3-Dimethyl-4-oxo-3,4-dihydro-2H-1,3-benzoxazin-7-yl)oxy]-5-{[(1S)-2-hydroxy-1-methylethyl]oxy}-N-(3-methyl-1,2,4-thiadiazol-5-yl)benzamide

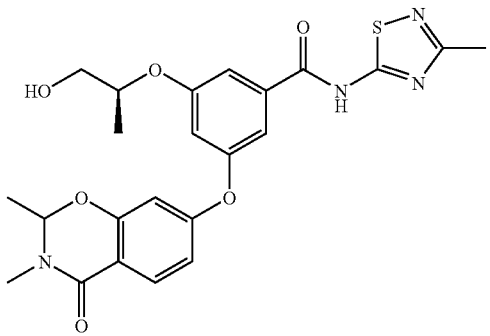

Cesium carbonate (489 mg, 1.5 mmol) was added to a solution of 3-hydroxy-5-{[(1S)-2-hydroxy-1-methylethyl]oxy}-N-(3-methyl-1,2,4-thiadiazol-5-yl)benzamide (155 mg, 0.5 mmol) and 8-fluoro-4-methyl-3,4-dihydro-1,4-benzoxazepin-5(2H)-one (117 mg, 0.6 mmol) in DMA (5 mL) and the stirred mixture heated at 160° C. in a microwave reactor for 8 hours. The mixture was cooled to RT and pressure, the DMA removed in vacuo, and the residue partitioned between water (25 mL) and ethyl acetate (30 mL). The mixture was adjusted to pH 2, the organic layer washed with brine, dried (MgSO$_4$) and evaporated in vacuo to a residue which was chromatographed on silica, eluting with ethyl acetate, to give desired compound (156 mg). $^1$H NMR δ (CDCl$_3$): 1.3 (d, 3H), 1.5 (d, 2H), 2.4 (s, 3H), 3.0 (s, 3H), 3.7 (d, 2H), 4.5 (m, 1H), 5.35 (q, 1H), 6.4 (s, 1H), 6.6 (d, 1H), 6.75 (s, 1H), 7.15 (s, 1H), 7.2 (s, 1H), 7.8 (d, 1H); m/z 485 (M+H)$^+$ The preparation of 8-fluoro-4-methyl-3,4-dihydro-1,4-benzoxazepin-5(2H)-one is described below.

8-Fluoro-4-methyl-3,4-dihydro-1,4-benzoxazepin-5(2H)-one

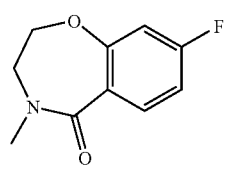

A mixture of 9-chloro-8-fluoro-4-methyl-3,4-dihydro-1,4-benzoxazepin-5(2H)-one (1 equivalent), 10% palladium on charcoal (0.1 equivalents) and ammonium formate (10 equivalents) in methanol was heated at reflux for 2 hours. The mixture was allowed to cool, filtered through Celite® and the filtrate concentrated in vacuo. The residue was partitioned between ethyl acetate and water, the organic phase washed with brine, dried (MgSO$_4$), concentrated in vacuo and chromatographed on alumina, eluting with ethyl acetate, to give the desired compound as a colourless solid.

$^1$H NMR δ (CDCl$_3$): 3.15 (s, 3H), 3.5 (t, 2H), 4.35 (t, 2H), 6.6 (dd, 1H), 6.75 (dt, 1H), 7.8 (t, 1H); m/z 196 (M+H)$^+$

The preparation of 9-chloro-8-fluoro-4-methyl-3,4-dihydro-1,4-benzoxazepin-5(2H)-one was described earlier.

The preparation of 3-hydroxy-5-{[(1S)-2-hydroxy-1-methylethyl]oxy}-N-(3-methyl-1,2,4-thiadiazol-5-yl)benzamide is described below.

3-Hydroxy-5-{[(1S)-2-hydroxy-1-methylethyl]oxy}-N-(3-methyl-1,2,4-thiadiazol-5-yl)benzamide

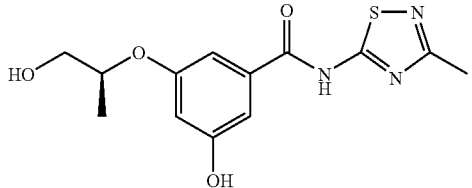

Iodotrimethylsilane (5.51 mL, 38.7 mmol) was added to 3-hydroxy-5-{[(1S)-2-methoxy-(1-methylethyl)oxy}-N-(3-methyl-1,2,4-thiadiazol-2-yl)benzamide (2.5 g, 7.73 mmol) in acetonitrile (25 mL) and the reaction stirred at RT for 48 hours. Methanol (15 mL) was added and the reaction stirred for 1 hour then a saturated solution of sodium thiosulphate (10 mL) was added and stirred for 20 mins. The volatiles were removed in vacuo and the aqueous residue extracted into ethyl acetate (2×150 mL). The organics were washed with water, brine, dried (MgSO$_4$), and reduced in vacuo to give a yellow solid. The solid was triturated with DCM and then with ethyl acetate to give the desired compound as a white solid (1.44 g).
$^1$H NMR δ (d$_6$-DMSO): 1.23 (d, 3H), 2.49 (s, 3H), 3.46-3.59 (m, 2H), 4.48-4.52 (m, 1H), 4.89 (t, 1H), 6.60 (s, 1H), 7.08 (s, 1H), 7.24 (s, 1H), 9.91 (s, 1H), 13.28 (s, 1H); m/z 310 (M+H)$^+$ 3-Hydroxy-5-{[(1S)-2-methoxy-(1-methylethyl)oxy}-N-(3-methyl-1,2,4-thiadiazol-2-yl)benzamide

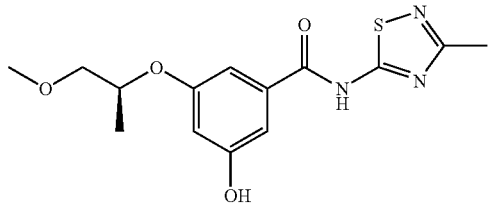

A solution of 3-{[(1S)-2-methoxy-(1-methylethyl)oxy}-5-{phenylmethyloxy}-N-(3-methyl-1,2,4-thiadiazol-2-yl)benzamide (9.53 g) and thioanisole (13.9 mL) in trifluoroacetic acid (45 mL) was stirred at ambient temperature for 16 hours. The trifluoroacetic acid was removed in vacuo and the residual oil partitioned between ethyl acetate (100 mL) and aqueous sodium hydrogen carbonate solution (300 mL). The aqueous layer was separated, extracted with ethyl acetate (2×100 mL), and the combined organic extracts washed with brine, dried (MgSO$_4$), and evaporated to a residue which was chromatographed on silica with 50% ethyl acetate in isohexane as eluant to give the desired compound (4.5 g).

¹H NMR δ (CDCl₃): 1.2 (d, 3H), 2.5 (s, 3H), 3.3 (s, 3H), 3.4-3.6 (m, 2H), 4.6-4.7 (m, 1H), 6.6 (s, 1H), 7.05 (s, 1H), 7.1 (s, 1H), 9.85 (s, 1H), 13.2 (s, 1H). m/z 324 (M+H)⁺

3-{[(1S)-2-Methoxy-(1-methylethyl)oxy}-5-{phenylmethyloxy}-N-(3-methyl-1,2,4-thiadiazol-2-yl)benzamide

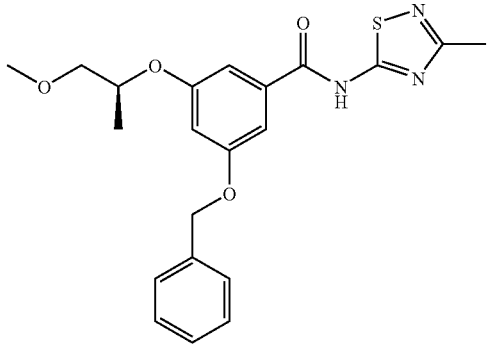

Oxalyl chloride (5.24 mL), followed by DMF (1 drop), were added to a solution of 3-[(1S)-2-methoxy-(1-methylethyl)oxy]-5-{[phenylmethyl]oxy}benzoic acid (15.8 g) in DCM (260 mL) and the mixture stirred at RT for 16 hours. The DCM and excess oxalyl chloride were removed in vacuo, the residual oil dissolved in DCM (50 mL) and added to a solution of 5-amino-3-methyl-1,2,4 thiadiazole (6.05 g) and triethylamine (14.6 mL) in DCM (150 mL) at 0-5° C., and the mixture stirred at RT for 16 hours. The DCM and excess triethylamine were removed in vacuo, and the residual oil partitioned between ethyl acetate (250 mL) and 1M hydrochloric acid (150 mL). The ethyl acetate layer was separated, washed sequentially with 1M hydrochloric acid, aqueous sodium hydrogen carbonate solution, and brine, dried (MgSO₄), and evaporated to a residue which was chromatographed on alumina with ethyl acetate as eluant, then on silica with 30% ethyl acetate in isohexane as eluant to give the desired compound (9.6 g).

¹H NMR δ (CDCl₃): 1.3 (d, 3H), 2.45 (s, 3H), 3.4 (s, 3H), 3.5-3.6 (m, 2H), 4.55-4.6 (m, 1H), 5.05 (s, 2H), 6.8 (s, 1H), 7.1 (m, 2H), 7.25 (m, 5H), 10.7 (s, 1H). m/z 414 (M+H)⁺

The preparation of 3-[(1S)-2-methoxy-(1-methylethyl)oxy]-5-{[phenylmethyl]oxy}benzoic acid was described earlier.

Example 40

3-{[(1S)-2-Hydroxy-1-methylethyl]oxy}-5-[(4-methyl-5-oxo-2,3,4,5-tetrahydro-1,4-benzoxazepin-8-yl)oxy]-N-(3-methyl-1,2,4-thiadiazol-5-yl)benzamide

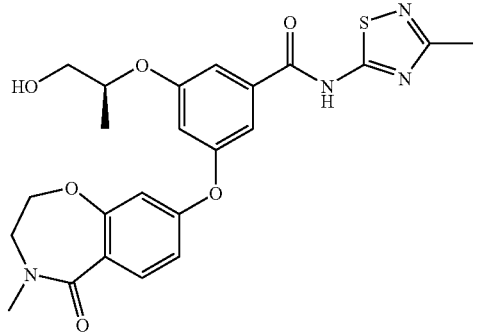

Trimethylsilyl iodide (0.95 mL, 6.7 mmol) was added to a solution of 3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(3-methyl-1,2,4-thiadiazol-5-yl)benzamide (335 mg, 0.67 mmol) in acetonitrile (20 mL) under an atmosphere of argon and the mixture stirred at RT for 18 hours. The mixture was poured onto saturated sodium hydrogen carbonate solution (50 mL), the acetonitrile removed in vacuo, and the aqueous layer extracted with ethyl acetate (3×50 mL). The combined organic layers were washed with sodium thiosulphate solution, brine, dried (MgSO₄) and evaporated in vacuo to a residue which was chromatographed on silica, eluting with ethyl acetate then with 2% methanol in DCM, to give the desired compound as a colourless solid (50 mg). ¹H NMR δ (CDCl₃): 1.3 (d, 3H), 2.5 (s, 3H), 3.2 (s, 3H), 3.6 (t, 2H), 3.75 (m, 2H), 4.4 (t, 2H), 4.55 (m, 1H), 6.55 (d, 1H), 6.7 (dd, 1H), 6.8 (d, 1H), 7.2 (s, 1H), 7.25 (s, 1H), 7.85 (d, 1H); m/z 485 (M+H)⁺

The preparation of 3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(3-methyl-1,2,4-thiadiazol-5-yl)benzamide was described earlier.

Example 41

3-[(7-Fluoro-5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide

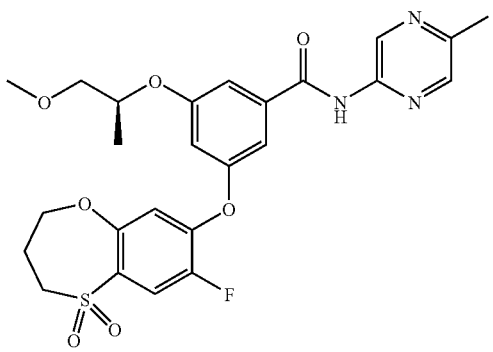

3-Hydroxy-5-{[(1S)-1-methyl-2-(methyloxy)ethyl]oxy}-N-(5-methylpyrazin-2-yl)benzamide (634 mg, 2 mmol), 3-[(2,4,5-trifluorophenyl)sulfonyl]dihydrofuran-2(3H)-one (560 mg, 2 mmol) and potassium carbonate (552 mg, 4 mmol) in acetonitrile (10 mL) were heated at 160° C. for 2 h and 170° C. for 30 minutes in a microwave reactor. Water was added to the reaction mixture and the phases separated. The aqueous phase was extracted with ethyl acetate (3×20 mL), and the combined organics washed with 1M hydrochloric acid, a saturated sodium bicarbonate solution, brine and dried (MgSO₄) and evaporated. The residue was dissolved in methanol and heated to reflux on a steam bath. The residual solid was removed by hot filtration and the filtrate evaporated to a residue which was chromatographed on alumina, eluting with 10% methanol in DCM, to give the desired compound as a clear foam (152 mg). ¹H NMR δ (CDCl₃): 1.27 (d, 3H), 2.32-2.38 (m, 2H), 2.49 (s, 3H), 3.31 (t, 2H), 3.34 (s, 3H), 3.43-3.47 (m, 1H), 3.49-3.54 (m, 1H), 4.15 (t, 2H), 4.53-4.57 (m, 1H), 6.72 (d, 1H), 6.77 (t, 1H), 7.08 (t, 1H), 7.25 (t, 1H), 7.71-7.74 (m, 1H), 8.07 (d, 1H), 8.25 (s, 1H), 9.45 (d, 1H); m/z 532 (M+H)⁺, 530 (M−H)⁻

The preparations of 3-hydroxy-5-{[(1S)-1-methyl-2-(methyloxy)ethyl]oxy}-N-(5-methylpyrazin-2-yl)benzamide and 3-[(2,4,5-trifluorophenyl)sulfonyl]dihydrofuran-2(3H)-one were described earlier.

Example 42

3-[(7-Fluoro-5,5-dioxido-3,4-dihydro-2H-1,5-benzoxathiepin-8-yl)oxy]-5-{[(1S)-1-methyl-2-(methyloxy)ethyl]oxy}-N-1H-pyrazol-3-ylbenzamide

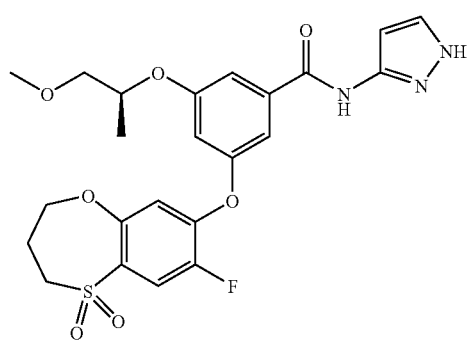

1,1-Dimethylethyl 3-{[(3-hydroxy-5-{[(1S)-1-methyl-2-(methyloxy)ethyl]oxy}phenyl) carbonyl]amino}-1H-pyrazole-1-carboxylate (145 mg, 0.5 mmol), 3-[(2,4,5-trifluorophenyl)sulfonyl]dihydrofuran-2(3H)-one (140 mg, 0.5 mmol) and potassium carbonate (138 mg, 2 mmol) in acetonitrile (4 mL) were heated at 130° C. for 1 hour then 160° C. for a further 1 hour in a microwave reactor. Water was added to the reaction mixture and the phases separated. The aqueous phase was extracted with ethyl acetate (3×20 mL), and the combined organics washed with 1M hydrochloric acid, a saturated sodium bicarbonate solution, brine, dried (MgSO$_4$), filtered and evaporated. The residue was chromatographed on alumina, eluting with 0-10% methanol in DCM, to give the desired compound as a white solid (58 mg).

$^1$H NMR δ (CDCl$_3$): 1.33 (d, 3H), 2.37-2.44 (m, 2H), 3.21-3.27 (m, 2H), 3.40 (s, 3H), 3.50-3.64 (m, 2H), 4.21 (t, 2H), 4.63-4.70 (m, 1H), 6.77 (d, 1H), 6.78-6.81 (m, 2H), 7.29 (s, 1H), 7.47-7.50 (m, 2H), 7.75 (d, 1H), 9.97 (s, 1H); m/z 506 (M+H)$^+$, 504 (M−H)$^-$

The preparation of 3-[(2,4,5-trifluorophenyl)sulfonyl]dihydrofuran-2(3H)-one was described earlier.

The preparation of 1,1-dimethylethyl 3-{[(3-hydroxy-5-{[(1S)-1-methyl-2-(methyloxy)ethyl]oxy}phenyl)carbonyl]amino}-1H-pyrazole-1-carboxylate is described below:

1,1-Dimethylethyl 3-{[(3-hydroxy-5-{[(1S)-1-methyl-2-(methyloxy)ethyl]oxy}phenyl)carbonyl]amino}-1H-pyrazole-1-carboxylate

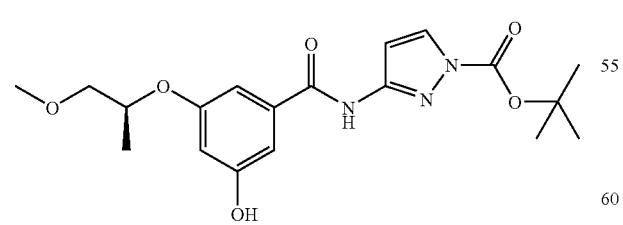

A solution of 1,1-dimethylethyl 3-[({3-{[(1S)-1-methyl-2-(methyloxy)ethyl]oxy}-5-[(phenylmethyl)oxy]phenyl}carbonyl)amino]-1H-pyrazole-1-carboxylate (23 g, 47.8 mmol) in THF (140 mL) and ethanol (140 mL) was evacuated and purged with nitrogen (×3). 10% Palladium on carbon (2.3 g; 10% w/w) was added and reaction mixture was evacuated and finally purged with hydrogen gas. The reaction mixture was left to stir at RT under a hydrogen balloon for 16 hours. The palladium on carbon was filtered through diatomaceous earth and the filtrate concentrated in vacuo to give a white foam (18 g).

$^1$H NMR δ (d$_6$-DMSO): 1.2 (d, 3H), 1.55 (s, 9H), 3.25 (s, 3H obscured by water peak), 3.4-3.5 (m, 2H), 4.7 (m, 1H), 6.5 (s, 1H), 6.95 (d, 1H), 7.0 (s, 1H), 7.1 (s, 1H), 8.2 (d, 1H), 9.65 (s, 1H), 11.2 (s, br, 1H); m/z 392 (M+H)$^+$ 1,1-Dimethylethyl 3-[({3-{[(1S)-1-methyl-2-(methyloxy)ethyl]oxy}-5-[(phenylmethyl)oxy]phenyl}carbonyl)amino]-1H-pyrazole-1-carboxylate

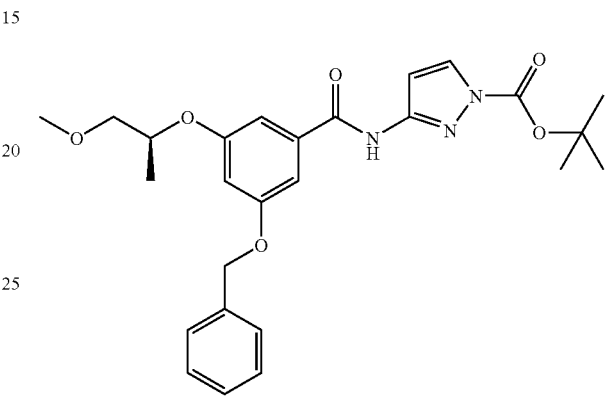

DIPEA (28.5 mL, 164 mmol) was added to a suspension of 3-[(1S)-2-methoxy-(1-methylethyl)oxy]-5-{[phenylmethyl]oxy}benzoic acid (20.7 g, 65.6 mmol), HATU (31.2 g, 82.0 mmol) and 1,1-dimethylethyl 3-amino-1H-pyrazole-1-carboxylate (15.0 g, 82.0 mmol) in DMF (30 mL) and the reaction mixture stirred for 16 hours at RT. Water (250 mL) was added and the reaction mixture extracted with diethyl ether (3×150 mL). The organic layer was washed with saturated brine solution and dried (MgSO$_4$). The filtrate was concentrated in vacuo and the residue crystallised on standing. The crystals were washed with isohexane to give to give the desired material as yellow crystals (23.4 g). m/z 482 (M+H)$^+$.

The preparation of 1,1-dimethylethyl 3-amino-1H-pyrazole-1-carboxylate was described earlier.

Example 43

3-[(7-Fluoro-5,5-dioxido-3,4-dihydro-2H-1,5-benzoxathiepin-8-yl)oxy]-5-{[(1S)-2-hydroxy-1-methylethyl]oxy}-N-(5-methylpyrazin-2-yl)benzamide

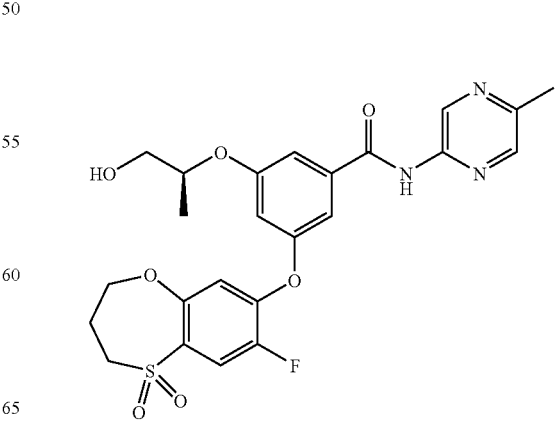

A solution of 3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide (100 mg, 0.19 mmol) in acetonitrile (3 mL) was treated with trimethylsilyl iodide (0.138 mL) and stirred at RT under argon for 16 hours. Sodium thiosulphate solution (30 mL) was added and the mixture extracted with ethyl acetate (6×30 mL). The combined organic extracts were dried (MgSO$_4$), filtered and evaporated to give a yellow oil. The oil was chromatographed on alumina, eluting with 0-50% methanol in DCM, to give the desired compound as an orange solid (19 mg). $^1$H NMR δ (CDCl$_3$): 1.25 (d, 3H), 2.35-2.42 (m, 2H), 2.52 (s, 3H), 3.32-3.41 (m, 2H), 3.46-3.71 (m, 2H), 3.75 (d, 1H), 4.19-4.22 (m, 2H), 4.53-4.57 (m, 1H), 6.78 (d, 1H), 6.80 (t, 1H), 7.18 (s, 1H), 7.35 (s, 1H), 7.80 (d, 1H), 8.18 (s, 1H), 8.37 (s, 1H), 9.50 (s, 1H); m/z 518 (M+H)$^+$, 516 (M−H)$^−$ Example 44

3-[(5,5-Dioxido-3,4-dihydro-2H-1,5-benzoxathiepin-8-yl)oxy]-5-{[(1S)-2-hydroxy-1-methylethyl]oxy}-N-(5-methylpyrazin-2-yl)benzamide

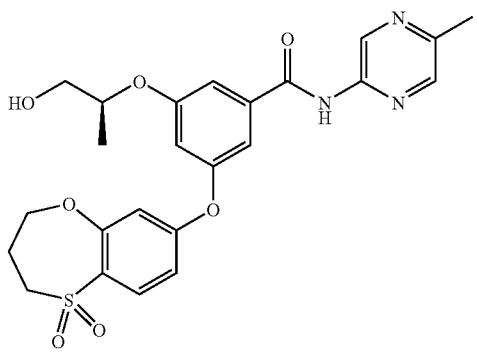

Iodotrimethylsilane (0.416 mL, 2.92 mmol) was added to a solution of 3-[(5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide (150 mg, 0.29 mmol) in acetonitrile (7 mL) and the reaction stirred at RT overnight. Methanol (35 mL) was added, the reaction stirred for 1 hour, then a saturated aqueous solution of sodium thiosulphate (30 mL) was added and the reaction stirred for a further 20 minutes. The mixture was evaporated in vacuo, and the product was extracted away from the inorganic residues by the addition of 20% methanol in DCM (40 mL) with stirring. The organics were reduced in vacuo to a volume of approximately 5 mL. The residue was chromatographed on silica, eluting with 0-20% methanol in DCM, to give the desired compound as a cream solid (79 mg).

$^1$H NMR δ (d$_6$-DMSO): 1.25 (d, 3H), 2.24 (d, 2H), 2.48 (s, 3H), 3.51-3.58 (m, 4H), 4.20 (t, 2H), 4.61 (q, 1H), 4.92 (t, 1H), 6.85 (d, 1H), 6.97-6.99 (m, 2H), 7.36 (s, 1H), 7.54 (d, 1H), 7.83-7.85 (m, 1H), 8.37 (d, 1H), 9.26 (d, 1H), 11.10 (s, 1H); m/z 500 (M+H)$^+$

The preparation of 3-[(5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide was described earlier.

Example 45

3-[(5,5-Dioxido-3,4-dihydro-2H-1,5-benzoxathiepin-8-yl)oxy]-5-{[(1S)-1-methyl-2-(methyloxy)ethyl]oxy}-N-1H-pyrazol-3-ylbenzamide

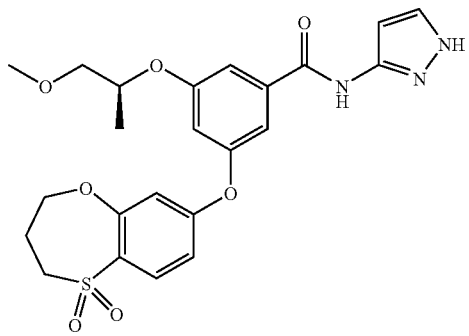

1-Chloro-N,N,2-trimethyl-1-propenylamine (0.076 mL, 0.57 mmol) was added to a mixture of 3-[(5,5-dioxido-3,4-dihydro-2H-1,5-benzoxathiepin-8-yl)oxy]-5-{[(1S)-1-methyl-2-(methyloxy)ethyl]oxy}benzoic acid (0.2 g, 0.47 mmol) in DCM (14 mL) and the mixture stirred at RT for 40 minutes. 1,1-Dimethylethyl 3-amino-1H-pyrazole-1-carboxylate (0.174 g, 0.95 mmol) and pyridine (0.95 mmol) were added and the mixture stirred for a further 3 hours at RT under an inert atmosphere. The solvent was removed in vacuo and the residue chromatographed on silica, eluting with 50-100% ethyl acetate in isohexane, to give the protected material. This material was dissolved in acetonitrile and heated in a microwave reactor at 150° C. for 12 minutes. The solvent was removed and the residue chromatographed on silica, eluting with 10% methanol in DCM, followed by trituration from diethyl ether to give the desired material as a colourless solid. $^1$H NMR δ (CDCl$_3$): 1.33 (d, 3H), 2.41-2.42 (m, 2H), 3.36 (t, 2H), 3.41 (s, 3H), 3.52-3.62 (m, 2H), 4.23 (t, 2H), 4.59-4.63 (m, 1H), 6.72 (d, 1H), 6.81 (t, 1H), 6.83-6.90 (m, 2H), 7.19 (s, 1H), 7.41 (s, 1H), 7.49 (d, 1H), 7.90 (d, 1H), 9.81 (s, 1H), 10.25 (brs, 1H); m/z 488 (M+H)$^+$ The preparation of 1,1-dimethylethyl 3-amino-1H-pyrazole-1-carboxylate was described earlier. The preparation of 3-[(5,5-dioxido-3,4-dihydro-2H-1,5-benzoxathiepin-8-yl)oxy]-5-{[(s)-1-methyl-2-(methyloxy)ethyl]oxy}benzoic acid is described below.

3-[(5,5-Dioxido-3,4-dihydro-2H-1,5-benzoxathiepin-8-yl)oxy]-5-{[(1S)-1-methyl-2-(methyloxy)ethyl]oxy}benzoic acid

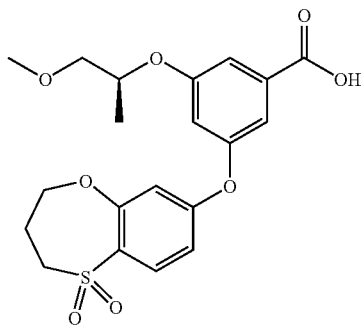

A mixture of 3-hydroxy-5-{[(1S)-1-methyl-2-(methyloxy)ethyl]oxy}benzoic acid (0.245 g, 1.08 mmol), 8-fluoro-3,4-dihydro-2H-1,5-benzoxathiepine 5,5-dioxide (235 mg, 1.08 mmol) and potassium carbonate (299 mg, 2.17 mmol) in acetonitrile (7.8 mL) was heated in a microwave reactor at 160° C. for 5 hours. The mixture was reduced in vacuo and the residue purified by preparative HPLC (on a C18 reversed phase using 5-95% acetonitrile (+0.2% TFA) in water (+0.2% TFA) as eluant) to give the desired compound as a beige solid (222 mg). $^1$H NMR δ (d$_6$-DMSO): 1.22 (d, 3H), 2.22-2.24 (m, 2H), 3.17 (s, 3H), 3.43-3.58 (m, 4H), 4.03-4.16 (m, 1H), 4.16-4.25 (m, 2H), 4.63-4.73 (m, 1H), 6.80-6.85 (m, 1H) 6.90-7.01 (m, 2H), 7.15 (s, 1H), 7.35 (s, 1H), 7.83 (d, 1H); m/z 421 (M–H)–

The preparations of 3-hydroxy-5-{[(1S)-1-methyl-2-(methyloxy)ethyl]oxy}benzoic acid and 8-fluoro-3,4-dihydro-2H-1,5-benzoxathiepine-5,5-dioxide were described earlier.

Biological Tests:

The biological effects of the compounds of formula (I) may be tested in the following way:

(1) Enzymatic Activity

Enzymatic activity of recombinant human pancreatic GLK may be measured by incubating GLK, ATP and glucose. The rate of product formation may be determined by coupling the assay to a G-6-P dehydrogenase, NADP/NADPH system and measuring the linear increase with time of optical density at 340 nm (Matschinsky et al 1993). Activation of GLK by compounds can be assessed using this assay in the presence or absence of GLKRP as described in Brocklehurst et al (Diabetes 2004, 53, 535-541).

Production of Recombinant GLK and GLKRP:

Human GLK and GLKRP cDNA was obtained by PCR from human pancreatic and hepatic mRNA respectively, using established techniques described in Sambrook J, Fritsch EF & Maniatis T, 1989. PCR primers were designed according to the GLK and GLKRP cDNA sequences shown in Tanizawa et al 1991 and Bonthron, D. T. et al 1994 (later corrected in Warner, J. P. 1995).

Cloning in Bluescript II Vectors

GLK and GLKRP cDNA was cloned in *E. coli* using pBluescript II, (Short et al 1998) a recombinant cloning vector system similar to that employed by Yanisch-Perron C et al (1985), comprising a colEI-based replicon bearing a polylinker DNA fragment containing multiple unique restriction sites, flanked by bacteriophage T3 and T7 promoter sequences; a filamentous phage origin of replication and an ampicillin drug resistance marker gene.

Transformations

*E. Coli* transformations were generally carried out by electroporation. 400 mL cultures of strains DH5a or BL21(DE3) were grown in L-broth to an OD 600 of 0.5 and harvested by centrifugation at 2,000 g. The cells were washed twice in ice-cold deionised water, resuspended in 1 mL 10% glycerol and stored in aliquots at –70° C. Ligation mixes were desalted using Millipore V Series™ membranes (0.0025 mm) pore size). 40 mL of cells were incubated with 1 mL of ligation mix or plasmid DNA on ice for 10 minutes in 0.2 cm electroporation cuvettes, and then pulsed using a Gene Pulser™ apparatus (BioRad) at 0.5 kVcm$^{-1}$, 250 mF. Transformants were selected on L-agar supplemented with tetracyline at 10 mg/mL or ampicillin at 100 mg/mL.

Expression

GLK was expressed from the vector pTB375NBSE in *E. coli* BL21 cells, producing a recombinant protein containing a 6-His tag immediately adjacent to the N-terminal methionine. Alternatively, another suitable vector is pET21 (+)DNA, Novagen, Cat number 697703. The 6-His tag was used to allow purification of the recombinant protein on a column packed with nickel-nitrilotriacetic acid agarose purchased from Qiagen (cat no 30250).

GLKRP was expressed from the vector pFLAG CTC (IBI Kodak) in *E. coli* BL21 cells, producing a recombinant protein containing a C-terminal FLAG tag. The protein was purified initially by DEAE Sepharose ion exchange followed by utilisation of the FLAG tag for final purification on an M2 anti-FLAG immunoaffinity column purchased from Sigma-Aldrich (cat no. A1205).

(2) Oral Glucose Tolerance Test (OGTT)

Oral glucose tolerance tests were done on conscious Zucker obese fa/fa rats (age 12-13 weeks or older) fed a high fat diet (45% kcal fat) for at least two weeks prior to experimentation. The animals were fasted for 2 hours before use for experiments. A test compound or a vehicle was given orally 120 minutes before oral administration of a glucose solution at a dose of 2 g/kg body weight. Blood glucose levels were measured using a Accucheck glucometer from tail bled samples taken at different time points before and after administration of glucose (time course of 60 minutes). A time curve of the blood glucose levels was generated and the area-under-the-curve (AUC) for 120 minutes was calculated (the time of glucose administration being time zero). Percent reduction in glucose excursion was determined using the AUC in the vehicle-control group as zero percent reduction.

Compounds of the invention generally have an activating activity for glucokinase with an EC$_{50}$ of less than about 500 nM, in particular less than 100 nm, for example less than 50 nm. For example, Example 3 has an EC$_{50}$ of 38 nm.

Example 3 exhibits 29% OGTT activity at 10 mg/kg.

References

1 Printz, R. L., Magnuson, M. A. and Granner, D. K. (1993) Annual Review of Nutrition 13, 463-96

2 DeFronzo, R. A. (1988) Diabetes 37, 667-87

3 Froguel, P., Zouali, H., Vionnet, N., Velho, G., Vaxillaire, M., Sun, F., Lesage, S., Stoffel, M., Takeda, J. and Passa, P. (1993) New England Journal of Medicine 328, 697-702

4 Bell, G. I., Pilkis, S. J., Weber, I. T. and Polonsky, K. S. (1996) Annual Review of Physiology 58, 171-86

5 Velho, G., Petersen, K. F., Perseghin, G., Hwang, J. H., Rothman, D. L., Pueyo, M. E., Cline, G. W., Froguel, P. and Shulman, G. I. (1996) Journal of Clinical Investigation 98, 1755-61

6 Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240-6

6a Gloyn, A. L., Noordam, K., Willemsen, M. A. A. P., Ellard, S., Lam, W. W. K., Campbell, I. W., Midgley, P., Shiota, C., Buettger, C., Magnuson, M. A., Matschinsky, F. M., and Hattersley, A. T.; Diabetes 52: 2433-2440

7 Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (1998) New England Journal of Medicine 338, 226-30

8 Caro, J. F., Triester, S., Patel, V. K., Tapscott, E. B., Frazier, N. L. and Dohm, G. L. (1995) Hormone & Metabolic Research 27, 19-22

9 Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287-95

10 Shiota, M., Postic, C., Fujimoto, Y., Jetton, T. L., Dixon, K., Pan, D., Grimsby, J., Grippo, J. F., Magnuson, M. A. and Cherrington, A. D. (2001) Diabetes 50, 622-9

11 Ferre, T., Pujol, A., Riu, E., Bosch, F. and Valera, A. (1996) Proceedings of the National Academy of Sciences of the United States of America 93, 7225-30

12 Seoane, J., Barbera, A., Telemaque-Potts, S., Newgard, C. B. and Guinovart, J. J. (1999) Journal of Biological Chemistry 274, 31833-8

13 Moore, M. C., Davis, S. N., Mann, S. L. and Cherrington, A. D. (2001) Diabetes Care 24, 1882-7

14 Alvarez, E., Roncero, I., Chowen, J. A., Vazquez, P. and Blazquez, E. (2002) Journal of Neurochemistry 80, 45-53

15 Lynch, R. M., Tompkins, L. S., Brooks, H. L., Dunn-Meynell, A. A. and Levin, B. E. (2000) Diabetes 49, 693-700

16 Roncero, I., Alvarez, E., Vazquez, P. and Blazquez, E. (2000) Journal of Neurochemistry 74, 1848-57

17 Yang, X. J., Kow, L. M., Funabashi, T. and Mobbs, C. V. (1999) Diabetes 48, 1763-1772

18 Schuit, F. C., Huypens, P., Heimberg, H. and Pipeleers, D. G. (2001) Diabetes 50, 1-11

19 Levin, B. E. (2001) International Journal of Obesity 25, supplement 5, S68-S72.

20 Alvarez, E., Roncero, I., Chowen, J. A., Thorens, B. and Blazquez, E. (1996) Journal of Neurochemistry 66, 920-7

21 Mobbs, C. V., Kow, L. M. and Yang, X. J. (2001) American Journal of Physiology-Endocrinology & Metabolism 281, E649-54

22 Levin, B. E., Dunn-Meynell, A. A. and Routh, V. H. (1999) American Journal of Physiology 276, R1223-31

23 Spanswick, D., Smith, M. A., Groppi, V. E., Logan, S. D. and Ashford, M. L. (1997) Nature 390, 521-5

24 Spanswick, D., Smith, M. A., Mirshamsi, S., Routh, V. H. and Ashford, M. L. (2000) Nature Neuroscience 3, 757-8

25 Levin, B. E. and Dunn-Meynell, A. A. (1997) Brain Research 776, 146-53

26 Levin, B. E., Govek, E. K. and Dunn-Meynell, A. A. (1998) Brain Research 808, 317-9

27 Levin, B. E., Brown, K. L. and Dunn-Meynell, A. A. (1996) Brain Research 739, 293-300

28 Rowe, I. C., Boden, P. R. and Ashford, M. L. (1996) Journal of Physiology 497, 365-77

29 Fujimoto, K., Sakata, T., Arase, K., Kurata, K., Okabe, Y. and Shiraishi, T. (1985) Life Sciences 37, 2475-82

30 Kurata, K., Fujimoto, K. and Sakata, T. (1989) Metabolism: Clinical & Experimental 38, 46-51

31 Kurata, K., Fujimoto, K., Sakata, T., Etou, H. and Fukagawa, K. (1986) Physiology & Behavior 37, 615-20

32 Jetton T. L., Liang Y., Pettepher C. C., Zimmerman E. C., Cox F. G., Horvath K., Matschinsky F. M., and Magnuson M. A., J. Biol. Chem., February 1994; 269: 3641-3654

33 Reimann F. and Gribble F. M., Diabetes 2002 51: 2757-2763

34 Cheung A. T., Dayanandan B., Lewis J. T., Korbutt G. S., Rajotte R. V., Bryer-Ash M., Boylan M. O., Wolfe M. M., Kieffer T. J., *Science, Vol* 290, Issue 5498, 1959-1962, 8 Dec. 2000

The invention claimed is:
1. A compound of Formula (I) or a pharmaceutically acceptable salt thereof:

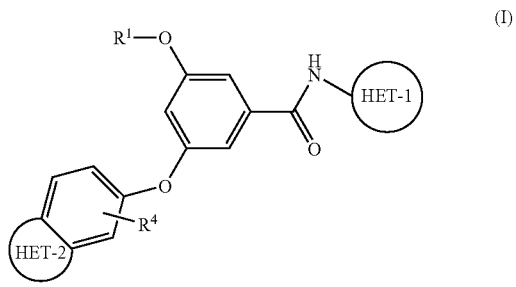

(I)

wherein:
R¹ is selected from isopropyl, but-2-yl, 1,1,1-trifluoroprop-2-yl, 1,3-difluoroprop-2-yl, but-1-yn-3-yl, 1-hydroxyprop-2-yl, hydroxybut-3-yl, 1-hydroxybut-2-yl, tetrahydrofuranyl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl, 1-fluoromethoxyprop-2-yl, 1,1-difluoromethoxyprop-2-yl, and 1-trifluoromethoxyprop-2-yl;

HET-1 is a 5- or 6-membered, C-linked heteroaryl ring containing a nitrogen atom in the 2-position and optionally 1 or 2 further ring heteroatoms independently selected from O, N, and S; which ring is optionally substituted on any nitrogen atom by a substituent selected from R⁷ and/or on any available carbon atom by 1 or 2 substituents independently selected from R⁶;

HET-2 is a 5- to 7-membered heterocyclic ring fused to the benzene ring, containing 1, 2, or 3 ring heteroatoms independently selected from O, S, and N wherein any ring carbon or sulfur atom may optionally be oxidised and wherein HET-2 is optionally substituted on any nitrogen atom by a substituent selected from R² and/or on any available carbon atom by 1 or 2 substituents independently selected from R³;

R² is selected from (1-4C)alkyl, (3-6C)cycloalkyl, benzyl, (1-4C)alkylcarbonyl, (1-4C)alkylsulphonyl, hydroxy (1-4C)alkyl, and (1-4C)alkoxy(1-4C)alkyl;

R³ is selected from (1-4C)alkyl, (3-6C)cycloalkyl, (1-4C) alkoxy, hydroxy, fluoro, and chloro;

R⁴ is selected from hydrogen, fluoro, and chloro;

R⁶ is independently selected from (1-4C)alkyl, halo, hydroxy(1-4C)alkyl, (1-4C)alkoxy(1-4C)alkyl, (1-4C) alkylS(O)$_p$(1-4C)alkyl, amino(1-4C)alkyl, (1-4C)alkylamino(1-4C)alkyl, di(1-4C)alkylamino(1-4C)alkyl, and HET-3;

R⁷ is independently selected from (1-4C)alkyl, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl, and HET-3;

HET-3 is a 5- or 6-membered, C- or N-linked unsubstituted heteroaryl ring containing 1, 2, or 3 ring heteroatoms independently selected from O, N, and S;

p is independently 0, 1, or 2.

2. A compound of the Formula (I) according to claim 1, or a pharmaceutically-acceptable salt thereof, wherein HET-1 is selected from optionally substituted thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, and triazolyl.

3. A compound of the Formula (I) according to claim 1, or a pharmaceutically-acceptable salt thereof, wherein HET-1 is selected from pyrazolyl, thiadiazolyl, and pyrazinyl, optionally substituted on carbon or nitrogen by methyl or ethyl.

4. A compound of the Formula (I) according to claim 1, or a pharmaceutically-acceptable salt thereof, wherein $R^1$ is of sub-formula X:

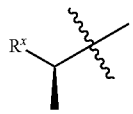
(X)

wherein $R^x$ is selected from methyl, trifluoromethyl, ethynyl, hydroxymethyl, hydroxyethyl, methoxymethyl, fluoromethoxymethyl, difluoromethoxymethyl and trifluoromethoxymethyl.

5. A compound of the Formula (I) according to claim 1, or a pharmaceutically-acceptable salt thereof, wherein $R^1$ is selected from 1-hydroxyprop-2-yl, 1-methoxyprop-2-yl, 1-hydroxybut-2-yl, isopropyl, tetrahydrofuranyl, and 1,3-difluoroprop-2-yl.

6. A compound of the Formula (I) according to claim 1, or a pharmaceutically-acceptable salt thereof, wherein HET-1 is selected from pyrazolyl, thiadiazolyl and pyrazinyl, optionally substituted on carbon or nitrogen by methyl or ethyl; and $R^1$ is selected from 1-hydroxyprop-2-yl, 1-methoxyprop-2-yl, 1-hydroxybut-2-yl, isopropyl, tetrahydrofuranyl, and 1,3-difluoroprop-2-yl; except that when HET-1 is unsubstituted pyrazolyl, $R^1$ is selected from 1-methoxyprop-2-yl, isopropyl, and tetrahydrofuranyl.

7. A compound of the Formula (I) according to claim 1, or a pharmaceutically-acceptable salt thereof, wherein the bicyclic system formed by HET-2 fused to the benzo ring is selected from Formulae A to M:

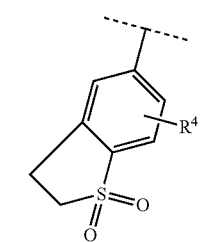
A

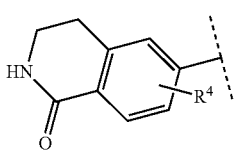
B

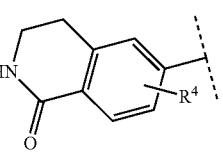
C

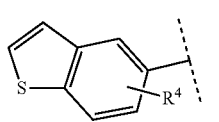
D

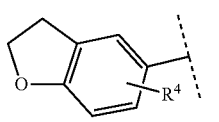

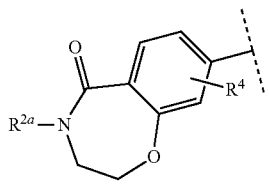
E

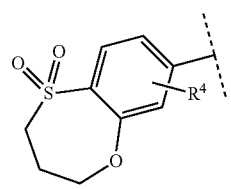
F

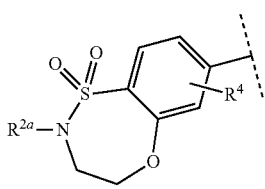
G

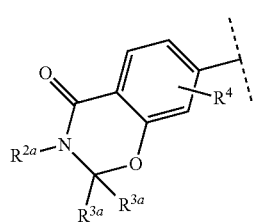
H

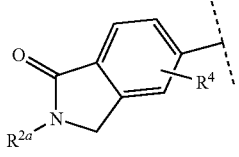
J

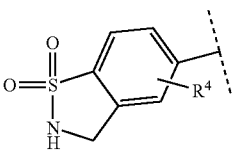
K

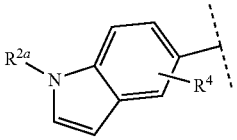
L

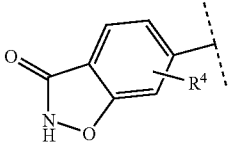
M wherein $R^{2a}$ is hydrogen or is selected from $R^2$ as defined in claim 1, $R^{3a}$ is hydrogen or is selected from $R^3$ as defined in claim 1, and each $R^4$ is as defined in claim 1.

8. A compound of the Formula (I) according to claim 7, or a pharmaceutically-acceptable salt thereof, wherein the bicyclic system formed by HET-2 fused to the benzo ring is selected from Formulae E, F, G and H.

9. A compound of the Formula (I) according to claim 7, or a pharmaceutically-acceptable salt thereof, wherein $R^{3a}$ is hydrogen, $R^{2a}$ is hydrogen or is methyl, and $R^4$ is hydrogen or fluoro.

10. A compound of the Formula (I) according to claim 1, or a pharmaceutically-acceptable salt thereof, wherein the bicyclic system formed by HET-2 fused to the benzo ring is of Formula (Z):

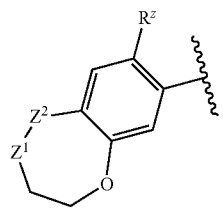

wherein $R^z$ is hydrogen or fluoro, $Z^1$ is $CH_2$ or $NR^{2a}$, $R^{2a}$ is hydrogen or methyl, and $Z^2$ is C(=O) or $SO_2$.

11. A compound of the Formula (I) according to claim 7, or a pharmaceutically-acceptable salt thereof, wherein:
   HET-1 is pyrazolyl, methylthiadiazolyl or optionally substituted pyrazinyl, wherein optional substituents are selected from methyl and ethyl;
   $R^1$ is 1-hydroxyprop-2-yl, 1-methoxyprop-2-yl, tetrahydrofuranyl, 1,3-difluoroprop-2-yl, isopropyl or 1-hydroxybut-2-yl; except that when HET-1 is unsubstituted pyrazolyl, $R^1$ is selected from 1-methoxyprop-2-yl, isopropyl, and tetrahydrofuranyl;
   the bicyclic system formed by HET-2 fused to the benzo ring is selected from Formulae E, F and G;
   each $R^{3a}$ is hydrogen;
   $R^{2a}$ is hydrogen or methyl;
   $R^4$ is hydrogen or fluoro.

12. A compound of Formula (I) according to claim 7, or a pharmaceutically-acceptable salt thereof, wherein HET-1 is 3-methyl-1,2,4-thiadiazol-5-yl.

13. A compound of the Formula (I) according to claim 1, which is one or more of the following:
   3-[(2,2-difluoro-1,3-benzodioxol-5-yl)oxy]-5-[(1S)-2-hydroxy-1-methylethoxy]-N-(1-methyl-1H-pyrazol-3-yl) benzamide;
   3-(1,3-benzodioxol-5-yloxy)-5-[(1S)-2-hydroxy-1-methylethoxy]-N-(1-methyl-1H-pyrazol-3-yl)benzamide;
   3-[(8-fluoro-2,3-dimethyl-4-oxo-3,4-dihydro-2H-1,3-benzoxazin-7-yl)oxy]-5-[(1S)-2-hydroxy-1-methylethoxy]-N-(1-methyl-1H-pyrazol-3-yl)benzamide;
   3-[(7-fluoro-5,5-dioxido-3,4-dihydro-2H-1,5-benzoxathiepin-8-yl)oxy]-5-[(1S)-2-hydroxy-1-methylethoxy]-N-(1-methyl-1H-pyrazol-3-yl)benzamide;
   3-[(1S)-2-hydroxy-1-methylethoxy]-5-[(1-methyl-1H-indol-5-yl)oxy]-N-(1-methyl-1H-pyrazol-3-yl)benzamide;
   3-(2,3-dihydro-1-benzofuran-5-yloxy)-5-[(1S)-2-hydroxy-1-methylethoxy]-N-(1-methyl-1H-pyrazol-3-yl) benzamide;
   3-[(1S)-2-hydroxy-1-methylethoxy]-5-(1H-indol-5-yloxy)-N-(1-methyl-1H-pyrazol-3-yl)benzamide;
   3-(1-benzothien-5-yloxy)-5-[(1S)-2-hydroxy-1-methylethoxy]-N-(1-methyl-1H-pyrazol-3-yl)benzamide;
   3-[(9-chloro-4-methyl-5-oxo-2,3,4,5-tetrahydro-1,4-benzoxazepin-8-yl)oxy]-5-[(1S)-2-hydroxy-1-methylethoxy]-N-(1-methyl-1H-pyrazol-3-yl)benzamide;
   3-[(4-benzyl-9-fluoro-5-oxo-2,3,4,5-tetrahydro-1,4-benzoxazepin-8-yl)oxy]-5-[(1S)-2-hydroxy-1-methylethoxy]-N-(1-methyl-1H-pyrazol-3-yl)benzamide;
   3-[(8-chloro-3-ethyl-2-methyl-4-oxo-3,4-dihydro-2H-1,3-benzoxazin-7-yl)oxy]-5-[(1S)-2-hydroxy-1-methylethoxy]-N-(1-methyl-1H-pyrazol-3-yl)benzamide; and
   3-[(1S)-2-hydroxy-1-methylethoxy]-5-[(4-methyl-5-oxo-2,3,4,5-tetrahydro-1,4-benzoxazepin-8-yl)oxy]-N-(1-methyl-1H-pyrazol-3-yl)benzamide; and/or
   3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-(1-methyl-1H-pyrazol-3-yl)benzamide; and
   3-[(1,1-dioxido-3,4-dihydro-2H-5,1,2-benzoxathiazepin-7-yl)oxy]-5-{[(1S)-2-hydroxy-1-methylethyl]oxy}-N-(1-methyl-1H-pyrazol-3-yl)benzamide; and/or
   3-[(9-chloro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide;
   3-[(8-chloro-2,3-dimethyl-4-oxo-3,4-dihydro-2H-1,3-benzoxazin-7-yl)oxy]-5-{[(1S)-1-methyl-2-(methyloxy)ethyl]oxy}-N-(1-methyl-1H-pyrazol-3-yl)benzamide;
   3-[(9-chloro-4-methyl-5-oxo-2,3,4,5-tetrahydro-1,4-benzoxazepin-8-yl)oxy]-N-(1-ethyl-1H-pyrazol-3-yl)-5-{[(1S)-1-methyl-2-(methyloxy)ethyl]oxy}benzamide;
   3-[(2,3-dimethyl-4-oxo-3,4-dihydro-2H-1,3-benzoxazin-7-yl)oxy]-5-{[(1S)-1-methyl-2-(methyloxy)ethyl]oxy}-N-(1-methyl-1H-pyrazol-3-yl)benzamide;
   N-(1-ethyl-1H-pyrazol-3-yl)-3-{[(1S)-1-methyl-2-(methyloxy)ethyl]oxy}-5-[(4-methyl-5-oxo-2,3,4,5-tetrahydro-1,4-benzoxazepin-8-yl)oxy]benzamide;
   3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(1-methyl-1H-pyrazol-3-yl)benzamide;
   3-{[2-fluoro-1-(fluoromethyl)ethyl]oxy}-5-[(9-fluoro-4-methyl-5-oxo-2,3,4,5-tetrahydro-1,4-benzoxazepin-8-yl)oxy]-N-(1-methyl-1H-pyrazol-3-yl)benzamide;
   3-[(9-chloro-4-methyl-5-oxo-2,3,4,5-tetrahydro-1,4-benzoxazepin-8-yl)oxy]-N-(1-ethyl-1H-pyrazol-3-yl)-5-{[(1S)-2-hydroxy-1-methylethyl]oxy}benzamide;
   3-[(9-chloro-4-methyl-5-oxo-2,3,4,5-tetrahydro-1,4-benzoxazepin-8-yl)oxy]-5-[(1-methylethyl)oxy]-N-(1-methyl-1H-pyrazol-3-yl)benzamide;
   3-[(1-methylethyl)oxy]-5-[(4-methyl-5-oxo-2,3,4,5-tetrahydro-1,4-benzoxazepin-8-yl)oxy]-N-(1-methyl-1H-pyrazol-3-yl)benzamide; and
   3-[(8-chloro-2,3-dimethyl-4-oxo-3,4-dihydro-2H-1,3-benzoxazin-7-yl)oxy]-5-{[(1S)-1-(hydroxymethyl)propyl]oxy}-N-(1-methyl-1H-pyrazol-3-yl)benzamide; and/or
   3-[(1,1-dioxido-2,3-dihydro-1-benzothien-5-yl)oxy]-5-{[(1S)-1-methyl-2-(methyloxy)ethyl]oxy}-N-(1-methyl-1H-pyrazol-3-yl)benzamide;
   N-(1-ethyl-1H-pyrazol-3-yl)-3-{[(1S)-2-hydroxy-1-methylethyl]oxy}-5-[(4-methyl-5-oxo-2,3,4,5-tetrahydro-1,4-benzoxazepin-8-yl)oxy]benzamide;
   N-(1-ethyl-1H-pyrazol-3-yl)-3-[(9-fluoro-4-methyl-5-oxo-2,3,4,5-tetrahydro-1,4-benzoxazepin-8-yl)oxy]-5-{[(1S)-1-methyl-2-(methyloxy)ethyl]oxy}benzamide;
   3-[(9-fluoro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide;
   3-[(7-fluoro-4-methyl-5-oxo-2,3,4,5-tetrahydro-1,4-benzoxazepin-8-yl)oxy]-5-{[(1S)-1-methyl-2-(methyloxy)ethyl]oxy}-N-(1-methyl-1H-pyrazol-3-yl)benzamide;

3-[(9-chloro-4-methyl-5-oxo-2,3,4,5-tetrahydro-1,4-benzoxazepin-8-yl)oxy]-N-(1-methyl-1H-pyrazol-3-yl)-5-[(3S)-tetrahydrofuran-3-yloxy]benzamide;

3-[(4-methyl-5-oxo-2,3,4,5-tetrahydro-1,4-benzoxazepin-8-yl)oxy]-N-(1-methyl-1H-pyrazol-3-yl)-5-[(3S)-tetrahydrofuran-3-yloxy]benzamide; and/or 3-{[(1S)-1-methyl-2-(methyloxy)ethyl]oxy}-N-(1-methyl-1H-pyrazol-3-yl)-5-[(2,2,3-trimethyl-4-oxo-3,4-dihydro-2H-1,3-benzoxazin-7-yl)oxy]benzamide;

N-(1-methyl-1H-pyrazol-3-yl)-3-[(3S)-tetrahydrofuran-3-yloxy]-5-[(2,2,3-trimethyl-4-oxo-3,4-dihydro-2H-1,3-benzoxazin-7-yl)oxy]benzamide;

3-{[(1S)-1-methyl-2-(methyloxy)ethyl]oxy}-N-(5-methylpyrazin-2-yl)-5-[(2,2,3-trimethyl-4-oxo-3,4-dihydro-2H-1,3-benzoxazin-7-yl)oxy]benzamide;

3-{[(1S)-1-methyl-2-(methyloxy)ethyl]oxy}-5-[(3-methyl-4-oxo-3,4-dihydro-2H-1,3-benzoxazin-7-yl)oxy]-N-(1-methyl-1H-pyrazol-3-yl)benzamide;

3-[(3-methyl-4-oxo-3,4-dihydro-2H-1,3-benzoxazin-7-yl)oxy]-N-(1-methyl-1H-pyrazol-3-yl)-5-[(3S)-tetrahydrofuran-3-yloxy]benzamide;

3-{[(1S)-1-methyl-2-(methyloxy)ethyl]oxy}-5-[(3-methyl-4-oxo-3,4-dihydro-2H-1,3-benzoxazin-7-yl)oxy]-N-(5-methylpyrazin-2-yl)benzamide;

3-({2,2-dimethyl-3-[(methyloxy)methyl]-4-oxo-3,4-dihydro-2H-1,3-benzoxazin-7-yl}oxy)-5-{[(1S)-1-methyl-2-(methyloxy)ethyl]oxy}-N-(1-methyl-1H-pyrazol-3-yl)benzamide;

3-({2,2-dimethyl-3-[(methyloxy)methyl]-4-oxo-3,4-dihydro-2H-1,3-benzoxazin-7-yl}oxy)-N-(5-methylpyrazin-2-yl)-5-[(3S)-tetrahydrofuran-3-yloxy]benzamide;

3-({2,2-dimethyl-3-[(methyloxy)methyl]-4-oxo-3,4-dihydro-2H-1,3-benzoxazin-7-yl}oxy)-N-(5-methylpyrazin-2-yl)-5-[(3S)-tetrahydrofuran-3-yloxy]benzamide;

3-{[(1S)-2-hydroxy-1-methylethyl]oxy}-5-[(3-methyl-4-oxo-3,4-dihydro-2H-1,3-benzoxazin-7-yl)oxy]-N-(5-methylpyrazin-2-yl)benzamide;

3-{[(1S)-2-hydroxy-1-methylethyl]oxy}-5-[(3-methyl-4-oxo-3,4-dihydro-2H-1,3-benzoxazin-7-yl)oxy]-N-(3-methyl-1,2,4-thiadiazol-5-yl)benzamide;

3-[(2,2-dimethyl-4-oxo-3,4-dihydro-2H-1,3-benzoxazin-7-yl)oxy]-N-(5-methylpyrazin-2-yl)-5-[(3S)-tetrahydrofuran-3-yloxy]benzamide;

3-[(2,2-dimethyl-4-oxo-3,4-dihydro-2H-1,3-benzoxazin-7-yl)oxy]-5-{[(1S)-1-methyl-2-(methyloxy)ethyl]oxy}-N-(5-methylpyrazin-2-yl)benzamide;

3-[(2-methyl-1,1-dioxido-3,4-dihydro-2H-5,1,2-benzoxathiazepin-7-yl)oxy]-5-{[(1S)-1-methyl-2-(methyloxy)ethyl]oxy}-N-(5-methylpyrazin-2-yl)benzamide;

3-[(1,1-dioxido-3,4-dihydro-2H-5,1,2-benzoxathiazepin-7-yl)oxy]-5-{[(1S)-1-methyl-2-(methyloxy)ethyl]oxy}-N-(5-methylpyrazin-2-yl)benzamide;

3-{[(1S)-1-methyl-2-(methyloxy)ethyl]oxy}-5-[(3-methyl-4-oxo-3,4-dihydro-2H-1,3-benzoxazin-7-yl)oxy]-N-1H-pyrazol-3-ylbenzamide;

3-[(3-methyl-4-oxo-3,4-dihydro-2H-1,3-benzoxazin-7-yl)oxy]-N-1H-pyrazol-3-yl-5-[(3S)-tetrahydrofuran-3-yloxy]benzamide;

3-[(1-methylethyl)oxy]-5-[(3-methyl-4-oxo-3,4-dihydro-2H-1,3-benzoxazin-7-yl)oxy]-N-1H-pyrazol-3-ylbenzamide;

3-[(3-methyl-4-oxo-3,4-dihydro-2H-1,3-benzoxazin-7-yl)oxy]-N-(5-methylpyrazin-2-yl)-5-[(3S)-tetrahydrofuran-3-yloxy]benzamide;

3-[(9-chloro-4-methyl-5-oxo-2,3,4,5-tetrahydro-1,4-benzoxazepin-8-yl)oxy]-N-(5-methylpyrazin-2-yl)-5-[(3S)-tetrahydrofuran-3-yloxy]benzamide;

N-(5-methylpyrazin-2-yl)-3-[(1-oxo-1,2,3,4-tetrahydroisoquinolin-6-yl)oxy]-5-[(3S)-tetrahydrofuran-3-yloxy]benzamide;

3-[(4-methyl-5-oxo-2,3,4,5-tetrahydro-1,4-benzoxazepin-8-yl)oxy]-N-1H-pyrazol-3-yl-5-[(3S)-tetrahydrofuran-3-yloxy]benzamide;

3-[(2-methyl-1,1-dioxido-3,4-dihydro-2H-5,1,2-benzoxathiazepin-7-yl)oxy]-5-{[(S)-1-methyl-2-(methyloxy)ethyl]oxy}-N-1H-pyrazol-3-ylbenzamide;

3-[(1,1-dioxido-3,4-dihydro-2H-5,1,2-benzoxathiazepin-7-yl)oxy]-5-{[(1S)-1-methyl-2-(methyloxy)ethyl]oxy}-N-1H-pyrazol-3-ylbenzamide;

3-[(5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide;

3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(5-methylpyrazin-2-yl)benzamide;

3-{[(1S)-1-methyl-2-(methyloxy)ethyl]oxy}-5-[(4-methyl-5-oxo-2,3,4,5-tetrahydro-1,4-benzoxazepin-8-yl)oxy]-N-1H-pyrazol-3-ylbenzamide;

3-{[(1S)-1-methyl-2-(methyloxy)ethyl]oxy}-5-[(4-methyl-5-oxo-2,3,4,5-tetrahydro-1,4-benzoxazepin-8-yl)oxy]-N-(3-methyl-1,2,4-thiadiazol-5-yl)benzamide;

3-[(1-methylethyl)oxy]-5-[(4-methyl-5-oxo-2,3,4,5-tetrahydro-1,4-benzoxazepin-8-yl)oxy]-N-1H-pyrazol-3-ylbenzamide;

3-{[(1S)-2-hydroxy-1-methylethyl]oxy}-5-[(4-methyl-5-oxo-2,3,4,5-tetrahydro-1,4-benzoxazepin-8-yl)oxy]-N-(5-methylpyrazin-2-yl)benzamide;

3-[(2,3-dimethyl-4-oxo-3,4-dihydro-2H-1,3-benzoxazin-7-yl)oxy]-5-{[(1S)-2-hydroxy-1-methylethyl]oxy}-N-(3-methyl-1,2,4-thiadiazol-5-yl)benzamide;

3-{[(1S)-2-hydroxy-1-methylethyl]oxy}-5-[(4-methyl-5-oxo-2,3,4,5-tetrahydro-1,4-benzoxazepin-8-yl)oxy]-N-(3-methyl-1,2,4-thiadiazol-5-yl)benzamide;

3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-(5-methylpyrazin-2-yl)benzamide;

3-[(7-fluoro-5,5-dioxido-3,4-dihydro-2H-1,5-benzoxathiepin-8-yl)oxy]-5-{[(1S)-1-methyl-2-(methyloxy)ethyl]oxy}-N-1H-pyrazol-3-ylbenzamide;

3-[(7-fluoro-5,5-dioxido-3,4-dihydro-2H-1,5-benzoxathiepin-8-yl)oxy]-5-{[(1S)-2-hydroxy-1-methylethyl]oxy}-N-(5-methylpyrazin-2-yl)benzamide;

3-[(5,5-dioxido-3,4-dihydro-2H-1,5-benzoxathiepin-8-yl)oxy]-5-{[(1S)-2-hydroxy-1-methylethyl]oxy}-N-(5-methylpyrazin-2-yl)benzamide; and 3-[(5,5-dioxido-3,4-dihydro-2H-1,5-benzoxathiepin-8-yl)oxy]-5-{[(1S)-1-methyl-2-(methyloxy)ethyl]oxy}-N-1H-pyrazol-3-ylbenzamide;

or a pharmaceutically-acceptable salt thereof.

14. A compound of the Formula (I) according to claim 1, which is 3-[(7-fluoro-5,5-dioxido-3,4-dihydro-2H-1,5-benzoxathiepin-8-yl)oxy]-5-[(1S)-2-hydroxy-1-methylethoxy]-N-(1-methyl-1H-pyrazol-3yl)benzamide or a pharmaceutically-acceptable salt thereof.

15. A pharmaceutical composition comprising a compound according to claim 1, or a pharmaceutically-acceptable salt thereof, together with a pharmaceutically acceptable diluent or carrier.

16. A method of treating type 2 diabetes comprising administering an effective amount of a compound of Formula (I) according to claim 1, or a pharmaceutically-acceptable salt thereof, to a mammal in need of such treatment.

17. A process for the preparation of a compound of Formula (I) according to claim 1, comprising any one of the processes (a) to (e):

(a) reacting an acid of Formula (III) or activated derivative thereof with a compound of Formula (IV), wherein $R^1$ is as hereinbefore defined or a protected version thereof;

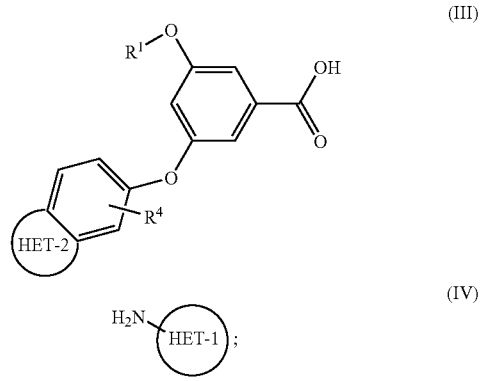

(III)

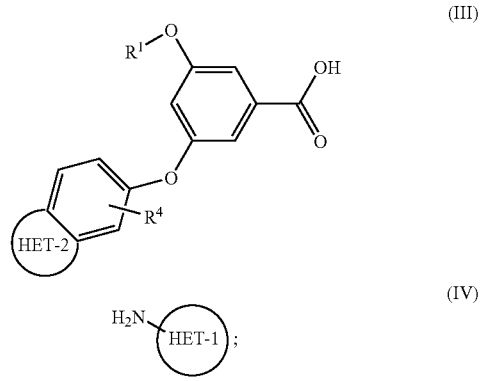

(IV)

or (b) reacting a compound of Formula (V) with a compound of Formula (VI), $R^1$—$X^1$     (V)

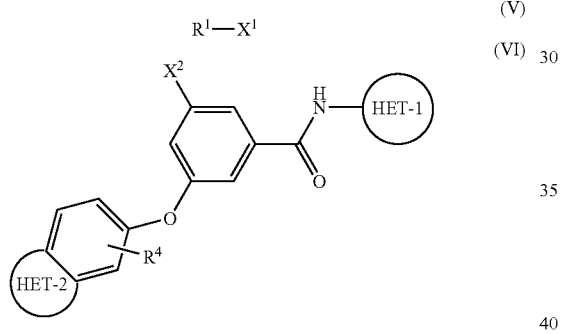

(VI)

wherein $X^1$ is a leaving group and $X^2$ is a hydroxyl group; or $X^1$ is a hydroxyl group and $X^2$ is a leaving group; and wherein $R^1$ is as hereinbefore defined or a protected version thereof;

or reacting a compound of Formula (V) with the intermediate ester of Formula (VII), wherein $P^1$ is a protecting group as hereinafter described, followed by ester hydrolysis and amide formation;

$R^1$—$X^1$     (V)

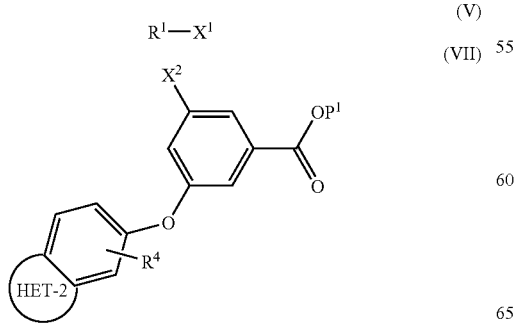

(VII)

or (c) reacting a compound of Formula (VIII) with a compound of Formula (IX)

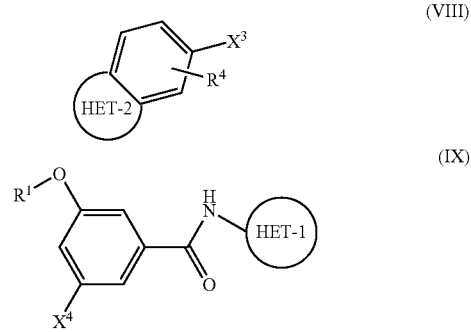

(VIII)

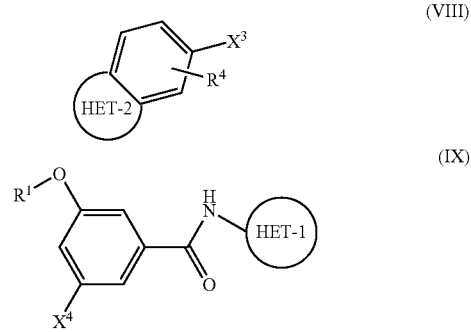

(IX)

wherein $X^3$ is a leaving group or an organometallic reagent and $X^4$ is a hydroxyl group; or $X^3$ is a hydroxyl group and $X^4$ is a leaving group or an organometallic reagent; and
wherein $R^1$ is as hereinbefore defined or a protected version thereof;

or reacting a compound of Formula (VIII) with the intermediate ester of Formula (X), followed by ester hydrolysis and amide formation;

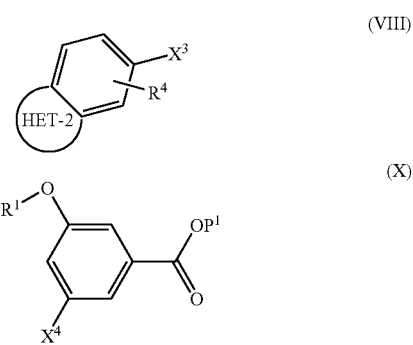

(VIII)

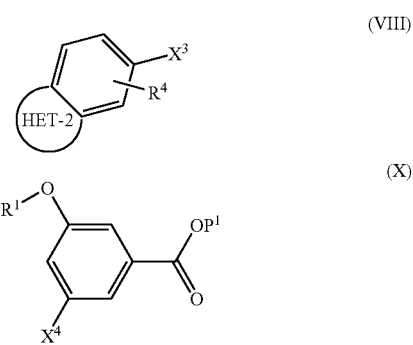

(X)

or (d) reacting a compound of Formula (XI) with a compound of Formula (XII),

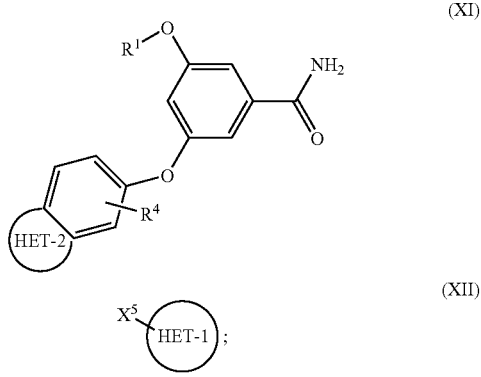

(XI)

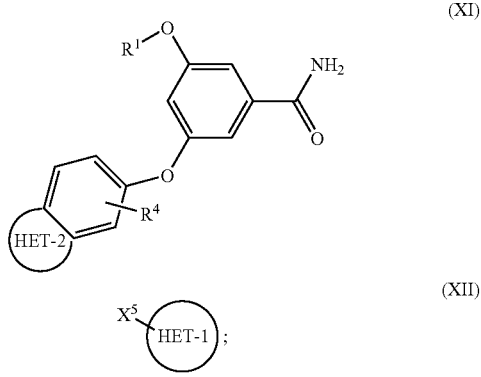

(XII)

wherein $X^5$ is a leaving group; and wherein $R^1$ is as hereinbefore defined or a protected version thereof;

or e) cyclizing a compound of Formula (XIII) to a compound of Formula (I)

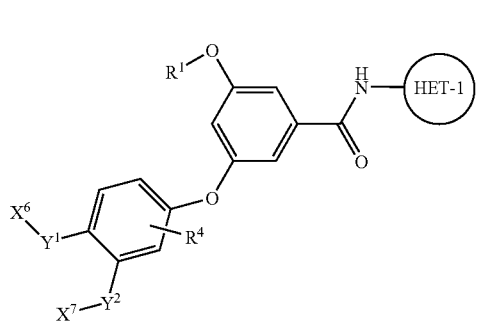

(XIII)

wherein $Y^1$ and $Y^2$ are 0-4 atom linkers, wherein each linker atom is independently selected from C, N, S, or O (wherein any C or S can be optionally oxidised and any atom can be optionally substituted provided it is not quaternised and there are no S—S or O—O bonds); $X^6$ is a nucleophilic species and $X^7$ is a leaving group or vice versa; and wherein $R^1$ is as hereinbefore defined or a protected version thereof;

or cyclizing the intermediate ester of Formula (XIV) to a compound of Formula (I), followed by ester hydrolysis and amide formation;

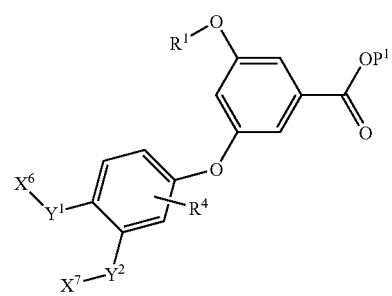

(XIV)

and thereafter, optionally:
i) converting a compound of Formula (I) into another compound of Formula (I);
ii) removing any protecting groups; and/or
iii) forming a pharmaceutically-acceptable salt thereof.

* * * * *